(12) United States Patent
McAdow et al.

(10) Patent No.: US 9,968,668 B2
(45) Date of Patent: May 15, 2018

(54) STAPHYLOCOCCAL COAGULASE ANTIGENS AND METHODS OF THEIR USE

(71) Applicant: UNIVERSITY OF CHICAGO, Chicago, IL (US)

(72) Inventors: Molly McAdow, Chicago, IL (US); Andrea Dedent, Chicaco, IL (US); Alice Cheng, Chicago, IL (US); Carla Emolo, Chicago, IL (US); Dominique Missiakas, Chicago, IL (US); Olaf Schneewind, Chicago, IL (US)

(73) Assignee: The University of Chicago, Chicago, IL (US)

(*) Notice: Subject to any disclaimer, the term of this patent is extended or adjusted under 35 U.S.C. 154(b) by 142 days.

(21) Appl. No.: 14/397,031

(22) PCT Filed: Mar. 14, 2013

(86) PCT No.: PCT/US2013/031695
§ 371 (c)(1),
(2) Date: Oct. 24, 2014

(87) PCT Pub. No.: WO2013/162746
PCT Pub. Date: Oct. 31, 2013

(65) Prior Publication Data
US 2015/0273040 A1 Oct. 1, 2015

Related U.S. Application Data

(60) Provisional application No. 61/638,831, filed on Apr. 26, 2012, provisional application No. 61/674,619, filed on Jul. 23, 2012.

(51) Int. Cl.
| | |
|---|---|
| *A61K 39/08* | (2006.01) |
| *C07K 14/31* | (2006.01) |
| *A61K 39/085* | (2006.01) |
| *C12N 9/52* | (2006.01) |
| *A61K 38/48* | (2006.01) |
| *A61K 45/06* | (2006.01) |
| *C07K 16/12* | (2006.01) |

(52) U.S. Cl.
CPC ............ *A61K 39/085* (2013.01); *A61K 38/48* (2013.01); *A61K 45/06* (2013.01); *C07K 14/31* (2013.01); *C12N 9/52* (2013.01); *C07K 16/1271* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,648,240 A | 7/1997 | Hook et al. | 435/69.3 |
| 5,801,234 A | 9/1998 | Hodgson et al. | 536/23.7 |
| 5,840,846 A | 11/1998 | Hook et al. | 530/350 |
| 6,008,341 A | 12/1999 | Foster et al. | 536/23.7 |
| 6,288,214 B1 | 9/2001 | Hook et al. | 530/387.1 |
| 7,608,276 B2* | 10/2009 | Masignani | A61K 39/085 424/184.1 |
| 8,287,884 B2* | 10/2012 | Masignani | A61K 39/085 424/234.1 |
| 8,398,996 B2* | 3/2013 | Masignani | A61K 39/085 424/234.1 |
| 8,465,750 B2* | 6/2013 | Masignani | A61K 39/085 424/234.1 |
| 8,679,505 B2* | 3/2014 | Bagnoli | C07K 14/31 424/190.1 |
| 8,703,148 B2* | 4/2014 | Biemans | A61K 39/085 424/184.1 |
| 8,732,783 B2* | 5/2014 | Kwak | G11B 27/10 725/135 |
| 8,747,864 B2* | 6/2014 | Masignani | A61K 39/085 424/234.1 |
| 8,753,650 B2* | 6/2014 | Masignani | A61K 39/085 424/234.1 |
| 8,758,765 B2* | 6/2014 | Missiakas | A61K 39/085 424/185.1 |
| 8,808,699 B2* | 8/2014 | Schneewind | A61K 39/085 424/139.1 |
| 8,821,894 B2* | 9/2014 | Schneewind | C07K 14/31 424/190.1 |
| 8,858,955 B2* | 10/2014 | Biemans | A61K 39/385 424/193.1 |
| 8,945,588 B2* | 2/2015 | Schneewind | C07K 14/31 424/130.1 |

(Continued)

FOREIGN PATENT DOCUMENTS

| | | |
|---|---|---|
| EP | 0786519 | 7/1997 |
| KR | 2007/082448 A1 * | 8/2007 |

(Continued)

OTHER PUBLICATIONS

Kinoshita et al, Microbiol Immunol 2008; 52: 334-348.*
McAdow, Molly Elizabeth [Ph.D.]; Schneewind, Olaf [advisor] CS The University of Chicago (0330) SO Dissertation Abstracts International, (2012) vol. 73, No. 11 B(E).*
Jansen et al, Vaccine 31 (2013) 2723-2730.*
Flower et al, Clin Microbiol Infect 2014; 20 (Suppl. 5): 66-75.*
Diep et al, Lancet 2006; 367: 731-39.*
McAdow et al, et al J. Innate Immunity, Jan. 2012, 4:141-148.*
Bagnoli et al,Frontiers in Cellular and Infection Microbiology, Feb. 2012, vol. 2/Article 16:1-4.*
Grundmeier et al, Infection and Immunity, Dec. 2004, 72/12:7155-7163.*
Bjerketorp et al, FEMS Microbiology Letters, 2004, 234:309-314.*
Abdallah et al., *Mol. Microbiol.*, 62, 667-679, 2006.
Abdallah et al., *Nat. Rev. Microbiol.*, 5, 883-891, 2007.
Andersen et al., *J Immunol.*, 154, 3359-3372, 1995.
Archer, *Clin. Infect. Dis.*, 26, 1179-1181, 1998.
Bjerketorp et al., *FEMS Microbiology Letters*, 234(2):309-314, 2010.
Bjerketorp, et al., *FEMS Microbiol Lett.* 234:309-314, 2004.
Bjerketorp, et al., *Microbiol.* 148:2037-2044, 2002.
Boake, *J Immunol.* 76:89-96, 1956.

(Continued)

Primary Examiner — Nita M Minnifield
(74) Attorney, Agent, or Firm — Norton Rose Fulbright US LLP

(57) ABSTRACT

The present invention concerns methods and compositions for treating or preventing a bacterial infection, particularly infection by a *Staphylococcus bacterium*. The invention provides methods and compositions for stimulating an immune response against the bacteria. In certain embodiments, the methods and compositions involve coagulase Domains 1-2 and variants thereof.

21 Claims, 18 Drawing Sheets

(56) References Cited

U.S. PATENT DOCUMENTS

| | | | |
|---|---|---|---|
| 9,085,631 B2* | 7/2015 | Moller | A61K 39/085 |
| 9,095,540 B2* | 8/2015 | Schneewind | |
| 9,181,329 B2* | 11/2015 | Bubeck-Wardenburg | |
| 9,212,219 B2* | 12/2015 | Schneewind | A61K 39/085 |
| 9,315,554 B2* | 4/2016 | Schneewind | A61K 39/085 |
| 2002/0061569 A1* | 5/2002 | Haselbeck | A61K 31/7088 |
| | | | 435/183 |
| 2002/0169288 A1 | 11/2002 | Hook et al. | 530/350 |
| 2004/0014178 A1* | 1/2004 | Guss | A61K 38/36 |
| | | | 435/69.6 |
| 2004/0029129 A1* | 2/2004 | Wang | C07K 14/195 |
| | | | 435/6.18 |
| 2005/0037444 A1* | 2/2005 | Meinke | C07K 14/195 |
| | | | 435/7.23 |
| 2005/0256299 A1* | 11/2005 | Foster | C07K 16/30 |
| | | | 530/300 |
| 2006/0115490 A1* | 6/2006 | Masignani | A61K 39/085 |
| | | | 424/190.1 |
| 2008/0038287 A1* | 2/2008 | Meinke | C07K 14/195 |
| | | | 424/190.1 |
| 2008/0085289 A1* | 4/2008 | Castado | A61K 39/085 |
| | | | 424/243.1 |
| 2008/0095777 A1* | 4/2008 | Castado | A61K 39/085 |
| | | | 424/139.1 |
| 2009/0269349 A1* | 10/2009 | Foster | C07K 16/30 |
| | | | 424/139.1 |
| 2010/0021503 A1* | 1/2010 | Denoel | A61K 31/70 |
| | | | 424/243.1 |
| 2010/0047267 A1* | 2/2010 | Masignani | A61K 39/085 |
| | | | 424/190.1 |
| 2010/0055130 A1* | 3/2010 | Masignani | A61K 39/085 |
| | | | 514/1.1 |
| 2010/0143399 A1* | 6/2010 | Biemans | A61K 39/385 |
| | | | 424/197.11 |
| 2010/0322959 A1* | 12/2010 | Biemans | A61K 39/085 |
| | | | 424/194.1 |
| 2011/0008385 A1* | 1/2011 | Castado | A61K 39/085 |
| | | | 424/197.11 |
| 2011/0206676 A1* | 8/2011 | Missiakas | A61K 39/085 |
| | | | 424/139.1 |
| 2011/0262477 A1* | 10/2011 | Cheng | A61K 39/085 |
| | | | 424/190.1 |
| 2012/0020890 A1* | 1/2012 | Masignani | A61K 39/085 |
| | | | 424/9.1 |
| 2012/0093850 A1* | 4/2012 | Bagnoli | C07K 14/31 |
| | | | 424/190.1 |
| 2012/0107340 A1* | 5/2012 | Bagnoli | C07K 14/31 |
| | | | 424/190.1 |
| 2012/0282247 A1* | 11/2012 | Schneewind | C07K 14/31 |
| | | | 424/130.1 |
| 2013/0136746 A1* | 5/2013 | Schneewind | A61K 39/085 |
| | | | 424/139.1 |
| 2013/0171183 A1* | 7/2013 | Schneewind | C07K 14/31 |
| | | | 424/190.1 |
| 2013/0230550 A1* | 9/2013 | Schneewind | A61K 39/085 |
| | | | 424/190.1 |
| 2014/0037650 A1* | 2/2014 | Kim | C07K 16/1271 |
| | | | 424/165.1 |
| 2014/0072556 A1* | 3/2014 | Moller | A61K 39/085 |
| | | | 424/133.1 |
| 2014/0170134 A1* | 6/2014 | Schneewind | C07K 16/1271 |
| | | | 424/131.1 |
| 2014/0178425 A1* | 6/2014 | Bagnoli | C07K 14/31 |
| | | | 424/190.1 |
| 2014/0335095 A1* | 11/2014 | Schneewind | A61K 39/085 |
| | | | 424/139.1 |
| 2015/0044251 A1* | 2/2015 | Contorni | A61K 39/085 |
| | | | 424/192.1 |
| 2015/0056240 A1* | 2/2015 | Schneewind | C07K 14/31 |
| | | | 424/190.1 |
| 2015/0210775 A1* | 7/2015 | Church | C07K 16/40 |
| | | | 424/133.1 |
| 2015/0273040 A1* | 10/2015 | McAdow | C07K 14/31 |
| | | | 424/243.1 |
| 2015/0322117 A1* | 11/2015 | Moller | A61K 39/085 |
| | | | 424/139.1 |
| 2015/0328302 A1* | 11/2015 | Castado | A61K 39/085 |
| | | | 424/139.1 |
| 2015/0368322 A1* | 12/2015 | McAdow | C07K 16/1271 |
| | | | 424/133.1 |
| 2016/0074497 A1* | 3/2016 | Falugi | C07K 14/31 |
| | | | 424/190.1 |

FOREIGN PATENT DOCUMENTS

| | | | |
|---|---|---|---|
| KR | 2007082442 A1 * | 8/2007 | |
| WO | WO 98/57994 | 12/1998 | |
| WO | WO 9933954 A1 | 7/1999 | |
| WO | WO 00/02523 | 1/2000 | |
| WO | WO 00/12132 | 3/2000 | |
| WO | WO 00/12689 | 3/2000 | |
| WO | WO 00/15238 | 3/2000 | |
| WO | WO 2002/28892 A1 * | 4/2001 | |
| WO | WO 01/34809 | 5/2001 | |
| WO | WO 01/60852 | 8/2001 | |
| WO | WO 2001/70955 A2 * | 9/2001 | |
| WO | WO 01/98499 | 12/2001 | |
| WO | WO 02/059148 | 8/2002 | |
| WO | WO 2002/77183 A2 * | 10/2002 | |
| WO | WO 02/094868 | 11/2002 | |
| WO | WO 2003/011899 A2 * | 2/2003 | |
| WO | WO 2006032472 | 3/2006 | |
| WO | WO 2006032475 | 3/2006 | |
| WO | WO 2006032500 | 3/2006 | |
| WO | WO 2007113222 | 10/2007 | |
| WO | WO 2007113223 | 10/2007 | |
| WO | WO 2008/081014 A2 * | 7/2008 | |
| WO | WO 2010/014304 A2 * | 2/2010 | |
| WO | WO 2010/042481 A1 * | 4/2010 | |
| WO | WO 2010/119343 A2 * | 10/2010 | |
| WO | WO 2010/142906 A2 * | 12/2010 | |
| WO | WO 2011/005341 A2 * | 1/2011 | |
| WO | WO 2011/127032 A1 * | 10/2011 | |
| WO | WO 2011127032 | 10/2011 | |
| WO | WO 2012/003474 A2 * | 1/2012 | |
| WO | WO 2012/034067 A1 * | 3/2012 | |
| WO | WO 2012/136653 A1 * | 10/2012 | |
| WO | WO 2013/092985 A1 * | 12/2012 | |
| WO | WO 2013/162746 A1 * | 10/2013 | |

OTHER PUBLICATIONS

Brown et al., *Biochemistry*, 37:4397-4406, 1998.
Burts et al., *Proc. Natl. Acad. Sci. USA*, 102:1169-1174, 2005.
Cedergren et al., *Protein Eng.*, 6:441-448, 1993.
Cespedes et al., *J. Infect. Dis.* 191(3):444-52, 2005.
Cheng et al., *PLoS Pathogens*, 6(8):e1001036, 2010.
Cheng, et al., *Trends Microbiol.* 19: 225-232, 2011.
Dalbey and Wickner, *J. Biol. Chem.*, 260:15925-15931, 1985.
DeDent et al., *EMBO J.* 27:2656-2668, 2008.
DeDent et al., *J. Bacteriol.* 189:4473-4484, 2007.
DeDent, et al., *Sem Immunopathol.* 34: 317-333, 2012.
Deisenhofer et al., *Hoppe-Seyh Zeitsch. Physiol. Chem.* 359:975-985, 1978.
Deisenhofer, *Biochemistry* 20:2361-2370, 1981.
Dinges et al., *Clin. Microbiol. Rev.*, 13:16-34, 2000.
Duthie, *J Gen Microbiol.* 6: 95-107, 1952.
Ekstedt & Yotis, *J Bacteriol.* 80:496-500, 1960.
Ekstedt, *Ann. N.Y. Acad. Sci.*, 65:119-131, 1956.
Enright, et al., *J Clin Microbiol.* 38: 1008-1015, 2000.
Field and Smith, *J. Comp. Pathol.*, 55:63, 1945.
Fortune et al., *Proc Natl. Acad. Sci. USA*, 102:10676-10681, 2005.
Foster, *Nat. Rev. Microbiol.*, 3:948-958, 2005.
Friedrich, et al., *Nature.* 425:535-539, 2003.
Gomez et al., *EMBO J.* 26:701-709, 2007.
Gomez et al., *J. Biol. Chem.* 281:20190-20196, 2006.
Gomez et al., *Nature Med.* 10:842-8, 2004.
Goodyear and Silverman, *J Exp. Med.*, 197:1125-1139, 2003.

(56) References Cited

OTHER PUBLICATIONS

Goodyear, et al., *PNAS USA*. 101:11392-11397, 2004.
Gouda et al., *Biochemistry*, 31(40):9665-72, 1992.
Graille et al., *Proc. Nat. Acad. Sci. USA* 97:5399-5404, 2000.
Guggenberger et al., *PLoS Pathogens*, 8(1):e1002434, 2012.
Guss et al., *Eur. J Biochem*. 138:413-420, 1984.
Hale & Smith, *Br J Exp Pathol*. 26: 209-216, 1945.
Harrison, *Br Med J* 2: 149-152, 1963.
Harrison, *J Pathol Bacterial*. 87: 145-150, 1964.
Hartleib, et al., *Blood*. 96:2149-2156, 2000.
Hsu et al., *Proc. Natl. Acad. Sci. USA*, 100:12420-12425, 2003.
International Search Report and Written Opinion for PCT/US2013/031695, dated Mar. 14, 2013.
Jansson et al., *FEMS Immunol. Med. Microbiol*. 20:69-78 1998.
Jensen, *Acta Path. Microbiol. Scandin*. 44:421-428, 1958.
Kanemitsu, et al., *Microbiol Immunol*. 45: 23-27, 2001.
Kennedy et al., *Proc. Natl. Acad. Sci. USA* 105:1327-1332, 2008.
Klevens et al., *Clin. Infect. Dis*., 2008; 47:927-30, 2008.
Klevens et al., *JAMA*, 298:1763-1771, 2007.
Koreen, et al., *J Clin Microbiol*. 42: 792-799, 2004.
Kroh, et al., *PNAS USA*. 106:7786-7791, 2009.
Lancefield, *J Exp Med*. 47: 91-103, 1928.
Lancefield, *J immunol*. 89: 307-313, 1962.
Lee, *Trends Microbiol*. 4(4):162-166, 1996.
Lominski & Roberts, *J Pathol Bacteriol*. 58: 187-199, 1946.
Lominski, et al., *Lancet*. 1: 1315-1318, 1962.
Lominski, *J Gen Microbiol*. 3: ix, 1949.
Lowy, *N Engl J Med*. 339:520-532, 1998.
MacGurn et al., *Mol. Microbiol*., 57:1653-1663, 2005.
Marraffmi et al., 2006.
Mazmanian et al., *Mol. Microbiol*., 40(5):1049-1057, 2001.
Mazmanian et al., *Proc. Natl. Acad. Sci. USA*, 97:5510-5515, 2000.
Mazmanian et al., *Science*, 285(5428):760-3, 1999.
McAdow, et al., *PLoS Pathogens*. 7: e1002307, 2011.
McAdow et al., *Infection and Immunity*, 80(10):3389-3398, 2012.
McAdow et al., *Journal of Innate Immunity*, 4(2):141-148, 2012.
McCarthy & Lindsay, *BMC Microbiol*. 10: 173, 2010.
McLaughlin et al., *PLoS Pathog*., 3:e105, 2007.
Mora, et al., *PNAS USA*. 102: 15641-15646, 2005.
Moreillon, et al., *Infect Immun*. 63:4738-4743, 1995.
Much, *Biochem Z* 14:143-155, 1908.
Navarre and Schneewind, *J. Biol. Chem*., 274:15847-15856, 1999.
NCBI, GenBank Accession No. ACF21985.1, 2008.
NCBI, GenBank Accession No. CAC36438.1, 2001.
Novick, *Mol. Microbiol*., 48:1429-1449, 2003.
Nuccitelli, et al., *PNAS USA*. 108: 10278-10283, 2011.
O'Seaghdha et al., *FEBS J*. 273:4831-4841, 2006.
O'Brien, et al., *Mol Microbiol*. 44:1033-1044, 2002.
Pallen, *Trends Microbiol*., 10:209-212, 2002.
Panizzi et al., *J Biol. Chem*., 281:1179-1187, 2006.
Panizzi, et al., *Cell Mol Life Sci*. 61: 2793-2798, 2004.
Panizzi, et al., *Nat Med*. 17: 1142-1146, 2011.
Patel, et al., *Infect Contr Hosp Epidemiol*. 32: 881-888, 2011.
Phonimdaeng, et al., *Mol Microbiol*. 4:393-404, 1990.
Pym et al., *Nat. Med*., 9:533-539, 2003.
Rammelkamp, et al., *Ann NY Acad Sci*. 65: 144-151, 1956.
Rammelkamp, et al., *J Exp Med*. 91: 295-307, 1950.
Roben et al., *J. Immunol*. 154:6437-6445, 1995.
Salid-Salim et al., *Infect. Control Hosp. Epidemiol*. 24:451-455, 2003.
Schneewind & Missiakas, *PNAS USA*. 108: 10029-10030, 2011.
Schneewind et al., *Cell* 70:267-281, 1992.
Schneewind, et al., *Science*. 268:103-106, 1995.
Shaw et al., *Microbiology*, 150:217-228, 2004.
Sibbald et al., *Microbiol. Mol Biol. Rev*., 70:755-788, 2006.
Sjodahl, *Eur. J. Biochem*. 73:343-351, 1977.
Sjoquist et al., *Eur. J. Biochem*. 30:190-194, 1972.
Smith & Johnstone. *Nature*. 178: 982-983, 1956.
Smith et al., *Brit. J. Exp. Pathol*., 28:57, 1947.
Stanley et al., *Proc. Natl. Acad. Sci. USA*, 100:13001-13006, 2003.
Stranger-Jones et al., *Proc. Nat. Acad. Sci. USA*, 103:16942-16947, 2006.
Streitfeld, et al., *Nature*. 184(Suppl 21): 1665-1666, 1959.
Tager & Hales, *J Immunol*. 60: 1-9, 1948.
Tenover, et al., *Antimicrob Agents Chemother*. 56: 1324-1330, 2012.
Tiedemann et al., *Proc. Natl. Acad. Sci. USA*, 92:12156-12159, 1995.
Ton-That et al., *Proc. Natl. Acad. Sci. USA*, 96(22):12424-9, 1999.
Uhlen et al., *J. Biol. Chem*. 259:1695-1702 and 13628 (Corr.) 1984.
van Wely et al., *FEMS MicrobioL Rev*., 25:437-454, 2001.
Watanabe, et al., *J Bacteriol*. 187:3698-3707, 2005.
Watanabe, et al., *PLoS One*. S, 4: e5714, 2009.
Xu et al., *Mol. Microbiol*., 66(3):787-800, 2007.
Boehringer Ingelheim Vetmedica, Inc., "Staphylococcus aureus Bacterin Lysigin", 2012. Retrieved from https://www.bi-vetmedica.com/content/dam/internet/ah/vetmedica/com_EN/product_files/lysigin/lysigin_label.pdf on Aug. 11, 2016.
Extended European Search Report for EP13781494.3, dated Sep. 7, 2016.
Murphy et al., *Human Vaccines* 7:51-59 (2011).

\* cited by examiner

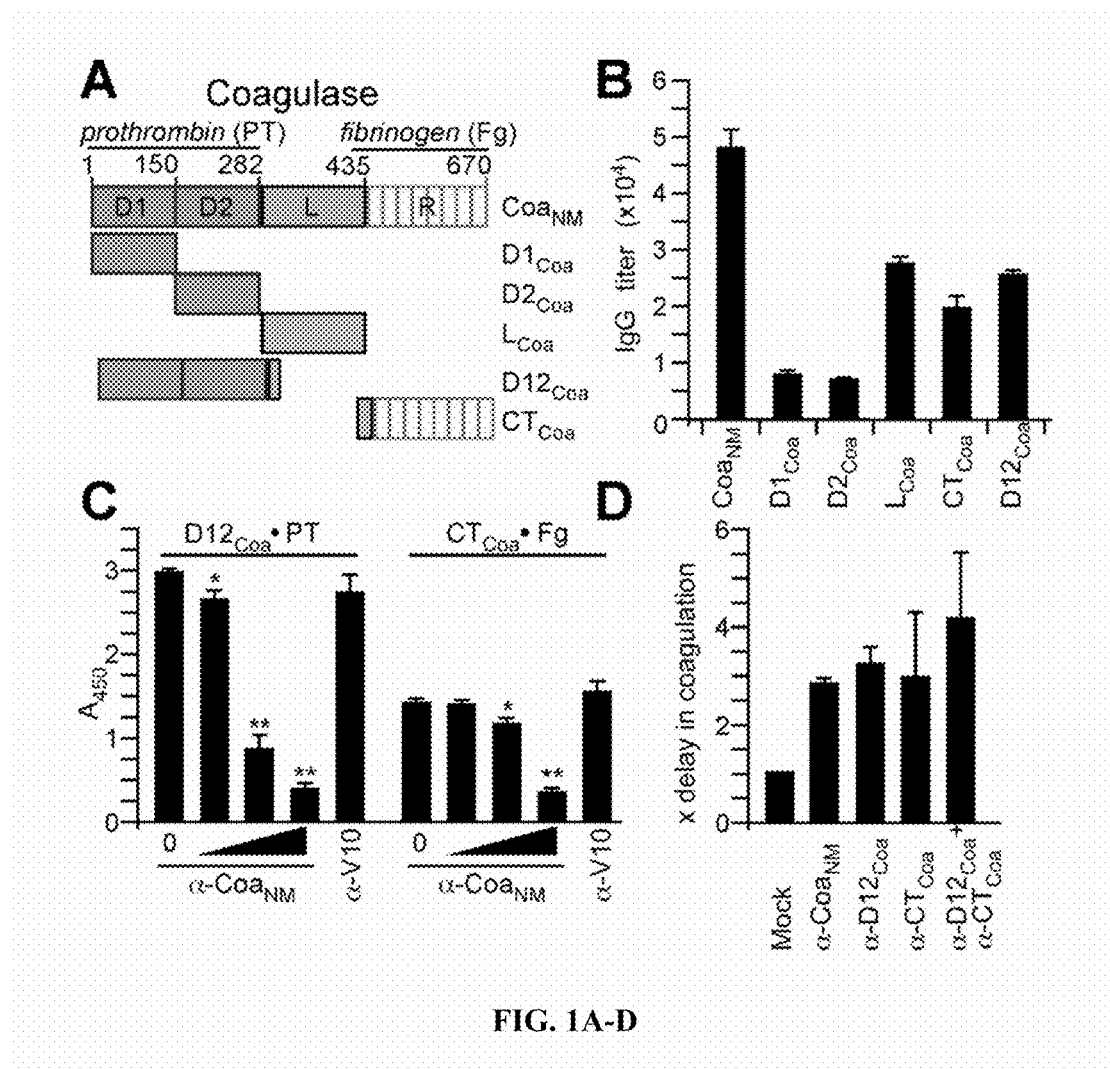
FIG. 1A-D

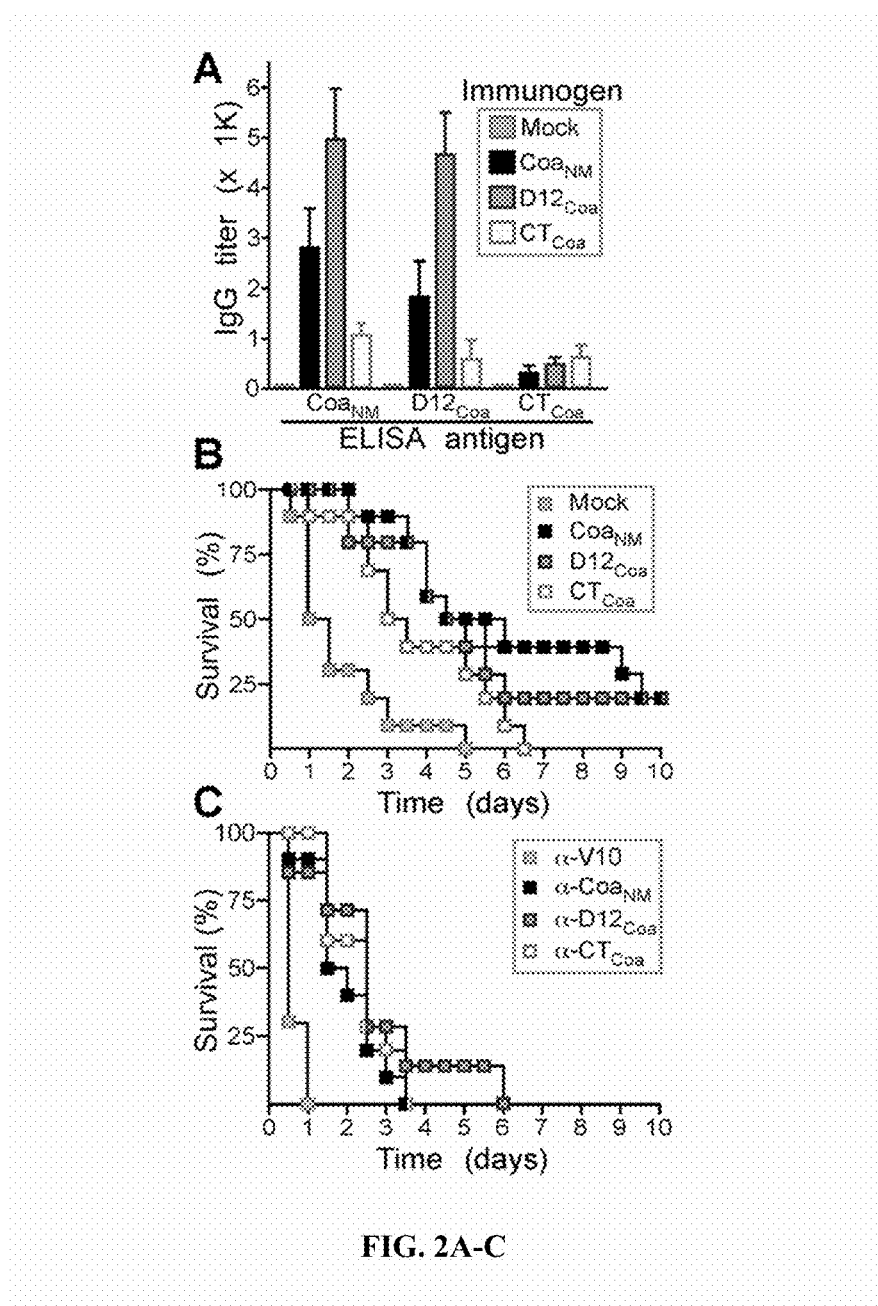
FIG. 2A-C

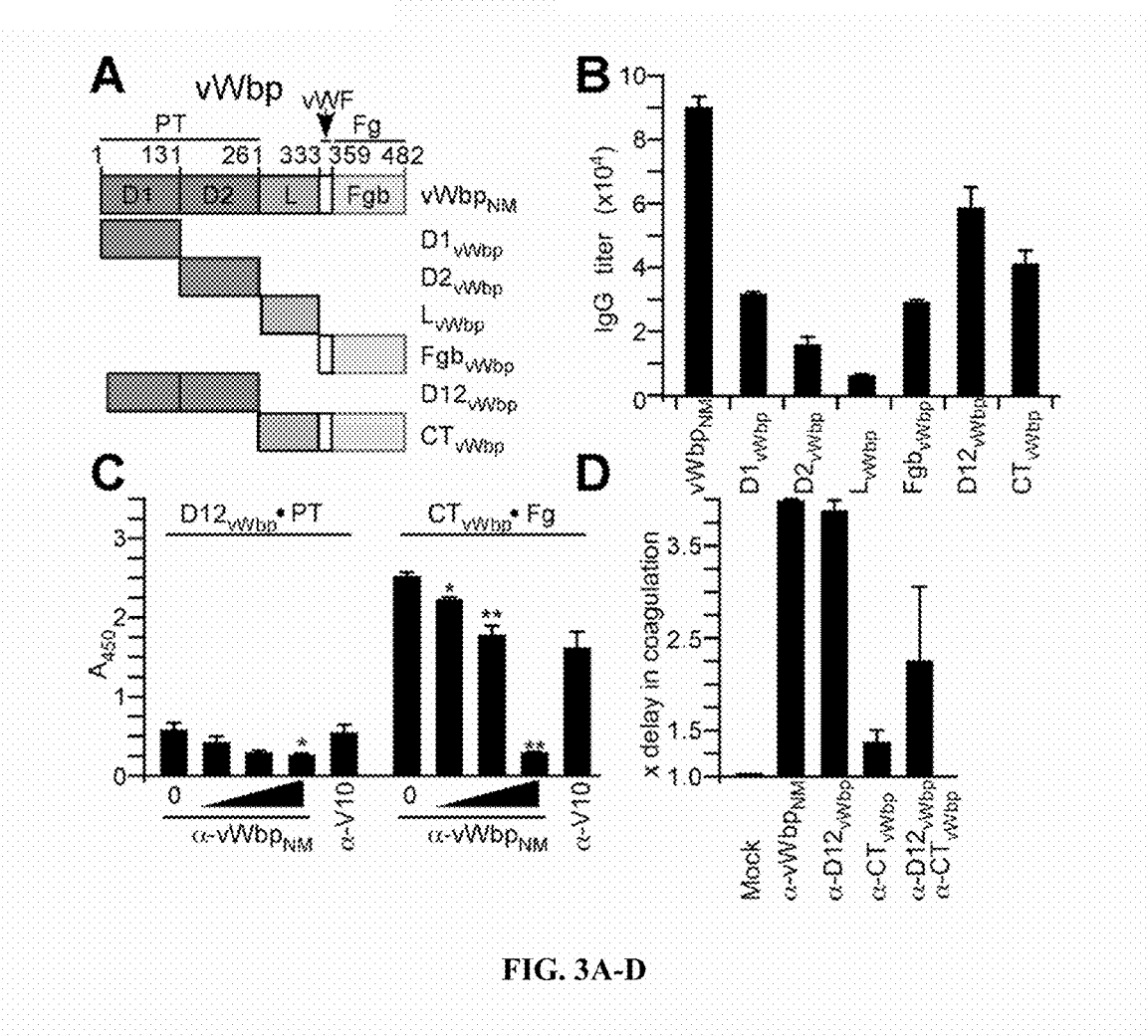
FIG. 3A-D

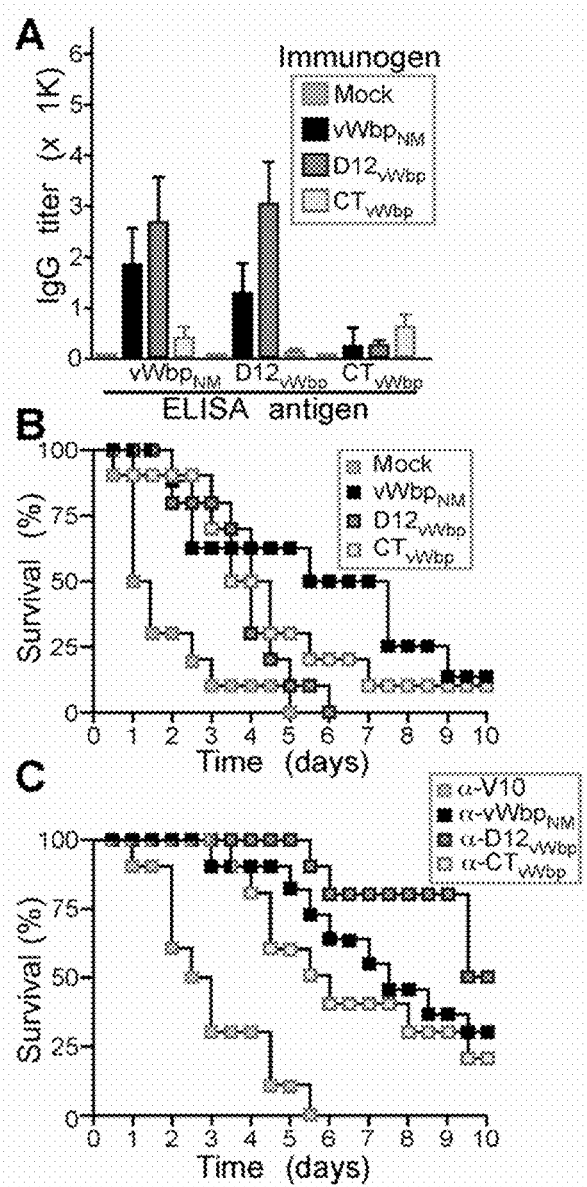
FIG. 4A-C

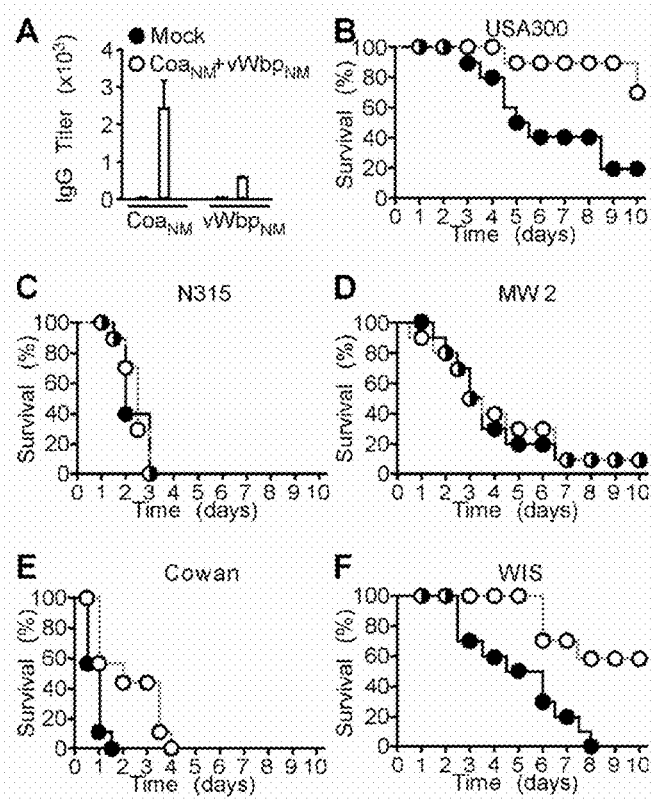
FIG. 5A-F
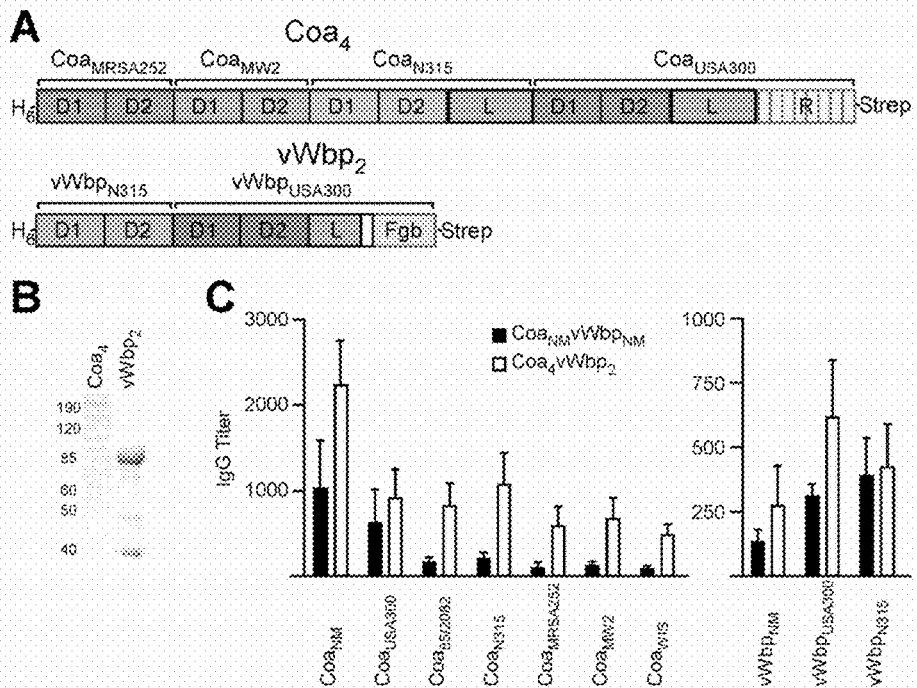
FIG. 6A-C

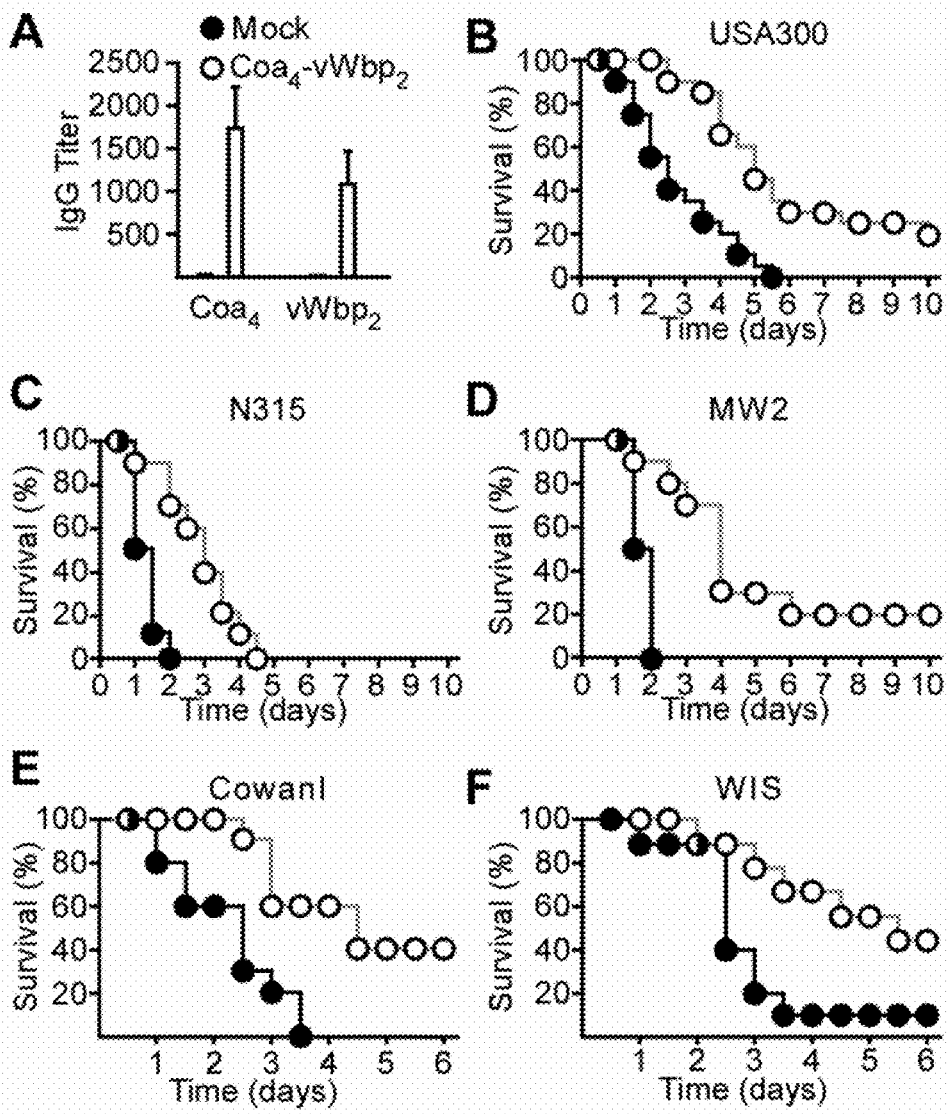
FIG. 7A-F

FIG. 8A

```
USA300_Coa    AAGAAATGATTGATGACTTAAATTCAATTATTGATGATTTCTTTATGGAAACTAAACA-A  771
N315_Coa      AAGAAATGATCGATGACTTAAATTCAATTATAGATGATTTCTTTATGGAGACTAAACA-A  756
MRSA252_Coa   AAGAAATGATGGATGATTTAAATTCTATTATTGATGATTTCTTTATGGATAC-AAACATG  771
MW2_Coa       AAGAAATGATTAAAGATTTAGAATCTATTATTGATGATTTCTTCATTGAAACCAAGTT-G  771
WIS_Coa       AAGAAATGATTAAAGATTTAGAATCTATTATTGATGATTTCTTCATTGAAACAAAGTT-G  693
              **********  * **  ***  *  **  ***** *********** ** ** ** **

USA300_Coa    AATAGACCGAAATCTATAACGAAATATAATCCTACAACACATAACTATAAAACAAATAGT  831
N315_Coa      AATAGACCGAATTCTATAACAAAATATGATCCAACAAAACACAATTTTAAAGAGAAGAGT  816
MRSA252_Coa   AATAGACCATTAAACATAACTAAATTTAATCCGAATATTCATGACTATACTAATAAGCCT  831
MW2_Coa       AATAGACCTAAACACATTACTAGGTATGATGGAACTAAACATGATTACCA---------T  822
WIS_Coa       AATAGACCTCAACACATTACTAGATATGATGGAACTAAACATGATTACCA---------T  744
              ********   ** **  *   *  **     *    **   * *              *

USA300_Coa    GATAATAAACCTAATTTTGATAAATTAGTTGAAGAAACGAAAAAAGCAGTTAAAGAAGCA  891
N315_Coa      GAAAATAAACCTAATTTTGATAAATTAGTTGAAGAAACAAAAAAAGCAGTTAAAGAAGCA  876
MRSA252_Coa   GAAAATAGAGATAACTTCGATAAATTAGTCAAAGAAACAAGAGAAGCAATCGCAAACGCT  891
MW2_Coa       AAACATAAAGATGGATTTGATGCTCTAGTTAAAGAAACAAGAAGAAGCCGGTTGCAAAGGCT  882
WIS_Coa       AAACATAAAGATGGATTTGATGCTTTAGTTAAAGAAACAAGAGAAGCGGTTTCTAAGGCT  804
              *  ***  *  *   **  ***     ****  *******  *  ****    *    * **

USA300_Coa    GATGATTCTTGGAAAAAGAAAACTGTCAAAAAATACGGAGAAACTGAAACAAAATCGCCA  951
N315_Coa      GACGAATCTTGGAAAAATAAAACTGTCAAAAAATACGAGGAAACTGTAACAAAATCTCCT  936
MRSA252_Coa   GACGAATCTTGGAAAACAAGAACCGTCAAAAAATTACGGTGAATCTGAAACAAAATCTCCT  951
MW2_Coa       GACGAATCTTGGAAAAATAAAACTGTCAAAAAATACGAGGAAACTGTAACAAAATCTCCA  942
WIS_Coa       GACGAATCTTGGAAAACTAAAACTGTCAAAAAATACGGGGAAACTGAAACAAAATATCCT  864
              ** ** **********  * *** ********  ****  *** *** *********    **

USA300_Coa    GTAGTAAAAGAAGAGAAGAAAGTTGAAGAACCTCAAGCACCTAAAGTTGATAACCAACAA  1011
N315_Coa      GTTGTAAAAGAAGAGAAGAAAGTTGAAGAACCTCAATTACCTAAAGTTGGAAACCAGCAA  996
MRSA252_Coa   GTTGTAAAAGAAGAGAAGAAAGTTGAAGAACCTCAATTACCTAAAGTTGGAAACCAGCAA  1011
MW2_Coa       GTTGTAAAAGAAGAGAAGAAAGTTGAAGAACCTCAATCACCTAAATTTGATAACCAACAA  1002
WIS_Coa       GTTGTAAAAGAAGAGAAGAAAGTTGAAGAACCTCAATCACCTAAAGTTTCTGAAAAAGTG  924
              ** ****************************  *******  *  ****        *   *

USA300_Coa    GAGGTTAAAACTACGGCTGGTAAAGCTGAAGAAACAACACAACCAGTTGCACAACCATTA  1071
N315_Coa      GAGGTTAAAACTACGGCTGGTAAAGCTGAAGAAACAACACAACCAGTTGCACAACCATTA  1056
MRSA252_Coa   GAGGATAAAATTACAGTTGGTACAACTGAAGAAGCACCATTACCAATTGCGCAACCACTA  1071
MW2_Coa       GAGGTTAAAATTACAGTTGATAAAGCTGAAGAAACAACACAACCAGTGGCACAGCCATTA  1062
WIS_Coa       GATGTTCAGGAAACGGTTGGTACAACTGAAGAAGCACCATTACCAATTGCGCAACCACTA  984
              **  *    ** **  * ** *  * ********   ** ** ** **  ** ** ** **

USA300_Coa    GTTAAAATTCCACAGGGCACAATTACAGGTGAAATTGTAAAAGGTCCGGAATATCCAACG  1131
N315_Coa      GTAAAAATTCCACAAGAAACAATCTATGGTGAAACTGTAAAAGGTCCAGAATATCCAACG  1116
MRSA252_Coa   GTTAAAATTCCACAGGGCACAATTCAAGGTGAAATTGTAAAAGGTCCGGAATATCTAACG  1131
MW2_Coa       GTTAAAATTCCACAGGGCACAATTACAGGTGAAATTGTAAAAGGTCCGGAATATCCAACG  1122
WIS_Coa       GTTAAATTACCACAAATTGGGACTCAAGGCGAAATTGTAAAAGGTCCCGACTATCCAACT  1044
              ** ***  * *****              ** ****  ************  **** ***

USA300_Coa    ATGGAAAATAAAACGGTACAAGGTGAAATCGTTCAAGGTCCCGATTTTCTAACAATGGAA  1191
N315_Coa      ATGGAAAATAAAACGTTACAAGGTGAAATCGTTCAAGGTCCCGATTTTCTAACAATGGAA  1176
MRSA252_Coa   ATGGAAAATAAAACGTTACAAGGTGAAATCGTTCAAGGTCCAGATTTCCCAACAATGGAA  1191
MW2_Coa       ATGGAAAATAAAACGGTACAAGGTGAAATCGTTCAAGGTCCAGATTTCCCAACAATGGAA  1182
WIS_Coa       ATGGAAAATAAAACGTTACAAGGTGTAATTGTTCAAGGTCCAGATTTCCCAACAATGGAA  1104
              ***************  ********  ***  *** *********   *****  * **********

USA300_Coa    CAAAGCGGCCCATCATTAAGCAATAATTATACAAACCCA---------------------  1230
N315_Coa      CAAAACAGACCATCTTTAAGCGATAATTATACTCAACCG---------------------  1215
MRSA252_Coa   CAAAACAGACCATCTTTAAGCGATAATTATACTCAACCG---------------------  1230
MW2_Coa       CAAAACAGACCATCTTTAAGCGATAATTATACTCAACCG---------------------  1221
WIS_Coa       CAAAACAGACCATCTTTAAGTGACAATTATACACAACCATCTGTGACTTTACCGTCAATT  1164
              ****   *  *****  ****  * ******** * **                  *  **

USA300_Coa    -------------CCGTTAACGAACCCTATTTTAGAAGGTCTTGAAGGTAGCTCATCTAAA  1278
N315_Coa      -------------ACGACACCGAACCCTATTTTAGAAGGTCTTGAAGGTAGCTCATCTAAA  1263
MRSA252_Coa   -------------ACGCACACCGAACCCTATTTTAAAAGGTATTGAAGGAAACTCAACTAAA  1278
MW2_Coa       -------------ACGACACCGAACCCTATTTTAGAAGGTCTTGAAGGTAGCTCATCTAAA  1269
WIS_Coa       ACAGGTGAAAGTACACCAACGAACCCTATTTTAAAAGGTATTGAAGGAAACTCATCTAAA  1224
                           *   * *************** ****** *  **** *  **** *****

USA300_Coa    CTTGAAATAAAACCACAAGGTACTGAATCAACGTTAAAAGGTACTCAAGGAGAATCAAGT  1338
N315_Coa      CTTGAAATAAAACCACAAGGTACTGAATCAACGTTAAAAGGTATTCAAGGAGAATCAAGT  1323
MRSA252_Coa   CTTGAAATAAAACCACAAGGTACTGAATCAACGTTAAAAGGTACTCAAGGAGAATCAAGT  1338
MW2_Coa       CTTGAAATAAAACCACAAGGTACTGAATCAACGTTAAAAGGTACTCAAGGAGAATCAAGT  1329
WIS_Coa       CTTGAAATAAAACCACAAGGTACTGAATCAACGTTGAAAGGTATTCAAGGAGAATCAAGT  1284
              ***********************************  *******  ***************

USA300_Coa    GATATTGAAGTTAAACCTCAAGCAACTGAAACAACAGAAGCTTCTCAATATGGTCCGAGA  1398
N315_Coa      GATATTGAAGTTAAACCTCAAGCAACTGAAACAACAGAAGCTTCTCAATATGGTCCGAGA  1383
MRSA252_Coa   GATATTGAAGTTAAACCTCAAGCAACTGAAACAACAGAAGCATCACATTATCCAGCGAGA  1398
MW2_Coa       GATATTGAAGTTAAACCTCAAGCAACTGAAACAACAGAAGCATCACATTATCCAGCAAGA  1389
WIS_Coa       GATATTGAAGTTAAACCTCAAGCAACTGAAACAACAGAAGCATCACATTATCCAGCGAGA  1344
              ***********************************     **  ** ***    * ***

USA300_Coa    CCGCAATTTAACAAAACACCTAAATATGTTAAATATAGAGATGCTGGTACAGGTATCCGT  1458
```

FIG. 8B

```
N315_Coa      CCGCAATTTAACAAAACACCTAAGTATGTGAAATATAGAGATGCTGGTACAGGTATCCGT 1443
MRSA252_Coa   CCTCAATTTAACAAAACACCTAAGTATGTGAAATATAGAGATGCTGGTACAGGTATCCGT 1458
MW2_Coa       CCTCAATTTAACAAAACACCTAAATATGTTAAATATAGAGATGCTGGTACAGGTATCCGT 1449
WIS_Coa       CCGCAATTTAACAAAACACCTAAATATGTGAAATATAGAGATGCTGGTACAGGTATTCGT 1404
              ** ******************** ***** ************************** ***

USA300_Coa    GAATACAACGATGGAACATTTGGATATGAAGCGAGACCAAGATTCAATAAGCCA------ 1512
N315_Coa      GAATACAACGATGGAACATTTGGATATGAAGCGAGACCAAGATTCAACAAGCCAAGTGAA 1503
MRSA252_Coa   GAATACAACGATGGAACATTTGGATATGAAGCGAGACCAAGATTCAACAAGCCAAG---- 1514
MW2_Coa       GAATACAACGATGGAACATTTGGATATGAAGCGAGACCAAGATTCAATAAGCCCATCAGAA 1509
WIS_Coa       GAATACAACGATGGAACTTTTGGATATGAAGCGAGACCAAGATTCAACAAGCCATCAGAA 1464
              ***************** ***************************** ****** ******

USA300_Coa    ------------------------TCA--------------------------------- 1515
N315_Coa      ACAAATGCATACAACGTAACGACAAATCAAGATGGCACAGTATCATACGGAGCTCGCCCA 1563
MRSA252_Coa   ------------------------C----------------------------------- 1515
MW2_Coa       ACAAACGCATACAACGTAACGACAAATCAAGATGGCACAGTAACATATGGCGCTCGCCCA 1569
WIS_Coa       ACAAACGCATACAACGTAACGACAAATCAAGATGGCACAGTATCATATGGGGCTCGCCCA 1524
                                      *

USA300_Coa    ------------------GAAACAAATGCATATAACGTAACAACACATGCAAATGGTCAA 1557
N315_Coa      ACACAAAACAAGCCAAGTGAAACAAACGCTATAACGTAACAACACATGCAAATGGTCAA 1623
MRSA252_Coa   ------------------GAAACAAATGCATACAACGTAACGACAAATCAAGATGGCACA 1557
MW2_Coa       ACACAAAACAAACCAAGCAAAACAAATGCATACAACGTAACAACACATGCAAATGGTCAA 1629
WIS_Coa       ACACAAAACAAGCCAAGCAAAACAAATGCATATAACGTAACAACACATGCAAACGGCCAA 1584
              *******  ***** ********* *** **  **  ** *

USA300_Coa    GTATCATACGGAGCTCGTCCGACA------------------------------------ 1581
N315_Coa      GTATCATACGGTGCTCGCCCAACA------------------------------------ 1647
MRSA252_Coa   GTATCATATGGCGCTCGCCCGACA------------------------------------ 1581
MW2_Coa       GTATCATATGGCGCTCGCCCGACA------------------------------------ 1653
WIS_Coa       GTATCATATGGCGCTCGCCCGACACATACAACAAGCCAAGTGAAACAAATGCATACAACGTA 1644
              ********  *  *****  **  ***

USA300_Coa    -----------------------------------------------CAAAACAAGCCAAGC 1596
N315_Coa      -----------------------------------------------CAAAAAAGCCAAGC 1662
MRSA252_Coa   -----------------------------------------------CAAAACAAGCCAAGC 1596
MW2_Coa       -----------------------------------------------CAAAACAAGCCAAGC 1668
WIS_Coa       ACGACAAATCGAGATGGCACAGTATCATATGGCGCTCGCCCGACACAAAAACAAGCCAAGC 1704
                                                             *****  ********

USA300_Coa    AAAACAAACGCATATAACGTAACAACACATGGAAACGGCCAAGTATCATATGGCGCTCGC 1656
N315_Coa      AAAACAAATGCATACAACGTAACAACACATGCAAATGGTCAAGTATCATATGGCGCTCGC 1722
MRSA252_Coa   GAAACAAACGCATATAACGTAACAACACATGCAAACGGCCAAGTATCATACGGAGCTCGT 1656
MW2_Coa       AAAACAAATGCATATAACGTAACAACACATGCAAATGGTCAAGTATCATACGGAGCTCGC 1728
WIS_Coa       GAAACGAATGCATATAACGTAACAACACACGGAAATGGCCAAGTATCATATGGCGCTCGT 1764
              ****  ** ***** **************  *** **  ****** ** ******* ** *****

USA300_Coa    CCAACACAAAACAAGCCAAGCAAAACAAATGCATACAACGTAACAACACATGCAAACGGT 1716
N315_Coa      CCGACACAAAAAAAGCCAAGCAAAACAAATGCATATAACGTAACAACACATGCAAATGGT 1782
MRSA252_Coa   CCGACACAAAACAAGCCAAGCGAAACGAACGCATATAACGTAACAACACATGCAAACGGT 1716
MW2_Coa       CCGACACAAAACAAGCCAAGCAAAACAAATGCATATAACGTAACAACACACGCAAACGGT 1788
WIS_Coa       CCGACACAAAAGAAGCCAAGCAAAACAAATGCATATAACGTAACAACACATGCAAACGGC 1824
              ** ********  ********* ***** ** ***** ****************** *****  **

USA300_Coa    CAAGTGTCATACGGAGCTCGCCCGACATACAAGAAGCCAAGTAAAACAAATGCATACAAT 1776
N315_Coa      CAAGTATCATACGGAGCTCGCCCGACATACAAGAAGCCAAGCGAAACAAATGCATACAAC 1842
MRSA252_Coa   CAAGTGTCATACGGAGCTCGCCCAACACAAAACAAGCCAAGTAAAACAAATGCATACAAT 1776
MW2_Coa       CAAGTGTCATACGGAGCTCGCCCGACATACAAGAAGCCAAGTAAAACAAATGCATACAAT 1848
WIS_Coa       CAAGTATCATATGGCGCTCGTCCGACATACAACAAGCCAAGTAAAACAAATGCATACAAT 1884
              ***** *****  **  *****  ** *****  *  **  ********  ******************

USA300_Coa    GTAACAACACATGCA--------------------------------------------- 1791
N315_Coa      GTAACAACACATGCAAATGGTCAAGTATCATATGGCGCTCGCCCGACACAAAAAAGCCA 1902
MRSA252_Coa   GTAACAACACATGCA--------------------------------------------- 1791
MW2_Coa       GTAACAACACATGCA--------------------------------------------- 1863
WIS_Coa       GTAACAACACATGCA--------------------------------------------- 1899
              ***************

USA300_Coa    ------------------------------------GATGGTACTGCGACATATGGGCCT 1815
N315_Coa      AGCGAAACAAACGCATATAACGTAACAACACATGCAGATGGTACTGCGACATATGGTCCT 1962
MRSA252_Coa   ------------------------------------GATGGTACTGCGACATATGGTCCT 1815
MW2_Coa       ------------------------------------GATGGTACTGCGACATATGGGCCT 1887
WIS_Coa       ------------------------------------GATGGTACTGCGACATATGGTCCT 1923
                                                  ******************** ***

USA300_Coa    AGAGTAACAAAATAA 1830
N315_Coa      AGAGTAACAAAATAA 1977
MRSA252_Coa   AGAGTAACAAAATAA 1830
MW2_Coa       AGAGTAACAAAATAA 1902
WIS_Coa       AGAGTAACAAAATAA 1938
              ***************
```

FIG. 8C

```
USA300_D1D2    IVTKDYSGKSQVNAGSKNGTLIDSRYLNSALYYLEDYIIYAIGLTNKYEYGDNIYKEAKD  60
Newman_D1D2    IVTKDYSGKSQVNAGSKNGTLIDSRYLNSALYYLEDYIIYAIGLTNKYEYGDNIYKEAKD  60
N315_D1D2      IVTKDYSKESRVNEKSKKGATVSDYYYWKIIDSLEAQFTGAIDLLEDYKYGDPIYKEAKD  60
MU50_D1D2      IVTKDYSKESRVNEKSKKGATVSDYYYWKIIDSLEAQFTGAIDLLEDYKYGDPIYKEAKD  60
MRSA252_D1D2   IVTKDYSKESRVNENSKYDTPIPDWYLGSILNRLGDQIYYAKELTNKYEYGEKEYKQAID  60
85/2082_D1D2   IVTKDYSKESRVNENSKYDTPIPDWYLGSILNRLGDQIYYAKELTNKYEYGEKEYKQAID  60
MW2_D1D2       IVTKDYSGKSQVNAGSKNGKQIADGYYWGIIENLENQFYNIFHLLDQHKYAEKEYKDAVD  60
WIS_D1D2       IVTKDYSGKSQVNAGSKNGKQIADGYYWGIIENLENQFYNIFHLLDQHKYAEKEYKDALD  60
               ******  : *:**   **  .    : .*     : *  :         *  :..::*.:   **:*.*

USA300_D1D2    RLLEKVLREDQYLLERKKSQYEDYKQWYANYKKENPRTDLKMANFHKYNLEELSMKEYNE  120
Newman_D1D2    RLLEKVLREDQYLLERKKSQYEDYKQWYANYKKENPRTDLKMANFHKYNLEELSMKEYNE  120
N315_D1D2      RLMTRVLGEDQYLLKKKIDEYELYKKWYKSSNK-----NTNMLTFHKYNLYNLTMNEYND  115
MU50_D1D2      RLMTRVLGEDQYLLKKKIDEYELYKKWYKSSNK-----NTNMLTFHKYNLYNLTMNEYND  115
MRSA252_D1D2   KLMTRVLGEDHYLLERKKAQYEAYKKWFEKHKSENPHSSLKKIKFDDFDLYRLTKKEYNE  120
85/2082_D1D2   KLMTRVLGEDHYLLERKKAQYEAYKKWFEKHKSENPHSSLKKIKFDDFDLYRLTKKEYNE  120
MW2_D1D2       KLKTRVLEEDQYLLERKKEKYEIYKELYKKYKKENPNTQVKMKAFDKYDLGDLTMEEYND  120
WIS_D1D2       KLKTRVLEEDQYLLERKKEKYEIYKELYKKYKKENPNTQVKMKAFDKYDLGDLTMEEYND  120
                :* :**  **:***::*   :** **:  : . :.    .  : *..::*  *: :***:

USA300_D1D2    LQDALKRALDDFHREVKDIKDKNSDLKTFNAAEEDKATKEVYDLVSEIDTLVVSYYGDKD  180
Newman_D1D2    LQDALKRALDDFHREVKDIKDKNSDLKTFNAAEEDKATKEVYDLVSEIDTLVVSYYGDKD  180
N315_D1D2      IFNSLKDAVYQFNKEVKEIEHKNVDLKQFDKDGEDKATKEVYDLVSEIDTLVVTYYADKD  175
MU50_D1D2      IFNSLKDAVYQFNKEVKEIEHKNVDLKQFDKDGEDKATKEVYDLVSEIDTLVVTYYADKD  175
MRSA252_D1D2   LHQSLKEAVDEFNSEVKNIQSKQKDLLPYDEATENRVTNGIYDFVCEIDTLYAAYFNHSQ  180
85/2082_D1D2   LHQSLKEAVDEFNSEVKNIQSKQKDLLPYDEATENRVTNGIYDFVCEIDTLYAAYFNHSQ  180
MW2_D1D2       LSKLLTKALDNFKLEVKKIESENPDLRPYSESEERTAYGKIDSLVDQAYSVYFAYVTDAQ  180
WIS_D1D2       LSKLLTKALDNFKLEVKKIESENPDLRPYSESEERTAYGKIDSLVDQAYSVYFAYVTDAQ  180
                :  . *.  *:  :*: ***.*:  :: **    :.      *    :  .:*  ::    :*  . :

USA300_D1D2    YGEHAKELRAKLDLILGDTDNPHKITNERIKKEMIDDLNSIIDDFFMETKQNRPKSITKY  240
Newman_D1D2    YGEHAKELRAKLDLILGDTDNPHKITNERIKKEMIDDLNSIIDDFFMETKQNRPKSITKY  240
N315_D1D2      YGEHAKELRAKLDLILGDTDNPHKITNERIKKEMIDDLNSIIDDFFMETKQNRPNSITKY  235
MU50_D1D2      YGEHAKELRAKLDLILGDTDNPHKITNERIKKEMIDDLNSIIDDFFMETKQNRPNSITKY  235
MRSA252_D1D2   YGHNAKELRAKLDIILGDAKDPVRITNERIRKEMMDDLNSIIDDFFMDTNMNRPLNITKF  240
85/2082_D1D2   YGHNAKELRAKLDIILGDAKDPVRITNERIRKEMMDDLNSIIDDFFMDTNMNRPLNITKF  240
MW2_D1D2       HKTEALNLRAKIDLILGDEKDPIRVTNQRTEKEMIKDLESIIDDFFIETKLNRPQHITRY  240
WIS_D1D2       HKTEALNLRAKIDLILGDEKDPIRVTNQRTEKEMIKDLESIIDDFFIETKLNRPQHITRY  240
                :   .* :****:*:****  .:*  ::**:* .***:.**:********::*:  ***   **::

USA300_D1D2    NPTTHNYKTNSDNKPNFDKLVEETKKAVKEADDSWKKKTVKK  282
Newman_D1D2    NPTTHNYKTNSDNKPNFDKLVEETKKAVKEADDSWKKKTVKK  282
N315_D1D2      DPTKHNFKEKSENKPNFDKLVEETKKAVKEADESWKNKTVKK  277
MU50_D1D2      DPTKHNFKEKSENKPNFDKLVEETKKAVKEADESWKNKTVKK  277
MRSA252_D1D2   NPNIHDYTNKPENRDNFDKLVKETREAIANADESWKTRTVKN  282
85/2082_D1D2   NPNIHDYTNKPENRDNFDKLVKETREAVANADESWKTRTVKN  282
MW2_D1D2       DGTKHDYHK---HKDGFDALVKETREAVAKADESWKNKTVKK  279
WIS_D1D2       DGTKHDYHK---HKDGFDALVKETREAVSKADESWKTKTVKK  279
                :  . *::       ::  .** **:**;:*; :**;***.:***;
```

FIG. 8D

Alignment of vwb from strains investigated

```
USA300_vwb    ------------------------------------------------------------
Newman_vwb    TTGAAAAATAAATTGCTAGTTTTATCATTGGGAGCATTATGTGTATCACAAATTTGGGAA 60
MW2_vwb       TTGAAAAATAAATTGCTAGTTTTATCATTGGGAGCATTATGTGTATCACAAATTTGGGAA 60
MRSA252_vwb   TTGAAAAATAAATTGCTAGTTTTATCATTGGGAGCATTATGTGTATCACAAATTTGGGAA 60
N315_vwb      TTGAAAAATAAATTGCTAGTTTTATCATTGGGAGCATTATGTGTATCACAAATTTGGGAA 60

USA300_vwb    ------------------GTGGTTTCTGGGGAGAAGAATCCATATGTATCTGAGTCGTTG 42
Newman_vwb    AGTAATCGTGCGAGTGCAGTGGTTTCTGGGGAGAAGAATCCATATGTATCTGAGTCGTTG 120
MW2_vwb       AGTAATCGTGCGAGTGCAGTGGTTTCTGGGGAGAAGAATCCATATGTATCTGAGTCGTTG 120
MRSA252_vwb   AGCAATCGTGCGAGTGCAGTGGTTTCTGGGGAGGAGAATCCATATAAATCTGAGTCATTG 120
N315_vwb      AGTAATCATGCGAGTGCAGTGGTTTCTGGGGAGAAGAATCCATATGTATCAAAAGCTTTA 120
                                ***************  ***********   ***    *   * **

USA300_vwb    AAACTGACTAATAATAAAAATAAATCTAGAAC-AGTAGAAGAGTATAAGAAAAGCTTGGA 101
Newman_vwb    AAACTGACTAATAATAAAAATAAATCTAGAAC-AGTAGAAGAGTATAAGAAAAGCTTGGA 179
MW2_vwb       AAACTGACTAATAATAAAAATAAATCTAGAAC-AGTAGAAGAGTATAAGAAAAGCTTGGA 179
MRSA252_vwb   AAATTAAATGGGAAAAGAAGTACTACAATAACTAGT-GATAAATATGAAGAAAATTTAGA 179
N315_vwb      GAATTGAAAGATAAAAGTAATAAATCCAATTCTTAC-GAAAATTATAGAGATAGTTTAGA 179
                **  *          **  *  ** *      *    **  ****         *  *   ** **

USA300_vwb    TGATTTAATATGGTCCTTTCCAAACTTAGATAATGAAAGATTTGATAATCCTGAATATAA 161
Newman_vwb    TGATTTAATATGGTCCTTTCCAAACTTAGATAATGAAAGATTTGATAATCCTGAATATAA 239
MW2_vwb       TGATTTAATATGGTCCTTTCCAAACTTAGATAATGAAAGATTTGATAATCCTGAATATAA 239
MRSA252_vwb   TATGTTAATATCGTCATTATCATTTGCAGATTATGAAAAATATGAGGAACCAGAATACAA 239
N315_vwb      AAGTTTGATTTCATCATTATCTTTTGCTGATTATGAAAAATATGAAGAGCCAGAATATGA 239
                 **  **   **  **   *          *** ****** **  ***  *  **  ***** *

USA300_vwb    AGAAGCTATGAAAAAATATCAACAGAGATTTATGGCTGAAGATGAGGCTTTGAAGAAATT 221
Newman_vwb    AGAAGCTATGAAAAAATATCAACAGAGATTTATGGCTGAAGATGAGGCTTTGAAGAAATT 299
MW2_vwb       AGAAGCTATGAAAAAATATCAACAGAGATTTATGGCTGAAGATGAGGCTTTGAAGAAATT 299
MRSA252_vwb   AGAAGCAGTTAAAAAGTATCAACAAAAATTTATGGCTGAAGATGATGCATT-AAAAAATT 298
N315_vwb      AAAGGCTGTAAAAAAATATCAACAAAAATTTATGGCTGAAGATGATGCATTAAAAAATTT 299
                *  ***   * ***** ********  *  ****************  ** **  ** **  **

USA300_vwb    TTTTAGTGAAGAGAAAAAAATAAAAAATGGAAATACTGATA---ATTTAGATTATCTA-- 276
Newman_vwb    TTTTAGTGAAGAGAAAAAAATAAAAAATGGAAATACTGATA---ATTTAGATTATCTA-- 354
MW2_vwb       TTTTAGTGAAGAGAAAAAAATAAAAAATGGAAATACTGATA---ATTTAGATTATCTA-- 354
MRSA252_vwb   TTTTAGTGAAGAGAAAAAAATAAAAAATAGAAATACTAATA---CATCAAATTATCTG-- 353
N315_vwb      TTTAAATGAAGAAAAAGAAGATAAAAAATGCAGATATTAGCAGAAAATCGAATAATTTATT 359
                ***  * ****** **  **  ********   *  ***    *   *     *  ** ** *

USA300_vwb    -GGATTATCTCATGAAAGATATGAAAGTGTATTTAATACTTTGAAAAAACAAAGTGAGGA 335
Newman_vwb    -GGATTATCTCATGAAAGATATGAAAGTGTATTTAATACTTTGAAAAAACAAAGTGAGGA 413
MW2_vwb       -GGATTATCTCATGAAAGATATGAAAGTGTATTTAATACTTTGAAAAAACAAAGTGAGGA 413
MRSA252_vwb   -GGATTAACACACGAAAGATATGAGTCAATTTATAATTCAATTTAAAAATCATCGTGAAGA 412
N315_vwb      AGGTTTAACACATGAAAGATATTCTTATATTTTTGATACATTAAAGAAAAATAAACAAGA 419
                ** ***  * **  **********    * * * ** *  **  **  *    *  **

USA300_vwb    GTTCTTAAAAGAAATTGAAGATATAAAAAAAGATAACCCTGAATTGAAAGACTTTAATGA 395
Newman_vwb    GTTCTTAAAAGAAATTGAAGATATAAAAAAAGATAACCCTGAATTGAAAGACTTTAATGA 473
MW2_vwb       GTTCTTAAAAGAAATTGAAGATATAAAAAAAGATAACCCTGAATTGAAAGACTTTAATGA 473
MRSA252_vwb   ATTTTCAAAAGAAATCGAAGAAATTAATAATAAAAATCCAGTGTTAAAAGAATATAACAA 472
N315_vwb      GTTTTTAAAAGATATTGAGAAATACAACTGAAAAATAGTGATTTAAGGACTTTAACAA 479
                 ** * ******  ** ***** **    *       * *** ** ** ** * *** *

USA300_vwb    AGAGGAGCAATTAAAGTGCGACTTAGAATTAAACAAATTAGAAAATCAGATATTAATGTT 455
Newman_vwb    AGAGGAGCAATTAAAGTGCGACTTAGAATTAAACAAATTAGAAAATCAGATATTAATGTT 533
MW2_vwb       ATAG-------------------------------------------------------- 477
MRSA252_vwb   TGAGGAACAAACTAAAGCTGATACGGAATTAAACACTCTTGAAAATCAAGTACTAATGAT 532
N315_vwb      TACAGAGCAACATAATGCCGACGTAGAAATAAACAATTTAGAAAATAAAGTATTAATGGT 539

USA300_vwb    AGGTAAAACATTTTATCAAAACTATAGAGATGATGTTGAAAGTTTATATAGTAAGTTAGA 515
Newman_vwb    AGGTAAAACATTTTATCAAAACTATAGAGATGATGTTGAAAGTTTATATAGTAAGTTAGA 593
MW2_vwb       ------------------------------------------------------------
MRSA252_vwb   AGGTTATACATTTTATCACTCGAATAAAAATGAAGTAGAAGATTTATATAACAAATTAGA 592
N315_vwb      AGGGTATACATTCTATAATACAAATAAGGACGAAGTTGAAGAATTATATAGTGAGTTAGA 599

USA300_vwb    TTTAATTATGGGATATAAAGATGAAGAAAGA---GCAAATAAAAAAGCAGTTAACAAAAG 572
Newman_vwb    TTTAATTATGGGATATAAAGATGAAGAAAGA---GCAAATAAAAAAGCAGTTAACAAAAG 650
MW2_vwb       ------------------------------------------------------------
MRSA252_vwb   TATGATTCTTGGTTATAAAGATGAAGAGAGA---AAAAAGAAGAGGGCTACCAATCAAAG 649
N315_vwb      TTTGATTGTTGGA---GAAGTTCAAGATAAGTCGGATAAAAAAAGAGCAGTAAATCAAAG 656

USA300_vwb    GATGTTAGAAAATAAAAAAGAAGACTTAGAAACCATAATTGATGAATTTTTAGTGATAT 632
Newman_vwb    GATGTTAGAAAATAAAAAAGAAGACTTAGAAACCATAATTGATGAATTTTTAGTGATAT 710
MW2_vwb       ------------------------------------------------------------
MRSA252_vwb   AATGTTCAATAATAAAAAAGAGGATTTAGAACATTATTGATGAATTCTTTGGAGAAAT 709
N315_vwb      GATGTTAAATAGAAAAAAAGAGGATTTAGAATTTATTATAGATAAATTTTTTAAAAAAAT 716
```

FIG. 9A

```
USA300_vwb    AGATAAAACAAGACCTAATAA-TATTCCTGTTTTAGAAGATGAAAAACAAGAAGAGAAAA  691
Newman_vwb    AGATAAAACAAGACCTAATAA-TATTCCTGTTTTAGAAGATGAAAAACAAGAAGAGAAAA  769
MW2_vwb       ------------------------------------------------------------
MRSA252_vwb   TGG-ACAACAAAGGCCAACATCTATACCAACATTAGCGCCTAAAGAAGAAAAAGAAACAA  768
N315_vwb      TCA-ACAAGAACGTCCAGAGAGTATACCAGCATTAACTAGTGAAAAA-AATCATAATCAG  774

USA300_vwb    ATCATAAAAATATGGCTCAATTAAAATCTGACACTGAAGCAGCAAAAAGTGATGAATCAA  751
Newman_vwb    ATCATAAAAATATGGCTCAATTAAAATCTGACACTGAAGCAGCAAAAAGTGATGAATCAA  829
MW2_vwb       ------------------------------------------------------------
MRSA252_vwb   ATATAAAAAATGCAAATAAATTAAAATCTGACACTGAAGCAGCAAAAAATGATGAAGCAA  828
N315_vwb      ACTATGGCATTA-----AAGTTAAAAGCAGATACAGAAGCTGCTAAAAATGACGTATCAA  829

USA300_vwb    AAAGAAGCAAGAGAAGTAAAAGAAGTTTAAATACTCAAAATCACAAACCTGCATCTCAAG  811
Newman_vwb    AAAGAAGCAAGAGAAGTAAAAGAAGTTTAAATACTCAAAATCACAAACCTGCATCTCAAG  889
MW2_vwb       ------------------------------------------------------------
MRSA252_vwb   AAAGAAG------------------TTTAAATACCCACAATCACAAATCTGTATCTCAAG  870
N315_vwb      AAAGAAG---------TAAAGAAGTTTAAATACTCAAAATAATAAATCTACAACACAAG  880

USA300_vwb    AAGTTTCTGAACAACAAAAAGCTGAATATGATAAAAGAGCAGAAGAAAGAAAAGCGAGAT  871
Newman_vwb    AAGTTTCTGAACAACAAAAAGCTGAATATGATAAAAGAGCAGAAGAAAGAAAAGCGAGAT  949
MW2_vwb       ------------------------------------------------------------
MRSA252_vwb   AAGTCTCTGAACAACAAAAAGCTGACTACGAAAGAAAAGCTGAAGAAAGAAAAGCGAGAT  930
N315_vwb      AAATTTCTGAAGAACAAAAAGCTGAATATCAAAGAAAGTCAGAGGCATTAAAAGAAAGAT  940

USA300_vwb    TTTTGGATAATCAAAAAATTAAGAAAACACCTGTAGTGTCATTAGAATATGATTTTGAGC  931
Newman_vwb    TTTTGGATAATCAAAAAATTAAGAAAACACCTGTAGTGTCATTAGAATATGATTTTGAGC  1009
MW2_vwb       ------------------------------------------------------------
MRSA252_vwb   TTTTAGATAAGCAAAAAAATAAGAAAACTCCTGTAGTTTCATTAGAATATGATTTTGAAC  990
N315_vwb      TTATAAACAGACAAAAATCTAAAAATGAGTCTGTGGTTTCACTAA---------TCGATG  991

USA300_vwb    ATAAACAACGTATTGACAACGAAAACGACAAGAAACTTGTGGTTTCTGCACCAACAAAGA  991
Newman_vwb    ATAAACAACGTATTGACAACGAAAACGACAAGAAACTTGTGGTTTCTGCACCAACAAAGA  1069
MW2_vwb       ------------------------------------------------------------
MRSA252_vwb   ATAAACAACGTGTTGACAACGAAAACGACAAGCAACTTGTGGTTTCTGAGCCATCAAAGA  1050
N315_vwb      ACGAAGA------CGACAACGAAAACGACAGGCAACTTGTGGTTTCTGCGCCATCAAAGA  1045

USA300_vwb    AACCAACATCACCGACTACATATACTGAAACAACGACACAGGTACCAATGCCTACAGTTG  1051
Newman_vwb    AACCAACATCACCGACTACATATACTGAAACAACGACACAGGTACCAATGCCTACAGTTG  1129
MW2_vwb       ------------------------------------------------------------
MRSA252_vwb   AACCAACAACACCGCCTACATACACTGAAACAACCACACAGCTACCAATGCCTACAGTTG  1110
N315_vwb      AACCAACAACACCGACTACATATACTGAAACAACGACTCAGGTACCAATGCCTACAGTTG  1105

USA300_vwb    AGCGTCAAACTCAGCAACAAATTATTTATAATGCACCAAAACAATTGGCTGGATTAAATG  1111
Newman_vwb    AGCGTCAAACTCAGCAACAAATTATTTATAATGCACCAAAACAATTGGCTGGATTAAATG  1189
MW2_vwb       ------------------------------------------------------------
MRSA252_vwb   AGCGTCAAACACAGCAACAAATCGTTTACAAAGCACCAAAACCATTAGCTGGATTAAATG  1170
N315_vwb      AGCGTCAAACTCAGCAACAAATCGTTTACAAAACACCAAAACCATTAGCTGGATTAAATG  1165

USA300_vwb    GTGAAAGTCATGATTTCACAACAACGCATCAATCACCAACAACTTCAAATCACACGCATA  1171
Newman_vwb    GTGAAAGTCATGATTTCACAACAACGCATCAATCACCAACAACTTCAAATCACACGCATA  1249
MW2_vwb       ------------------------------------------------------------
MRSA252_vwb   GTGAAAGTCATGATTTCACAACAACGCATCAATCACCAACTACTTCAAATCACACGCATA  1230
N315_vwb      GTGAAAGTCATGATTTCACAACAACGCATCAATCACCAACAACTTCAAATCATACGCATA  1225

USA300_vwb    ATAATGTTGTTGAATTTGAAGAAACGTCTGCTTTACCTGGTAGAAAATCAGGATCACTGG  1231
Newman_vwb    ATAATGTTGTTGAATTTGAAGAAACGTCTGCTTTACCTGGTAGAAAATCAGGATCACTGG  1309
MW2_vwb       ------------------------------------------------------------
MRSA252_vwb   ATCATCTTATTGAAATTGAAGAAACATCTGCTTTACCTGGTAGAAAGACAGGTTCATTGG  1290
N315_vwb      ATAATGTTGTTGAATTTGAAGAAACGTCTGCTTTACCTGGTAGAAAATCAGGATCACTGG  1285

USA300_vwb    TTGGTATAAGTCAAATTGATTCTTCTCATCTAACTGAACGTGAGAAGCGTGTAATTAAGC  1291
Newman_vwb    TTGGTATAAGTCAAATTGATTCTTCTCATCTAACTGAACGTGAGAAGCGTGTAATTAAGC  1369
MW2_vwb       ------------------------------------------------------------
MRSA252_vwb   TTGGTTTGAGTCAAATTGATTCTTCGCATTTAACTGAACGTGAGAAGCGCGTGATTAAAC  1350
N315_vwb      TTGGTATAAGTCAAATTGATTCTTCTCATCTAACTGAACGTGAGAAGCGTGTAATCAAGC  1345

USA300_vwb    GTGAACACGTTAGAGAAGCTCAAAAGTTAGTTGATAATTATAAAGATACACATAGTTATA  1351
Newman_vwb    GTGAACACGTTAGAGAAGCTCAAAAGTTAGTTGATAATTATAAAGATACACATAGTTATA  1429
MW2_vwb       ------------------------------------------------------------
MRSA252_vwb   GTGAACACGTGAGAGAAGCTCAAAAGTTAGTTGATAATTATAAAGATACACATAGTTATA  1410
N315_vwb      GTGAACACGTTAGAGAAGCTCAAAAGTTAGTTGATAATTATAAAGATACACATAGTTATA  1405
```

FIG. 9B

```
USA300_vwb     AAGACCGAATAAATGCACAACAAAAAGTAAATACTTTAAGTGAAGGTCATCAAAAACGTT 1411
Newman_vwb     AAGACCGAATAAATGCACAACAAAAAGTAAATACTTTAAGTGAAGGTCATCAAAAACGTT 1489
MW2_vwb        ------------------------------------------------------------
MRSA252_vwb    AAGACCGATTAAATGCCCAACAAAAAGTAAATACTTTAAGTGCAGGTCATCAAAAACGTT 1470
N315_vwb       AAGACCGATTAAATGCACAACAAAAAGTAAATACTTTAAGTGAAGGTCATCAAAAACGTT 1465

USA300_vwb     TTAATAAACAAATCAATAAAGTATATAATGGCAAATAA---------------------- 1449
Newman_vwb     TTAATAAACAAATCAATAAAGTATATAATGGCAAATAA---------------------- 1527
MW2_vwb        ------------------------------------------------------------
MRSA252_vwb    TTAATAAACAAATTAATAAAGTATATAATGGCAAATAATTAATGCATGGCTGCAAAGGAA 1530
N315_vwb       TTAATAAACAAATCAATAAAGTATACAATGGCAAATAA---------------------- 1503

USA300_vwb     ------------------------------------------------------------
Newman_vwb     ------------------------------------------------------------
MW2_vwb        ------------------------------------------------------------
MRSA252_vwb    ATAATGAGTTTGCCGTAAAAATAACAACATTTTAAACTAGCAATAAATAATATCAAAGTC 1590
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    ATCATTTCAATGATGCAATCTAGTATAGTCCACATTCTAAACAGGTGTGGACTATTACTT 1650
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    TTTTCACTTTATATTACGAAAAAATTATTATGCTTAACTATCAATATCAATAATTAATTT 1710
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    TAAGCTGAAAAACAATAAAAATGTTAAGACAACGTTTACTTCAAGTTAATTATTATACTG 1770
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    AAAATTCTGGTATATAATGCTGTTAGTGAATATAACAGGAAAATTAAATTGGTTATGATA 1830
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    TTGAGTCTATATAAAGGAGAAATAACAGATGAAAAAGAAATTATTAGTTTTAACTATGAG 1890
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    CACGCTATTTGCTACACAATTTATGAATTCAAATCACGCTAATGCATCAACAGAAAGTGT 1950
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    TGATAAAAACTTTGTAGTTCCAGAATCGGGTATTAATAAAATTATTCCAACTTACGATGA 2010
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    ATTTAAAAAAGCACCAAAAGTAAATGTTAGTAATTTAGCTGACAACAAAAACTTTGTAGC 2070
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    TTCTGAAGATAAATTGAATAAGATTGCAGATCCATCGGCAGCTAGTAAAATTGTAGATAA 2130
N315_vwb       ------------------------------------------------------------

USA300_vwb     ------------------------------------------------------------
```

FIG. 9C

```
Newman_vwb          ------------------------------------------------------------
MW2_vwb             ------------------------------------------------------------
MRSA252_vwb         AAACTTTGCCGTACCAGAATCAAAATTAGGAATCATTGTACCAGAGTATAAAGAAATCAA 2190
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         TAATCGAGTGAATGTAACAACAAACAATCCAGCTTCAAAACAAGTTGACAAGCAAATTGT 2250
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         TGCTAAAGACCCAGAGGTGAATAGATTTATTACGCAAAATAAAGTAAACCATCGTTTCAT 2310
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         TACTACGCAAACCCACTATAAGAAAGTTATTACTTCATACAAATCAACACATGTACATAA 2370
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         ACATGTAAACCATGCAACATCTTCTATCCATCATCACTTTACTATTAAACCATCAGAAGC 2430
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         ACCTAGATATACACACCCATCTCAATCTCAATCGTTAATTATAAATCATCATTTTGCAGT 2490
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         TCCTGGATACCATGGTCATAAAGTTGTAACACCAGGACAAGCTAGTATTAGAATTCATCA 2550
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         CTTTTGTGCTGTACCTCAAATAAATAGTTTTAAGGTCATTCCATCATATGGTCACAATTC 2610
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         ACATCGTATGCATGTACCAAGTTTCCAAAATAACACAACAGCAACACATCAAAATGCAAA 2670
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         AGTAAATAAAACTTATAACTATAAATATTTTTATACTTATAAAGTAGTCAAAGGTGTAAA 2730
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         AAAACATTTCTCATTTTCAAAATCACATGGTTGTAAAATTGTTAAACCAGCATTAAACAT 2790
N315_vwb            ------------------------------------------------------------

USA300_vwb          ------------------------------------------------------------
Newman_vwb          ------------------------------------------------------------
MW2_vwb             ------------------------------------------------------------
MRSA252_vwb         CAAAAATGTAAATTATCAATATGCTGTTCCAAGTAATAGCCCTACACACGTTGTTCCTGA 2850
N315_vwb            ------------------------------------------------------------

USA300_vwb          ------------------------------------------------------------
Newman_vwb          ------------------------------------------------------------
```

FIG. 9D

```
MW2_vwb          ------------------------------------------------------------
MRSA252_vwb      GTTTCAGGGTATCTTACCAGCACCACGAGTATAAAAATTGACATTAAGTTTACGAGATAT 2910
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      GATAAATACCTATTATTTTAAACATAGTCTGCAATCTATGAGGTTGTAGGCTATGTTTTT 2970
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      TGCAGTTTATCAATAAACACCCATCAACAAATTATACCGTTTTTCTACTTTAAAAGTTGG 3030
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      AAGTAACATAATCTTAAATAAATATATTATTAATTAAGATAAATATAAGACTCGAGATTA 3090
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      TTGTTAATAGTTTGTTCATCGCAAGTTAATTATTGTTTCTAAAATATTGGTATATAATTT 3150
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      TCAATGGCGAAGAAAACAGGGTAAAAAAGTCGGTTTTTAAATCAAAGCAAATAAGGAGTA 3210
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      AAAAATGAAAAGGAAAGTACTAGTATTAACAATGGGCGTACTTTGTGCGACACAATTATG 3270
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      GCAAACGAATAATGCAAAAGCTTTAGTGACAGAGAGTGGCGTTAATGATACTAAGCAATT 3330
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      TACTGAAGTAACATCGGAAGAAAAAGTTATAAAAGATGCTATTTCGAAAGTCAATGAAAG 3390
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      CTTTATTTACTATCCCCAAAATGATTTGAAGGGATTAGGTGGAGAACACAACGATTACGA 3450
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      AAAAATTACATATAGCACTTCTTCTAATAATGTTTTAGAATTATCAATGAGTTCAAAATA 3510
N315_vwb         ------------------------------------------------------------

USA300_vwb       ------------------------------------------------------------
Newman_vwb       ------------------------------------------------------------
MW2_vwb          ------------------------------------------------------------
MRSA252_vwb      CGTAGGCGGTAAATCAGGAGCTATGGTTGGTTATAGTGAAATTTACTCATCACATTTCAC 3570
N315_vwb         ------------------------------------------------------------

USA300_vwb       ------------------------------------------------------------
Newman_vwb       ------------------------------------------------------------
MW2_vwb          ------------------------------------------------------------
```

FIG. 9E

```
MRSA252_vwb    AGACCGCGACAAACGTGCTATCAGACGTGATCATGTTAAAGAAGCACAAAACTTGATTAA 3630
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    TGATTATAAATATACGCAAATATATGAAGACTTTGCTAAAGCTACTGCAAAGGTAAGTAC 3690
N315_vwb       ------------------------------------------------------------

USA300_vwb     ------------------------------------------------------------
Newman_vwb     ------------------------------------------------------------
MW2_vwb        ------------------------------------------------------------
MRSA252_vwb    ACTTAGTCAGTCTCACCAAAATTATTTAAATAAACAAATTGATAAAGTGAATAATAAGAT 3750
N315_vwb       ------------------------------------------------------------

USA300_vwb     ----------------------
Newman_vwb     ----------------------
MW2_vwb        ----------------------
MRSA252_vwb    AGAGAAAACTGAAAAACGCTAA 3772
N315_vwb       ----------------------
```

FIG. 9F

```
MW2_vWbp       VVSGEKNPYVSESLKLTNNKNKSRTVEEYKKSLDDLIWSFPNLQNERFDNPEYKEAMKKY  60
Newman_vWbp    VVSGEKNPYVSESLKLTNNKNKSRTVEEYKKSLDDLIWSFPNLQNERFDNPEYKEAMKKY  60
USA300_vWbp    VVSGEKNPYVSESLKLTNNKNKSRTVEEYKKSLDDLIWSFPNLQNERFDNPEYKEAMKKY  60
N315_vWbp      VVSGEKNPYVSKSLELKDKNNSYENIKQSLESLISSLSFADYEKYEEPEYKEAVKKY    60
MRSA252_vWbp   VVSGEENPYKSESLKLNGKRSTTITSDKYEENLDMLISSLSFADYERYEEPEYKEAVKKY  60
               *****:***  *::*:*.. ..:  : ::*...*: ** *:.  *  *:::***:*:***

MW2_vWbp       QQRFMAEDEALKKFFSEEKKIKNGNTDN--LDYLGLSHERYESVFNTLKKQSEEFLKEIE 118
Newman_vWbp    QQRFMAEDEALKKFFSEEKKIKNGNTDN--LDYLGLSHERYESVFNTLKKQSEEFLKEIE 118
USA300_vWbp    QQRFMAEDEALKKFFSEEKKIKNGNTDN--LDYLGLSHERYESVFNTLKKQSEEFLKEIE 118
N315_vWbp      QQRFMAEDEALKKFLSEEKNIKNADSEKSNNLIGLTHERYSYIFDRLKKNQEFLRDIE   120
MRSA252_vWbp   QQKFMAEDDALKNPLVKRKK---------------------------------------  80
               **:*****:***:*:  :.**

MW2_vWbp       DIKKDNPELKDFNE---------------------------------------------- 132
Newman_vWbp    DIKKDNPELKDFNEEQLKCDLELNKLENQILMLGKTFYQNYRDDVESLYSKLDLIMGYK 178
USA300_vWbp    DIKKDNPELKDFNEEQLKCDLELNKLENQILMLGKTFYQNYRDDVESLYSKLDLIMGYK 178
N315_vWbp      DIKKDNPELKDFNEEQHNADVEINNLENKVLMVGYTFYNTNKDEVEELYSELDLIVGEV 180
MRSA252_vWbp   ------------------------------------------------------------

MW2_vWbp       ------------------------------------------------------------
Newman_vWbp    DEERANKKAVNKPMLENKKEDLETIIDEFFSDIDKTRPNNIPVLEDEKQEEKNHKNMAQL 238
USA300_vWbp    DEERANKKAVNKRMLENKKEDLETIIDEFFSDIDKTRPNNIPVLEDEKQEEKNHKNMAQL 238
N315_vWbp      QDKSDKKRAVNQRMLNRKKEDLEFIIDKFFKKIQQERPESIPALTSEKN---RNQTMALKL 238
MRSA252_vWbp   ------------------------------------------------------------

MW2_vWbp       ------------------------------------------------------------
Newman_vWbp    KSDTEAAKSDESKRSKRSKRSLNTQNHKPASQEVSEQQKAEYDKRAEERKARFLDNQKIK 298
USA300_vWbp    KSDTEAAKSDESKRSKRSKRSLNTQNHKPASQEVSEQQKAEYDKRAEERKARFLDNQKIK 298
N315_vWbp      KADTEAAKNDVSKRSKRS---LNTQNNKSTTQEISEEQKAEYQRKSEALKERFINRQKSK 295
MRSA252_vWbp   ------------------------------------------------------------

MW2_vWbp       ------------------------------------------------------------
Newman_vWbp    KTPVVSLEYDFEHKQRIDNENDKKLVVSAPTKKPTSPTTYTETTTQVPMPTVERQTQQQI 358
USA300_vWbp    KTPVVSLEYDFEHKQRIDNENDKKLVVSAPTKKPTSPTTYTETTTQVPMPTVERQTQQQI 358
N315_vWbp      NESVVSLIDDED-----DNENDRQLVVSAPSKKPTTPTTYTETTTQVPMPTVERQTQQQI 350
MRSA252_vWbp   ------------------------------------------------------------

MW2_vWbp       ------------------------------------------------------------
Newman_vWbp    IYNAPKQLAGLNGESHDFTTTHQSPTTSNHTHNNVVEFEETSALPGRKSGSLVGISQIDS 418
USA300_vWbp    IYNAPKQLAGLNGESHDFTTTHQSPTTSNHTHNNVVEFEETSALPGRKSGSLVGISQIDS 418
N315_vWbp      VYKTPKPLAGLNGESHDFTTTHQSPTTSNHTHNNVVEFEETSALPGRKSGSLVGISQIDS 410
MRSA252_vWbp   ------------------------------------------------------------

MW2_vWbp       ------------------------------------------------------------
Newman_vWbp    SHLTEREKRVIKREHVREAQKLVDNYKDTHSYKDRINAQQKVNTLSEGHQKRFNKQINKV 478
USA300_vWbp    SHLTEREKRVIKREHVREAQKLVDNYKDTHSYKDRINAQQKVNTLSEGHQKRFNKQINKV 478
N315_vWbp      SHLTEREKRVIKREHVREAQKLVDNYKDTHSYKDRINAQQKVNTLSEGHQKRFNKQINKV 470
MRSA252_vWbp   ------------------------------------------------------------

MW2_vWbp       ----
Newman_vWbp    YNGK 482
USA300_vWbp    YNGK 482
N315_vWbp      YNGK 474
MRSA252_vWbp   ----
```

FIG. 9G

```
USA300_vWbp   VVSGEKNPYVSESLKLTNNKNKSRTVEEYKKSLDDLIWSFPNLDNERFDNPEYKEAMKKY  60
Newman_vWbp   VVSGEKNPYVSESLKLTNNKNKSRTVEEYKKSLDDLIWSFPNLDNERFDNPEYKEAMKKY  60
N315_vWbp     VVSGEKNPYVSKALELKDKSNKSNSYENYRDSLESLISSLSFADYEKYEEPEYEKAVKKY  60
              ***********  :*.:: .*** :  *;*:. **: ** *:.   * *::.***:*:***

USA300_vWbp   QQRFMAEDEALKKFFSEEKKIKNGNTDN--LDYLGLSHERYESVFNTLKKQSEEFLKEIE  118
Newman_vWbp   QQRFMAEDEALKKFFSEEKKIKNGNTDN--LDYLGLSHERYESVFNTLKKQSEEFLKEIE  118
N315_vWbp     QQKFMAEDDALKNFLNEEKKIKNADISRKSNNLLGLTHERYSYIFDTLKKNKQEFLKDIE  120
              **:*****:***:*: ******.:  ..    : ***:****. :*:****::**:**:**

USA300_vWbp   DIKKDNPELKDFNEEEQLKCDLELNKLENQILMLGKTFYQNYRDDVESLYSKLDLIMGYK  178
Newman_vWbp   DIKKDNPELKDFNEEEQLKCDLELNKLENQILMLGKTFYQNYRDDVESLYSKLDLIMGYK  178
N315_vWbp     EIQLKNSDLKDFNNTEQHNADVEINNLENKVLMVGYTFYNTNKDEVEELYSELDLIVGEV  180
              :*: .*.:*****:  ** :.*:*:*:****:.:**:*:*:.* ***:. .*:**.****:*

USA300_vWbp   DEERANKKAVNKRMLENKKEDLETIIDEFFSDIDKTRPNNIFVLEDEKQEERNHKNMAQL  238
Newman_vWbp   DEERANKKAVNKRMLENKKEDLETIIDEFFSDIDKTRPNNIPVLEDEKQEEKNHKNMAQL  238
N315_vWbp     QDKSDEKRAVNQRMLNRKKEDLEFIIDKFFKKIQQERPESIPALTSEKN--HNQTMALKL  238
              ::: .:*:***:***. :****** ***:**. :: ::*: :.*: * .**: . :*

USA300_vWbp   KSDTEAAKSDESKRSKRSKRSLNTQNHKPASQEVSEQQKAEYDKPAEERKARFLDNQKIK  298
Newman_vWbp   KSDTEAAKSDESKRSKRSKRSLNTQNHKPASQEVSEQQKAEYDKRAEEPKARFLDNQKIK  298
N315_vWbp     KADTEAAKNDVSKRSKRS---LNTQNNKSTTQEISEEQKAEYQRKSEALKERFINRQKSK  295
              *:******..* ******    ******:*  ::**:**:****::::: *  **::.** *

USA300_vWbp   KTPVVSLEYDFEHKQRIDNENDKKLVVSAPTKKPTSPTTYTETTTQVPMPTVERQTQQQI  358
Newman_vWbp   KTPVVSLEYDFEHKQRIDNENDKKLVVSAPTKKPTSPTTYTETTTQVPMPTVERQTQQQI  358
N315_vWbp     NESVVSLIDDED-----DNENDRQLVVSAPSKKPTTPTTYTETTTQVPMPTVERQTQQQI  350
              : .****. * :      *****:.*****:****:****************************

USA300_vWbp   IYNAPKQLAGLNGESHDFTTTHQSPTTSNHTHNNVVEFEETSALPGRKSGSLVGISQIDS  418
Newman_vWbp   IYNAPKQLAGLNGESHDFTTTHQSPTTSNHTHNNVVEFEETSALPGRKSGSLVGISQIDS  418
N315_vWbp     VYKTPKPLAGLNGESHDFTTTHQSPTTSNHTHNNVVEFEETSALPGRKSGSLVGISQIDS  410
              :*::.** *****************************************************

USA300_vWbp   SHLTEREKRVIKREHVREAQKLVDNYKDTHSYKDRINAQQKVNTLSEGHQKRFNKQINKV  478
Newman_vWbp   SHLTEREKRVIKREHVREAQKLVDNYKDTHSYKDRINAQQKVNTLSEGHQKRFNKQINKV  478
N315_vWbp     SHLTEREKRVIKREHVREAQKLVDNYKDTHSYKDRLNAQQKVNTLSEGHQKRFNKQINKV  470
              ***********************************:************************

USA300_vWbp   YNGK 482
Newman_vWbp   YNGK 482
N315_vWbp     YNGK 474
              ****
```

FIG. 9H

STAPHYLOCOCCAL COAGULASE ANTIGENS AND METHODS OF THEIR USE

This application is a national phase application under 35 U.S.C. § 371 of International Application No. PCT/US2013/031695, filed Mar. 14, 2013, which claims priority to U.S. Provisional Patent Application 61/638,831 filed on Apr. 26, 2012 and U.S. Provisional Patent Application 61/674,619 filed on Jul. 23, 2012. The entire contents of each of the above-referenced disclosures are specifically incorporated herein by reference without disclaimer.

This invention was made with government support under AI057153 and AI092711 awarded by the National Institutes of Health. The government has certain rights in the invention.

BACKGROUND OF THE INVENTION

I. Field of the Invention

The present invention relates generally to the fields of immunology, microbiology, and pathology. More particularly, it concerns methods and compositions involving bacterial coagulase variants, which can be used to invoke an immune response against the bacteria.

II. Background

The number of both community acquired and hospital acquired infections have increased over recent years with the increased use of intravascular devices. Hospital acquired (nosocomial) infections are a major cause of morbidity and mortality, more particularly in the United States, where it affects more than 2 million patients annually. The most frequent infections are urinary tract infections (33% of the infections), followed by pneumonia (15.5%), surgical site infections (14.8%) and primary bloodstream infections (13%) (Emorl and Gaynes, 1993).

The major nosocomial pathogens include *Staphylococcus aureus*, coagulase-negative *Staphylococci* (mostly *Staphylococcus epidermidis*), enterococcus spp., *Escherichia coli* and *Pseudomonas aeruginosa*. Although these pathogens cause approximately the same number of infections, the severity of the disorders they can produce combined with the frequency of antibiotic resistant isolates balance this ranking towards *S. aureus* and *S. epidermidis* as being the most significant nosocomial pathogens.

*Staphylococci* can cause a wide variety of diseases in humans and other animals through either toxin production or invasion. Staphylococcal toxins are also a common cause of food poisoning, as the bacteria can grow in improperly-stored food.

*Staphylococcus epidermidis* is a normal skin commensal which is also an important opportunistic pathogen responsible for infections of impaired medical devices and infections at sites of surgery. Medical devices infected by *S. epidermidis* include cardiac pacemakers, cerebrospinal fluid shunts, continuous ambulatory peritoneal dialysis catheters, orthopedic devices and prosthetic heart valves.

*Staphylococcus aureus* is the most common cause of nosocomial infections with a significant morbidity and mortality. It is the cause of some cases of osteomyelitis, endocarditis, septic arthritis, pneumonia, abscesses, and toxic shock syndrome. *S. aureus* can survive on dry surfaces, increasing the chance of transmission. Any *S. aureus* infection can cause the staphylococcal scalded skin syndrome, a cutaneous reaction to exotoxin absorbed into the bloodstream. It can also cause a type of septicemia called pyaemia that can be life-threatening. Problematically, Methicillin-resistant *Staphylococcus aureus* (MRSA) has become a major cause of hospital-acquired infections.

*S. aureus* and *S. epidermidis* infections are typically treated with antibiotics, with penicillin being the drug of choice, whereas vancomycin is used for methicillin resistant isolates. The percentage of staphylococcal strains exhibiting wide-spectrum resistance to antibiotics has become increasingly prevalent, posing a threat for effective antimicrobial therapy. In addition, the recent emergence of vancomycin resistant *S. aureus* strain has aroused fear that MRSA strains are emerging and spreading for which no effective therapy is available.

An alternative to antibiotic treatment for staphylococcal infections is under investigation that uses antibodies directed against staphylococcal antigens. This therapy involves administration of polyclonal antisera (WO00/15238, WO00/12132) or treatment with monoclonal antibodies against lipoteichoic acid (WO98/57994).

An alternative approach would be the use of active vaccination to generate an immune response against staphylococci. The *S. aureus* genome has been sequenced and many of the coding sequences have been identified (WO02/094868, EP0786519), which can lead to the identification of potential antigens. The same is true for *S. epidermidis* (WO01/34809). As a refinement of this approach, others have identified proteins that are recognized by hyperimmune sera from patients who have suffered staphylococcal infection (WO01/98499. WO02/059148).

*S. aureus* secretes a plethora of virulence factors into the extracellular milieu (Archer, 1998; Dinges et al., 2000; Foster, 2005; Shaw et al., 2004; Sibbald et al., 2006). Like most secreted proteins, these virulence factors are translocated by the Sec machinery across the plasma membrane. Proteins secreted by the Sec machinery bear an N-terminal leader peptide that is removed by leader peptidase once the pre-protein is engaged in the Sec translocon (Dalbey and Wickner, 1985; van Wely et al., 2001). Recent genome analysis suggests that Actinobacteria and members of the Firmicutes encode an additional secretion system that recognizes a subset of proteins in a Sec-independent manner (Pallen, 2002). ESAT-6 (early secreted antigen target 6 kDa) and CFP-10 (culture filtrate antigen 10 kDa) of *Mycobacterium tuberculosis* represent the first substrates of this novel secretion system termed ESX-1 or Snm in *M. tuberculosis* (Andersen et al., 1995; Hsu et al., 2003; Pym et al., 2003; Stanley et al., 2003). In *S. aureus*, two ESAT-6 like factors designated EsxA and EsxB are secreted by the Ess pathway (ESAT-6 secretion system) (Burts et al., 2005).

The first generation of vaccines targeted against *S. aureus* or against the exoproteins it produces have met with limited success (Lee, 1996). There remains a need to develop effective vaccines against staphylococcal infections. Additional compositions for treating staphylococcal infections are also needed.

SUMMARY OF THE INVENTION

During infection, *Staphylococcus aureus* secrets two coagulases, Coa and vWbp, which upon association with host prothrombin and fibrinogen, convert soluble fibrinogen to insoluble fibrin, induce the formation of fibrin clots and enable the establishment of staphylococcal disease. Due to the fact that Coa and vWbp are important factors for staphylococcal coagulation and agglutination, which promote the pathogenesis of *S. aureus* abscess formation and lethal bacteremia in mice. Here the inventors demonstrate that antibodies directed against the variable prothrombin-binding portion of coagulases confer type-specific immunity through neutralization of *S. aureus* clotting activity and protect from staphylococcal disease. In particular, by combining variable portions of coagulases from North-American isolates into hybrid Coa and vWbp proteins, a subunit vaccine was derived that provides protection against challenge with different coagulase-type *S. aureus* strains.

Certain embodiments an immunogenic composition is provided comprising a staphylococcal coagulase Domains 1-2 (e.g., a Domains 1-2 from a staphylococcal Coa or vWbp protein). For example, the Domains 1-2 can comprise or consist of an amino acid sequence that is at least 80, 85, 90, 95, 98, 99 or 100% identical to an amino acid sequence of SEQUENCE TABLE NO. 1 (SEQ ID NOs: 33-37) or SEQUENCE TABLE NO. 2 (SEQ ID NOs: 38-41). In some aspects, a staphylococcal coagulase Domains 1-2 is comprised in a less than full-length coagulase protein. For example, the Domains 1-2 can be comprised in a less than full-length Coa protein (e.g., that lacks all or part of a L or R Domain segment) or in a less than full-length vWbp protein (e.g., that lacks all or part of a L or F Domain segment). In some aspects, a Domain 1-2 is a Domain 1-2 segment wherein the secretion signal sequence has been removed.

In certain embodiments, an immunogenic composition is provided comprising at least two different staphylococcal coagulase Domains 1-2. For example, a composition can comprise at least two different staphylococcal coagulase Domains 1-2 from a staphylococcal Coa or vWbp protein, wherein at least one Domain 1-2 is comprised in a less than full-length coagulase protein. In certain aspects, the sequence of the Domains 1-2 comprises or consists of an amino acid sequence that is at least 80% identical to an amino acid sequence of SEQUENCE TABLE NO. 1 (SEQ ID NOs: 33-37) or SEQUENCE TABLE NO. 2 (SEQ ID NOs: 38-41). In certain aspects, the sequence of the Domains 1-2 comprises or consists of an amino acid sequence that is at least 85, 90, 95, 98, 99 or 100% identical to an amino acid sequence of SEQUENCE TABLE NO. 1 (SEQ ID NOs: 33-37) or SEQUENCE TABLE NO. 2 (SEQ ID NOs: 38-41). In further aspects, at least one of the Domains 1-2 is comprised in a less than full-length coagulase protein sequence. In particular embodiments, the full length coagulase protein is a Coa protein comprising the sequence of SEQ ID NO: 42. In particular aspects, the full length coagulase protein is a vWbp protein comprising the sequence of SEQ ID NO: 75. In still further aspects, the a less than full-length Coa protein lacks all or part of a L or R Domain segment. In still further aspects, the truncated vWbp protein lacks all or part of a L or F Domain segment. The term "truncated" protein is used to refer to a protein or a polypeptide that does not achieve its full length, and thus is missing one or more of the amino acid residues that are present in a normal protein. The term "truncated relative to a full-length coagulase protein" is used to refer to a protein or a polypeptide that does not have the full length of a coagulase protein, and thus is missing at least one amino acid residues that are present in a coagulase protein.

In certain embodiments, one of the staphylococcal coagulase Domains 1-2 is from *S. aureus* Newman, 85/2082, MW2, MSSA476, N315, Mu50, MRSA252, CowanI, WIS or USA300 strain, or any other *S. aureus* strain. In some embodiments, one of the coagulase Domains 1-2 comprises a vWbp domains 1-2 from a *S. aureus* N315 or USA300.

In some aspects, one of the Domains 1-2 comprises a Coa Domains 1-2 at least 80% identical to an amino acid sequence of SEQUENCE TABLE NO. 1 (SEQ ID NOs: 33-37). In further aspects, one of the Domains 1-2 comprises a Coa Domains 1-2 at least 85, 90, 95, 98, 99% identical to an amino acid sequence of SEQUENCE TABLE NO. 1 (SEQ ID NOs: 33-37).

In another aspects, one of the Domains 1-2 comprises a vWbp Domains 1-2 at least 80% identical to a sequence of SEQUENCE TABLE NO. 2 (SEQ ID NOs: 38-41). In further aspects, one of the Domains 1-2 comprises a vWbp Domains 1-2 at least 85, 90, 95, 98, 99% identical to a sequence of SEQUENCE TABLE NO. 2 (SEQ ID NOs: 38-41).

In certain embodiments, one of the Domains 1-2 is a Coa Domains 1-2, further comprising an L or R domain from a staphylococcal Coa protein.

In certain embodiments, one of the Domains 1-2 is a vWbp Domains 1-2, further comprising an L or Fgb domain from a staphylococcal vWbp protein.

In some aspects, an immunogenic composition comprises at least three, four, or five different staphylococcal coagulase Domains 1-2. In further aspects, an immunogenic composition comprise at least four different staphylococcal coagulase Domains 1-2. In particular embodiments, the at least four different staphylococcal coagulase Domains 1-2 are staphylococcal Coa Domains 1-2 from strains MRSA252, MW2, N315 and USA300.

In some embodiments, it is contemplated that an immunogenic composition comprises at least two different staphylococcal coagulase Domains 1-2 that are comprised in a fusion protein.

In further embodiments, the immunogenic composition further comprises one or more additional staphylococcal antigen(s). In additional embodiments, the immunogenic composition may also include an adjuvant. In particular embodiments, the additional staphylococcal antigen(s) is Emp, EsxA, EsxB, EsaC, Eap, Ebh, EsaB, Coa, vWbp, vWh, Hla, SdrC, SdrD, SdrE, IsdA, IsdB, IsdC, ClfA, ClfB, SasF or a nontoxigenic SpA.

Embodiments include a recombinant polypeptide comprising at least two different staphylococcal coagulase Domains 1-2. The sequences of the Domains 1-2 are at least 80% identical to an amino acid sequence of SEQUENCE TABLE NO. 1 (SEQ ID NOs: 33-37) or SEQUENCE TABLE NO. 2 (SEQ ID NOs: 38-41). In some aspects, the sequence of the Domains 1-2 are at least 85, 90, 95, 98, 99% identical to an amino acid sequence of SEQUENCE TABLE NO. 1 (SEQ ID NOs: 33-37) or SEQUENCE TABLE NO. 2 (SEQ ID NOs: 38-41).

In further embodiments, a polynucleotide molecule comprising a nucleic acid sequence encoding a recombinant polypeptide comprising sequence encoding at least two different staphylococcal coagulase Domains 1-2 is contemplated. In further aspects, an expression vector comprises the nucleic acid sequence operably linked to an expression control sequence. In still further aspects, a host cell comprising the expression vector is also contemplated.

Embodiments include the use of the composition, the recombinant polypeptide, the polynucleotide molecule and the expression vector described herein to treat or prevent a staphylococcal infection in a subject. In some aspects, a composition comprising at least two different staphylococcal coagulase Domains 1-2 is used to treat or prevent a staphylococcal infection. The sequences of the Domains 1-2 are at least 80% identical to an amino acid sequence of SEQUENCE TABLE NO. 1 (SEQ ID NOs: 33-37) or SEQUENCE TABLE NO. 2 (SEQ ID NOs: 38-41) and at least one of the Domains 1-2 is a truncated coagulase protein sequence.

In some embodiments, a method to manufacture an immunogenic composition comprising mixing at least two different staphylococcal coagulase Domains 1-2 polypeptides is contemplated. The sequences of the Domains 1-2 are at least 80% identical to an amino acid sequence of SEQUENCE TABLE NO. 1 (SEQ ID NOs: 33-37) or SEQUENCE TABLE NO. 2 (SEQ ID NOs: 38-41) and at least one of the Domains 1-2 is a truncated coagulase protein sequence.

Embodiments include the use of at least two different staphylococcal coagulase Domains 1-2 described herein in methods and compositions for the treatment of bacterial and/or staphylococcal infection. Furthermore, certain embodiments provide methods and compositions that can be used to treat (e.g., limiting staphylococcal abscess formation and/or persistence in a subject) or prevent bacterial infection. In some cases, methods for stimulating an immune response involve administering to the subject an effective amount of the immunogenic composition described herein and in certain aspects other bacterial proteins. Other bacterial proteins include, but are not limited to (i) a secreted virulence factor, and/or a cell surface protein or peptide, or (ii) a recombinant nucleic acid molecule encoding a secreted virulence factor, and/or a cell surface protein or peptide.

In other aspects, the subject can be administered with the immunogenic composition, the recombinant polypeptide, or the vector described herein. The recombinant polypeptide or the vector can be formulated in a pharmaceutically acceptable composition. The composition can further comprise one or more of at least or at most 1, 2, 3, 4, 5, 6, 7, 8, 9, 10, 11, 12, 13, 14, 15, 16, 17, 18, or 19 additional staphylococcal antigen or immunogenic fragment thereof (e.g., Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC. SasF, vWbp, or vWh). Additional staphylococcal antigens that can be used include, but are not limited to 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341). Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234). SsaA, SSP-1, SSP-2, and/or Vitronectin binding protein (see PCT publications WO2007/113222, WO2007/113223, WO2006/032472, WO2006/032475. WO2006/032500, each of which is incorporated herein by reference in their entirety).

The staphylococcal antigen or immunogenic fragment can be administered concurrently with the immunogenic composition comprising at least two different coagulase Domains 1-2, the recombinant polypeptide comprising at least two different Domains 1-2, and/or the vector comprising a nucleic acid sequence encoding at least two different Domains 1-2 described herein. The staphylococcal antigen or immunogenic fragment can be administered in the same composition with the immunogenic composition comprising at least two different Domains 1-2, the recombinant polypeptide comprising at least two different Domains 1-2, and/or the vector comprising a nucleic acid sequence encoding at least two different Domains 1-2 described herein. As used herein, the term "modulate" or "modulation" encompasses the meanings of the words "enhance," or "inhibit." "Modulation" of activity may be either an increase or a decrease in activity. As used herein, the term "modulator" refers to compounds that effect the function of a moiety, including up-regulation, induction, stimulation, potentiation, inhibition, down-regulation, or suppression of a protein, nucleic acid, gene, organism or the like.

A recombinant nucleic acid molecule can encode at least two different staphylococcal coagulase Domains 1-2 and at least one staphylococcal antigen or immunogenic fragment thereof. In particular aspects, one of the at least two different staphylococcal coagulase Domains 1-2 is a Coa Domains 1-2 at least 80% identical to an amino acid sequence of SEQUENCE TABLE NO. 1 (SEQ ID NOs: 33-37). In still further aspects, one of the at least two different staphylococcal coagulase Domains 1-2 is a vWbp Domains 1-2 at least 80% identical to a sequence of SEQUENCE TABLE NO. 2 (SEQ ID NOs: 38-41). In some aspects, the recombinant nucleic acid molecule comprises a sequence that encodes a truncated coagulase protein and the truncated coagulase protein includes either one of the at least two different staphylococcal coagulase Domains 1-2. In particular embodiments, the coagulase protein is a Coa protein comprising the sequence of SEQ ID NO: 42. In particular aspects, the coagulase protein is a vWbp protein comprising the sequence of SEQ ID NO: 75.

In certain embodiments, the composition or the polypeptide comprising at least two different staphylococcal coagulase Domains 1-2 may be used in combination with secreted factors or surface antigens including, but not limited to one or more of an isolated Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, or vWh polypeptide or immunogenic segment thereof. Additional staphylococcal antigens that can be used include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In certain embodiments, 1, 2, 3, 4, 5, 6, 7, 8, 9, 10 or more of Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008, 341), Fibronectin binding protein (U.S. Pat. No. 5,840,846), FnbA, FnbB, GehD (US 2002/0169288), HarA. HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein, can be specifically excluded from a formulation of the invention.

The following table lists the various combinations of staphylococcal coagulase Domains 1-2 and various other Staphylococcal antigens:

TABLE 1

Staphylococcal coagulase Domains 1-2 and staphylococcal antigen combinations.

| | | | | | | | | | | | | | | | | | | | | | |
|---|---|---|---|---|---|---|---|---|---|---|---|---|---|---|---|---|---|---|---|---|---|
| Eap | + | + | + | + | + | + | + | + | + | + | + | + | + | + | + | + | + | + | + | + | + |
| Ebh | | + | + | + | + | + | + | + | + | + | + | + | + | + | + | + | + | + | + | + | + |
| Emp | | | + | + | + | + | + | + | + | + | + | + | + | + | + | + | + | + | + | + | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |
| SdrC | | | | | | | | + | + | + | + | + | + | + | + | + | + | + | + | + | + |
| SdrD | | | | | | | | | + | + | + | + | + | + | + | + | + | + | + | + | + |
| SdrE | | | | | | | | | | + | + | + | + | + | + | + | + | + | + | + | + |
| IsdA | | | | | | | | | | | + | + | + | + | + | + | + | + | + | + | + |
| IsdB | | | | | | | | | | | | + | + | + | + | + | + | + | + | + | + |
| ClfA | | | | | | | | | | | | | + | + | + | + | + | + | + | + | + |
| ClfB | | | | | | | | | | | | | | + | + | + | + | + | + | + | + |
| Coa | | | | | | | | | | | | | | | + | + | + | + | + | + | + |
| Hla | | | | | | | | | | | | | | | | + | + | + | + | + | + |
| $Hla_{H35A}$ | | | | | | | | | | | | | | | | | + | + | + | + | + |
| IsdC | | | | | | | | | | | | | | | | | | + | + | + | + |
| SasF | | | | | | | | | | | | | | | | | | | + | + | + |
| vWbp | | | | | | | | | | | | | | | | | | | | + | + |
| vWh | | | | | | | | | | | | | | | | | | | | | + |
| Ebh | | + | + | + | + | + | + | + | + | + | + | + | + | + | + | + | + | + | + | + | + |
| Emp | | | + | + | + | + | + | + | + | + | + | + | + | + | + | + | + | + | + | + | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |
| SdrC | | | | | | | | + | + | + | + | + | + | + | + | + | + | + | + | + | + |
| SdrD | | | | | | | | | + | + | + | + | + | + | + | + | + | + | + | + | + |
| SdrE | | | | | | | | | | + | + | + | + | + | + | + | + | + | + | + | + |
| IsdA | | | | | | | | | | | + | + | + | + | + | + | + | + | + | + | + |
| IsdB | | | | | | | | | | | | + | + | + | + | + | + | + | + | + | + |
| ClfA | | | | | | | | | | | | | + | + | + | + | + | + | + | + | + |
| ClfB | | | | | | | | | | | | | | + | + | + | + | + | + | + | + |
| Coa | | | | | | | | | | | | | | | + | + | + | + | + | + | + |
| Hla | | | | | | | | | | | | | | | | + | + | + | + | + | + |
| $Hla_{H35A}$ | | | | | | | | | | | | | | | | | + | + | + | + | + |
| IsdC | | | | | | | | | | | | | | | | | | + | + | + | + |
| SasF | | | | | | | | | | | | | | | | | | | + | + | + |
| vWbp | | | | | | | | | | | | | | | | | | | | + | + |
| vWh | | | | | | | | | | | | | | | | | | | | | + |
| Emp | | | + | + | + | + | + | + | + | + | + | + | + | + | + | + | + | + | + | + | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |
| SdrC | | | | | | | | + | + | + | + | + | + | + | + | + | + | + | + | + | + |
| SdrD | | | | | | | | | + | + | + | + | + | + | + | + | + | + | + | + | + |
| SdrE | | | | | | | | | | + | + | + | + | + | + | + | + | + | + | + | + |
| IsdA | | | | | | | | | | | + | + | + | + | + | + | + | + | + | + | + |
| IsdB | | | | | | | | | | | | + | + | + | + | + | + | + | + | + | + |
| ClfA | | | | | | | | | | | | | + | + | + | + | + | + | + | + | + |
| ClfB | | | | | | | | | | | | | | + | + | + | + | + | + | + | + |
| Coa | | | | | | | | | | | | | | | + | + | + | + | + | + | + |
| Hla | | | | | | | | | | | | | | | | + | + | + | + | + | + |
| $Hla_{H35A}$ | | | | | | | | | | | | | | | | | + | + | + | + | + |
| IsdC | | | | | | | | | | | | | | | | | | + | + | + | + |
| SasF | | | | | | | | | | | | | | | | | | | + | + | + |
| vWbp | | | | | | | | | | | | | | | | | | | | + | + |
| vWh | | | | | | | | | | | | | | | | | | | | | + |
| EsaB | | | | + | + | + | + | + | + | + | + | + | + | + | + | + | + | + | + | + | + |
| EsaC | | | | | + | + | + | + | + | + | + | + | + | + | + | + | + | + | + | + | + |
| EsxA | | | | | | + | + | + | + | + | + | + | + | + | + | + | + | + | + | + | + |
| EsxB | | | | | | | + | + | + | + | + | + | + | + | + | + | + | + | + | + | + |
| SdrC | | | | | | | | + | + | + | + | + | + | + | + | + | + | + | + | + | + |
| SdrD | | | | | | | | | + | + | + | + | + | + | + | + | + | + | + | + | + |
| SdrE | | | | | | | | | | + | + | + | + | + | + | + | + | + | + | + | + |
| IsdA | | | | | | | | | | | + | + | + | + | + | + | + | + | + | + | + |

TABLE 1-continued

Staphylococcal coagulase Domains 1-2 and staphylococcal antigen combinations.

| Antigen | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| IsdB | | | | | | | | + | + | + | + | + | + | + | + | + | + |
| ClfA | | | | | | | | | + | + | + | + | + | + | + | + | + |
| ClfB | | | | | | | | | | + | + | + | + | + | + | + | + |
| Coa | | | | | | | | | | | + | + | + | + | + | + | + |
| Hla | | | | | | | | | | | | + | + | + | + | + | + |
| $Hla_{H35A}$ | | | | | | | | | | | | | + | + | + | + | + |
| IsdC | | | | | | | | | | | | | | + | + | + | + |
| SasF | | | | | | | | | | | | | | | + | + | + |
| vWbp | | | | | | | | | | | | | | | | + | + |
| vWh | | | | | | | | | | | | | | | | | + |

| Antigen | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| EsaC | + | + | + | + | + | + | + | + | + | + | + | + | + | + | + | + | + |
| EsxA | | + | + | + | + | + | + | + | + | + | + | + | + | + | + | + | + |
| EsxB | | | + | + | + | + | + | + | + | + | + | + | + | + | + | + | + |
| SdrC | | | | + | + | + | + | + | + | + | + | + | + | + | + | + | + |
| SdrD | | | | | + | + | + | + | + | + | + | + | + | + | + | + | + |
| SdrE | | | | | | + | + | + | + | + | + | + | + | + | + | + | + |
| IsdA | | | | | | | + | + | + | + | + | + | + | + | + | + | + |
| IsdB | | | | | | | | + | + | + | + | + | + | + | + | + | + |
| ClfA | | | | | | | | | + | + | + | + | + | + | + | + | + |
| ClfB | | | | | | | | | | + | + | + | + | + | + | + | + |
| Coa | | | | | | | | | | | + | + | + | + | + | + | + |
| Hla | | | | | | | | | | | | + | + | + | + | + | + |
| $Hla_{H35A}$ | | | | | | | | | | | | | + | + | + | + | + |
| IsdC | | | | | | | | | | | | | | + | + | + | + |
| SasF | | | | | | | | | | | | | | | + | + | + |
| vWbp | | | | | | | | | | | | | | | | + | + |
| vWh | | | | | | | | | | | | | | | | | + |

| Antigen | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| EsxA | | + | + | + | + | + | + | + | + | + | + | + | + | + | + | + | + |
| EsxB | | | + | + | + | + | + | + | + | + | + | + | + | + | + | + | + |
| SdrC | | | | + | + | + | + | + | + | + | + | + | + | + | + | + | + |
| SdrD | | | | | + | + | + | + | + | + | + | + | + | + | + | + | + |
| SdrE | | | | | | + | + | + | + | + | + | + | + | + | + | + | + |
| IsdA | | | | | | | + | + | + | + | + | + | + | + | + | + | + |
| IsdB | | | | | | | | + | + | + | + | + | + | + | + | + | + |
| ClfA | | | | | | | | | + | + | + | + | + | + | + | + | + |
| ClfB | | | | | | | | | | + | + | + | + | + | + | + | + |
| Coa | | | | | | | | | | | + | + | + | + | + | + | + |
| Hla | | | | | | | | | | | | + | + | + | + | + | + |
| $Hla_{H35A}$ | | | | | | | | | | | | | + | + | + | + | + |
| IsdC | | | | | | | | | | | | | | + | + | + | + |
| SasF | | | | | | | | | | | | | | | + | + | + |
| vWbp | | | | | | | | | | | | | | | | + | + |
| vWh | | | | | | | | | | | | | | | | | + |

| Antigen | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| EsxB | | | + | + | + | + | + | + | + | + | + | + | + | + | + | + | + |
| SdrC | | | | + | + | + | + | + | + | + | + | + | + | + | + | + | + |
| SdrD | | | | | + | + | + | + | + | + | + | + | + | + | + | + | + |
| SdrE | | | | | | + | + | + | + | + | + | + | + | + | + | + | + |
| IsdA | | | | | | | + | + | + | + | + | + | + | + | + | + | + |
| IsdB | | | | | | | | + | + | + | + | + | + | + | + | + | + |
| ClfA | | | | | | | | | + | + | + | + | + | + | + | + | + |
| ClfB | | | | | | | | | | + | + | + | + | + | + | + | + |
| Coa | | | | | | | | | | | + | + | + | + | + | + | + |
| Hla | | | | | | | | | | | | + | + | + | + | + | + |
| $Hla_{H35A}$ | | | | | | | | | | | | | + | + | + | + | + |
| IsdC | | | | | | | | | | | | | | + | + | + | + |
| SasF | | | | | | | | | | | | | | | + | + | + |
| vWbp | | | | | | | | | | | | | | | | + | + |
| vWh | | | | | | | | | | | | | | | | | + |

| Antigen | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| SdrC | | | | + | + | + | + | + | + | + | + | + | + | + | + | + | + |
| SdrD | | | | | + | + | + | + | + | + | + | + | + | + | + | + | + |
| SdrE | | | | | | + | + | + | + | + | + | + | + | + | + | + | + |
| IsdA | | | | | | | + | + | + | + | + | + | + | + | + | + | + |
| IsdB | | | | | | | | + | + | + | + | + | + | + | + | + | + |
| ClfA | | | | | | | | | + | + | + | + | + | + | + | + | + |
| ClfB | | | | | | | | | | + | + | + | + | + | + | + | + |
| Coa | | | | | | | | | | | + | + | + | + | + | + | + |
| Hla | | | | | | | | | | | | + | + | + | + | + | + |
| $Hla_{H35A}$ | | | | | | | | | | | | | + | + | + | + | + |
| IsdC | | | | | | | | | | | | | | + | + | + | + |

TABLE 1-continued

Staphylococcal coagulase Domains 1-2 and staphylococcal antigen combinations.

| | | | | | | | | | | | | | |
|---|---|---|---|---|---|---|---|---|---|---|---|---|---|
| SasF | | | | | | | | | | | + | + | + |
| vWbp | | | | | | | | | | | | + | + |
| vWh | | | | | | | | | | | | | + |

| | | | | | | | | | | | | | |
|---|---|---|---|---|---|---|---|---|---|---|---|---|---|
| SdrD | + | + | + | + | + | + | + | + | + | + | + | + | + |
| SdrE | | + | + | + | + | + | + | + | + | + | + | + | + |
| IsdA | | | + | + | + | + | + | + | + | + | + | + | + |
| IsdB | | | | + | + | + | + | + | + | + | + | + | + |
| ClfA | | | | | + | + | + | + | + | + | + | + | + |
| ClfB | | | | | | + | + | + | + | + | + | + | + |
| Coa | | | | | | | + | + | + | + | + | + | + |
| Hla | | | | | | | | + | + | + | + | + | + |
| $Hla_{H35A}$ | | | | | | | | | + | + | + | + | + |
| IsdC | | | | | | | | | | + | + | + | + |
| SasF | | | | | | | | | | | + | + | + |
| vWbp | | | | | | | | | | | | + | + |
| vWh | | | | | | | | | | | | | + |

| | | | | | | | | | | | | |
|---|---|---|---|---|---|---|---|---|---|---|---|---|
| SdrE | + | + | + | + | + | + | + | + | + | + | + | + |
| IsdA | | + | + | + | + | + | + | + | + | + | + | + |
| IsdB | | | + | + | + | + | + | + | + | + | + | + |
| ClfA | | | | + | + | + | + | + | + | + | + | + |
| ClfB | | | | | + | + | + | + | + | + | + | + |
| Coa | | | | | | + | + | + | + | + | + | + |
| Hla | | | | | | | + | + | + | + | + | + |
| $Hla_{H35A}$ | | | | | | | | + | + | + | + | + |
| IsdC | | | | | | | | | + | + | + | + |
| SasF | | | | | | | | | | + | + | + |
| vWbp | | | | | | | | | | | + | + |
| vWh | | | | | | | | | | | | + |

| | | | | | | | | | | | |
|---|---|---|---|---|---|---|---|---|---|---|---|
| IsdA | + | + | + | + | + | + | + | + | + | + | + |
| IsdB | | + | + | + | + | + | + | + | + | + | + |
| ClfA | | | + | + | + | + | + | + | + | + | + |
| ClfB | | | | + | + | + | + | + | + | + | + |
| Coa | | | | | + | + | + | + | + | + | + |
| Hla | | | | | | + | + | + | + | + | + |
| $Hla_{H35A}$ | | | | | | | + | + | + | + | + |
| IsdC | | | | | | | | + | + | + | + |
| SasF | | | | | | | | | + | + | + |
| vWbp | | | | | | | | | | + | + |
| vWh | | | | | | | | | | | + |

| | | | | | | | | | | |
|---|---|---|---|---|---|---|---|---|---|---|---|
| IsdB | + | + | + | + | + | + | + | + | + | + | |
| ClfA | | + | + | + | + | + | + | + | + | + | |
| ClfB | | | + | + | + | + | + | + | + | + | |
| Coa | | | | + | + | + | + | + | + | + | |
| Hla | | | | | + | + | + | + | + | + | |
| $Hla_{H35A}$ | | | | | | + | + | + | + | + | |
| IsdC | | | | | | | + | + | + | + | |
| SasF | | | | | | | | + | + | + | |
| vWbp | | | | | | | | | + | + | |
| vWh | | | | | | | | | | + | |

| | | | | | | | | | |
|---|---|---|---|---|---|---|---|---|---|---|
| ClfA | + | + | + | + | + | + | + | + | + | |
| ClfB | | + | + | + | + | + | + | + | + | |
| Coa | | | + | + | + | + | + | + | + | |
| Hla | | | | + | + | + | + | + | + | |
| $Hla_{H35A}$ | | | | | + | + | + | + | + | |
| IsdC | | | | | | + | + | + | + | |
| SasF | | | | | | | + | + | + | |
| vWbp | | | | | | | | + | + | |
| vWh | | | | | | | | | + | |

| | | | | | | | | |
|---|---|---|---|---|---|---|---|---|---|
| ClfB | + | + | + | + | + | + | + | + | |
| Coa | | + | + | + | + | + | + | + | |
| Hla | | | + | + | + | + | + | + | |
| $Hla_{H35A}$ | | | | + | + | + | + | + | |
| IsdC | | | | | + | + | + | + | |
| SasF | | | | | | + | + | + | |
| vWbp | | | | | | | + | + | |
| vWh | | | | | | | | + | |

| | | | | | | |
|---|---|---|---|---|---|---|
| Coa | + | + | + | + | + | + |
| Hla | | + | + | + | + | + |
| $Hla_{H35A}$ | | | + | + | + | + |
| IsdC | | | | + | + | + |
| SasF | | | | | + | + |

TABLE 1-continued

Staphylococcal coagulase Domains 1-2 and staphylococcal antigen combinations.

| | | | | | | |
|---|---|---|---|---|---|---|
| vWbp | | | | | + | + |
| vWh | | | | | | + |

| | | | | | | |
|---|---|---|---|---|---|---|
| Hla | + | + | + | + | + | + |
| Hla$_{H35A}$ | | + | + | + | + | + |
| IsdC | | | + | + | + | + |
| SasF | | | | + | + | + |
| vWbp | | | | | + | + |
| vWh | | | | | | + |

| | | | | | |
|---|---|---|---|---|---|
| Hla$_{H35A}$ | + | + | + | + | + |
| IsdC | | + | + | + | + |
| SasF | | | + | + | + |
| vWbp | | | | + | + |
| vWh | | | | | + |

| | | | | |
|---|---|---|---|---|
| IsdC | + | + | + | + |
| SasF | | + | + | + |
| vWbp | | | + | + |
| vWh | | | | + |

| | | | |
|---|---|---|---|
| SasF | + | + | + |
| vWbp | | + | + |
| vWh | | | + |

| | | |
|---|---|---|
| vWbp | + | + |
| vWh | | + |

| | |
|---|---|
| vWh | + |

In still further aspects, the isolated recombinant polypeptide comprising at least two different staphylococcal coagulase Domains 1-2 described herein is multimerized, e.g., dimerized or a linear fusion of two or more polypeptides or peptide segments. In certain aspects of the invention, a composition comprises multimers or concatamers of 1, 2, 3, 4, 5, 6, 7, 8, 9, 10, 11, 12, 13, 14, 15, 16, 17, 18, 19, 20 or more isolated cell surface proteins or segments thereof. Concatamers are linear polypeptides having one or more repeating peptide units. The at least two different staphylococcal coagulase Domains 1-2 can be consecutive or separated by a spacer or other peptide sequences, e.g., one or more additional bacterial peptide. In a further aspect, the other polypeptides or peptides contained in the multimer or concatamer can include, but are not limited to 1, 2, 3, 4, 5, 6, 7, 8, 9, 10, 11, 12, 13, 14, 15, 16, 17, 18, 19 of Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, vWh or immunogenic fragments thereof. Additional staphylococcal antigens that can be used in combination with at least two different staphylococcal coagulase Domains 1-2, include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein.

Certain embodiments include methods for eliciting an immune response against a staphylococcus bacterium or staphylococci in a subject comprising providing to the subject an effective amount of an immunogenic composition or a recombinant polypeptide comprising at least two different staphylococcal coagulase Domains 1-2 or a vector comprising a nucleic acid sequence encoding the same. In certain aspects, the methods for eliciting an immune response against a staphylococcus bacterium or staphylococci in a subject comprising providing to the subject an effective amount of 1, 2, 3, 4, 5, 6, 7, 8, 9, 10, 11, 12, 13, 14, 15, 16, 17, 18, 19 or more secreted proteins and/or cell surface proteins or segments/fragments thereof. A secreted protein or cell surface protein includes, but is not limited to Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, and/or vWh proteins and immunogenic fragments thereof. Additional staphylococcal antigens that can be used include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase. RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein.

Embodiments of the invention include compositions that include a polypeptide, peptide, or protein that comprises a sequence that is or is at least 70%, 75%, 80%, 85%, 90%, 95%, 96%, 97%, 98%, or 99% identical or similar to a staphylococcal coagulase Domains 1-2, in particular, a Coa Domains 1-2 (see, SEQUENCE TABLE NO. 1 (SEQ ID NOs: 33-37)) or a vWbp Domains 1-2 (see, SEQUENCE TABLE NO. 2 (SEQ ID NOs: 38-41)), or a second protein or peptide that is a secreted bacterial protein or a bacterial cell surface protein. Similarity or identity, with identity being preferred, is known in the art and a number of different programs can be used to identify whether a protein (or nucleic acid) has sequence identity or similarity to a known sequence. Sequence identity and/or similarity is determined using standard techniques known in the art, including, but not limited to, the local sequence identity algorithm of Smith & Waterman (1981), by the sequence identity alignment algorithm of Needleman & Wunsch (1970), by the search for similarity method of Pearson & Lipman (1988), by computerized implementations of these algorithms (GAP, BEST-FIT. FASTA, and TFASTA in the Wisconsin Genetics Software Package, Genetics Computer Group, 575 Science Drive, Madison, Wis.), the Best Fit sequence program described by Devereux et al. (1984), preferably using the default settings, or by inspection. Preferably, percent identity is calculated by using alignment tools known to and readily ascertainable to those of skill in the art. Percent identity is essentially the number of identical amino acids divided by the total number of amino acids compared times one hundred.

Still further embodiments include methods for stimulating in a subject a protective or therapeutic immune response against a staphylococcus bacterium comprising administering to the subject an effective amount of a composition including (i) a immunogenic composition comprising at least two different staphylococcal coagulase Domains 1-2, e.g., a Coa Domains 1-2 (see, SEQUENCE TABLE NO. 1 (SEQ ID NOs: 33-37)) or a vWbp Domains 1-2 (see, SEQUENCE TABLE NO. 2 (SEQ ID NOs: 38-41)) or a homologue thereof; or, (ii) a recombinant polypeptide comprising at least two different staphylococcal coagulase Domains 1-2 or homogues thereof; or, (iii) a nucleic acid molecule comprises a sequence encoding the at least two different staphylococcal Domains 1-2 or homologue thereof, or (iv) administering any of (i)-(iii) with any combination or permutation of bacterial proteins described herein. In a preferred embodiment the composition is not a staphylococcus bacterium. In certain aspects the subject is a human or a cow. In a further aspect the composition is formulated in a pharmaceutically acceptable formulation. The staphylococci may be *Staphylococcus aureus*.

Yet still further embodiments include vaccines comprising a pharmaceutically acceptable composition having at least two different staphylococcal coagulase Domains 1-2 described herein, or any other combination or permutation of protein(s) or peptide(s) described herein, wherein the composition is capable of stimulating an immune response against a staphylococcus bacterium. The vaccine may comprise at least two different staphylococcal coagulase Domains 1-2 described herein, or any other combination or permutation of protein(s) or peptide(s) described. In certain aspects, at least two different staphylococcal coagulase Domains 1-2 described herein, or any other combination or permutation of protein(s) or peptide(s) described are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other Staphylococcal proteins. A composition may further comprise an isolated non-coagulase polypeptide. Typically the vaccine comprises an adjuvant. In certain aspects a protein or peptide of the invention is linked (covalently or non-covalently) to the adjuvant, preferably the adjuvant is chemically conjugated to the protein.

In still yet further embodiments, a vaccine composition is a pharmaceutically acceptable composition having a recombinant nucleic acid encoding a recombinant polypeptide containing at least two different staphylococcal coagulase Domains 1-2 described herein, or any other combination or permutation of protein(s) or peptide(s) described herein, wherein the composition is capable of stimulating an immune response against a staphylococcus bacteria. In certain embodiments the recombinant nucleic acid contains a heterologous promoter. Preferably the recombinant nucleic acid is a vector. More preferably the vector is a plasmid or a viral vector. In some aspects the vaccine includes a recombinant, non-staphylococcus bacterium containing the nucleic acid. The recombinant non-staphylococci may be *Salmonella* or another gram-positive bacteria. The vaccine may comprise a pharmaceutically acceptable excipient, more preferably an adjuvant.

Still further embodiments include methods for stimulating in a subject a protective or therapeutic immune response against a staphylococcus bacterium comprising administering to the subject an effective amount of a composition of at least two different staphylococcal coagulase Domains 1-2 described herein, or a recombinant polypeptide containing at least two different staphylococcal coagulase Domains 1-2, or a nucleic acid encoding the same, and further comprising one or more of a Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, or vWh protein or peptide thereof. In a preferred embodiment the composition comprises a non-staphylococcus bacterium. In a further aspect the composition is formulated in a pharmaceutically acceptable formulation. The staphylococci for which a subject is being treated may be *Staphylococcus aureus*. Methods of the invention may also additionally include 1, 2, 3, 4, 5, 6, 7, 8, 9, 10, 11, 12, 13, 14, 15, 16, 17, 18, 19 or more secreted virulence factors and/or cell surface proteins, such as Eap, Ebh, Emp, EsaC, EsxA, EsxB, SdrC, SdrD, SdrE, IsdA, IsdB, ClfA, ClfB. Coa, Hla, IsdC, SasF, vWbp, or vWh in various combinations. In certain aspects a vaccine formulation includes Eap, Ebh, Emp, EsaC, EsxA, EsxB, SdrC, SdrD, SdrE, IsdA, IsdB, ClfA, ClfB, Coa, Hla, IsdC, SasF, vWbp, and vWh.

In certain aspects an antigen combination can include (1) at least two different staphylococcal coagulase Domains 1-2 and IsdA; (2) at least two different staphylococcal coagulase Domains 1-2 and ClfB; (3) at least two different staphylococcal coagulase Domains 1-2 and SdrD; (4) at least two different staphylococcal coagulase Domains 1-2 and Hla or Hla variant; (5) at least two different staphylococcal coagulase Domains 1-2 and ClfB, SdrD, and Hla or Hla variant; (6) at least two different staphylococcal coagulase Domains 1-2, IsdA, SdrD, and Hla or Hla variant; (7) at least two different staphylococcal coagulase Domains 1-2, IsdA. ClfB, and Hla or Hla variant; (8) at least two different staphylococcal coagulase Domains 1-2, IsdA, ClfB, and SdrD; (9) at least two different staphylococcal coagulase Domains 1-2, IsdA, ClfB, SdrD and Hla or Hla variant; (10) at least two different staphylococcal coagulase Domains 1-2, IsdA, ClfB, and SdrD; (11) at least two different staphylococcal coagulase Domains 1-2, IsdA, SdrD, and Hla or Hla variant; (12) at least two different staphylococcal coagulase Domains 1-2, IsdA, and Hla or Hla variant; (13) at least two different staphylococcal coagulase Domains 1-2, IsdA, ClfB, and Hla or Hla variant; (14) at least two different staphylococcal coagulase Domains 1-2, ClfB, and SdrD; (15) at least two different staphylococcal coagulase Domains 1-2, ClfB, and Hla or Hla variant; or (16) at least two different staphylococcal coagulase Domains 1-2, SdrD, and Hla or Hla variant.

In certain aspects, a bacterium delivering a composition of the invention will be limited or attenuated with respect to prolonged or persistent growth or abscess formation. In yet a further aspect, at least two different staphylococcal coagulase Domains 1-2 can be overexpressed in an attenuated bacterium to further enhance or supplement an immune response or vaccine formulation.

The term "EsxA protein" refers to a protein that includes isolated wild-type EsxA polypeptides from staphylococcus bacteria and segments thereof, as well as variants that stimulate an immune response against staphylococcus bacteria EsxA proteins.

The term "EsxB protein" refers to a protein that includes isolated wild-type EsxB polypeptides from staphylococcus bacteria and segments thereof, as well as variants that stimulate an immune response against staphylococcus bacteria EsxB proteins.

The term "SdrD protein" refers to a protein that includes isolated wild-type SdrD polypeptides from staphylococcus bacteria and segments thereof, as well as variants that stimulate an immune response against staphylococcus bacteria SdrD proteins.

The term "SdrE protein" refers to a protein that includes isolated wild-type SdrE polypeptides from staphylococcus bacteria and segments thereof, as well as variants that stimulate an immune response against staphylococcus bacteria SdrE proteins.

The term "IsdA protein" refers to a protein that includes isolated wild-type IsdA polypeptides from staphylococcus bacteria and segments thereof, as well as variants that stimulate an immune response against staphylococcus bacteria IsdA proteins.

The term "IsdB protein" refers to a protein that includes isolated wild-type IsdB polypeptides from staphylococcus bacteria and segments thereof, as well as variants that stimulate an immune response against staphylococcus bacteria IsdB proteins.

The term "Eap protein" refers to a protein that includes isolated wild-type Eap polypeptides from staphylococcus bacteria and segments thereof, as well as variants that stimulate an immune response against staphylococcus bacteria Eap proteins.

The term "Ebh protein" refers to a protein that includes isolated wild-type Ebh polypeptides from staphylococcus bacteria and segments thereof, as well as variants that stimulate an immune response against staphylococcus bacteria Ebh proteins.

The term "Emp protein" refers to a protein that includes isolated wild-type Emp polypeptides from staphylococcus bacteria and segments thereof, as well as variants that stimulate an immune response against staphylococcus bacteria Emp proteins.

The term "EsaB protein" refers to a protein that includes isolated wild-type EsaB polypeptides from staphylococcus bacteria and segments thereof, as well as variants that stimulate an immune response against staphylococcus bacteria EsaB proteins.

The term "EsaC protein" refers to a protein that includes isolated wild-type EsaC polypeptides from staphylococcus bacteria and segments thereof, as well as variants that stimulate an immune response against staphylococcus bacteria EsaC proteins.

The term "SdrC protein" refers to a protein that includes isolated wild-type SdrC polypeptides from staphylococcus bacteria and segments thereof, as well as variants that stimulate an immune response against staphylococcus bacteria SdrC proteins.

The term "ClfA protein" refers to a protein that includes isolated wild-type ClfA polypeptides from staphylococcus bacteria and segments thereof, as well as variants that stimulate an immune response against staphylococcus bacteria ClfA proteins.

The term "ClfB protein" refers to a protein that includes isolated wild-type ClfB polypeptides from staphylococcus bacteria and segments thereof, as well as variants that stimulate an immune response against staphylococcus bacteria ClfB proteins.

The term "Coa protein" refers to a protein that includes isolated wild-type Coa polypeptides from staphylococcus bacteria and segments thereof, as well as variants that stimulate an immune response against staphylococcus bacteria Coa proteins.

The term "Hla protein" refers to a protein that includes isolated wild-type Hla polypeptides from staphylococcus bacteria and segments thereof, as well as variants that stimulate an immune response against staphylococcus bacteria Hla proteins.

The term "IsdC protein" refers to a protein that includes isolated wild-type IsdC polypeptides from staphylococcus bacteria and segments thereof, as well as variants that stimulate an immune response against staphylococcus bacteria IsdC proteins.

The term "SasF protein" refers to a protein that includes isolated wild-type SasF polypeptides from staphylococcus bacteria and segments thereof, as well as variants that stimulate an immune response against staphylococcus bacteria SasF proteins.

The term "vWbp protein" refers to a protein that includes isolated wild-type vWbp (von Willebrand factor binding protein) polypeptides from staphylococcus bacteria and segments thereof, as well as variants that stimulate an immune response against staphylococcus bacteria vWbp proteins.

The term "vWh protein" refers to a protein that includes isolated wild-type vWh (von Willebrand factor binding protein homolog) polypeptides from staphylococcus bacteria and segments thereof, as well as variants that stimulate an immune response against staphylococcus bacteria vWh proteins.

An immune response refers to a humoral response, a cellular response, or both a humoral and cellular response in an organism. An immune response can be measured by assays that include, but are not limited to, assays measuring the presence or amount of antibodies that specifically recognize a protein or cell surface protein, assays measuring T-cell activation or proliferation, and/or assays that measure modulation in terms of activity or expression of one or more cytokines.

In still further embodiments of the invention a composition may include a polypeptide, peptide, or protein that is or is at least 70%, 75%, 80%, 85%, 90%, 95%, 96%, 97%, 98%, or 99% identical or similar to an EsxA protein.

In still further embodiments of the invention a composition may include a polypeptide, peptide, or protein that is or is at least 70%, 75%, 80%, 85%, 90%, 95%, 96%, 97%, 98%, or 99% identical or similar to an EsxB protein.

In yet still further embodiments of the invention a composition may include a polypeptide, peptide, or protein that is or is at least 70%, 75%, 80%, 85%, 90%, 95%, 96%, 97%, 98%, or 99% identical or similar to an SdrD protein.

In further embodiments of the invention a composition may include a polypeptide, peptide, or protein that is or is at least 70%, 75%, 80%, 85%, 90%, 95%, 96%, 97%, 98%, or 99% identical or similar to an SdrE protein.

In still further embodiments of the invention a composition may include a polypeptide, peptide, or protein that is or is at least 70%, 75%, 80%, 85%, 90%, 95%, 96%, 97%, 98%, or 99% identical or similar to an IsdA protein.

In yet still further embodiments of the invention a composition may include a polypeptide, peptide, or protein that is or is at least 70%, 75%, 80%, 85%, 90%, 95%, 96%, 97%, 98%, or 99% identical or similar to an IsdB protein.

Embodiments of the invention include compositions that include a polypeptide, peptide, or protein that is or is at least 70%, 75%, 80%, 85%, 90%, 95%, 96%, 97%, 98%, or 99% identical or similar to a EsaB protein.

In a further embodiments of the invention a composition may include a polypeptide, peptide, or protein that is or is at least 70%, 75%, 80%, 85%, 90%, 95%, 96%, 97%, 98%, or 99% identical or similar to a ClfB protein.

In still further embodiments of the invention a composition may include a polypeptide, peptide, or protein that is or is at least 70%, 75%, 80%, 85%, 90%, 95%, 96%, 97%, 98%, or 99% identical or similar to an IsdC protein.

In yet further embodiments of the invention a composition may include a polypeptide, peptide, or protein that is or is at least 70%, 75%, 80%, 85%, 90%, 95%, 96%, 97%, 98%, or 99% identical or similar to a SasF protein.

In yet still further embodiments of the invention a composition may include a polypeptide, peptide, or protein that is or is at least 70%, 75%, 80%, 85%, 90%, 95%, 96%, 97%, 98%, or 99% identical or similar to a SdrC protein. In yet still further embodiments of the invention a composition may include a polypeptide, peptide, or protein that is or is at least 70%, 75%, 80%, 85%, 90%, 95%, 96%, 97%, 98%, or 99% identical or similar to a ClfA protein.

In yet still further embodiments of the invention a composition may include a polypeptide, peptide, or protein that is or is at least 70%, 75%, 80%, 85%, 90%, 95%, 96%, 97%, 98%, or 99% identical or similar to an Eap protein.

In yet still further embodiments of the invention a composition may include a polypeptide, peptide, or protein that is or is at least 70%, 75%, 80%, 85%, 90%, 95%, 96%, 97%, 98%, or 99% identical or similar to an Ebh protein.

In yet still further embodiments of the invention a composition may include a polypeptide, peptide, or protein that is or is at least 70%, 75%, 80%, 85%, 90%, 95%, 96%, 97%, 98%, or 99% identical or similar to an Emp protein.

In yet still further embodiments of the invention a composition may include a polypeptide, peptide, or protein that is or is at least 70%, 75%, 80%, 85%, 90%, 95%, 96%, 97%, 98%, or 99% identical or similar to an EsaC protein. Sequence of EsaC polypeptides can be found in the protein databases and include, but are not limited to accession numbers ZP_02760162 (GI:168727885), NP_645081.1 (GI: 21281993), and NP_370813.1 (GI:15923279), each of which is incorporated herein by reference as of the priority date of this application.

In yet still further embodiments of the invention a composition may include a polypeptide, peptide, or protein that is or is at least 70%, 75%, 80%, 85%, 90%, 95%, 96%, 97%, 98%, or 99% identical or similar to a Coa protein.

In yet still further embodiments of the invention a composition may include a polypeptide, peptide, or protein that is or is at least 70%, 75%, 80%, 85%, 90%, 95%, 96%, 97%, 98%, or 99% identical or similar to a Hla protein.

In yet still further embodiments of the invention a composition may include a polypeptide, peptide, or protein that is or is at least 70%, 75%, 80%, 85%, 90%, 95%, 96%, 97%, 98%, or 99% identical or similar to a vWa protein.

In yet still further embodiments of the invention a composition may include a polypeptide, peptide, or protein that is or is at least 70%, 75%, 80%, 85%, 90%, 95%, 96%, 97%, 98%, or 99% identical or similar to a vWbp protein.

In certain aspects, a polypeptide or segment/fragment can have a sequence that is at least 85%, at least 90%, at least 95%, at least 98%, or at least 99% or more identical to the amino acid sequence of the reference polypeptide. The term "similarity" refers to a polypeptide that has a sequence that has a certain percentage of amino acids that are either identical with the reference polypeptide or constitute conservative substitutions with the reference polypeptides.

The polypeptides described herein may include 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of the sequence of SEQUENCE TABLE NO. 1 (SEQ ID NOs: 33-37) or SEQUENCE TABLE NO. 2 (SEQ ID NOs: 38-41).

A polypeptide segment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of the sequence of SEQUENCE TABLE NO. 1 (SEQ ID NOs: 33-37) or SEQUENCE TABLE NO. 2 (SEQ ID NOs: 38-41).

In yet still further embodiments, a composition may include a polynucleotide that is or is at least 70%, 75%, 80%, 85%, 90%, 95%, 96%, 97%, 98%, or 99% identical or similar to a nucleic acid sequence encoding a Coa protein. In certain aspects, the nucleic acid sequence encoding a Coa protein of strain USA300 will have all or part of the nucleic acid sequence provided herein. In certain aspects, the nucleic acid sequence encoding a Coa protein of strain N315 will have all or part of the nucleic acid sequence provided herein In certain aspects, the nucleic acid sequence encoding a Coa protein of strain MW2 will have all or part of the nucleic acid sequence of provided herein. In certain aspects, the nucleic acid sequence encoding a Coa protein of strain MRSA252 will have all or part of the nucleic acid sequence of provided herein. In certain aspects, the nucleic acid sequence encoding a Coa protein of strain WIS will have all or part of the nucleic acid sequence of provided herein. In certain aspects, the nucleic acid sequence encoding a Coa protein of strain MU50 will have all or part of the nucleic acid sequence of provided herein. In certain aspects, the nucleic acid sequence encoding a Coa protein of strain 85/2082 will have all or part of the nucleic acid sequence of provided herein. In certain aspects, the nucleic acid sequence encoding a Coa protein of strain Newman will have all or part of the nucleic acid sequence of provided herein.

In yet still further embodiments, a composition may include a polynucleotide that is or is at least 70%, 75%, 80%, 85%, 90%, 95%, 96%, 97%, 98%, or 99% identical or similar to a nucleic acid sequence encoding a vWbp fusion protein. In certain aspects, the nucleic acid sequence encoding a vWpb protein of strain USA300 will have all or part of the nucleic acid sequence provided herein. In certain aspects, the nucleic acid sequence encoding a vWbp protein of strain N315 will have all or part of the nucleic acid sequence provided herein. In certain aspects, the nucleic acid sequence encoding a vWbp protein of strain Newman will have all or part of the nucleic acid sequence provided herein. In certain aspects, the nucleic acid sequence encoding a vWbp protein of strain MRSA252 will have all or part of the nucleic acid sequence provided herein. In certain aspects, the nucleic acid sequence encoding a vWbp protein of strain MW2 will have all or part of the nucleic acid sequence provided herein.

In yet still further embodiments, a composition may include a polynucleotide that is or is at least 70%, 75%, 80%, 85%, 90%, 95%, 96%, 97%, 98%, or 99% identical or similar to a nucleic acid sequence encoding a Coa Domains 1-2. In certain aspects, the nucleic acid sequence encoding a Coa Domains 1-2 of strain N315 will have all or part of the nucleic acid sequence provided herein. In certain aspects, the nucleic acid sequence encoding a Coa Domains 1-2 of strain MW2 will have all or part of the nucleic acid sequence provided herein. In certain aspects, the nucleic acid sequence encoding a Coa Domains 1-2 of strain MRSA252 will have all or part of the nucleic acid sequence provided herein. In certain aspects, the nucleic acid sequence encoding a Coa Domains 1-2 of strain WIS will have all or part of the nucleic acid sequence provided herein.

In particular aspects, a composition may comprise a polynucleotide that is or is at least 70%, 75%, 80%, 85%, 90%, 95%, 96%, 97%, 98%, or 99% identical or similar to a nucleic acid sequence encoding five different Coa Domains 1-2 from strains WIS, MRSA252, N315, MW2, and USA300, respectively. In still further aspects, the nucleic acid sequence encoding five different Coa Domains 1-2 will have all or part of the nucleic acid sequence provided herein.

In yet still further embodiments, a composition may include a polynucleotide that is or is at least 70%, 75%, 80%, 85%, 90%, 95%, 96%, 97%, 98%, or 99% identical or similar to a nucleic acid sequence encoding a vWbp Domains 1-2. In certain aspects, the nucleic acid sequence encoding a vWbp Domains 1-2 of strain N315 will have all or part of the nucleic acid sequence provided herein. In certain aspects, the nucleic acid sequence encoding a vWbp Domains 1-2 of strain MW2 will have all or part of the nucleic acid sequence provided herein. In certain aspects, the nucleic acid sequence encoding a vWbp Domain 1-2 of strain MRSA252 will have all or part of the nucleic acid sequence provided herein.

The compositions may be formulated in a pharmaceutically acceptable composition. In certain aspects of the invention the staphylococcus bacterium is an *S. aureus* bacterium.

In further aspects, a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous, intramuscular, intravenous, or various combinations thereof, including inhalation or aspiration.

In still further embodiments, a composition comprises a recombinant nucleic acid molecule encoding a polypeptide described herein or segments/fragments thereof. Typically a recombinant nucleic acid molecule encoding a polypeptide described herein contains a heterologous promoter. In certain aspects, a recombinant nucleic acid molecule of the invention is a vector, in still other aspects the vector is a plasmid. In certain embodiments the vector is a viral vector. In certain aspects a composition includes a recombinant, non-staphylococcus bacterium containing or expressing a polypeptide described herein. In particular aspects the recombinant non-staphylococcus bacteria is *Salmonella* or another gram-positive bacteria. A composition is typically administered to mammals, such as human subjects, but administration to other animals that are capable of eliciting an immune response is contemplated. In further aspects the staphylococcus bacterium containing or expressing the polypeptide is *Staphylococcus aureus*. In further embodiments the immune response is a protective immune response.

In further embodiments a composition comprises a recombinant nucleic acid molecule encoding all or part of one or more of a Eap, Ebh, Emp, EsaB, EsaC, EsxA, EsxB, SdrC, SdrD, SdrE, IsdA, IsdB, ClfA, ClfB, Coa, Hla, IsdC, SasF, SpA, vWbp, or vWh protein or peptide or variant thereof. Additional staphylococcal antigens that can be used in combination with the polypeptides described herein include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In particular aspects, a bacteria is a recombinant non-staphylococcus bacteria, such as a *Salmonella* or other gram-positive bacteria.

Compositions discussed herein are typically administered to human subjects, but administration to other animals that are capable of eliciting an immune response to a staphylococcus bacterium is contemplated, particularly cattle, horses, goats, sheep and other domestic animals, i.e., mammals.

In certain aspects the staphylococcus bacterium is a *Staphylococcus aureus*. In further embodiments the immune response is a protective immune response. In still further aspects, the methods and compositions of the invention can be used to prevent, ameliorate, reduce, or treat infection of tissues or glands, e.g., mammary glands, particularly mastitis and other infections. Other methods include, but are not limited to prophylactically reducing bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

Any embodiment discussed with respect to one aspect of the invention applies to other aspects of the invention as well. In particular, any embodiment discussed in the context of a composition comprising at least two different staphylococcal coagulse Domains 1-2 or a recombinant polypeptide comprising the same or a nucleic acid encoding the same may be implemented with respect to other antigens, such as Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288, 214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (or nucleic acids), and vice versa. It is also understood that any one or more of Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008, 341). Fibronectin binding protein (U.S. Pat. No. 5,840,846). FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523). SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein can be specifically excluded from a claimed composition.

Embodiments include compositions that contain or do not contain a bacterium. A composition may or may not include an attenuated or viable or intact staphylococcal bacterium. In certain aspects, the composition comprises a bacterium that is not a staphylococcal bacterium or does not contain staphylococcal bacteria. In certain embodiments a bacterial composition comprises an isolated or recombinantly expressed at least two different staphylococcal coagulase Domains 1-2 described herein or a nucleotide encoding the same. The composition may be or include a recombinantly engineered staphylococcus bacterium that has been altered in a way that comprises specifically altering the bacterium with respect to a secreted virulence factor or cell surface protein. For example, the bacteria may be recombinantly modified to express more of the virulence factor or cell surface protein than it would express if unmodified.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The subject will have (e.g., are diagnosed with a staphylococcal infection), will be suspected of having, or will be at risk of developing a staphylococcal infection. Compositions of the present invention include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

The embodiments in the Example section are understood to be embodiments of the invention that are applicable to all aspects of the invention.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIGS. 1A-1D. Immune responses to coagulase. (A) Drawing to illustrate the primary structure of coagulase from *S. aureus* Newman ($Coa_{NM}$), which was purified via an N-terminal $His_6$ tag from *E. coli*. $Coa_{NM}$ encompasses the D1 and D2 domains involved in prothrombin binding, the linker (L) domain and the Repeat (R) domain, which is comprised of tandem repeats of a 27 residue peptide sequence that binds to fibrinogen. In addition to $Coa_{NM}$, the $D1_{Coa}$, $D2_{Coa}$, $D12_{Coa}$, $L_{Coa}$, and $R_{Coa}$, domains were purified. (B) Rabbits were immunized with purified $Coa_{NM}$ and immune sera examined by ELISA for serum IgG reactive with $Coa_{NM}$, $D1_{Coa}$, $D2_{Coa}$, $D12_{Coa}$, $L_{Coa}$ or $CT_{Coa}$. (C) The association of $D12_{Coa}$ with human prothrombin or the binding of $CT_{Coa}$ to fibrinogen were measured by ELISA and perturbed with increasing concentrations rabbit IgG directed against $Coa_{NM}$ or the plague vaccine antigen V10 as a control. (D) Affinity purified rabbit IgG specific for $Coa_{NM}$ ($\alpha$-$Coa_{NM}$), $D12_{Coa}$ ($\alpha$-$D12_{Coa}$) or $CT_{Coa}$ ($\alpha$-$CT_{Coa}$) were added to citrate-treated mouse blood and inoculated with *S. aureus* Newman to monitor the inhibition of staphylococcal coagulation.

FIGS. 2A-2C. Coagulase domains as vaccine antigens. (A) Recombinant purified $Coa_{NM}$, $D12_{Coa}$ and $CT_{Coa}$ were used to immunize BALB/c mice (n=5) with a prime-booster regimen and immune sera were analyzed by ELISA for reactivity of mouse serum IgG towards purified $Coa_{NM}$, $D12_{Coa}$ or $CT_{Coa}$. (B) Cohorts of BALB/c mice (n=10) with a prime-booster regimen of purified $Coa_{NM}$, $D12_{Coa}$ and $CT_{Coa}$ and challenged by intravenous injection with *S. aureus* Newman (1×10⁸ CFU). Survival of animals was monitored over 10 days. (C) Affinity purified rabbit IgG specific for $Coa_{NM}$ ($\alpha$-$Coa_{NM}$), $D12_{Coa}$ ($\alpha$-$D12_{Coa}$), $CT_{Coa}$ ($\alpha$-$CT_{Coa}$) or V10 ($\alpha$-V10) was injected at a concentration of 5 mg/kg body weight into the peritoneal cavity of naïve BALB/c mice. Passively immunized mice were challenged by intravenous injection with *S. aureus* Newman (1×10⁸ CFU) and survival of animals was monitored over 10 days.

FIGS. 3A-3D. Immune responses to von Willebrand Factor binding protein (vWbp). (A) Drawing to illustrate the primary structure of vWbp from *S. aureus* Newman ($vWbp_{NM}$), which was purified via an N-terminal $His_6$ tag from *E. coli*. $vWbp_{NM}$ encompasses the D1 and D2 domains involved in prothrombin binding, the linker (L) domain and the fibrinogen binding (Fgb) domain. In addition to $vWbp_{NM}$, the $D1_{vWbp}$, $D2_{vWbp}$, $D12_{vWbp}$, $L_{vWbp}$, $Fgb_{vWbp}$ and the $CT_{vWbp}$ domains were purified. (B) Rabbits were immunized with purified $vWbp_{NM}$ and immune sera examined by ELISA for serum IgG reactive with $vWbp_{NM}$, the $D1_{vWbp}$, $D2_{vWbp}$, $D12_{vWbp}$, $L_{vWbp}$, $Fgb_{vWbp}$, and the $CT_{vWbp}$. (C) The association of $D12_{vWbp}$ with human prothrombin or the binding of $CT_{vWbp}$ to fibrinogen were measured by ELISA and perturbed with increasing concentrations rabbit IgG directed against $vWbp_{NM}$ or the plague vaccine antigen V10 as a control. (D) Affinity purified rabbit IgG specific for $vWbp_{NM}$ ($\alpha$-$vWbp_{NM}$), $D12_{vWbp}$ ($\alpha$-$D12_{vWbp}$) or $CT_{vWbp}$ ($\alpha$-$CT_{vWbp}$) were added to citrate-treated mouse blood and inoculated with *S. aureus* Newman to monitor the inhibition of staphylococcal coagulation.

FIGS. 4A-4C. von Willebrand Factor binding protein (vWbp) domains as vaccine antigens. (A) Recombinant purified $vWbp_{NM}$, $D12_{vWbp}$, and $CT_{vWbp}$ were used to immunize BALB/c mice (n=5) with a prime-booster regimen and immune sera were analyzed by ELISA for reactivity of mouse serum IgG towards purified $vWbp_{NM}$, $D12_{vWbp}$ and $CT_{vWbp}$. (B) Cohorts of BALB/c mice (n=10) with a prime-booster regimen of purified $vWbp_{NM}$, $D12_{vWbp}$, and $CT_{vWbp}$ and challenged by intravenous injection with *S. aureus* Newman (1×10⁸ CFU). Survival of animals was monitored over 10 days. (C) Affinity purified rabbit IgG specific for $vWbpp_{NM}$ ($\alpha$-$vWbp_{NM}$), $D12_{vWbp}$, ($\alpha$-$D12_{vWbp}$), $CT_{vWbp}$ ($\alpha$-$CT_{vWbp}$) or V10 ($\alpha$-V10) was injected at a concentration of 5 mg/kg body weight into the peritoneal cavity of naïve BALB/c mice. Passively immunized mice were challenged by intravenous injection with *S. aureus* Newman (1×10⁸ CFU) and survival of animals was monitored over 10 days.

FIGS. 5A-5F. Immunization of mice with $Coa_{NM}$/$vWbp_{NM}$ vaccine and the spectrum of disease protection against different *S. aureus* isolates. (A) Recombinant $Coa_{NM}$/$vWbp_{NM}$ or mock (PBS) vaccine were used to immunize BALB/c mice (n=5) with a prime-booster regimen. Immune sera were analyzed by ELISA for reactivity of mouse serum IgG towards purified $Coa_{NM}$ and $vWbp_{NM}$. Cohorts of BALB/c mice (n=10) were immunized with a prime-booster regimen of purified $Coa_{NM}$/$vWbp_{NM}$ or mock vaccine and challenged by intravenous injection with *S. aureus* USA300 (B), N315 (C), MW2 (D), CowanI (E) or WIS (F). Survival of animals was monitored over 10 days.

FIGS. 6A-6C Immunogenicity of the Coa$_4$/vWbp$_2$ vaccine. (A) Drawing to illustrate the design of the Coa$_4$ and vWbp$_2$ vaccine components. Coa$_4$ is comprised of an N-terminal His6 tag, the Coa D12 domains of *S. aureus* strains MRSA252, MW2, N315 and the full length mature sequence of Coa from strain USA300 in addition to a C-terminal STREP tag. vWbp$_2$ is comprised of an N-terminal His6 tag, the vWBp D12 domains of *S. aureus* N315 and the full length mature sequence of vWbp from strain USA300 in addition to a C-terminal STREP tag. (B) Coa$_4$ and vWbp$_2$ were purified from *E. coli* via Ni-NTA and Streptavidin affinity chromatography and analyzed by Coomassie stained SDS-PAGE.

FIGS. 7A-7F Immunization of mice with the Coa$_4$/vWbp$_2$ vaccine and the spectrum of disease protection against different *S. aureus* isolates. (A) Coa$_4$/vWbp$_2$ or mock (PBS) vaccine were used to immunize BALB/c mice (n=5) with a prime-booster regimen. Immune sera were analyzed by ELISA for reactivity of mouse serum IgG towards purified Coa$_4$ and vWbp$_2$. (B) Cohorts of BALB/c mice (n=10) were immunized with a prime-booster regimen of purified Coa$_4$/vWbp$_2$ or mock vaccine and challenged by intravenous injection with *S. aureus* USA300 (B). N315 (C), MW2 (D), CowanI (E) or WIS (F). Survival of animals was monitored over 10 days.

Figure 8A:
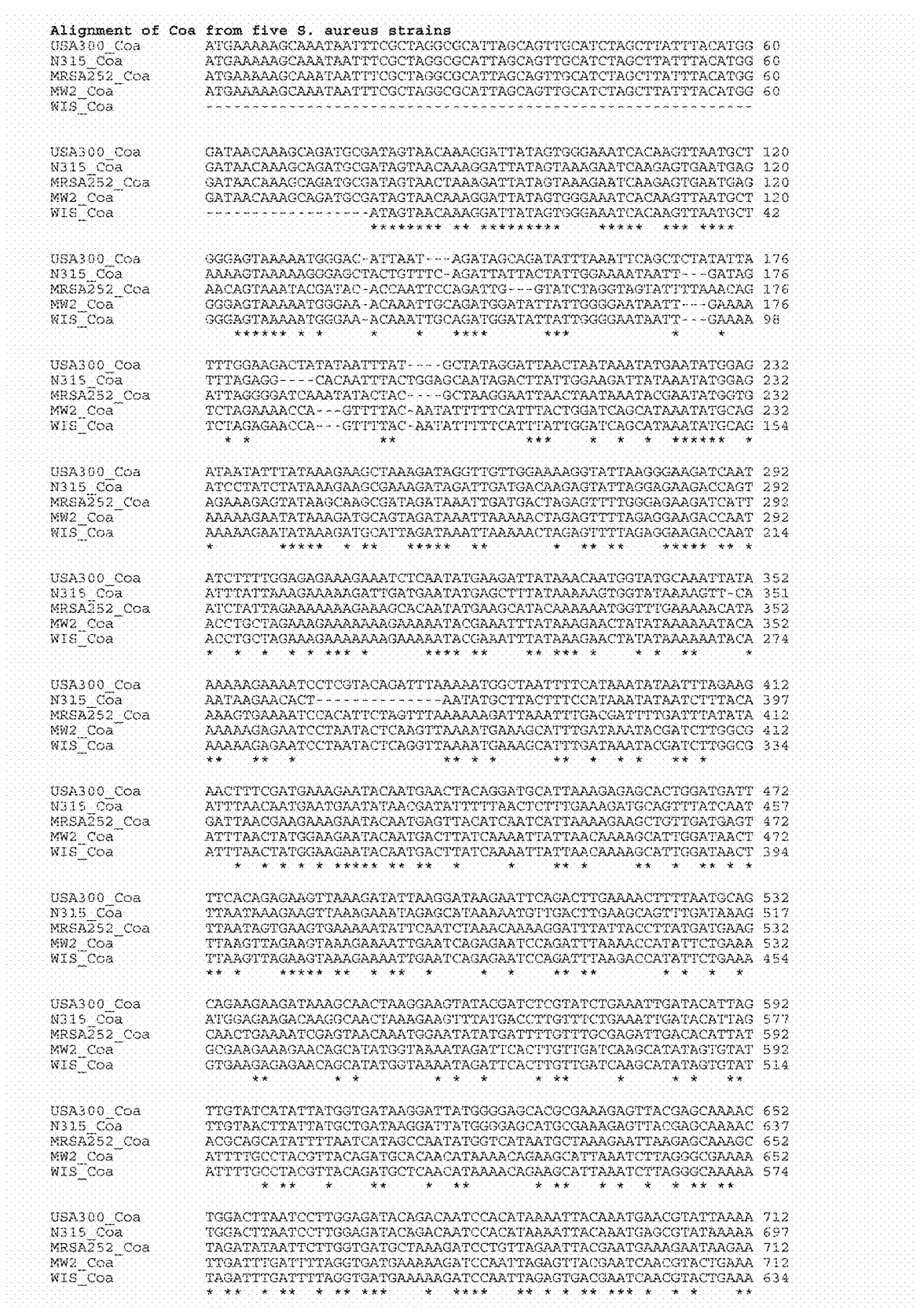

FIGS. 8A-D: Coa sequence alignments. (A-C) Alignment of Coa nucleic acid sequences from five *S. aureus* strains. (D) Alignment of amino acid sequences of Coa Domains 1-2 from selected *S. aureus* strains.

FIGS. 9A-H: vWbp sequence alignments. (A-F) Alignment of vWbp nucleic acid sequences from five *S. aureus* strains. (G) Alignment of amino acid sequences of vWbp (Domain 1 sequence is shaded) from selected *S. aureus* strains. (H) Alignment of amino acid sequences of vWbp from selected *S. aureus* strains without the two truncated alleles.

DETAILED DESCRIPTION

*Staphylococcus aureus*, a Gram-positive microbe that colonizes the human skin and nares, causes invasive diseases such as skin and soft tissue infections, bacteremia, sepsis and endocarditis (Lowy 1998). The emergence of antibiotic-resistant strains, designated community-acquired (CA-MRSA) or hospital-acquired methicillin-resistant *S. aureus* (HA-MRSA), presents a formidable therapeutic challenge (Klevens 2008). Although several vaccine development efforts have been launched, an FDA-licensed *S. aureus* vaccine is not yet available (DeDent 2012).

A hallmark of *S. aureus* isolates is their ability to form clots when inoculated into human citrate-plasma or blood (Much 1908). This phenotype has been linked to the secretion of coagulase (Coa) (Cheng 2010), which binds prothrombin and alters the enzyme's active site through insertion of their N-terminal residues at exosite 1, thereby converting fibrinogen to fibrin (Friedrich 2003). The mature form of Coa is comprised of the N-terminal D1 and D2 domains, which provide for association with and activation of prothrombin (Panizzi 2004) (FIG. 1A). A linker domain (L) connects D12 and the R region with tandem repeats of a 27 residue peptide that bind fibrinogen (Panizzi 2006) (FIG. 1A). Prothrombin Coa complex (staphylocoagulase) converts soluble fibrinogen to insoluble fibrin, forming the mesh network of a clot (Friedrich 2003; Kroh 2009).

When injected into animals, purified Coa clots blood in vivo and this is thought to promote staphylococcal escape from phagocytic killing (Hale 1945; Smith 1956). More recently, coagulase typing, i.e. the neutralization of *S. aureus* coagulation of citrate-plasma with specific antiserum was used to distinguish ten different serological Coa types (Kanemitsu 2001). Coagulase (Coa) types were also analyzed by DNA sequencing, which revealed significant variation within coa sequences for the D1-2 domain and little variation for the linker and repeat regions, respectively (Watanabe 2005). To address the question whether sequence variation within *S. aureus* coa genes is the result of negative selection, as might occur when infected individuals develop antibody responses against secreted Coa, Watanabe and colleagues sequenced the coa genes from 126 *S. aureus* isolates, which were simultaneously analyzed for coagulase-serotype and clonal cluster (CC) type. The latter is accomplished via multi-locus sequence typing (MLST), which examines sequences from seven different genes (arc, aro, glp, gmk, pta, tpi, and yqi) (Enright 2000). With the exception of CC1 and CC8 strains, most of the isolates that were defined by MLST were of the same coa sequence-type (Watanabe 2009). Variation of coa sequences is likely generated via horizontal gene transfer (phage transduction or DNA transformation), as coa genes of the same sequence-type are found scattered across the MLST tree (Watanabe 2009). Together with the observation that pooled human immunoglobulin neutralizes most, but not all, coagulase-types (Streitfeld 1959), these results suggest that coa gene diversification may enable *S. aureus* to circumvent the humoral immune responses of hosts with prior exposure to the pathogen (Watanabe 2009). Thus, Coa may represent a protective antigen of *S. aureus* and should be carefully analyzed for its possible use as a vaccine antigen.

Nearly a century after the first description of staphylococcal coagulase, Bjerketorp and colleagues discovered vWbp (Bjerketorp 2002). vWbp is a secreted protein that, in addition to binding von Willebrand Factor, also associates with prothrombin to convert fibrinogen to fibrin (Friedrich 2003; Kroh 2009; Bjerketorp 2004). vWbp displays sequence homology to the Coa D12 domains (Watanabe 2005; Bjerketorp 2004), however its C-terminal domain lacks the L and R domains of Coa, which are replaced by unique vWF and fibrinogen binding sites (Cheng 2010; Bjerketorp 2002). Genome sequencing discovered two distinct vwb alleles with variation in the predicted D1-2 domains (Watanabe 2005). Immunization of mice with purified recombinant Coa or vWbp alone were not sufficient to elicit protective immune responses against challenge with the same coagulase-type *S. aureus* strain, however antibodies against both, Coa and vWbp, protected animals against *S. aureus* abscess formation and lethal bacteremia (Cheng 2010). Similarly, *S. aureus* Newman mutants lacking coa and vwb, but not variants with single gene deletions, displayed significant defects in mouse models of abscess formation or lethal bacteremia (Cheng 2010). Coa and vWbp secretion enables *S. aureus* to agglutinate in the presence of plasma, resulting in thrombo-embolic lesions as well as endocarditis and promoting the lethal outcome of staphylococcal bacteremia (McAdow 2011; Panizzi 2011). Blocking coagulases with univalent direct thrombin inhibitors delays the time-to-death associated with lethal *S. aureus* challenge, further highlighting the importance of coagulases for staphylococcal disease (McAdow 2011).

Early work on coagulase demonstrated that, following *S. aureus* infection, humans as well as animals generate Coa-specific antibodies (Tager 1948; Lominski 1946). When transferred to naïve rabbits, these antibodies may neutralize *S. aureus* coagulation and, at least in some cases, may confer immunity to challenge with *S. aureus* (Lominski 1949;

Lominski 1962). Active immunization of rabbits with preparations containing coagulase could prolong the life of rabbits that had been challenged by intravenous inoculation with lethal doses of S. aureus (Boake 1956). Comparison of different (phage-typed) S. aureus isolates for inhibition of plasma clotting by coagulase-antiserum revealed both phage type-specific and non-specific neutralization (Lominski 1946; Lominski 1962; Rammelkamp 1950; Duthie 1952; Harrison 1964). These data supported a general concept for the existence of serological types of Coa, which are not strictly linked to S. aureus phage-types (Rammelkamp 1956).

Purified coagulase toxoid, encompassing purified Coa from S. aureus strains M1 and Newman adsorbed to aluminum phosphate, was examined for therapeutic immunization of 71 patients with chronic furunculosis (Harrison 1963). As compared to placebo, coagulase immunization generated a rise in coagulase-specific antibody titers but failed to improve the clinical outcome of chronic furunculosis (Harrison 1963). Of note, the development of neutralizing antibodies or the possibility of type-specific immunity were not examined (Harrison 1963). Thus, although early work revealed preclinical efficacy of coagulase subunit vaccines, clinical studies failed to demonstrate efficacy in a human trial. As most of these studies were conducted from 1945-1965, one must consider the limited tools for the isolation of highly purified coagulases as well as the inability to type S. aureus strains or coagulase vaccine preparations on the basis of their nucleotide sequence. Further, earlier studies were conducted without knowledge of vWbp or of the molecular mechanisms of Coa- and vWbp-mediated prothrombin activation and fibrinogen cleavage (Friedrich 2003; Kroh 2009).

The inventors recently observed that both coagulases secreted by S. aureus Newman, Coa a and $vWbp_{NM}$, are sufficient for the ability of this strain to cause abscess formation and rapidly lethal bacteremia in mice (Cheng 2010). In active and passive immunization experiments, antibodies against both $Coa_{NM}$ and $vWbp_{NM}$ were required to confer protection against abscess formation or lethal bacteremia (Cheng 2010). On the basis of these observations, the inventors hypothesize that coagulases may function as protective antigens that elicit antibody responses against Coa and vWbp, which protect animals and humans against S. aureus disease (Cheng 2010). In agreement with this model, expression of coa and vwb is a universal trait of S. aureus strains (Cheng 2011). Of note, the coa gene of S. aureus isolates is variable (McCarthy 2010), with greater variation in amino acid sequence than even the tandem repeats of the protein A (spa) gene; the variation in spa is used for epidemiological typing experiments (Watanabe 2009; Koreen 2004). S. aureus mutants that are unable to express coa have not yet been isolated from humans with manifest staphylococcal disease. The vwb gene is less variable (McCarthy 2010). Analyzing currently available S. aureus genome sequences for vwb homology, the inventors identified three alleles. Two of the vwb alleles varied in their coding sequence for the D12 domain (S. aureus N315 and USA300 are representatives for these alleles), whereas the third allele harbored a nucleotide deletion in codon 102, creating a frameshift that results in a nonsense mutation in codon 107 (S. aureus MRSA252).

Enabled by these observations, the inventors examined immune responses to coagulases and demonstrated that antibodies against the D1-2 domain neutralize staphylococcal coagulation in a type-specific manner. By injecting mice with a $Coa_4/vWbp_2$ vaccine that harbors antigenic determinants from the major North American isolates [CC1, CC5 (USA100), CC8 (USA300), CC30, CC45](Klevens 2007; Patel 2011), mice could be protected against challenge with several different S. aureus strains.

Coa and vWbp immunization of rabbits or mice generated predominantly antibodies against the D1-2 domain of $Coa_{NM}$ or $vWbp_{NM}$. D1-2-specific antibodies neutralized the coagulase activities of S. aureus Newman and, when transferred to naïve animals, conferred protection against lethal bacteremia. Neutralization and disease protection of $Coa_{NM}$- and $vWbp_{NM}$- specific antibodies occurred in a type-specific manner, not unlike the type-specific immunity reported for Streptococcus pyogenes M proteins (Lancefield 1928; Lancefield 1962) or the pilus (T) antigens of S. pyogenes and Streptococcus agalactiae (Mora 2005; Niccitelli 2011). Informed by the structural vaccinology approach for pilus antigens (Nuccitelli 2011; Schneewind 2011), the inventors engineered two polypeptides that encompasses the D1-2 domains of the major Coa and vWbp types from the North American S. aureus isolates: CC1, CC5, CC8, CC30 and CC45 strains (Tenover 2012). The purified products, $Coa_4$ and $vWbp_2$, were used as antigens and elicited antibody responses against the D12 domains of every Coa and vWbp type examined. Immunization of mice with $Coa_4/vWbp_2$ provided protection against lethal bacteremia challenge with representative S. aureus CC1, CC5. CC8, CC30 and CC45 strains. Thus, the design criteria of the $Coa_4/vWbp_2$ vaccine, to generate universal immune responses against Coa and vWbp against clinically relevant S. aureus, have been met. In addition to type-specific neutralization of Coa and vWbp via antibodies directed against the D12 domain, antibodies against the R (Coa) and CT domains (vWbp) also provided protection against S. aureus disease.

I. Staphylococcal Antigens

A. Staphylococcal Coagulases

Coagulases are enzymes produced by Staphylococcus bacteria that convert fibrinogen to fibrin. Coa and $vW_h$ activate prothrombin without proteolysis (Friedrich et al., 2003). The coagulase-prothrombin complex recognizes fibrinogen as a specific substrate, converting it directly into fibrin. The crystal structure of the active complex revealed binding of the D1 and D2 domains to prothrombin and insertion of its Ile1-Val$^2$ N-terminus into the Ile$^{16}$ pocket, inducing a functional active site in the zymogen through conformational change (Friedrich et al., 2003). Exosite I of α-thrombin, the fibrinogen recognition site, and proexosite I on prothrombin are blocked by the D2 of Coa (Friedrich et al., 2003). Nevertheless, association of the tetrameric (Coa.prothrombin)$_2$ complex binds fibrinogen at a new site with high affinity (Panizzi et al., 2006). This model explains the coagulant properties and efficient fibrinogen conversion by coagulase (Panizzi et al., 2006). Fibrinogen is a large glycoprotein (Mr~340,000), formed by three pairs of Aα-, Bβ-, and γ-chains covalently linked to form a "dimer of trimers," where A and B designate the fibrinopeptides released by thrombin cleavage (Panizzi et al., 2006). The elongated molecule folds into three separate domains, a central fragment E that contains the N-termini of all six chains and two flanking fragments D formed mainly by the C-termini of the Bβ- and γ-chains. These globular domains are connected by long triple-helical structures. Coagulase-prothrombin complexes, which convert human fibrinogen to the self-polymerizing fibrin, are not targeted by circulating thrombin inhibitors (Panizzi et al., 2006). Thus, staphylococcal coagulases bypass the physiological blood coagulation pathway.

All *S. aureus* strains secrete coagulase and vWbp (Bjerketorp et al., 2004; Field and Smith, 1945). Although early work reported important contributions of coagulase to the pathogenesis of staphylococcal infections (Ekstedt and Yotis, 1960; Smith et al., 1947), more recent investigations with molecular genetics tools challenged this view by observing no virulence phenotypes with endocarditis, skin abscess and mastitis models in mice (Moreillon et al., 1995; Phonimdaeng et al., 1990). Generating isogenic variants of *S. aureus* Newman, a fully virulent clinical isolate (Duthie et al., 1952), it is described herein that coa mutants indeed display virulence defects in a lethal bacteremia and renal abscess model in mice. In the inventors experience, *S. aureus* 8325-4 is not fully virulent and it is presumed that mutational lesions in this strain may not be able to reveal virulence defects in vivo. Moreover, antibodies raised against Coa or vWbp perturb the pathogenesis of *S. aureus* Newman infections to a degree mirroring the impact of gene deletions. Coa and vWbp contribute to staphylococcal abscess formation and lethal bacteremia and may also function as protective antigens in subunit vaccines.

Biochemical studies document the biological value of antibodies against Coa and vWbp. By binding to antigen and blocking its association with clotting factors, the antibodies prevent the formation of Coa-prothrombin and vWbp-prothrombin complexes. Passive transfer studies revealed protection of experimental animals against staphylococcal abscess formation and lethal challenge by Coa and vWbp antibodies. Thus, Coa and vWbp neutralizing antibodies generate immune protection against staphylococcal disease.

Earlier studies revealed a requirement of coagulase for resisting phagocytosis in blood (Smith et al., 1947) and the inventors observed a similar phenotype for Δcoa mutants in lepirudin-treated mouse blood (see Example 3 below). As vWbp displays higher affinity for human prothrombin than the mouse counterpart, it is suspected the same may be true for ΔvWbp variants in human blood. Further, expression of Coa and vWbp in abscess lesions as well as their striking distribution in the eosinophilic pseudocapsule surrounding (staphylococcal abscess communities (SACs) or the peripheral fibrin wall, suggest that secreted coagulases contribute to the establishment of these lesions. This hypothesis was tested and, indeed, Δcoa mutants were defective in the establishment of abscesses. A corresponding test, blocking Coa function with specific antibodies, produced the same effect. Consequently, it is proposed that the clotting of fibrin is a critical event in the establishment of staphylococcal abscesses that can be targeted for the development of protective vaccines. Due to their overlapping function on human prothrombin, both Coa and vWbp are considered excellent candidates for vaccine development.

A. Staphylcoccal Protein A (SpA)

All *Staphylococcus aureus* strains express the structural gene for Protein A (spa) (Jensen, 1958; Said-Salim et al., 2003), a well characterized virulence factor whose cell wall anchored surface protein product (SpA) encompasses five highly homologous immunoglobulin binding domains designated E, D. A, B, and C (Sjodahl, 1977). These domains display 80% identity at the amino acid level, are 56 to 61 residues in length, and are organized as tandem repeats (Uhlen et al., 1984). SpA is synthesized as a precursor protein with an N-terminal YSIRKGS signal peptide and a C-terminal LPXTG motif sorting signal (DeDent et al., 2008; Schneewind et al., 1992). Cell wall anchored Protein A is displayed in great abundance on the staphylococcal surface (DeDent et al., 2007; Sjoquist et al., 1972). Each of its immunoglobulin binding domains is composed of anti-parallel α-helices that assemble into a three helix bundle and bind the Fec domain of immunoglobulin G (IgG) (Deisenhofer, 1981; Deisenhofer et al., 1978), the VH3 heavy chain (Fab) of IgM (i.e., the B cell receptor) (Graille et al., 2000), the von Willebrand factor at its A1 domain [vWF A1 is a ligand for platelets](O'Seaghdha et al., 2006) and the tumor necrosis factor α (TNF-α) receptor I (TNFRI) (Gomez et al., 2006), which is displayed on surfaces of airway epithelia (Gomez et al., 2004; Gomez et al., 2007).

SpA impedes neutrophil phagocytosis of staphylococci through its attribute of binding the Fc component of IgG (Jensen, 1958; Uhlen et al., 1984). Moreover, SpA is able to activate intravascular clotting via its binding to von Willebrand factor AI domains (Hartleib et al., 2000). Plasma proteins such as fibrinogen and fibronectin act as bridges between staphylococci (ClfA and ClfB) and the platelet integrin GPIIb/IIIa (O'Brien et al., 2002), an activity that is supplemented through Protein A association with vWF AI, which allows staphylococci to capture platelets via the GPIb-α platelet receptor (Foster, 2005; O'Seaghdha et al., 2006). SpA also binds TNFRI and this interaction contributes to the pathogenesis of staphylococcal pneumonia (Gomez et al., 2004). SpA activates proinflammatory signaling through TNFR1 mediated activation of TRAF2, the p38/c-Jun kinase, mitogen activate protein kinase (MAPK) and the Rel-transcription factor NF-KB. SpA binding further induces TNFR1 shedding, an activity that appears to require the TNF-converting enzyme (TACEXGomez et al., 2007). All of the aforementioned SpA activities are mediated through its five IgG binding domains and can be perturbed by the same amino acid substitutions, initially defined by their requirement for the interaction between Protein A and human IgG 1 (Cedergren et al., 1993.

SpA also functions as a B cell superantigen by capturing the Fab region of VH3 bearing IgM, the B cell receptor (Gomez et al., 2007; Goodyear et al., 2003; Goodyear and Silverman, 2004; Roben et al., 1995). Following intravenous challenge, staphylococcal Protein A (SpA) mutations show a reduction in staphylococcal load in organ tissues and dramatically diminished ability to form abscesses (described herein). During infection with wildtype *S. aureus*, abscesses are formed within forty-eight hours and are detectable by light microscopy of hematoxylin-cosin stained, thin-sectioned kidney tissue, initially marked by an influx of polymorphonuclear leukocytes (PMNs). On day 5 of infection, abscesses increase in size and enclosed a central population of staphylococci, surrounded by a layer of eosinophilic, amorphous material and a large cuff of PMNs. Histopathology revealed massive necrosis of PMNs in proximity to the staphylococcal nidus at the center of abscess lesions as well as a mantle of healthy phagocytes. The inventors also observed a rim of necrotic PMNs at the periphery of abscess lesions, bordering the eosinophilic pseudocapsule that separated healthy renal tissue from the infectious lesion. Staphylococcal variants lacking Protein A are unable to establish the histopathology features of abscesses and are cleared during infection.

In previous studies, Cedergren et al. (1993) engineered five individual substitutions in the Fc fragment binding sub-domain of the B domain of SpA, L17D, N28A, I31A and K35A. These authors created these proteins to test data gathered from a three dimensional structure of a complex between one domain of SpA and Fct. Cedergren et al. determined the effects of these mutations on stability and binding, but did not contemplate use of such substitutions for the production of a vaccine antigen.

Brown et al. (1998) describe studies designed to engineer new proteins based on SpA that allow the use of more favorable elution conditions when used as affinity ligands. The mutations studied included single mutations of Q13A, Q14H, N15A, N15H, F17H, Y18F, L21H, N32H, or K39H. Brown et al. report that Q13A, N15A, N15H, and N32H substitutions made little difference to the dissociation constant values and that the Y18F substitution resulted in a 2 fold decrease in binding affinity as compared to wild type SpA. Brown et al. also report that L21H and F17H substitutions decrease the binding affinity by five-fold and a hundred-fold respectively. The authors also studied analogous substitutions in two tandem domains. Thus, the Brown et al. studies were directed to generating a SpA with a more favorable elution profile, hence the use of His substitutions to provide a pH sensitive alteration in the binding affinity. Brown et al. ia silent on the use of SpA as a vaccine antigen.

Graille et al. (2000) describe a crystal structure of domain D of SpA and the Fab fragment of a human IgM antibody. Graille et al. define by analysis of a crystal structure the D domain amino acid residues that interact with the Fab fragment as residues Q26, G29, F30, Q32, S33, D36, D37. Q40, N43, E47, or L51, as well as the amino acid residues that form the interface between the domain D sub-domains. Graille et al. define the molecular interactions of these two proteins, but is silent in regard to any use of substitutions in the interacting residues in producing a vaccine antigen.

O'Seaghdha et al. (2006) describe studies directed at elucidating which sub-domain of domain D binds vWF. The authors generated single mutations in either the Fc or VH3 binding sub-domains, i.e., amino acid residues F5A, Q9A, Q10A, F13A, Y14A, L17A, N28A, I31A, K35A, G29A, F30A, S33A, D36A, D37A, Q40A, E47A, or Q32A. The authors discovered that vWF binds the same sub-domain that binds Fc. O'Seaghda et al. define the sub-domain of domain D responsible for binding vWF, but is silent in regard to any use of substitutions in the interacting residues in producing a vaccine antigen.

Gomez et al. (2006) describe the identification of residues responsible for activation of the TNFR1 by using single mutations of F5A, F13A, Y14A, L17A, N21A, I31A, Q32A, and K35A. Gomez et al. is silent in regard to any use of substitutions in the interacting residues in producing a vaccine antigen.

Recombinant affinity tagged Protein A, a polypeptide encompassing the five IgG domains (EDCAB) (Sjodahl, 1977) but lacking the C-terminal Region X (Guss et al., 1984), was purified from recombinant E. coli and used as a vaccine antigen (Stranger-Jones et al., 2006). Because of the attributes of SpA in binding the Fc portion of IgG, a specific humoral immune response to Protein A could not be measured (Stranger-Jones et al., 2006). The inventors have overcome this obstacle through the generation of SpA-DQ9, 10K; D36,37A. BALB/c mice immunized with recombinant Protein A (SpA) displayed significant protection against intravenous challenge with S. aureus strains: a 2.951 log reduction in staphylococcal load as compared to the wild-type (P>0.005; Student's t-test) (Stranger-Jones et al., 2006). SpA specific antibodies may cause phagocytic clearance prior to abscess formation and/or impact the formation of the aforementioned eosinophilic barrier in abscesses that separate staphylococcal communities from immune cells since these do not form during infection with Protein A mutant strains. Each of the five SpA domains (i.e., domains formed from three helix bundles designated E, D, A, B, and C) exerts similar binding properties (Jansson et al., 1998). The solution and crystal structure of the domain D has been solved both with and without the Fc and VH3 (Fab) ligands, which bind Protein A in a non-competitive manner at distinct sites (Graille et al., 2000). Mutations in residues known to be involved in IgG binding (FS, Q9, Q10, S11, F13, Y14, L17, N28, 131 and K35) are also required for vWF AI and TNFR1 binding (Cedergren et al., 1993; Gomez et al., 2006; O'Seaghdha et al., 2006), whereas residues important for the VH3 interaction (Q26, G29, F30, S33, D36, D37, Q40, N43, E47) appear to have no impact on the other binding activities (Graille et al., 2000; Jansson et al., 1998). SpA specifically targets a subset of B cells that express VH3 family related IgM on their surface, i.e., VH3 type B cell receptors (Roben et al., 1995). Upon interaction with SpA, these B cells proliferate and commit to apoptosis, leading to preferential and prolonged deletion of innate-like B lymphocytes (i.e., marginal zone B cells and follicular B2 cells)(Goodyear et al., 2003; Goodyear et al., 2004).

Molecular Basis of Protein a Surface Display and Function.

Protein A is synthesized as a precursor in the bacterial cytoplasm and secreted via its YSIRK signal peptide at the cross wall, i.e. the cell division septum of staphylococci (DeDent et al., 2007; DeDent et al., 2008). Following cleavage of the C-terminal LPXTG sorting signal, Protein A is anchored to bacterial peptidoglycan crossbridges by sortase A (Mazmanian et al., 1999; Schneewind et al., 1995; Mazmanian et al., 2000). Protein A is the most abundant surface protein of staphylococci; the molecule is expressed by virtually all *S. aureus* strains (Cespedes et al., 2005; Kennedy et al., 2008; Said-Salim et al., 2003). Staphylococci turn over 15-20% of their cell wall per division cycle (Navarre and Schneewind, 1999). Murine hydrolases cleave the glycan strands and wall peptides of peptidoglycan, thereby releasing Protein A with its attached C-terminal cell wall disaccharide tetrapeptide into the extracellular medium (Ton-That et al., 1999). Thus, by physiological design, Protein A is both anchored to the cell wall and displayed on the bacterial surface but also released into surrounding tissues during host infection (Marraffini et al., 2006).

Protein A captures immunoglobulins on the bacterial surface and this biochemical activity enables staphylococcal escape from host innate and acquired immune responses (Jensen, 1958; Goodyear et al., 2004). Interestingly, region X of Protein A (Guss et al., 1984), a repeat domain that tethers the IgG binding domains to the LPXTG sorting signal/cell wall anchor, is perhaps the most variable portion of the staphylococcal genome (Said-Salim, 2003; Schneewind et al., 1992). Each of the five immunoglobulin binding domains of Protein A (SpA), formed from three helix bundles and designated E, D, A, B, and C, exerts similar structural and functional properties (Sjodahl, 1977; Jansson et al., 1998). The solution and crystal structure of the domain D has been solved both with and without the Fc and $V_H3$ (Fab) ligands, which bind Protein A in a non-competitive manner at distinct sites (Graille 2000).

In the crystal structure complex, the Fab interacts with helix II and helix III of domain D via a surface composed of four VH region β-strands (Graille 2000). The major axis of helix II of domain D is approximately 50° to the orientation of the strands, and the interhelical portion of domain D is most proximal to the C0 strand. The site of interaction on Fab is remote from the Ig light chain and the heavy chain constant region. The interaction involves the following domain D residues: Asp-36 of helix II, Asp-37 and Gln-40 in the loop between helix II and helix III and several other residues (Graille 2000). Both interacting surfaces are composed predominantly of polar side chains, with three negatively charged residues on domain D and two positively charged residues on the 2A2 Fab buried by the interaction, providing an overall electrostatic attraction between the two molecules. Of the five polar interactions identified between Fab and domain D, three are between side chains. A salt bridge is formed between Arg-H19 and Asp-36 and two hydrogen bonds are made between Tyr-H59 and Asp-37 and between Asn-H82a and Ser-33. Because of the conservation of Asp-36 and Asp-37 in all five IgG binding domains of Protein A, the inventors mutated these residues.

The SpA-D sites responsible for Fab binding are structurally separate from the domain surface that mediates Fcγ binding. The interaction of Fcγ with domain D primarily involves residues in helix I with lesser involvement of helix II (Gouda et al., 1992; Deisenhofer, 1981). With the exception of the Gln-32, a minor contact in both complexes, none of the residues that mediate the Fey interaction are involved in Fab binding. To examine the spatial relationship between these different Ig-binding sites, the SpA domains in these complexes have been superimposed to construct a model of a complex between Fab, the SpA-domain D, and the Fcγ molecule. In this ternary model, Fab and Fcγ form a sandwich about opposite faces of the helix II without evidence of steric hindrance of either interaction. These findings illustrate how, despite its small size (i.e., 56-61 aa), an SpA domain can simultaneously display both activities, explaining experimental evidence that the interactions of Fab with an individual domain are noncompetitive. Residues for the interaction between SpA-D and Fcγ are Gln-9 and Gln-10.

In contrast, occupancy of the Fc portion of IgG on the domain D blocks its interaction with vWF A1 and probably also TNFRI (O'Seaghdha et al., 2006). Mutations in residues essential for IgG Fc binding (F5, Q9, Q10, S11, F13, Y14, L17, N28, 131 and K35) are also required for vWF A1 and TNFR1 binding (O'Seaghdha et al., 2006; Cedergren et al., 1993; Gomez et al., 2006), whereas residues critical for the VH3 interaction (Q26, G29, F30, S33, D36, D37, Q40, N43, E47) have no impact on the binding activities of IgG Fc, vWF A1 or TNFRI (Jansson et al., 1998; Graille et al., 2000). The Protein A immunoglobulin Fab binding activity targets a subset of B cells that express $V_H3$ family related IgM on their surface, i.e., these molecules function as VH3type B cell receptors (Roben et al., 1995). Upon interaction with SpA, these B cells rapidly proliferate and then commit to apoptosis, leading to preferential and prolonged deletion of innate-like B lymphocytes (i.e., marginal zone B cells and follicular B2 cells) (Goodyear and Silverman, 2004; Goodyear and Silverman, 2003). More than 40% of circulating B cells are targeted by the Protein A interaction and the $V_H3$ family represents the largest family of human B cell receptors to impart protective humoral responses against pathogens (Goodyear and Silverman, 2004; Goodyear and Silverman, 2003). Thus, Protein A functions analogously to staphylococcal superantigens (Roben et al., 1995), albeit that the latter class of molecules, for example SEB, TSST-1, TSST-2, form complexes with the T cell receptor to inappropriately stimulate host immune responses and thereby precipitating characteristic disease features of staphylococcal infections (Roben et al., 1995; Tiedemann et al., 1995). Together these findings document the contributions of Protein A in establishing staphylococcal infections and in modulating host immune responses.

C. Other Staphylococcal Antigens

Research over the past several decades identified *S. aureus* exotoxins, surface proteins and regulatory molecules as important virulence factors (Foster, 2005; Mazmanian et al., 2001; Novick, 2003). Much progress has been achieved regarding the regulation of these genes. For example, staphylococci perform a bacterial census via the secretion of auto-inducing peptides that bind to a cognate receptor at threshold concentration, thereby activating phospho-relay reactions and transcriptional activation of many of the exotoxin genes (Novick, 2003). The pathogenesis of staphylococcal infections relies on these virulence factors (secreted exotoxins, exopolysaccharides, and surface adhesins). The development of staphylococcal vaccines is hindered by the multifaceted nature of staphylococcal invasion mechanisms. It is well established that live attenuated micro-organisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. Embodiments of the invention are directed to compositions and methods including variant coagulase polypeptides and peptides, in particular, one or more coagulase Domains 1-2, as well as other immunogenic extracellular proteins, polypeptides, and peptides (including both secreted and cell surface proteins or peptides) of gram positive bacteria for the use in mitigating or immunizing against infection. In particular embodiments the bacteria is a staphylococcus bacteria. Extracellular proteins, polypeptides, or peptides include, but are not limited to secreted and cell surface proteins of the targeted bacteria.

The human pathogen *S. aureus* secretes EsxA and EsxB, two ESAT-6 like proteins, across the bacterial envelope (Burts et al., 2005, which is incorporated herein by reference). Staphylococcal esxA and esxB are clustered with six other genes in the order of transcription: esxA esaA essA esaB essB essC esaC esxB. The acronyms esa, ess, and esx stand for ESAT-6 secretion accessory, system, and extracellular, respectively, depending whether the encoded proteins play an accessory (esa) or direct (ess) role for secretion, or are secreted (esx) in the extracellular milieu. The entire cluster of eight genes is herein referred to as the Ess cluster. EsxA, esxB, essA, essB, and essC are all required for synthesis or secretion of EsxA and EsxB. Mutants that fail to produce EsxA, EsxB, and EssC display defects in the pathogenesis of *S. aureus* murine abscesses, suggesting that this specialized secretion system may be a general strategy of human bacterial pathogenesis. Secretion of non-WXG 100 substrates by the ESX-1 pathway has been reported for several antigens including EspA, EspB, Rv3483c, and Rv3615c (Fortune et al., 2005; MacGurn et al., 2005; McLaughlin et al., 2007; Xu et al., 2007). The alternate ESX-5 pathway has also been shown to secrete both WXG 100 and non-WXG 100 proteins in pathogenic mycobacteria (Abdallah et al., 2007; Abdallah et al., 2006).

The *Staphylococcus aureus* Ess pathway can be viewed as a secretion module equipped with specialized transport components (Ess), accessory factors (Esa) and cognate secretion substrates (Esx). EssA, EssB and EssC are required for EsxA and EsxB secretion. Because EssA, EssB and EssC are predicted to be transmembrane proteins, it is contemplated that these proteins form a secretion apparatus. Some of the proteins in the ess gene cluster may actively transport secreted substrates (acting as motor) while others may regulate transport (regulator). Regulation may be achieved, but need not be limited to, transcriptional or post-translational mechanisms for secreted polypeptides, sorting of specific substrates to defined locations (e.g., extracellular medium or host cells), or timing of secretion events during infection. At this point, it is unclear whether all secreted Esx proteins function as toxins or contribute indirectly to pathogenesis.

Staphylococci rely on surface protein mediated-adhesion to host cells or invasion of tissues as a strategy for escape from immune defenses. Furthermore, *S. aureus* utilize surface proteins to sequester iron from the host during infection. The majority of surface proteins involved in staphylococcal pathogenesis carry C-terminal sorting signals, i.e., they are covalently linked to the cell wall envelope by sortase. Further, staphylococcal strains lacking the genes required for surface protein anchoring, i.e., sortase A and B, display a dramatic defect in the virulence in several different mouse models of disease. Thus, surface protein antigens represent a validated vaccine target as the corresponding genes are essential for the development of staphylococcal disease and can be exploited in various embodiments of the invention. The sortase enzyme superfamily are Gram-positive transpeptidases responsible for anchoring surface protein virulence factors to the peptidoglycan cell wall layer. Two sortase isoforms have been identified in *Staphylococcus aureus*, SrtA and SrtB. These enzymes have been shown to recognize a LPXTG motif in substrate proteins. The SrtB isoform appears to be important in heme iron acquisition and iron homeostasis, whereas the SrtA isoform plays a critical role in the pathogenesis of Gram-positive bacteria by modulating the ability of the bacterium to adhere to host tissue via the covalent anchoring of adhesins and other proteins to the cell wall peptidoglycan. In certain embodiments the coagulase variants, in particular, one or more coagulase Domains 1-2 described herein can be used in combination with other staphylococcal proteins such as Coa, Eap, Ebh, Emp, EsaC, EsaB, EsxA, EsxB, Hla, SdrC, SdrD, SdrE, IsdA, IsdB, ClfA, ClfB, IsdC, SasF, vWbp, and/or vWh proteins.

Certain aspects of the invention include methods and compositions concerning proteinaceous compositions including polypeptides, peptides, or nucleic acid encoding coagulase variants, in particular, one or more coagulase Domains 1-2 described herein and other staphylococcal antigens such as other proteins transported by the Ess pathway, or sortase substrates. These proteins may be modified by deletion, insertion, and/or substitution.

The Esx polypeptides include the amino acid sequence of Esx proteins from bacteria in the Staphylococcus genus. The Esx sequence may be from a particular staphylococcus species, such as *Staphylococcus aureus*, and may be from a particular strain, such as Newman. In certain embodiments, the EsxA sequence is SAV0282 from strain Mu50 (which is the same amino acid sequence for Newman) and can be accessed using Genbank Accession Number Q99WU4 (gi|68565539), which is hereby incorporated by reference. In other embodiments, the EsxB sequence is SAV0290 from strain Mu50 (which is the same amino acid sequence for Newman) and can be accessed using Genbank Accession Number Q99WT7 (gi|68565532), which is hereby incorporated by reference. In further embodiments, other polypeptides transported by the Ess pathway may be used, the sequences of which may be identified by one of skill in the art using databases and internet accessible resources.

The sortase substrate polypeptides include, but are not limited to the amino acid sequence of SdrC, SdrD, SdrE, IsdA, IsdB, ClfA, ClfB, IsdC or SasF proteins from bacteria in the Staphylococcus genus. The sortase substrate polypeptide sequence may be from a particular staphylococcus species, such as *Staphylococcus aureus*, and may be from a particular strain, such as Newman. In certain embodiments, the SdrD sequence is from strain N315 and can be accessed using Genbank Accession Number NP_373773.1 (gi|15926240), which is incorporated by reference. In other embodiments, the SdrE sequence is from strain N315 and can be accessed using Genbank Accession Number NP_373774.1 (gi|15926241), which is incorporated by reference. In other embodiments, the IsdA sequence is SAV1130 from strain Mu50 (which is the same amino acid sequence for Newman) and can be accessed using Genbank Accession Number NP_371654.1 (gi|15924120), which is incorporated by reference. In other embodiments, the IsdB sequence is SAV1129 from strain Mu50 (which is the same amino acid sequence for Newman) and can be accessed using Genbank Accession Number NP_371653.1 (gi|15924119), which is incorporated by reference. In further embodiments, other polypeptides transported by the Ess pathway or processed by sortase may be used, the sequences of which may be identified by one of skill in the art using databases and internet accessible resources.

Examples of various proteins that can be used in the context of the present invention can be identified by analysis of database submissions of bacterial genomes, including but not limited to accession numbers NC_002951 (GI:57650036 and GenBank CP000046), NC_002758 (GI:57634611 and GenBank BA000017), NC_002745 (GI:29165615 and GenBank BA000018), NC_003923 (GI:21281729 and GenBank BA000033), NC_002952 (GI:49482253 and GenBank BX571856), NC_002953 (GI:49484912 and GenBank BX571857), NC_007793 (GI:87125858 and GenBank CP000255), NC_007795 (GI:87201381 and GenBank CP000253) each of which are incorporated by reference.

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of coagulases, in particular, of coagulase Domains 1-2, SpA and other polypeptides of the invention can be substitutional, insertional, or deletion variants. A variation in a polypeptide of the invention may affect 1, 2, 3, 4, 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., a sequence of SEQUENCE TABLE NO. 1 (SEQ ID NOs: 33-37) or SEQUENCE TABLE NO. 2 (SEQ ID NOs: 38-41). A variant can include 2, 3, 4, 5, 6, 7, 8, 9, 10, 11, 12, 13, 14, 15, 16, 17, 18, 19, 20, or more substitute amino acids. A polypeptide processed or secreted by the Ess pathway or other surface proteins (see Table 1) or sortase substrates from any staphylococcus species and strain are contemplated for use in compositions and methods described herein.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

TABLE 2

Exemplary surface proteins of *S. aureus* strains.

| SAV # | SA# | Surface | MW2 | Mu50 | N315 | Newman | MRSA252* | MSSA476* |
|---|---|---|---|---|---|---|---|---|
| SAV0111 | SA0107 | Spa | 492 | 450 | 450 | 520 | 516 | 492 |
| SAV2503 | SA2291 | FnBPA | 1015 | 1038 | 1038 | 741 | — | 1015 |
| SAV2502 | SA2290 | FnBPB | 943 | 961 | 961 | 677 | 965 | 957 |
| SAV0811 | SA0742 | ClfA | 946 | 935 | 989 | 933 | 1029 | 928 |
| SAV2630 | SA2423 | ClfB | 907 | 877 | 877 | 913 | 873 | 905 |
| Np | Np | Cna | 1183 | — | — | — | 1183 | 1183 |
| SAV0561 | SA0519 | SdrC | 955 | 953 | 953 | 947 | 906 | 957 |
| SAV0562 | SA0520 | SdrD | 1347 | 1385 | 1385 | 1315 | — | 1365 |
| SAV0563 | SA0521 | SdrE | 1141 | 1141 | 1141 | 1166 | 1137 | 1141 |
| Np | Np | Pls | — | — | — | — | — | — |
| SAV2654 | SA2447 | SasA | 2275 | 2271 | 2271 | 2271 | 1351 | 2275 |
| SAV2160 | SA1964 | SasB | 686 | 2481 | 2481 | 2481 | 2222 | 685 |
|  | SA1577 | SasC | 2186 | 213 | 2186 | 2186 | 2189 | 2186 |
| SAV0134 | SA0129 | SasD | 241 | 241 | 241 | 241 | 221 | 241 |
| SAV1130 | SA0977 | SasE/IsdA | 350 | 350 | 350 | 350 | 354 | 350 |
| SAV2646 | SA2439 | SasF | 635 | 635 | 635 | 635 | 627 | 635 |
| SAV2496 |  | SasG | 1371 | 525 | 927 | — | — | 1371 |
| SAV0023 | SA0022 | SasH | 772 | — | 772 | 772 | 786 | 786 |
| SAV1731 | SA1552 | SasI | 895 | 891 | 891 | 891 | 534 | 895 |
| SAV1129 | SA0976 | SasJ/IsdB | 645 | 645 | 645 | 645 | 652 | 645 |

TABLE 2-continued

Exemplary surface proteins of S. aureus strains.

| SAV # | SA# | Surface | MW2 | Mu50 | N315 | Newman | MRSA252* | MSSA476* |
|---|---|---|---|---|---|---|---|---|
|  | SA2381 | SasK | 198 | 211 | 211 | — | — | 197 |
|  | Np | SasL | — | 232 | — | — | — | — |
| SAV1131 | SA0978 | IsdC | 227 | 227 | 227 | 227 | 227 | 227 |

Proteins of the invention may be recombinant, or synthesized in vitro. Alternatively, a non-recombinant or recombinant protein may be isolated from bacteria. It is also contemplated that a bacteria containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see Table 3, below).

TABLE 3

Codon Table

| Amino Acids |  |  | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC ACU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence, and in its underlying DNA coding sequence, and nevertheless produce a protein with a desirable property. It is thus contemplated by the inventors that various changes may be made in the DNA sequences of genes.

It is contemplated that in compositions of the invention, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be a coagulase Domains 1-2 or a coagulase or its variant and may be used in combination with other peptides or polypeptides, such as other bacterial peptides and/or antigens.

The present invention contemplates the administration of staphylococcal coagulase Domains 1-2 or variants thereof to effect a preventative therapy or therapeutic effect against the development of a disease or condition associated with infection by a staphylococcus pathogen.

In certain aspects, combinations of staphylococcal antigens are used in the production of an immunogenic composition that is effective at treating or preventing staphylococcal infection. Staphylococcal infections progress through several different stages. For example, the staphylococcal life cycle involves commensal colonization, initiation of infection by accessing adjoining tissues or the bloodstream, and/or anaerobic multiplication in the blood. The interplay between *S. aureus* virulence determinants and the host defense mechanisms can induce complications such as endocarditis, metastatic abscess formation, and sepsis syndrome. Different molecules on the surface of the bacterium are involved in different steps of the infection cycle. Combinations of certain antigens can elicit an immune response which protects against multiple stages of staphylococcal infection. The effectiveness of the immune response can be measured either in animal model assays and/or using an opsonophagocytic assay.

B. Polypeptides and Polypeptide Production

The present invention describes polypeptides, peptides, and proteins and immunogenic fragments thereof for use in various embodiments of the present invention. For example, specific polypeptides are assayed for or used to elicit an immune response. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Another embodiment of the present invention uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HepG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk−, hgprt− or aprt− cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a native or recombinant protein or optionally a protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, 20 amino acids, 30 amino acids, 40 amino acids, 50 amino acids, or 100 amino acids, including all values and ranges there between, taken contiguously from the amino acid sequence of the protein. In addition, such immunogenic fragments are immunologically reactive with antibodies generated against the Staphylococcal proteins or with antibodies generated by infection of a mammalian host with Staphylococci. Immunogenic fragments also include fragments that when administered at an effective dose, (either alone or as a hapten bound to a carrier), elicit a protective or therapeutic immune response against Staphylococcal infection, in certain aspects it is protective against S. aureus and/or S. epidermidis infection. Such an immunogenic fragment may include, for example, the protein lacking an N-terminal leader sequence, and/or a transmembrane domain and/or a C-terminal anchor domain. In a preferred aspect the immunogenic fragment according to the invention comprises substantially all of the extracellular domain of a protein which has at least 80% identity, at least 85% identity, at least 90% identity, at least 95% identity, or at least 97-99% identity, including all values and ranges there between, to a sequence selected segment of a polypeptide described or referenced herein.

Also included in immunogenic compositions of the invention are fusion proteins composed of one or more Staphylococcal proteins, or immunogenic fragments of staphylococcal proteins. Such fusion proteins may be made recombinantly and may comprise one portion of at least 1, 2, 3, 4, 5, or 6 staphylococcal proteins or segments. Alternatively, a fusion protein may comprise multiple portions of at least 1, 2, 3, 4 or 5 staphylococcal proteins. These may combine different Staphylococcal proteins and/or multiples of the same protein or protean fragment, or immunogenic fragments in the same protein (forming a multimer or a concatamer). Alternatively, the invention also includes individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

II. Nucleic Acids

In certain embodiments, the present invention concerns recombinant polynucleotides encoding the proteins, polypeptides, peptides of the invention. The nucleic acid sequences for coagulases, coagulases Domains 1-2, SpA, and other bacterial proteins are included, all of which are incorporated by reference, and can be used to prepare peptides or polypeptides.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene." "polynucleotide." or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein (see Table 3 above).

In particular embodiments, the invention concerns isolated nucleic acid segments and recombinant vectors incorporating nucleic acid sequences that encode one or more coagulase Domains 1-2, or variants thereof. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a coagulase polypeptide or peptide or a variant thereof to generate an immune response in a subject. In various embodiments the nucleic acids of the invention may be used in genetic vaccines.

The nucleic acid segments used in the present invention can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain other embodiments, the invention concerns isolated nucleic acid segments and recombinant vectors that include within their sequence a contiguous nucleic acid sequence encoding one of the sequence of SEQUENCE TABLE NO. 1 (SEQ ID NOs: 33-37) or SEQUENCE TABLE NO. 2 (SEQ ID NOs: 38-41) or any other nucleic acid sequences encoding coagulases or other secreted virulence factors and/or surface proteins including proteins transported by the Ess pathway, processed by sortase, or proteins incorporated herein by reference.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using the methods described herein (e.g., BLAST analysis using standard parameters).

The invention also contemplates the use of polynucleotides which are complementary to all the above described polynucleotides.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding one or more coagulase Domains 1-2 or variant thereof, the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989). Prealbumin (Transthyretin) (Costa et al., 1988), Elastase I (Omitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II—Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); 3-Interferon—poly(rI)x/poly(rc) (Tavernier et al., 1983); Adenovirus 5 E2-E1A (Imperiale et al., 1984); Collagenase—Phorbol Ester (TPA) (Angel et al., 1987a); Stromelysin—Phorbol Ester (TPA) (Angel et al., 1987b); SV40—Phorbol Ester (TPA) (Angel et al., 1987b); Murine MX Gene—Interferon, Newcastle Disease Virus (Hug et al., 1988); GRP78 Gene—A23187 (Resendez et al., 1988); α-2-Macroglobulin—IL-6 (Kunz et al., 1989); Vimentin—Serum (Rittling et al., 1989); MHC Class I Gene H-2κb—Interferon (Blanar et al., 1989); HSP70-E1A/SV40 Large T Antigen (Taylor et al., 1989, 1990a, 1990b); Proliferin—Phorbol Ester/TPA (Mordacq et al., 1989); Tumor Necrosis Factor—PMA (Hensel et al., 1989); and Thyroid Stimulating Hormone α Gene—Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of at least two different staphylococcal conagulase Domains 1-2 for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5'☐ methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed." which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULO-VIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. Polysaccharides

The immunogenic compositions of the invention may further comprise capsular polysaccharides including one or more of PIA (also known as PNAG) and/or *S. aureus* Type V and/or type VIII capsular polysaccharide and/or *S. epidermidis* Type I, and/or Type II and/or Type III capsular polysaccharide.

A. PIA (PNAG)

It is now clear that the various forms of staphylococcal surface polysaccharides identified as PS/A, PIA and SAA are the same chemical entity—PNAG (Maira-Litran et al., 2004). Therefore the term PIA or PNAG encompasses all these polysaccharides or oligosaccharides derived from them.

PIA is a polysaccharide intercellular adhesin and is composed of a polymer of β-(1→6)-linked glucosamine substituted with N-acetyl and O-succinyl constituents. This polysaccharide is present in both *S. aureus* and *S. epidermidis* and can be isolated from either source (Joyce et al., 2003; Maira-Litran et al., 2002). For example, PNAG may be isolated from *S. aureus* strain MN8m (WO04/43407). PIA isolated from *S. epidermidis* is a integral constituent of biofilm. It is responsible for mediating cell-cell adhesion and probably also functions to shield the growing colony from the host's immune response. The polysaccharide previously known as poly-N-succinyl-β-(1→6)-glucosamine (PNSG) was recently shown not to have the expected structure since the identification of N— succinylation was incorrect (Maira-Litran et al., 2002). Therefore the polysaccharide formally known as PNSG and now found to be PNAG is also encompassed by the term PIA.

PIA (or PNAG) may be of different sizes varying from over 400 kDa to between 75 and 400 kDa to between 10 and 75 kDa to oligosaccharides composed of up to 30 repeat units (of β-(1→6)-linked glucosamine substituted with N-acetyl and O-succinyl constituents). Any size of PIA polysaccharide or oligosaccharide may be use in an immunogenic composition of the invention, in one aspect the polysaccharide is over 40 kDa. Sizing may be achieved by any method known in the art, for instance by microfluidization, ultrasonic irradiation or by chemical cleavage (WO 03/53462, EP497524, EP497525). In certain aspects PIA (PNAG) is at least or at most 40-400 kDa, 40-300 kDa, 50-350 kDa, 60-300 kDa, 50-250 kDa and 60-200 kDa.

PIA (PNAG) can have different degree of acetylation due to substitution on the amino groups by acetate. PIA produced in vitro is almost fully substituted on amino groups (95-100%). Alternatively, a deacetylated PIA (PNAG) can be used having less than 60%, 50%, 40%, 30%, 20%, 10% acetylation. Use of a deacetylated PIA (PNAG) is preferred since non-acetylated epitopes of PNAG are efficient at mediating opsonic killing of Gram positive bacteria, preferably *S. aureus* and/or *S. epidermidis*. In certain aspects, the PIA (PNAG) has a size between 40 kDa and 300 kDa and is deacetylated so that less than 60%, 50%, 40%, 30% or 20% of amino groups are acetylated.

The term deacetylated PNAG (dPNAG) refers to a PNAG polysaccharide or oligosaccharide in which less than 60%, 50%, 40%, 30%, 20% or 10% of the amino a groups are acetylated. In certain aspects, PNAG is deaceylated to form dPNAG by chemically treating the native polysaccharide. For example, the native PNAG is treated with a basic solution such that the pH rises to above 10. For instance the PNAG is treated with 0.1-5 M, 0.2-4 M, 0.3-3 M, 0.5-2 M, 0.75-1.5 M or 1 M NaOH, KOH or $NH_4OH$. Treatment is for at least 10 to 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

The polysaccharide(s) can be conjugated or unconjugated to a carrier protein.

B. Type 5 and Type 8 Polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al., (1990) and Fournier et al., (1984). Both have FucNAcp in their repeat unit as well as ManNAcA which can be used to introduce a sulfhydryl group. The structures are:

→4)-β-D-ManNAcA(3OAc)-(1→4)-α-L-FucNAc
(1→3)-β-D-FucNAc-(1→  Type 5

→3)-β-D-ManNAcA(4OAc)-(1→3)-α-L-FucNAc
(1→3)-β-D-FucNAc-(1→  Type 8

Recently (Jones, 2005) NMR spectroscopy revised the structures to:

→4)-β-D-ManNAcA-(1→4)-α-L-FucNAc(3OAc)-
(1→3)-β-D-FucNAc-(1→  Type 5

→3)-β-D-ManNAcA(4OAc)-(1→3)-α-L-FucNAc
(1→3)-α-D-FucNAc(1→  Type 8

Polysaccharides may be extracted from the appropriate strain of *S. aureus* using method well known to of skill in the art, See U.S. Pat. No. 6,294,177. For example, ATCC 12902 is a Type 5 *S. aureus* strain and ATCC 12605 is a Type 8 *S. aureus* strain.

Polysaccharides are of native size or alternatively may be sized, for instance by microfluidisation, ultrasonic irradiation, or by chemical treatment. The invention also covers oligosaccharides derived from the type 5 and 8 polysaccharides from *S. aureus*. The type 5 and 8 polysaccharides included in the immunogenic composition of the invention are preferably conjugated to a carrier protein as described below or are alternatively unconjugated. The immunogenic compositions of the invention alternatively contains either type 5 or type 8 polysaccharide.

C. *S. aureus* 336 Antigen

In an embodiment, the immunogenic composition of the invention comprises the *S. aureus* 336 antigen described in U.S. Pat. No. 6,294,177. The 336 antigen comprises β-linked hexosamine, contains no O-acetyl groups, and specifically binds to antibodies to *S. aureus* Type 336 deposited under ATCC 55804. In an embodiment, the 336 antigen is a polysaccharide which is of native size or alternatively may be sized, for instance by microfluidisation, ultrasonic irradiation, or by chemical treatment. The invention also covers oligosaccharides derived from the 336 antigen. The 336 antigen can be unconjugated or conjugated to a carrier protein.

D. Type I, II and III Polysaccharides from *S. epidermidis*

Amongst the problems associated with the use of polysaccharides in vaccination, is the fact that polysaccharides per se are poor immunogens. It is preferred that the polysaccharides utilized in the invention are linked to a protein carrier which provide bystander T-cell help to improve immunogenicity. Examples of such carriers which may be conjugated to polysaccharide immunogens include the Diphtheria and Tetanus toxoids (DT, DT CRM197 and TT respectively), Keyhole Limpet Haemocyanin (KLH), and the purified protein derivative of Tuberculin (PPD), *Pseudonmonas aeruginosa* exoprotein A (rEPA), protein D from *Haemophilus influenzae*, pneumolysin or fragments of any of the above. Fragments suitable for use include fragments encompassing T-helper epitopes. In particular the protein D fragment from *H. influenza* will preferably contain the N-terminal ⅓ of the protein. Protein D is an IgD-binding protein from *Haemophilus influenzae* (EP 0 594 610 B1) and is a potential immunogen. In addition, staphylococcal proteins may be used as a carrier protein in the polysaccharide conjugates of the invention.

A carrier protein that would be particularly advantageous to use in the context of a staphylococcal vaccine is staphylococcal alpha toxoid. The native form may be conjugated to a polysaccharide since the process of conjugation reduces toxicity. Preferably genetically detoxified alpha toxins such as the His35Leu or His35Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

The polysaccharides may be linked to the carrier protein(s) by any known method (for example those methods described in U.S. Pat. Nos. 4,372,945, 4,474,757, and 4,356,170). Preferably, CDAP conjugation chemistry is carried out (see WO95/08348). In CDAP, the cyanylating reagent 1-cyano-dimethylaminopyridinium tetrafluoroborate (CDAP) is preferably used for the synthesis of polysaccharide-protein conjugates. The cyanilation reaction can be performed under relatively mild conditions, which avoids hydrolysis of the alkaline sensitive polysaccharides. This synthesis allows direct coupling to a carrier protein.

Conjugation preferably involves producing a direct linkage between the carrier protein and polysaccharide. Optionally a spacer (such as adipic dihydride (ADH)) may be introduced between the carrier protein and the polysaccharide.

IV. Immune Response and Assays

As discussed above, the invention concerns evoking or inducing an immune response in a subject against a coagulase or one or more coagulase Domains 1-2 or variants thereof. In one embodiment, the immune response can protect against or treat a subject having, suspected of having, or at risk of developing an infection or related disease, particularly those related to staphylococci. One use of the immunogenic compositions of the invention is to prevent nosocomial infections by inoculating a subject prior to undergoing procedures in a hospital or other environment having an increased risk of infection.

A. Immunoassays

The present invention includes the implementation of serological assays to evaluate whether and to what extent an immune response is induced or evoked by compositions of the invention. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of Bacterial Infection

In addition to the use of proteins, polypeptides, and/or peptides, as well as antibodies binding these polypeptides, proteins, and/or peptides, to treat or prevent infection as described above, the present invention contemplates the use of these polypeptides, proteins, peptides, and/or antibodies in a variety of ways, including the detection of the presence of Staphylococci to diagnose an infection, whether in a patient or on medical equipment which may also become infected. In accordance with the invention, a preferred method of detecting the presence of infections involves the steps of obtaining a sample suspected of being infected by one or more staphylococcal bacteria species or strains, such as a sample taken from an individual, for example, from one's blood, saliva, tissues, bone, muscle, cartilage, or skin. Following isolation of the sample, diagnostic assays utilizing the polypeptides, proteins, peptides, and/or antibodies of the present invention may be carried out to detect the presence of staphylococci, and such assay techniques for determining such presence in a sample are well known to those skilled in the art and include methods such as radioimmunoassay, western blot analysis and ELISA assays. In general, in accordance with the invention, a method of diagnosing an infection is contemplated wherein a sample suspected of being infected with staphylococci has added to it the polypeptide, protein, peptide, antibody, or monoclonal antibody in accordance with the present invention, and staphylococci are indicated by antibody binding to the polypeptides, proteins, and/or peptides, or polypeptides, proteins, and/or peptides binding to the antibodies in the sample.

Accordingly, antibodies in accordance with the invention may be used for the prevention of infection from staphylococcal bacteria (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. Specific examples of the generation of an antibody to a bacterial protein can be found in U.S. Patent Application Pub. No. 20030153022, which is incorporated herein by reference in its entirety.

Any of the above described polypeptides, proteins, peptides, and/or antibodies may be labeled directly with a detectable label for identification and quantification of staphylococcal bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the invention, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides have different functionalities according to the present invention. While according to one aspect, a polypeptide is derived from an immunogen designed to induce an active immune response in a recipient, according to another aspect of the invention, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to staphylococcus bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge with the antigenic composition ("hyperimmune globulin"), that contains antibodies directed against staphylococcus or other organism. A subject thus treated would donate plasma from which hyperimmune globulin would then be obtained, via conventional plasma-fractionation methodology, and administered to another subject in order to impart resistance against or to treat staphylococcus infection. Hyperimmune globulins according to the invention are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Memaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

D. Treatment Methods

A method of the present invention includes treatment for a disease or condition caused by a staphylococcus pathogen. An immunogenic polypeptide of the invention can be given to induce an immune response in a person infected with staphylococcus or suspected of having been exposed to staphylococcus. Methods may be employed with respect to individuals who have tested positive for exposure to staphylococcus or who are deemed to be at risk for infection based on possible exposure.

In particular, the invention encompasses a method of treatment for staphylococcal infection, particularly hospital acquired nosocomial infections. The immunogenic compositions and vaccines of the invention are particularly advantageous to use in cases of elective surgery. Such patients will know the date of surgery in advance and could be inoculated in advance. The immunogenic compositions and vaccines of the invention are also advantageous to use to inoculate health care workers.

In some embodiments, the treatment is administered in the presence of adjuvants or carriers or other staphylococcal antigens. Furthermore, in some examples, treatment comprises administration of other agents commonly used against bacterial infection, such as one or more antibiotics.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

V. Vaccine and Other Pharmaceutical Compositions and Administration

A. Vaccines

The present invention includes methods for preventing or ameliorating staphylococcal infections, particularly hospital acquired nosocomial infections. As such, the invention contemplates vaccines for use in both active and passive immunization embodiments. Immunogenic compositions, proposed to be suitable for use as a vaccine, may be prepared from immunogenic coagulases or a fragment thereof or a variant thereof, e.g., one or more coagulase Domains 1-2. In other embodiments, coagulases, a fragment thereof or a variant thereof, can be used in combination with other secreted virulence proteins, surface proteins or immunogenic fragments thereof. In certain aspects, antigenic material is extensively dialyzed to remove undesired small molecular weight molecules and/or lyophilized for more ready formulation into a desired vehicle.

Other options for a protein/peptide-based vaccine involve introducing nucleic acids encoding the antigen(s) as DNA vaccines. In this regard, recent reports described construction of recombinant vaccinia viruses expressing either 10 contiguous minimal CTL epitopes (Thomson, 1996) or a combination of B cell, cytotoxic T-lymphocyte (CTL), and T-helper (Th) epitopes from several microbes (An, 1997), and successful use of such constructs to immunize mice for priming protective immune responses. Thus, there is ample evidence in the literature for successful utilization of peptides, peptide-pulsed antigen presenting cells (APCs), and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against a coagulase and or its variant, such as one or more coagulase Domains 1-2, or any other bacterial protein or combination contemplated herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., *C. parvum*), endotoxins or lipopolysaccharide components of Gram-negative bacteria; emulsion in physiologically acceptable oil vehicles (e.g., mannide monooleate (Aracel A)); or emulsion with a 20% solution of a perfluorocarbon (Fluosol-DA®) used as a block substitute may also be employed to produce an adjuvant effect.

Examples of and often preferred adjuvants include complete Freund's adjuvant (a non-specific stimulator of the immune response containing killed *Mycobacterium tuberculosis*), incomplete Freund's adjuvants, and aluminum hydroxide.

In some aspects, it is preferred that the adjuvant be selected to be a preferential inducer of either a Th1 or a Th2 type of response. High levels of Th1-type cytokines tend to favor the induction of cell mediated immune responses to a given antigen, while high levels of Th2-type cytokines tend to favor the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ T cell clones by Mosmann and Coffman (Mosmann, and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidine (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

B. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine (Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

C. Combination Therapy

The compositions and related methods of the present invention, particularly administration of a secreted virulence factor or surface protein, including a coagulase Domains 1-2 or a variant thereof, and/or other bacterial peptides or proteins to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a polypeptide vaccine and/or therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the immunogenic molecule given as part of an immune therapy regime, such as an antigen, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the immunogenic compositions of the present invention to a patient/subject will follow general protocols for the administration of such compounds, taking into account the toxicity, if any, of the coagulase Domains 1-2 composition, or other compositions described herein. It is expected that the treatment cycles would be repeated as necessary. It also is contemplated that various standard therapies, such as hydration, may be applied in combination with the described therapy.

D. General Pharmaceutical Compositions

In some embodiments, pharmaceutical compositions are administered to a subject. Different aspects of the present invention involve administering an effective amount of a composition to a subject. In some embodiments of the present invention, staphylococcal antigens, members of the Ess pathway, including polypeptides or peptides of the Esa or Esx class, and/or members of sortase substrates may be administered to the patient to protect against infection by one or more staphylococcus pathogens. Alternatively, an expression vector encoding one or more such polypeptides or peptides may be given to a patient as a preventative treatment. Additionally, such compounds can be administered in combination with an antibiotic or an antibacterial. Such compositions will generally be dissolved or dispersed in a pharmaceutically acceptable carrier or aqueous medium.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active compounds of the present invention can be formulated for parenteral administration, e.g., formulated for injection via the intravenous, intramuscular, subcutaneous, or even intraperitoneal routes. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In Vitro, Ex Vivo, or In Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject.

In certain aspects of the present invention, the compositions may be administered either in vitro, ex vivo, or in vivo. In certain in vitro embodiments, autologous B-lymphocyte cell lines are incubated with a virus vector of the instant invention for 24 to 48 hours or with a cogaulase Domains 1-2 and/or a variant thereof and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

F. Antibodies And Passive Immunization

Another aspect of the invention is a method of preparing an immunoglobulin for use in prevention or treatment of staphylococcal infection comprising the steps of immunizing a recipient or donor with the vaccine of the invention and isolating immunoglobulin from the recipient or donor. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of staphylococcal disease. A method for treatment or prevention of staphylococcal infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well known techniques such as affinity chromatography (Harlow and Lane, 1988). Antibodies can include antiserum preparations from a variety of commonly used animals, e.g. goats, primates, donkeys, swine, horses, guinea pigs, rats or man.

An immunoglobulin produced in accordance with the present invention can include whole antibodies, antibody fragments or subfragments. Antibodies can be whole immunoglobulins of any class (e.g., IgG, IgM, IgA, IgD or IgE), chimeric antibodies or hybrid antibodies with dual specificity to two or more antigens of the invention. They may also be fragments (e.g., F(ab')2, Fab', Fab, Fv and the like) including hybrid fragments. An immunoglobulin also includes natural, synthetic, or genetically engineered proteins that act like an antibody by binding to specific antigens to form a complex.

A vaccine of the present invention can be administered to a recipient who then acts as a source of immunoglobulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals, or where treatment is required and there is no time for the individual to produce antibodies in response to vaccination.

An additional aspect of the invention is a pharmaceutical composition comprising two of more monoclonal antibodies (or fragments thereof: preferably human or humanised) reactive against at least two constituents of the immunogenic composition of the invention, which could be used to treat or prevent infection by Gram positive bacteria, preferably staphylococci, more preferably *S. aureus* or *S. epidermidis*. Such pharmaceutical compositions comprise monoclonal antibodies that can be whole immunoglobulins of any class, chimeric antibodies, or hybrid antibodies with specificity to two or more antigens of the invention. They may also be fragments (e.g., F(ab')2, Fab', Fab, Fv and the like) including hybrid fragments.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be humanized or part humanized by known methods.

VI. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Coagulases as Determinants of Protective Immune Responses Against *Staphylococcus Aureus*

A. Results

Antibodies Against Coagulase Domains

Rabbits were immunized with affinity purified His-tagged Coa derived from the coagulase gene of *S. aureus* Newman ($Coa_{NM}$). Immune serum was examined by ELISA, which revealed serum IgG antibody responses to antigen (FIGS. 1A-1B). To analyze the antibody responses against specific subdomains, affinity-purified recombinant proteins ($D1_{Coa}$, $D2_{Coa}$, $D12_{Coa}$ and $CT_{Coa}$) were subjected to ELISA (FIG. 1B). Immune serum harbored antibodies against each of the domains tested (FIG. 1B). Of note, antibodies against $L_{Coa}$ were more abundant than antibodies that recognized the repeat domain ($CT_{Coa}$) ($L_{Coa}$ vs. $CT_{Coa}$, P<0.05). Antibodies against $D12_{Coa}$ were more abundant than those that recognized the repeat domain, but this difference did not achieve statistical significance ($D12_{Coa}$, vs. $CT_{Coa}$, P=0.066). To probe the biological function of antibodies in the immune serum, the inventors used variable amounts of affinity purified Coans antibodies to perturb the association of $D12_{Coa}$ with human prothrombin or the association of $CT_{Coa}$ with fibrinogen (FIG. 1C). The inventors calculated that 120 nM α-Coa IgG blocked $D12_{Coa}$ binding to prothrombin, whereas 1.7 µM α-Coa IgG blocked the association of $CT_{Coa}$ with fibrinogen (FIG. 1C).

Rabbit $Coa_{NM}$ immune serum was subjected to affinity chromatography using either full length $Coa_{NM}$ (α-$Coa_{NM}$), $D12_{Coa}$ (α-$D12_{Coa}$) or $CT_{Coa}$ (α-$CT_{Coa}$). Equimolar amounts of affinity purified IgG were added to citrate-blood samples obtained from naïve BALB/c mice, which were subsequently inoculated with S. aureus CC8 strain Newman (Baba 2007). Compared to control samples without antibody, both α-$Coa_{NM}$ and α-$D12_{Coa}$ IgG caused a significant delay in clotting time, whereas α-$CT_{Coa}$ did not (FIG. 1D). Thus, rabbits respond to immunization with $Coa_{NM}$ by generating antigen-specific IgG molecules that are predominantly directed against $D12_{Coa}$ and $L_{Coa}$ and interfere with the clotting activity of secreted Coa. In contrast, antibodies against $CT_{Coa}$ are generated in lesser abundance and do not interfere with S. aureus Newman in vitro coagulation of blood.

Type-Specific and Cross-Protective Inhibition of S. aureus Coagulation

To examine the ability of α-$Coa_{NM}$ to block the coagulation of other strains isolated from human infections, antigen-specific IgG was added to citrate-blood samples from naive mice that were subsequently inoculated with S. aureus 85/2082 (CC8), MW2 (CC1), MSSA476 (CC1), N315 (CC5), Mu50 (CC5), MRSA252 (CC30), CowanI (CC30), WIS (CC45) and USA600 (CC45) (Table 4). $Coa_{NM}$-specific IgG delayed the clotting of S. aureus Newman (CC8), 85/2082 (CC8) and MW2 (CC1), but not of MSSA476 (CC1), N315 (CC5), Mu50 (CC1), MRSA252 (CC30), Cowan (CC3), WIS (CC45) and USA600 (CC45) (Table 4). These results suggested that antibodies against $Coa_{NM}$ interfere not only with the coagulation of S. aureus strains from the same CC type (or Coa-type), but that they may also interfere with the coagulation of strains from other types (MW2 and MSSA476). The observed pattern of cross-protection is not universal, as strains from the same MLST (or Coa-type) were not affected for coagulation by antibodies against $Coa_{NM}$. To examine the generality of type-specific and cross-protective inhibition, $Coa_{85/2082}$, $Coa_{MW2}$, $Coa_{N315}$, $Coa_{MRSA252}$ and $Coa_{WIS}$ were purified and rabbit immune sera were generated (Table 4). $Coa_{85/2082}$-specific IgG inhibited the coagulation of S. aureus Newman (CC8) and 85/2082 (CC8) and, to a lesser degree, that of N315 (CC5) and Mu50 (CC5). Antibodies directed against $Coa_{N315}$ inhibited the clotting of S. aureus N315 (CC5), Mu50 (CC5), Newman (CC8) and 85/2082 (CC8) as well as MRSA252 (CC30); however, these antibodies did not affect the coagulation of S. aureus CowanI (the other CC30 isolate) or of CC1 and CC45 strains. Antibodies against $Coa_{MRSA252}$ inhibited clotting of S. aureus CC1 and CC5 strains but did not affect the clotting of the CC30 or CC45 isolates. Antibodies against the CC45 isolate (WIS) inhibited clotting of S. aureus CC1 strains but did not affect the clotting of CC1, CC5, CC30, or CC45 strains. In summary, coagulation of mouse blood by S. aureus strains was invariably inhibited by antibodies raised against the corresponding Coa (CC8, CC5, CC1 and CC30 isolates). Cross-neutralization of coagulation is observed for antibodies directed against the two coagulases from CC8 strains and for one each of the coagulase of CC1 and CC5 strains. Finally, antibodies directed against Coa from the CC1, CC5, CC8, CC30 and CC45 strains did not neutralize the clotting of S. aureus CC45 strains or of CowanI (CC30). We presume that blood clotting in these isolates may be dependent on another factor, for example vWbp (vide infra).

TABLE 4

Type-specific or cross-protective inhibition of staphylococcal coagulation by Coa antibodies

| S. aureus | CC type | Coa-specific antibodies raised against coagulases from different S. aureus strains | | | | | |
|---|---|---|---|---|---|---|---|
| | | α-$Coa_{Newman}$ | α-$Coa_{85/2082}$ | α-$Coa_{MW2}$ | α-$Coa_{N315}$ | α-$Coa_{MRSA252}$ | α-$Coa_{WIS}$ |
| Newman | 8 | 1.7 | 1.5 | 1.7 | 1.9 | 1.7 | 1.7 |
| 85/2082 | 8 | 1.5 | 1.8 | 1.3 | 1.5 | 1.6 | 1.4 |
| MW2 | 1 | 1.2 | 1.1 | 1.1 | 0.8 | 1.1 | 1.0 |
| MSSA476 | 1 | 1.0 | 1.1 | 1.2 | 0.9 | 1.4 | 1.2 |
| N315 | 5 | 1.1 | 1.2 | 1.3 | 1.2 | 1.3 | 1.2 |
| Mu50 | 5 | 1.0 | 1.2 | 1.2 | 1.2 | 1.1 | 0.9 |
| MRSA252 | 30 | 0.9 | 1.2 | 1.2 | 1.3 | 1.0 | 0.9 |
| CowanI | 30 | 0.9 | 1.0 | 1.0 | 0.9 | 1.0 | 0.8 |
| WIS | 45 | 1.1 | 1.2 | 1.2 | 0.8 | 1.2 | 0.9 |
| USA600 | 45 | 0.8 | 1.0 | 1.2 | 1.2 | 0.8 | 0.8 |

Coagulase Antibodies and their Protective Effect on Staphylococcal Disease

Purified $Coa_{NM}$, $D12_{Coa}$ or $CT_{Coa}$ were emulsified and injected as a prime-booster regimen into BALB/c mice (n=10). Sera of mock (PBS) or $Coa_{NM}$, $D12_{Coa}$ and $CT_{Coa}$ immunized animals were examined by ELISA for IgG responses to antigen, revealing specific immune responses in vaccinated animals but not in control mice (FIGS. 2A-2B). Of note, immunization of mice with $Coa_{NM}$ raised predominantly antibodies against $D12_{Coa}$ and, to a lesser degree, antibodies that were directed against $CT_{Coa}$ (FIG. 2A). $D12_{Coa}$ immunization raised high titer antibodies that reacted with full length $Coa_{NM}$ [(FIG. 26A)] (FIG. 2A). In contrast, $CT_{Coa}$ immunization generated weak antibody responses (FIG. 2A). Mice were challenged by intravenous injection with S. aureus Newman and a 10-day observation period was used to assess protection against lethal sepsis (FIG. 2B). As compared to mock immunized animals, vaccination with $Coa_{NM}$, $D12_{Coa}$ or $CT_{Coa}$ resulted in increased time-to-death ($Coa_{NM}$ vs. PBS, P<0.001; $D12_{Coa}$ vs. PBS, P<0.01; $CT_{Coa}$ vs. PBS, P<0.05). Immune responses against $Coa_{NM}$ did not significantly outperform vaccination with either $D12_{Coa}$ or $CT_{Coa}$ in generating protection against lethal S. aureus challenge ($Coa_{NM}$ vs. $CT_{Coa}$, P>0.05; $D12_{Coa}$ vs. $CT_{Coa}$, P>0.05).

Whether antibodies directed against $D12_{Coa}$ or $CT_{Coa}$ provide protection against S. aureus lethal challenge was tested. Affinity purified rabbit IgG was injected into the peritoneal cavity of naïve BALB/c mice at a concentration of 5 mg/kg body weight (FIG. 2C). Twenty-four hours later, animals were challenged by intravenous injection of S.

*aureus* Newman (FIG. 2C). As compared to control antibodies [IgG (α-V10) specific for the V10 plague protective antigen (DeBord 2006)], IgG directed against $Coa_{NM}$, $D12_{Coa}$ or $CT_{Coa}$ each caused a delay in time-to-death for the corresponding cohort of challenged animals (all vaccines vs. PBS, P<0.05)(FIG. 2C). No significant differences in disease protection were detected between antibodies directed against $D12_{Coa}$, $CT_{Coa}$ or full length $Coa_{NM}$ (FIG. 2C). Thus, when compared to $D12_{Coa}$ and $L_{Coa}$, immunization with the $CT_{Coa}$ domain elicits low antibody responses, however passive transfer of antibodies against $D12_{Coa}$ and $CT_{Coa}$ provide similar levels of protection against *S. aureus* Newman lethal challenge. These data suggest that antibody-mediated neutralization of *S. aureus* Newman coagulase activity is not a prerequisite for disease protection. Following exposure to full length $Coa_{NM}$, BALB/c mice mount robust immune responses against $D12_{Coa}$ and $L_{Coa}$, but generate few antibodies against $CT_{Coa}$.

Antibodies Against Von-Willebrand-Factor-Binding-Protein Domains

Rabbits were immunized with affinity purified His-tagged vWbp derived from the vwb gene of *S. aureus* Newman ($vWbp_{NM}$). Immune serum was examined by ELISA, which revealed serum IgG antibody responses to antigen (FIGS. 3A-3B). To analyze the antibody responses against specific subdomains, affinity-purified $D1_{vWbp}$, $D2_{vWbp}$, $D12_{vWbp}$, $L_{vWbp}$ and $CT_{vWbp}$ were subjected to ELISA (FIG. 3B). Immune serum harbored antibodies against each of the subdomains tested (FIG. 3B). Of note, antibodies against the $D1_{vWbp}$ and $D2_{vWbp}$ and were less abundant than antibodies that recognized these two domains together ($D12_{vWbp}$). Compared with immune responses against $D12_{vWbp}$, antibodies directed against the $CT_{vWbp}$ were 30% less abundant ($D12_{vWbp}$ vs. $CT_{vWbp}$, P>0.05). To probe the biological function of antibodies in the immune serum, the inventors used variable amounts of $vWbp_{NM}$-specific IgG to perturb the association of $D12_{vWbp}$ with human prothrombin and the association of $CT_{vWbp}$ with fibrinogen (FIGS. 3C-3D). The inventors calculated that 1.3 µM α-vWbp IgG blocked $D12_{vWbp}$ binding to prothrombin, whereas 1.3 µM α-vWbp IgG blocked the association of $CT_{vWbp}$ with fibrinogen (FIG. 3D).

Equimolar amounts of affinity purified IgG were added to citrate-blood samples obtained from naïve BALB/c mice, which were subsequently inoculated with a coa mutant derived from *S. aureus* Newman (Cheng 2010). Compared to control samples without antibody, both α-vWbp and α-$D12_{vWbp}$ caused small delays in clotting time, whereas α-$CT_{vWbp}$ did not delay clotting time (FIG. 3D). Thus, rabbits respond to immunization with $vWbp_{NM}$ by generating antigen-specific IgG molecules that are directed against $D12_{vWbp}$, $L_{vWbp}$, and $CT_{vWbp}$. Antibodies against $D12_{vWbp}$ interfere with vWbp-mediated coagulation of mouse blood in vitro.

Antibodies Against vWbp Domains and their Protective Effect on Staphylococcal Disease Purified vWbpNM, D12vWbp or CTvWbp were emulsified and injected as a prime-booster regimen into BALB/c mice (n=10). Sera of mock (PBS) or vWbpNM, D12vWbp and CTvWbp immunized animals were examined by ELISA for IgG responses to antigen, revealing specific immune responses in vaccinated animals but not in control mice (FIGS. 4A-4B). Of note, immunization of mice with vWbpNM raised predominantly antibodies against D12vWbp and, to a lesser degree, antibodies that were directed against CTvWbp (FIG. 4A). D12vWbp immunization raised high titer antibodies that reacted with full length vWbpNM (FIG. 4A). In contrast, CTvWbp immunization generated weak antibody responses [(FIG. 28A)] (FIG. 4A). Mice were challenged by intravenous injection with *S. aureus* Newman and a 10 day observation period was used to assess protection against lethal sepsis (FIG. 4B). As compared to mock immunized animals, vaccination with vWbpNM, D12vWbp or CTvWbp resulted in increased time-to-death (vWbpNM vs. PBS, P<0.01; D12vWbp vs. PBS, P<0.05; CTvWbp vs. PBS, P<0.05). Immune responses against vWbpNM outperformed vaccination with D12vWbp but not CTvWbp in generating protection against lethal *S. aureus* challenge (vWbpNM vs. D12vWbp, P<0.05; vWbpNM vs. CTvWbp, P>0.05)(FIG. 4B).

Whether antibodies directed against $D12_{vWbp}$ or $CT_{vWbp}$ provide protection against *S. aureus* lethal challenge were examined. Affinity purified rabbit IgG was injected into the peritoneal cavity of naïve BALB/c mice at a concentration of 5 mg/kg body weight (FIG. 4C). Twenty-four hours later, animals were challenged by intravenous injection of *S. aureus* Newman (FIG. 4C). As compared to control antibodies (α-V10), IgG directed against $vWbp_{NM}$, $D12_{vWbp}$ or $CT_{vWbp}$ each caused a delay in time-to-death for the corresponding cohort of challenged animals (all vaccines vs. PBS, P<0.05)(FIG. 4C). No significant differences in disease protection were detected between antibodies directed against $D12_{vWbp}$, $CT_{vWbp}$ or full length $vWbp_{NM}$ (FIG. 4C). Thus, in contrast to $D12_{vWbp}$, immunization with the $CT_{vWbp}$, domain elicits low antibody responses. Passive transfer of antibodies against $D12_{vWbp}$ and $CT_{vWbp}$ provide similar levels of protection against *S. aureus* Newman lethal challenge. These data suggest that antibody mediated neutralization of *S. aureus* Newman vWbp, which can occur by antibodies directed against either $D12_{vWbp}$ or $CT_{vWbp}$, correlates with disease protection. Following exposure to full length $vWbp_{NM}$, BALB/c mice mount robust immune responses against $D12_{vWbp}$ and $L_{vWbp}$ but generate few antibodies against $CT_{vWbp}$.

Cross-Protective Attributes of the $Coa_{NM}/vWbp_{NM}$ Vaccine

Purified recombinant $Coa_{NM}$ and $vWbp_{NM}$ were emulsified and injected into BALB/c mice (n=10) as a prime-booster immunization regimen. Sera of mock (PBS) and $Coa_{NM}/vWbp_{NM}$ immunized animals were examined by ELISA for IgG responses to $Coa_{NM}$ as well as $vWbp_{NM}$, which revealed antigen-specific immune responses in vaccinated but not in control mice (FIG. 5A). Intravenous injection of mice with *S. aureus* and a 10 day observation period were used to assess vaccine protection against lethal challenge with various strains (FIG. 5). As a control, $Coa_{NM}/vWbp_{NM}$ immunization raised protection against *S. aureus* Newman (CC8) (Cheng 2010) (data not shown) and USA300 (CC8), but not against MW2 (CC1) or N315 (CC5) (FIGS. 5B-5D). Nevertheless, $Coa_{NM}/vWbp_{NM}$ immunization generated protection against challenge with *S. aureus* CowanI (CC30) and WIS (CC45). Taken together, these data indicate that the $Coa_{NM}/vWbp_{NM}$ vaccine provided type-specific immunity as well as cross-protection against some, but not all, coagulase type strains (FIGS. 5E-5F).

Immune Responses Elicited by the $Coa_4/vWbp_2$ Vaccine

The engineered polypeptide $Coa_4$ harbors the D12 domains of $Coa_{MRSA252}$, $Coa_{MW2}$, $Coa_{N315}$ and full length $Coa_{USA300}$ in addition to N-terminal $His_6$ and C-terminal STREP tags (FIG. 6A). $Coa_4$ was purified by affinity chromatography on StrepTactin-sepharose (FIG. 6B). When analyzed by Coomassie-stained SDS-PAGE, affinity purified $Coa_4$ was revealed as a 190 kDa polypeptide [(FIG. 30B)] (FIG. 6B). $Coa_4$ encompasses the D12 domains from the most frequent coagulase-type S. aureus isolates from North American patients (CC1, CC5, CC8, CC30, CC45) (DeLeo 2010). The vWbp$_2$ polypeptide encompasses the D12 domain of vWbp$_{N315}$ and full length vWbp$_{USA300}$ in addition to N-terminal His$_6$ and C-terminal STREP tags (FIG. 6A). vWbp$_2$ was purified by affinity chromatography, which yielded a polypeptide migrating with the expected mass of 85 kDa on Coomassie-stained SDS-PAGE (FIG. 6B). Mice (n=5) were immunized with a prime-booster regimen of Coa$_{NM}$/vWbp$_{NM}$ or Coa$_4$/vWbp$_2$ and immune responses to various coagulase and von-Willebrand-Factor-binding protein types were examined by ELISA [(FIGS. 6C-6D)] (FIG. 6C). Coa$_{NM}$/vWbp$_{NM}$ vaccine raised antibodies in mice that bound to the coagulases from CC8 strains but displayed little cross-reactivity towards Coa$_{N315}$, Coa$_{MRSA252}$, Coa$_{MW2}$ or Coa$_{WIS}$. By comparison, Coa$_4$ immunization raised higher titer antibodies not only against CC8 type coagulases, but also against the coagulases from CC1, CC5, CC30 and CC45 strains. As compared to vWbp$_{NM}$, vWbp$_2$ raised high titer antibodies against vWbp of CC5 and CC8 strains [(FIG. 6D)].

Cross-Protective Attributes of the Coa$_4$/vWbp$_2$ Vaccine

Purified recombinant Coa$_4$/vWbp$_2$ was emulsified and injected into BALB/c mice (n=10) using a prime-booster immunization regimen. Sera of mock (PBS) and Coa$_4$/vWbp$_2$ immunized animals were examined by ELISA for IgG responses to Coa$_4$ as well as vWbp$_2$, which revealed antigen-specific immune responses in vaccinated but not in control mice (FIG. 7A). Intravenous injection of mice with S. aureus and a 10 day observation period were used to assess vaccine protection against lethal challenge with various strains (FIG. 7). As expected, Coa$_4$/vWbp$_2$ immunization raised protection against S. aureus CC8 strain USA300 (Cheng 2010). Similar to Coa$_{NM}$/vWbp$_{NM}$ immunization, Coa$_4$/vWbp$_2$ vaccine raised protection against S. aureus CowanI (CC30) and WIS (CC45) challenge. Unlike Coa$_{NM}$/vWbp$_{NM}$, Coa$_4$/vWbp$_2$ protected mice against lethal challenge with either S. aureus N315 (CC5) or MW2 (CC1) (FIGS. 7B-7D). Taken together, these data indicate that the Coa$_{NM}$/vWbp$_{NM}$ vaccine provided type-specific immunity as well as cross-protection against some, but not all, coagulase type strains (FIGS. 7E-7F). Further, Coa$_4$/vWbp$_2$ vaccine protected animals against a challenge with the relevant S. aureus CC types isolated from North American patients with staphylococcal disease.

The inventors also examined whether Coa$_4$/vWbp$_2$ immunization can protect mice against staphylococcal abscess formation. BALB/c mice were immunized with a prime-booster regimen of Coa$_4$/vWbp$_2$ or mock control and challenged by intravenous inoculation of a sublethal dose of S. aureus strains USA300, N315, MW2 or CowanI. Five days after challenge, animals were euthanized, necropsied and kidneys removed. The tissues for one of the two kidneys from each mouse were fixed, thin-sectioned and stained with hematoxylin/ceosin for subsequent histopathology analysis (Table 5). Tissues of the other kidneys were homogenized and spread on agar plates to enumerate the staphylococcal load as colony forming units (Table 5). Coa$_4$/vWbp$_2$ immunization affected the bacterial load in renal tissues of mice infected with various S. aureus strains, leading to a significant reduction for S. aureus MW2 and CowanI, but not for USA300 and N315. This is an expected result, as Coa- or vWbp-specific antibodies do not promote opsonophagocytic killing of bacteria, but interfere with staphylococcal abscess formation, thereby reducing the ability of staphylococci to replicate within the protective environment of these lesions (Cheng 2010). As compared to mock-immunized animals, Coa$_4$/vWbp$_2$ immunization reduced staphylococcal abscess formation in renal tissues five days following challenge with the S. aureus strains USA300, CowanI, MW2 or N315 (Table 5).

TABLE 5

Active immunization of mice with Coa$_4$/vWbp$_2$ and protection against challenge with S. aureus strains USA300, N315, MW2, or CowanI

| Vaccine | Staphylococcal load in renal tissue | | | Abscess formation | |
| --- | --- | --- | --- | --- | --- |
| | $^a$log$_{10}$ CFU · g$^{-1}$ (SEM) | $^b$Significance (P value) | $^c$Reduction (log$_{10}$ CFU · g$^{-1}$) | $^d$Number of lesions | $^e$Significance (P value) |
| S. aureus USA300 | | | | | |
| Mock | 7.31 (0.37) | — | — | 8.8 (1.72) | — |
| Coa$_4$/vWbp$_2$ | 8.48 (0.41) | 0.150 | 0.835 | 4.3 (1.11) | 0.0434 |
| S. aureus N315 | | | | | |
| Mock | 7.25 (0.13) | — | — | 16.8 (1.49) | — |
| Coa$_4$/vWbp$_2$ | 7.10 (0.24) | 0.805 | 0.151 | 11.3 (0.84) | 0.0205 |
| S. aureus MW2 | | | | | |
| Mock | 8.04 (0.25) | — | — | 66.5 (8.41) | — |
| Coa$_4$/vWbp$_2$ | 7.25 (0.20) | 0.029 | 0.789 | 27.5 (4.39) | 0.0011 |
| S. aureus CowanI | | | | | |
| Mock | 6.94 (0.16) | — | — | 7.9 (1.27) | — |
| Coa$_4$/vWbp$_2$ | 5.59 (0.51) | 0.028 | 1.35 | 4.6 (0.73) | 0.0279 |

Early work on coagulase demonstrated that, following S. aureus infection, humans as well as animals generate Coa-specific antibodies (Tager 1948; Lominski 1946). When transferred to naïve rabbits, these antibodies may neutralize S. aureus coagulation and, at least in some cases, may confer immunity to challenge with S. aureus (Lominski 1949; Lominski 1962). Active immunization of rabbits with preparations containing coagulase could prolong the life of rabbits that had been challenged by intravenous inoculation with lethal doses of S. aureus (Boake 1956). Comparison of different (phage-typed) S. aureus isolates for inhibition of plasma clotting by coagulase-antiserum revealed both phage type-specific and non-specific neutralization (Lominski 1946; Lominski 1962; Rammelkamp 1950; Duthie 1952; Harrison 1964). These data supported a general concept for the existence of serological types of Coa, which are not strictly linked to *S. aureus* phage-types (Rammelkamp 1956).

Purified coagulase toxoid, encompassing purified Coa from *S. aureus* strains M1 and Newman adsorbed to aluminum phosphate, was examined for therapeutic immunization of 71 patients with chronic furunculosis (Harrison 1963). As compared to placebo, coagulase immunization generated a rise in coagulase-specific antibody titers but failed to improve the clinical outcome of chronic furunculosis (Harrison 1963). Of note, the development of neutralizing antibodies or the possibility of type-specific immunity were not examined (Harrison 1963). Thus, although early work revealed preclinical efficacy of coagulase subunit vaccines, clinical studies failed to demonstrate efficacy in a human trial. As most of these studies were conducted from 1945-1965, one must consider the limited tools for the isolation of highly purified coagulases as well as the inability to type *S. aureus* strains or coagulase vaccine preparations on the basis of their nucleotide sequence. Further, earlier studies were conducted without knowledge of vWbp or of the molecular mechanisms of Coa- and vWbp-mediated prothrombin activation and fibrinogen cleavage (Friedrich 2003; Kroh 2009). We recently observed that both coagulases secreted by *S. aureus* Newman, $Coa_{NM}$ and $vWbp_{NM}$, are sufficient for the ability of this strain to cause abscess formation and rapidly lethal bacteremia in mice (Cheng 2010). In active and passive immunization experiments, antibodies against both $Coa_{NM}$ and $vWbp_{NM}$ were required to confer protection against abscess formation or lethal bacteremia (Cheng 2010). On the basis of these observations, we hypothesize that coagulases may function as protective antigens that elicit antibody responses against Coa and vWbp, which protect animals and humans against *S. aureus* disease (Cheng 2010). In agreement with this model, expression of coa and vwb is a universal trait of *S. aureus* strains (Cheng 2011). Of note, the coa gene of *S. aureus* isolates is variable (McCarthy 2010), with greater variation in amino acid sequence than even the tandem repeats of the protein A (spa) gene; the variation in spa is used for epidemiological typing experiments (Watanabe 2009; Koreen 2004). *S. aureus* mutants that are unable to express coa have not yet been isolated from humans with manifest staphylococcal disease. The vwb gene is less variable (McCarthy 2010). Analyzing currently available *S. aureus* genome sequences for vwb homology, we identified three alleles. Two of the vwb alleles varied in their coding sequence for the D12 domain (*S. aureus* N315 and USA300 are representatives for these alleles), whereas the third allele harbored a nucleotide deletion in codon 102, creating a frameshift that results in a nonsense mutation in codon 107 (*S. aureus* MRSA252).

Enabled by these observations, we report here that Coa and vWbp immunization of rabbits or mice generated predominantly antibodies against the D12 domain of $Coa_{NM}$ or $vWbp_{NM}$. D12-specific antibodies neutralized the coagulase activities of *S. aureus* Newman and, when transferred to naïve animals, conferred protection against lethal bacteremia. Neutralization and disease protection of $Coa_{NM}$- and $vWbp_{NM}$-specific antibodies occurred in a type-specific manner, not unlike the type-specific immunity reported for *Streptococcus pyogenes* M proteins (Lancefield 1928; Lancefield 1962) or the pilus (T) antigens of *S. pyogenes* and *Streptococcus agalactiae* (Mora 2005; Nuccitelli 2011). Informed by the structural vaccinology approach for pilus antigens (Nuccitelli 2011; Schneewind 2011), we engineered two polypeptides that encompasses the D12 domains of the major Coa and vWbp types from the North American *S. aureus* isolates: CC1, CC5, CC8, CC30 and CC45 strains (Tenover 2012). The purified products, $Coa_4$ and $vWbp_2$, were used as antigens and elicited antibody responses against the D12 domains of every Coa and vWbp type examined. Immunization of mice with $Coa_4/vWbp_2$ provided protection against lethal bacteremia challenge with representative *S. aureus* CC1, CC5, CC8, CC30 and CC45 strains. Thus, the design criteria of the $Coa_4/vWbp_2$ vaccine, to generate universal immune responses against Coa and vWbp against clinically relevant *S. aureus*, have been met.

In addition to type-specific neutralization of Coa and vWbp via antibodies directed against the D12 domain, antibodies against the R (Coa) and CT domains (vWbp) also provided protection against *S. aureus* disease. As antibodies against the R and CT domains do not affect coagulation of fibrin via secreted Coa.prothrombin and vWbp.prothrombin complexes, we surmise that these adaptive immune mechanisms target coagulases via another mechanism. We currently do not appreciate how antibodies against the R domain of Coa or the CT domain of vWbp provide protection. It seems plausible that these antibodies may mediate Coa and vWbp removal from circulation via the binding to of immune complexes to Fc receptors on macrophages. Until the molecular mechanism of protection is revealed, the overall value of a vaccine strategy that targets the R and CT domains of Coa and vWbp cannot be appreciated.

B. Materials and Methods

Bacterial Strains and Growth of Cultures

*S. aureus* strains were cultured on tryptic soy agar or broth at 37° C. *E. coli* strains DH5α and BL21 (DE3) were cultured on Luria Bertani agar or broth at 37° C. Ampicillin (100 μg/mL) was used for pET15b and pGEX2tk selection. Primers used for the amplification of staphylococcal DNA are found in Table 6.

TABLE 6

Primers used

| Primer name | Sequence |
| --- | --- |
| F-N315coa | CGCGGATCCATAGTAACAAAGGATTATAGTAAAGAATCAAG (SEQ ID NO: 1) |
| R-N315coa | TCCCCCGGGTTATTTTGTTACTCTAGGCCCATA (SEQ ID NO: 2) |
| R-MW2coa | CGCGGATCCATAGTAACAAAGGATTATAGTGGGAAA (SEQ ID NO: 3) |

TABLE 6-continued

Primers used

| Primer name | Sequence |
| --- | --- |
| R-MW2coa | TCCCCCGGGTTATTTTGTTACTCTAGGCCCATA (SEQ ID NO: 4) |
| F-M252coa | CGCGGATCCATAGTAACTAAAGATTATAGTAAAGAATCAAGAG (SEQ ID NO: 5) |
| R-M252coa | TCCCCCGGGTTATTTTGTTACTCTAGGACCATATGTC (SEQ ID NO: 6) |
| F-U300coa | CGCGGATCCATAGTAACAAAGGATTATAGTGGGAAAT (SEQ ID NO: 7) |
| R-U300coa | TCCCCCGGGTTATTTTGTTACTCTAGGCCCATA (SEQ ID NO: 8) |
| F-WIScoa | CGCGGATCCATAGTAACAAAGGATTATAGTGGGAAAT (SEQ ID NO: 9) |
| R-WIScoa | TCCCCCGGGTTATTTTGTTACTCTAGGACCATATGTC (SEQ ID NO: 10) |
| F-85coa | CGCGGATCCATAGTAACTAAAGATTATAGTAAAGAATCAAGAG (SEQ ID NO: 11) |
| R-85coa | TCCCCCGGGTTATTTTGTTACTCTAGGACCATATGTC (SEQ ID NO: 12) |
| F-VUSA300FL-XhoI | CCGCTCGAGGTGGTTTCTGGGGAGAAG (SEQ ID NO: 13) |
| R-VUSA300FL-Bam-HI | CGGGATCCTTATTTGCCATTATATACTTTATTGATTT (SEQ ID NO: 14) |
| F-VN315FL-XhoI | CCGCTCGAGGTGGTTTCTGGGGAGAAG (SEQ ID NO: 15) |
| R-VN315FL-BamHI | CGGGATCCTTATTTGCCATTGTATACTTTATTG (SEQ ID NO: 16) |
| F-CUSA300-NcoI | CATGCCATGGCCTAGGATAGTAACAAAGGATTATAGTGGGAAAT (SEQ ID NO: 17) |
| R-CUSA300-BamHI | CGGGATCCTTATTTTGTTACTCTAGGCCCATA (SEQ ID NO: 18) |
| F-CN315-NcoI | CATGCCATGGCTCGAGATAGTAACAAAGGATTATAGTAAAGAATC (SEQ ID NO: 19) |
| R-CN315-AvrII | CCTAGGCGGACCATATTGAGAAGC (SEQ ID NO: 20) |
| F-CMW2-NcoI | CATGCCATGGCCGCGGATAGTAACAAAGGATTATAGTGGGAAA (SEQ ID NO: 21) |
| R-CMW2-XhoI | GGCTCGAGTTTTTTGACAGTTTTATTTTCCA (SEQ ID NO: 22) |
| F-CMRSA-NcoI | CATGCCATGGCCCGGGATAGTAACTAAAGATTATAGTAAAGAATCAAGAG (SEQ ID NO: 23) |
| R-CMRSA-SacII | TCCCCGCGGATTTTTGACGGTTCTTGTTTTCCAAGATT (SEQ ID NO: 24) |
| F-VUSA300-NcoI | CATGCCATGGCCTAGGGTGGTTTCTGGGGAGAAG (SEQ ID NO: 25) |
| R-VUSA300-BamHI | CGGGATCCTTATTTGCCATTATATACTTTATTGATTT (SEQ ID NO: 26) |
| F-VN315-NcoI | CATGCCATGGCTCGAGGTGGTTTCTGGGGAGAAG (SEQ ID NO: 27) |
| R-VN315-AvrII | CCTAGGTGTATTGTTAAAGTCCTTTAAATCAC (SEQ ID NO: 28) |
| F-His-CMRSA | CATGCCATGGGCAGCAGCCATCATCATCATCATCACAGCAGCATAGTAACTAAAGATTATAGTAAAGAATCAAGAG (SEQ ID NO: 29) |
| F-His-VN315 | CATGCCATGGGCAGCAGCCATCATCATCATCATCACAGCAGCGTGGTTTCTGGGGAGAAG (SEQ ID NO: 30) |

TABLE 6-continued

Primers used

| Primer name | Sequence |
|---|---|
| R-USA300CoaStrep | CGGGATCCTTACTTCTCAAATTGAGGATGAGACCATTTTGTTAC TCTAGGCCCATA (SEQ ID NO: 31) |
| R-USA300vwbStrep | CGGGATCCTTACTTCTCAAATTGAGGATGAGACCATTTGCCATT ATATACTTTATTGATTT (SEG ID NO: 32) |

$Coa_4$ and $vWbp_2$

To generate the hybrid proteins, coa and vwb from strain USA300 were PCR amplified. The 5' primer included the restriction site (NcoI) to insert onto the vector (pET15b) as well as an additional restriction enzyme (AvrII) for future use. The 3' primer included the restriction site (BamHI) for vector insertion. The inserts were cloned into E. coli strain DH5α. In each subsequent cloning round, the D12 from the next allele was added to the vector 5' to the previous insert. In each case, the 5' primer included the vector site (NcoI) and an additional restriction enzyme site for future use. The 3' primer for each sequential insert contained the restriction site (AvrII for N315) included in the 5' primer for the previous insert. The promoter region and His tag was restored in a subsequent round of cloning, and a C-terminal STREP tag was added in another round of cloning. The entire vector was sequenced to verify DNA sequence quality. Finally, each vector was transformed into E. coli strain BL21 for protein expression and purification.

Protein Purification

E. coli BL21(DE3) harboring expression vectors containing coa from S. aureus Newman, vwb from S. aureus strains Newman, USA3000, and N315; or the subdomains of coa and vwb; and expression vectors containing the genetic sequence for the hybrid proteins $Coa_4$ and $vWbp_2$, were grown at 37° C. and induced with 100 mM IPTG overnight at room temperature. Because of degradation during the purification of Coa, pGEX2tk expression vectors in E. coli DH5a were used to express coa from USA300, N315, MW2, MRSA252, 85/2082, and WIS as GST-tagged constructs. Three hours following induction, cells were centrifuged at 7,000×g, suspended in 1× column buffer (0.1 M Tris-HCl, pH 7.5, 0.5 M NaCl) and lysed in a French pressure cell at 14,000 lb/in². Lysates were subjected to ultracentrifugation at 40,000×g for 30 min. The supernatant of pET15b constructs was subjected to Ni-NTA chromatography, washed with column buffer and 10 mM imidazole, and eluted with 500 mM imidazole. For strep-tagged proteins, lysate supernatants were subjected to chromatography over StrepTactin Sepharose (GE Healthcare), washed in 1× strep wash buffer (0.1 M Tris-HCl, pH 8, 0.150 M NaCl, 0.1 M EDTA), and eluted in 1× strep wash buffer containing 2.5 mM desthiobiotin. For GST-tagged proteins, the supernatant of cleared lysates was subjected to glutathione-sepharose chromatography. To remove the GST tag, following washing with column buffer, the column buffer was switched to PreScission protease cleavage buffer containing 10 mM DTT, and the column was incubated with PreScission protease (GE Healthcare) overnight at the unit definition provided by GE. Liberated protein lacking the GST tag was then collected with additional protease cleavage buffer. Eluates were dialyzed against PBS. To remove endotoxin, 1:100 Triton-X114 was added and the solution was chilled for 10 min, incubated at 37° C. for 10 min, and centrifuged at 13,000×g. This was repeated twice. Supernatant was loaded onto a HiTrap desalting column to remove remnants of Triton-XI 14.

Rabbit Antibodies

Protein concentration was determined using a BCA kit (Pierce). Purity was verified by SDS-PAGE analysis and Coomassie Brilliant Blue staining. Six-month-old New-Zealand white female rabbits were immunized with 500 µg protein emulsified in CFA (Difco) for initial immunization or IFA for booster immunizations on day 24 and 48. On day 60, rabbits were bled and serum recovered for immunoblotting or passive transfer experiments. For antibody purification, recombinant $His_6$-Coa, $His_6$-vWbp, or $His_6$-ClfA (5 mg) was covalently linked to HiTrap NHS-activated HP columns (GE Healthcare). This antigen-matrix was then used for affinity chromatography of 10-20 mL of rabbit serum at 4° C. Charged matrix was washed with 50 column volumes of PBS, antibodies eluted with elution buffer (1 M glycine pH 2.5, 0.5 M NaCl) and immediately neutralized with 1 M Tris-HCl (pH 8.5). Purified antibodies were dialyzed overnight against PBS, 0.5 M NaCl at 4° C.

Coagulation Assay

Overnight cultures of staphylococcal strains were diluted 1:100 into fresh TSB and grown at 37° C. until they reached an $OD_{600}$ 0.4. One mL of culture was centrifuged, and staphylococci washed and suspended in 1 mL of sterile PBS to generate a suspension of $1 \times 10^8$ CFU/mL. Whole blood from naïve BALB/c mice was collected and sodium citrate was added to a final concentration 1% (w/v). To assess bacterial blood coagulating activity in the presence of antibodies, 10 µL of the stock bacterial culture was mixed with 10 µL of PBS containing 30 µM of anti-Coa and anti-vWbp mixture in a sterile plastic test tube (BD Falcon) and incubated for fifteen minutes. To each tube, 80 µL of anti-coagulated mouse blood in a sterile plastic test tube (BD falcon) to achieve a final concentration of 1×10 CFU/mL. Test tubes were incubated at 37° C. and blood coagulation was verified by tipping the tubes to 45° angles at timed intervals. For human blood experiments, consenting individuals were bled for 10 mL of blood, which was treated with sodium citrate to a final concentration of 1% (w/v). The blood was then tested in the manner described above. All experiments were repeated in at least two independent experiments.

Active Immunization

Three week-old BALB/c mice (n=10) were injected with 50 µg protein emulsified in 60 µL incomplete Freund's adjuvant, and 40 µL complete Freund's adjuvant. Eleven days post vaccination these mice were boosted with 50 µg protein each emulsified in 100 µL incomplete Freund's adjuvant. On day 21, mice were anesthetized with ketamine/xylazine and blood was collected by retro-orbital bleeding using micro-hematocrit capillary tubes (Fisher) in Z-Gel microtubes (Sarstedt) for determining half maximal titers.

Tubes were centrifuged at 10,000×g for three minutes, and serum was collected. Half maximal antibody titers were measured by enzyme-linked immunosorbant assay (ELISA).

Passive Transfer of Antibodies

Six hours prior to infection, six week old BALB/c mice (n=10) were injected intraperitoneally with affinity purified antibodies against full-length or subdomain constructs of Coa or vWbp or of V10 (control IgG specific for the LcrV plague antigen) at a dose of 5 mg/kg body weight.

Sepsis

Overnight cultures of staphylococcal strains were diluted 1:100 into fresh TSB and grown until they reached an $OD_{600}$ of 0.4. Bacteria were centrifuged at 7,000×g, washed, and suspended in the one-tenth volume of PBS. Six week-old female BALB/c mice (n=15) (Charles River) were injected retro-orbitally with $1×10^8$ CFU (*S. aureus* Newman, N315. CowanI, and WIS), $5×10^7$ CFU (*S. aureus* USA300), or $2×10^8$ CFU (*S. aureus* MW2) suspensions in 100 µL of PBS. Mice were monitored for survival over 10 days.

Renal Abscess

*S. aureus* strains were prepared as described for sepsis but following washing, bacterial pellets were resuspended in an equal volume resulting in one log fewer CFU compared to sepsis. To enumerate staphylococcal load in kidney tissue five days post-infection, mice were euthanized by $CO_2$ asphyxiation and kidneys were removed during necropsy. One kidney per mouse was homogenized in PBS, 1% Triton X— 100. Serial dilutions of homogenate were spread on TSA and incubated for colony formation. The bacterial load in tissue was analyzed in pairwise comparisons between wild-type and mutant strains with the unpaired two-tailed Student's t-test. For histopathology, the alternate kidney was fixed in 10% formalin for 24 hours at room temperature. Tissues were embedded in paraffin, thin-sectioned, stained with hematoxylin and eosin, and examined by light microscopy to enumerate pathological lesions per organ. Data were analyzed in pairwise comparisons between wild-type and mutant strains with the unpaired two-tailed Student's t-test.

Measurement of Coagulase Activity $5×10^{-8}$ M prothrombin (Innovative Research) was pre-incubated for 10 min with an equimolar amount of functional Coa at room temperature, followed by addition of S-2238 (a chromogenic substrate) to a final concentration of 1 mM in a total reaction buffer of 100 µL PBS. The change in absorbance was measured at 450 nm for 10 minutes in a spectrophotometer, plotted as a function of time, and fit to a linear curve. The slope of the curve (dA/dt) was interpreted to be the rate of S-2238 hydrolysis, and thus reflective of enzymatic function. The assay was repeated in presence of polyclonal antibodies added at $5×10^{-9}$ M and data were normalized to the average activity without inhibition. All experiments were performed in triplicate.

Coagulase Activity.

Purified recombinant Coa or vWbp (100 nM) were mixed with human prothrombin (Innovative Research) in 1% sodium citrate/PBS. After an initial reading, fibrinogen (3 µM) (Sigma) was added and conversion of fibrinogen to fibrin was measured as an increase in turbidity at 450 nm in a plate reader (BioTek) at 2.5 min intervals. As controls, the enzymatic activity of human alpha-thrombin (Innovative Research) or prothrombin alone were measured.

SEQUENCE TABLE 1

D1-2 domains of Coa from strain MRSA252:

| | | | | |
|---|---|---|---|---|
| IVTKDYSKES | RVNENSKYDT | PIPDWYLGSI | LNRIGDQIYY | AKELTNKYEY | 50 |
| GEKEYKQAID | KLMTRVLGED | HYLLEKKKAQ | YEAYKKWFEK | HKSENPHSSL | 100 |
| KKIKFDDFDL | YRLTKKEYNE | LHQSLKEAVD | EFNSEVKNIQ | SKQKDLLPYD | 150 |
| EATENRVTNG | IYDFVCEIDT | LYAAYFNMSQ | YGHNAKELRA | KLDIILGDAK | 200 |
| DPVRITNERI | RKEMMDDLNS | IIDDFFMDTN | MNRPLNITKF | NPNIHDYTNK | 250 |
| PENRDNFDKL | VKETREAIAN | ADESWKTRTV | KN (SEQ ID NO: 33) | | |

D1-2 Domains of Coa from strain MW2:

| | | | | |
|---|---|---|---|---|
| IVTKDYSGKS | QVNAGSKNGK | QIADGYYWGI | IENLENQFYN | IFHLLDQHKY | 50 |
| AEKEYKDAVD | KLKTRVLEED | QYLLEREKEK | YEIYKELYKK | YKKENPNTQV | 100 |
| KMKAFDKYDL | GDLTMEEYND | LSKLLTKALD | NFKLEVKKIE | SENPDLKPYS | 150 |
| ESEERTAYGK | IDSLVDQAYS | VYFAYVTDAQ | HKTEALNLRA | KIDLILGDEK | 200 |
| DPIRVTNQRT | EKEMIKDLES | IIDDFFIETK | LNRPKHITRY | DGIKHDYHKH | 250 |
| KDGFDALVKE | TREAVAKADE | SWKNKTVKK (SEQ ID NO: 34) | | | |

D1-2 Domains of Coa from strain WIS:

| | | | | |
|---|---|---|---|---|
| IVTKDYSGKS | QVNAGSKNGK | QIADGYYWGI | IENLENQFYN | IFHLLDQHKY | 50 |
| AEKEYKDALD | KLKTRVLEED | QYLLERKKEK | YEIYKELYKK | YKKENPNTQV | 100 |
| KMKAFDKYDL | GDLTMEEYND | LSKLLTKALD | NFKLEVKKIE | SENPDLRPYS | 150 |
| ESEERTAYGK | IDSLVDQAYS | VYFAYVTDAQ | HKTEALNLRA | KIDLILGDEK | 200 |
| DPIRVTNQRT | EKEMIKDLES | IIDDFFIETK | LNRPQHITRY | DGTKHDYHKH | 250 |
| KDGFDALVKE | TREAVSKADE | SWKTKTVKK (SEQ ID NO: 35) | | | |

D1-2 Domains of Coa from strain N315:

| | | | | |
|---|---|---|---|---|
| IVTKDYSKES | RVNEKSKKGA | TVSDYYYWKI | IDSLEAQFTG | AIDLLEDYKY | 50 |
| GDPIYKEAKD | RLMTRVLGED | QYLLKKKIDE | YELYKKWYKS | SNKNTNMLTF | 100 |
| HKYNLYNLTM | NEYNDIFNSL | KDAVYQFNKE | VKEIEHKNVD | LKQEDKDGED | 150 |

SEQUENCE TABLE 1-continued

```
KATKEVYDLV SEIDTLVVTY YADKDYGEHA KELRAKLDLI LGDTDNIPHKI    200
TNERIKKEMI DDLNSIIDDF FMETKQNRPN SITKYDPTKH NFKEKSENKP     250
NFDKLVEETK KAVKEADESW KNKTVKK (SEQ ID NO: 36)
```

D1-2 Domains of Coa from strain USA300:

```
IVTKDYSGKS QVNAGSKNGT LIDSRYLNSA LYYLEDYIIY AIGLTNKYEY      50
GDNIYKEAKD RLLEKVLRED QYLLERKKSQ YEDYKQWYAN YKKENPRTDL     100
KMANPHKYNL EELSMKEYNE LQDALKRALD DPHREVKDIF DKNSDLKTFN     150
AAEEDKATKE VYDLVSEIDT LVVSYYGDKD YGEHAKELRA KLDLILGDTD     200
NPHKITNERI KKEMIDDLNS IIDDFFMETK QNRPKSITKY NPTTHNYKTN     250
SDNKPNFDKL VEETKKAVKE ADDSWKKKTV KK (SEQ ID NO: 37)
```

SEQUENCE TABLE NO. 2

D1-2 domains of vWbp from strain N315:

```
VVSGEKNPYV SKALELKDKS NKSNSYENYR DSLESLISSL SFADYEKYEE      50
PEYEKAVKKY QQKFMAEDDA LKNFLNEEKK IKNADISRKS NNLLGLTHER     100
YSYIFDTLKK NKQEFLKDIE EIQLKNSDLK DFNNT (SEQ ID NO: 38)
```

D1-2 domains of vWbp from strain MW2:

```
VVSGEKNPYV SESLKLTNNK NKSRTVEEYK KSLDDLIWSF PNLDNERFDN      50
PEYKEAMKKY QQRFMAEDEA LKKFFSEEKK IKNGNTDNLD YLGLSHERYE     100
SVFNTLKKQS EEFLKEIEDI KKDNPELKDF NE (SEQ ID NO: 39)
```

D1-2 domains L and Fgb Domains from strain USA300

```
VVSGEKNPYV SESLKLTNNK NKSRTVEEYK KSLDDLIWSF PNLDNERFDN      50
PEYKEAMKKY QQRFMAEDEA LKKFFSEEKK IKNGNTDNLD YLGLSHERYE     100
SVFNILKKQS EEFLKEIEDI KKDNPELKDF NEEEQLKCDL ELNKLENQIL     150
MLGKTFYQNY RDDVESLYSK LDLIMGYKDE ERANKKAVNK RMLENKKEDL     200
ETIIDEFFSD IDKTRPNNIP VLEDEKQEEK NHKNMAQLKS DTEAAKSDES     250
KRSKRSKRSL NTQNHKPASQ EVSEQQKAEY DKRAEERKAR FLDNQKIKKT     300
PVVSLEYDFE HKQRIDNEND KKLVVSAPTK KPTSPTTYTE TTTQVPMPTV     350
ERQTQQQIIY NAPKQLAGLN GESHDFTTTH QSPTTSNHTH NNVVEFEETS     400
ALPGRESGSL VGISQIDSSH LTEREKRVIK REHVREAQKL VDNYKDTHSY     450
KDRINAQQKV NTLSEGHQKR FNKQINKVYN GK (SEQ ID NO: 40)
```

Additional sequences:
D1-2 and L Domains of Coa from strain N315:

```
IVTKDYSKES RVNEKSKKGA TVSDYYYWKI IDSLEAQFTG AIDLLEDYKY      50
GDPIYKEAKD RLMTRVLGED QYLLKKKIDE YELYKKWYKS SNKNTNMLTF     100
HKYNLYNLTM NEYNDIFNSL KDAVYQFNKE VKEIEHKNVD LKQFDKDGED     150
KATKEVYDLV SEIDTLVVTY YADKDYGEHA KELRAKLDLI LGDTDNPHKI     200
TNERIKKEMI DDLNSIIDDF FMETKQNRPN SITKYDPTKH NFKEKSENKP     250
NFDKLVEETK KAVKEADESW KNYTVKKYEE TVTKSPVVKE EKKVEEPQLP     300
KVGNQQEVKT TAGKAEETTQ PVAQPLVKIP QETIYGETVK GPEYPTMENK     350
TLQGEIVQGP DFLTMEQNRP SLSDNYTQPT TPNPILEGLE GSSSKLEIKP     400
QGTESTLKGI QGESSDIEVK PQATETTEAS QYGP (SEQ ID NO: 41)
```

Full length Coa polypeptide:
Strain USA300

```
MKKQIISLGA LAVASSLFTW DNKADAIVTK DYSGKSQVNA GSKNGTLTDS      50
RYLNSALYYL EDYIIYAIGL TNKYEYGDNI YKEAKDRLLE KVLREDQYLL     100
ERKKSQYEDY KQWYANYKKE NPRTDLKMAN FHKYNLEELS MKEYNELQDA     150
LKRALDDFHR EVKDIKDKNS DLKTFNAAEE DKATKEVYDL VSEIDTLVVS     200
YYGDKDYGEH AKELRAKLDL ILGDTDNPHK ITNERIKKEM IDDLNSIIDD     250
FFMETKQNRP KSITKYNPTT HNYKTNSDNK PNFDKLVEET KKAVKEADDS     300
WKKKTVKKYG ETETKSPVVK EEKKVEEPQA PKVDNQQEVK TTAGKAEETT     350
QPVAQPLVKI PQGTITGEIV KGPEYPTMEN KTVQGEIVQG PDFLTMEQSG     400
PSLSNNYTNP PLTNPILEGL EGSSSKLEIK PQGTESTLKG TQGESSDIEV     450
KPQATETTEA SQYGPRTQFN KTPKYVKYRD AGTGIREYND GTFGYEARPR     500
FNKPSETNAY NVTTHANGQV SYGARPTQNK PSKTNAYNVT THGNGQVSYG     550
ARPTQNKPSK TNAYNVTTHA NGQVSYGARP TYKKPSKTNA YNVTTHADGT     600
ATYGPRVTK (SEQ ID NO: 42)
```

Further COA nucleic acid sequences (domains are indicated)
USA300
D1-

```
    ATAGTAACAAAGGATTATAGTGGGAAATCACAAGTTAATGCTGGGAGTAAAAATGGG
ACATTAATAGATAGCAGATATTTAAATTCAGCTCTATATTATTTGGAAGACTATATAATTTA
TGCTATAGGATTAACTAATAAATATGAATATGGAGATAATATTTATAAAGAAGCTAAAGATA
GGTTGTTGGAAAAGGTATTAAGGGAAGATCAATATCTTTTGGAGAGAAAGAAATCTCAATAT
```

SEQUENCE TABLE NO. 2-continued

GAAGATTATAAACAATGGTATGCAAATTATAAAAAAGAAAATCCTCGTACAGATTTAAAAAT
GGCTAATTTTCATAAATATAATTTAGAAGAACTTTCGATGAAAGAATACAATGAACTACAGG
ATGCATTAAAGAGAGCACTGGATGATTTTCACAGAGAAGTTAAAGATATTAAGGATAAGAAT
TCAGACTTGAAAACTTTT (SEQ ID NO: 43)

D2-
AATGCAGCAGAAGAAGATAAAGCAACTAAGGAAGTATACGATCTCGTATCTGAAATT
GATACATTAGTTGTATCATATTATGGTGATAAGGATTATGGGGAGCACGCGAAAGAGTTACG
AGCAAAACTGGACTTAATCCTTGGAGATACAGACAATCCACATAAAATTACAAATGAACGTA
TTAAAAAAGAAATGATTGATGACTTAAATTCAATTATTGATGATTTCTTTATGGAAACTAAA
CAAAATAGACCGAAATCTATAACGAAATATAATCCTACAACACATAACTATAAACAAATAG
TGATAATAAACCTAATTTTGATAAATTAGTTGAAGAAACGAAAAAAGCAGTTAAAGAAGCAG
ATGATTCTTGGAAAAAGAAAACTGTCAAAAAA (SEQ ID NO: 44)

L-
TACGGAGAAACTGAAACAAAATCGCCAGTAGTAAAAGAAGAGAAGAAAGTTGAAGAA
CCTCAAGCACCTAAAGTTGATAACCAACAAGAGGTTAAAACTACGGCTGGTAAAGCTGAAGA
AACAACACAACCAGTTGCACAACCATTAGTTAAAATTCCACAGGGCACAATTACAGGTGAAA
TTGTAAAAGGTCCGGAATATCCAACGATGGAAAATAAAACGGTACAAGGTGAAATCGTTCAA
GGTCCCGATTTTCTAACAATGGAACAAAGCGGCCCATCATTAAGCAATAATTATACAAACCC
ACCGTTAACGAACCCTATTTTAGAAGGTCTTGAAGGTAGCTCATCTAAACTTGAAATAAAAC
CACAAGGTACTGAATCAACGTTAAAAGGTACTCAAGGAGAATCAAGTGATATTGAAGTTAAA
CCTCAAGCAACTGAAACAACAGAAGCTTCTCAATATGGTCCG (SEQ ID NO: 45)

R-
AGACCGCAATTTAACAAAACACCTAAATATGTTAAATATAGAGATGCTGGTACAGGTATCCG
TGAATACAACGATGGAACATTTGGATATGAAGCGAGACCAAGATTCAATAAGCCATCAGAAA
CAAATGCATATAACGTAACAACACATGCAAATGGTCAAGTATCATACGGAGCTCGTCCGACA
CAAAACAAGCCAAGCAAAACAAACGCATATAACGTAACAACACATGGAAACGGCCAAGTATC
ATATGGCGCTCGCCCAACACAAAACAAGCCAAGCAAAACAAATGCATACAACGTAACAACAC
ATGCAAACGGTCAAGTGTCATACGGAGCTCGCCCGACATACAAGAAGCCAAGTAAAACAAAT
GCATACAATGTAACAACACATGCAGATGGTACTGCGACATATGGGCCTAGAGTAACAAAATA
A (SEQ ID NO: 46)

N315
D1-
ATGAAAAAGCAAATAATTTCGCTAGGCGCATTAGCAGTTGCATCTAGCTTATTTACA
TGGGATAACAAAGCAGATGCGATAGTAACAAAGGATTATAGTAAAGAATCAAGAGTGAATGA
GAAAAGTAAAAAGGGAGCTACTGTTTCAGATTATTACTATTGGAAAATAATTGATAGTTTAG
AGGCACAATTTACTGGAGCAATAGACTTATTGGAAGATTATAAATATGGAGATCCTATCTAT
AAAGAAGCGAAAGATAGATTGATGACAAGAGTATTAGGAGAAGACCAGTATTTATTAAAGAA
AAAGATTGATGAATATGAGCTTTATAAAAAGTGGTATAAAAGTTCAAATAAGAACACTAATA
TGCTTACTTTCCATAAATATAATCTTTACAATTTAACAATGAATGAATATAACGATATTTTT
AACTCTTTGAAAGATGCAGTTTATCAATTTAATAAAGAAGTTAAAGAAATAGAGCATAAAAA
TGTTGACTTGAAGCAGTTT (SEQ ID NO: 47)

D2-
GATAAAGATGGAGAAGACAAGGCAACTAAAGAAGTTTATGACCTTGTTTCTGAAATT
GATACATTAGTTGTAACTTATTATGCTGATAAGGATTATGGGGAGCATGCGAAAGAGTTACG
AGCAAAACTGGACTTAATCCTTGGAGATACAGACAATCCACATAAAATTACAAATGAGCGTA
TAAAAAAAGAAATGATCGATGACTTAAATTCAATTATAGATGATTTCTTTATGGAGACTAAA
CAAAATAGACCCAATTCTATAACAAAATATGATCCAACAAAACACAATTTTAAAGAGAAGAG
TGAAAATAAACCTAATTTTGATAAATTAGTTGAAGAAACAAAAAAAGCAGTTAAAGAAGCAG
ACGAATCTTGGAAAAATAAAACTGTCAAAAAA (SEQ ID NO: 48)

L-
TACGAGGAAACTGTAACAAAATCTCCTGTTGTAAAAGAAGAGAAGAAAGTTGAAGAA
CCTCAATTACCTAAAGTTGGAAACCAGCAAGAGGTTAAAACTACGGCTGGTAAAGCTGAAGA
AACAACACAACCAGTGGCACAGCCATTAGTAAAAATTCCACAAGAAACAATCTATGGTGAAA
CTGTAAAAGGTCCAGAATATCCAACGATGGAAAATAAAACGTTACAAGGTGAAATCGTTCAA
GGTCCCGATTTTCTAACAATGGAACAAACAGACCATCTTTAAGCGATAATTATACTCAACC
GACGACACCGAACCCTATTTTAGAAGGTCTTGAAGGTAGCTCATCTAAACTTGAAATAAAAC
CACAAGGTACTGAATCAACGTTGAAAGGTATTCAAGGAGAATCAAGTGATATTGAAGTTAAA
CCTCAAGCAACTGAAACAACAGAAGCTTCTCAATATGGTCCG (SEQ ID NO: 49)

R-
AGACCGCAATTTAACAAAACACCTAAGTATGTGAAATATAGAGATGCTGGTACAGGT
ATCCGTGAATACAACGATGGAACATTTGGATATGAAGCGAGACCAAGATTCAACAAGCCAAG
TGAAACAAATGCATACAACGTAACGACAAATCAAGATGGCACAGTATCATACGGAGCTCGCC
CAACACAAAACAAGCCAAGTGAAACAAACGCATATAACGTAACAACACATGCAAATGGTCAA
GTATCATACGGTGCTCGCCCAACACAAAAAAAGCCAAGCAAAACAAATGCATACAACGTAAC
AACACATGCAAATGGTCAAGTATCATATGGCGCTCGCCCGACACAAAAAAAGCCAAGCAAAA

SEQUENCE TABLE NO. 2-continued

```
CAAATGCATATAACGTAACAACACATGCAAATGGTCAAGTATCATACGGAGCTCGCCCGACA
TACAAGAAGCCAAGCGAAACAAATGCATACAACGTAACAACACATGCAAATGGTCAAGTATC
ATATGGCGCTCGCCCGACACAAAAAAAGCCAAGCGAAACAAACGCATATAACGTAACAACAC
ATGCAGATGGTACTGCGACATATGGGCCTAGAGTAACAAAATAA (SEQ ID NO: 50)
```

Strain MW2
D1-
```
      ATGAAAAAGCAAATAATTTCGCTAGGCGCATTAGCAGTTGCATCTAGCTTATTTACA
TGGGATAACAAAGCAGATGCGATAGTAACAAAGGATTATAGTGGGAAATCACAAGTTAATGC
TGGGAGTAAAAATGGGAAACAAATTGCAGATGGATATTATTGGGGAATAATTGAAAATCTAG
AAAACCAGTTTTACAATATTTTTCATTTACTGGATCAGCATAAATATGCAGAAAAAGAATAT
AAAGATGCAGTAGATAAATTAAAAACTAGAGTTTTAGAGGAAGACCAATACCTGCTAGAAAG
AAAAAAAGAAAAATACGAAATTTATAAAGAACTATATAAAAAATACAAAAAGAGAATCCTA
ATACTCAAGTTAAAATGAAAGCATTTGATAAATACGATCTTGGCGATTTAACTATGGAAGAA
TACAATGACTTATCAAAATTATTAACAAAAGCATTGGATAACTTTAAGTTAGAAGTAAAGAA
AATTGAATCAGAGAATCCAGATTTAAAACCATAT (SEQ ID NO: 51)
```

D2-
```
TCTGAAAGCGAAGAAAGAACAGCATATGGTAAAATAGATTCACTTGTTGATCAAGCATATAG
TGTATATTTTGCCTACGTTACAGATGCACAACATAAAACAGAAGCATTAAATCTTAGGGCGA
AAATTGATTTGATTTTAGGTGATGAAAAAGATCCAATTAGAGTTACGAATCAACGTACTGAA
AAAGAAATGATTAAAGATTTAGAATCTATTATTGATGATTTCTTCATTGAAACCAAGTTGAA
TAGACCTAAACACATTACTAGGTATGATGGAACTAAACATGATTACCATAAACATAAAGATG
GATTTGATGCTCTAGTTAAAGAAACAAGAGAAGCGGTTGCAAAGGCTGACGAATCTTGGAAA
AATAAAACTGTCAAAAAA (SEQ ID NO: 52)
```

L-
```
      TACGAGGAAACTGTAACAAAATCTCCAGTTGTAAAAGAAGAGAAGAAAGTTGAAGAA
CCTCAATCACCTAAATTTGATAACCAACAAGAGGTTAAAATTACAGTTGATAAAGCTGAAGA
AACAACACAACCAGTGGCACAGCCATTAGTTAAAATTCCACAGGGCACAATTACAGGTGAAA
TTGTAAAAGGTCCGGAATATCCAACGATGGAAAATAAAACGTTACAAGGTGAAATCGTTCA
GGTCCAGATTTCCCAACAATGGAACAAAACAGACCATCTTTAAGCGATAATTATACTCAACC
GACGACACCGAACCCTATTTTAGAAGGTCTTGAAGGTAGCTCATCTAAACTTGAAATAAAAC
CACAAGGTACTGAATCAACGTTAAAAGGTACTCAAGGAGAATCAAGTGATATTGAAGTTAAA
CCTCAAGCATCTGAAACAACAGAAGCATCACATTATCCAGCAAGACCTCAATTTAACAAAAC
ACCTAAATATGTTAAATATAGAGATGCTGGTACAGGTATCCGTGAATACAACGATGGAACAT
TTGGATATGAA (SEQ ID NO: 53)
```

R-
```
GCGAGACCAAGATTCAATAAGCCATCAGAAACAAACGCATACAACGTAACGACAAATCAAGA
TGGCACAGTAACATATGGCGCTCGCCCAACACAAAACAAACCAAGCAAAACAATGCATACA
ACGTAACAACACATGCAAATGGTCAAGTATCATATGGCGCTCGCCCGACACAAAACAAGCCA
AGCAAAACAAATGCATATAACGTAACAACACATGCAAATGGTCAAGTATCATACGGAGCTCG
CCCGACACAAAACAAGCCAAGCAAAACAAATGCATATAACGTAACAACACACGCAAACGGTC
AAGTGTCATACGGAGCTCGCCCGACATACAAGAAGCCAAGTAAAACAAATGCATACAATGTA
ACAACACATGCAGATGGTACTGCGACATATGGGCCTAGAGTAACAAAATAA (SEQ ID NO: 54)
```

Strain MRSA252
D1-
```
ATGAAAAAGCAAATAATTTCGCTAGGCGCATTAGCAGTTGCATCTAGCTTATTTACATGGGA
TAACAAAGCAGATGCGATAGTAACTAAAGATTATAGTAAAGAATCAAGAGTGAATGAGAACA
GTAAATACGATACACCAATTCCAGATTGGTATCTAGGTAGTATTTTAAACAGATTAGGGGAT
CAAATATACTACGCTAAGGAATTAACTAATAAATACGAATATGGTGAGAAAGAGTATAAGCA
AGCGATAGATAAATTGATGACTAGAGTTTTGGGAGAAGATCATTATCTATTAGAAAAAAGA
AAGCACAATATGAAGCATACAAAAATGGTTTGAAAAACATAAAAGTGAAATCCACATTCT
AGTTTAAAAAGATTAAATTTGACGATTTTGATTTATATAGATTAACGAAGAAAGAATACAA
TGAGTTACATCAATCATTAAAAGAAGCTGTTGATGAGTTTAATAGTGAAGTGAAAAATATTC
AATCTAAACAAAAGGATTTATTACCTTAT (SEQ ID NO: 55)
```

D2-
```
GATGAAGCAACTGAAAATCGAGTAACAAATGGAATATATGATTTTGTTTGCGAGATTGACAC
ATTATACGCAGCATATTTTAATCATAGCCAATATGGTCATAATGCTAAAGAATTAAGAGCAA
AGCTAGATATAATTCTTGGTGATGCTAAAGATCCTGTTAGAATTACGAATGAAAGATAAGA
AAAGAAATGATGGATGATTTAAATTCTATTATTGATGATTTCTTTATGGATACAAACATGAA
TAGACCATTAAACATAACTAAATTTAATCCGAATATTCATGACTATACTAATAAGCCTGAAA
ATAGAGATAACTTCGATAAATTAGTCAAAGAAACAAGAGAAGCAATCGCAAACGCTGACGAA
TCTTGGAAAACAAGAACCGTCAAAAAT (SEQ ID NO: 56)
```

L-
```
TACGGTAATCTGAAACAAAATCTCCTGTTGTAAAAGAAGAGAAGAAAGTTGAAGAACCTCA
ATTACCTAAAGTTGGAAACCAGCAAGAGGATAAAATTACAGTTGGTACAACTGAAGAAGCAC
CATTACCAATTGCGCAACCACTAGTTAAAATTCCACAGGGCACAATTCAAGGTGAAATTGTA
AAAGGTCCGGAATATCTAACGATGGAAAATAAAACGTTACAAGGTGAAATCGTTCAAGGTCC
AGATTTCCCAACAATGGAACAAAACAGACCATCTTTAAGCGATAATTATACTCAACCGACGA
CACCGAACCCTATTTTAAAAGGTATTGAAGGAAACTCAACTAAACTTGAAATAAAACCACAA
```

SEQUENCE TABLE NO. 2-continued

```
GGTACTGAATCAACGTTAAAAGGTACTCAAGGAGAATCAAGTGATATTGAAGTTAAACCTCA
AGCAACTGAAACAACAGAAGCATCACATTATCCAGCGAGACCTCAATTTAACAAAACACCTA
AGTATGTGAAATATAGAGATGCTGGTACAGGTATCCGTAATACAACGATGGAACATTTGGA
TATGAA (SEQ ID NO: 57)

R-
GCGAGACCAAGATTCAACAAGCCAAGCGAAACAAATGCATACAACGTAACGACAAATCAAGA
TGGCACAGTATCATATGGCGCTCGCCCGACACAAAACAAGCCAAGCGAAACAAACGCATATA
ACGTAACAACACATGCAAACGGCCAAGTATCATACGGAGCTCGTCCGACACAAAACAAGCCA
AGCGAAACGAACGCATATAACGTAACAACACATGCAAACGGTCAAGTGTCATACGGAGCTCG
CCCAACACAAAACAAGCCAAGTAAAACAAATGCATACAATGTAACAACACATGCAGATGGTA
CTGCGACATATGGTCCTAGAGTAACAAAATAA (SEQ ID NO: 58)

Strain WIS
D1-
    ATAGTAACAAAGGATTATAGTGGGAAATCACAAGTTAATGCTGGGAGTAAAAATGGG
AAACAAATTGCAGATGGATATTATTGGGGAATAATTGAAAATCTAGAGAACCAGTTTTACAA
TATTTTTCATTTATTGGATCAGCATAAATATGCAGAAAAAGAATATAAAGATGCATTAGATA
AATTAAAAACTAGAGTTTTAGAGGAAGACCAATACCTGCTAGAAAGAAAAAAGAAAAATAC
GAAATTTATAAAGAACTATATAAAAAATACAAAAAAGAGAATCCTAATACTCAGGTTAAAAT
GAAAGCATTTGATAAATACGATCTTGGCGATTTAACTATGGAAGAATACAATGACTTATCA
AATTATTAACAAAAGCATTGGATAACTTTAAGTTAGAAGTAAAGAAAATTGAATCAGAGAAT
CCAGATTTAAGACCATAT (SEQ ID NO: 59)

D2-
TCTGAAAGTGAAGAGAGAACAGCATATGGTAAAATAGATTCACTTGTTGATCAAGCATATAG
TGTATATTTTGCCTACGTTACAGATGCTCAACATAAAACAGAAGCATTAAATCTTAGGGCAA
AAATAGATTTGATTTTAGGTGATGAAAAAGATCCAATTAGAGTGACGAATCAACGTACTGAA
AAAGAAATGATTAAAGATTTAGAATCTATTATTGATGATTTCTTCATTGAAACAAAGTTGAA
TAGACCTCAACACATTACTAGATATGATGGAACTAAACATGATTACCATAAACATAAAGATG
GATTTGATGCTTTAGTTAAAGAAACAAGAGAAGCGGTTTCTAAGGCTGACGAATCTTGGAAA
ACTAAAACTGTCAAAAAA (SEQ ID NO: 60)

L-
TACGGGGAAACTGAAACAAAATATCCTGTTGTAAAAGAAGAGAAGAAAGTTGAAGAACCTCA
ATCACCTAAAGTTTCTGAAAAAGTGGATGTTCAGGAAACGGTTGGTACAACTGAAGAAGCAC
CATTACCAATTGCGCAACCACTAGTTAAATTACCACAAATTGGGACTCAAGGCGAAATTGTA
AAAGGTCCCGACTATCCAACTATGGAAAATAAAACGTTACAAGGTGTAATTGTTCAAGGTCC
AGATTTCCCAACAATGGAACAAAACAGACCATCTTTAAGTGACAATTATACACAACCATCTG
TGACTTTACCGTCAATTACAGGTGAAAGTACACCAACGAACCCTATTTTAAAAGGTATTGAA
GGAAACTCATCTAAACTTGAAATAAAACCACAAGGTACTGAATCAACGTTGAAAGGTATTCA
AGGAGAATCAAGTGATATTGAAGTTAAACCTCAAGCAACTGAAACAACAGAAGCATCACATT
ATCCAGCGAGACCGCAATTTAACAAAACACCTAAATATGTGAAATATAGAGATGCTGGTACA
GGTATTCGTGAATACAACGATGGAACTTTTGGATATGAA (SEQ ID NO: 61)

R-
GCGAGACCAAGATTCAACAAGCCATCAGAAACAAACGCATACAACGTAACGACAAATCAAGA
TGGCACAGTATCATATGGGGCTCGCCCAACACAAAACAAGCCAAGCAAACAAATGCATATA
ACGTAACAACACATGCAAACGGCCAAGTATCATATGGCGCTCGCCCGACATACAACAAGCCA
AGTGAAACAAATGCATACAACGTAACGACAAATCGAGATGGCACAGTATCATATGGCGCTC
CCCGACACAAAACAAGCCAAGCGAAACGAATGCATATAACGTAACAACACACGGAAATGGCC
AAGTATCATATGGCGCTCGTCCGACACAAAAGAAGCCAAGCAAACAAATGCATATAACGTA
ACAACACATGCAAACGGCCAAGTATCATATGGCGCTCGTCCGACATACAACAAGCCAAGTAA
AACAAATGCATACAATGTAACAACACATGCAGATGGTACTGCGACATATGGTCCTAGAGTAA
CAAAATAA (SEQ ID NO: 62)

MU50
D1-
GATTGGGCAATTACATTTTGGAGGAATTAAAAAATTATGAAAAAGCAAATAATTTCGCTAGG
CGCATTAGCAGTTGCATCTAGCTTATTTACATGGGATAACAAAGCAGATGCGATAGTAACAA
AGGATTATAGTAAAGAATCAAGAGTGAATGAGAAAGTAAAAAGGGAGCTACTGTTTCAGAT
TATTACTATTGGAAAATAATTGATAGTTTAGAGGCACAATTTACTGGAGCAATAGACTTATT
GGAAGATTATAAATATGGAGATCCTATCTATAAAGAAGCGAAAGATAGATTGATGACAAGAG
TATTAGGAGAAGACCAGTATTTATTAAAGAAAAAGATTGATGAATATGAGCTTTATAAAAAG
TGGTATAAAAGTTCAAATAAGAACACTAATATGCTTACTTTCCATAAATATAATCTTTACAA
TTTAACAATGAATGAATATAACGATATTTTAACTCTTTGAAAGATGCAGTTTATCAATTTA
ATAAAGAAGTTAAAGAAATAGAGCATAAAAATGTTGACTTGAAGCAGTTT (SEQ ID NO: 63)

D2-
     GATAAAGATGGAGAAGACAAGGCAACTAAAGAAGTTTATGACCTTGTTTCTGAAATT
GATACATTAGTTGTAACTTATTATGCTGATAAGGATTATGGGGAGCATGCGAAAGAGTTACG
AGCAAAACTGGACTTAATCCTTGGAGATACAGACAATCCACATAAAATTACAAATGAGCGTA
TAAAAAAAGAAATGATCGATGACTTAAATTCAATTATAGATGATTTCTTTATGGAGACTAAA
CAAAATAGACCGAATTCTATAACAAAATATGATCCAACAAAACACAATTTTAAAGAGAAGAG
TGAAAATAAACCTAATTTTGATAAATTAGTTGAAGAACAAAAAAAGCAGTTAAAGAAGCAG
ACGAATCTTGGAAAAATAAAACTGTCAAAAAA (SEQ ID NO: 64)

L-
TACGAGGAAACTGTAACAAAATCTCCTGTTGTAAAAGAAGAGAAGAAAGTTGAAGAACCTCA
ATTACCTAAAGTTGGAAACCAGCAAGAGGTTAAAACTACGGCTGGTAAAGCTGAAGAAACAA
```

SEQUENCE TABLE NO. 2-continued

```
CACAACCAGTGGCACAGCCATTAGTAAAAATTCCACAAGAAACAATCTATGGTGAAACTGTA
AAAGGTCCAGAATATCCAACGATGGAAAATAAAACGTTACAAGGTGAAATCGTTCAAGGTCC
CGATTTTCTAACAATGGAACAAAACAGACCATCTTTAAGCGATAATTATACTCAACCGACGA
CACCGAACCCTATTTTAGAAGGTCTTGAAGGTAGCTCATCTAAACTTGAAATAAAACCACAA
GGTACTGAATCAACGTTGAAAGGTATTCAAGGAGAATCAAGTGATATTGAAGTTAAACCTCA
AGCAACTGAAACAACAGAAGCTTCTCAATATGGTCCG (SEQ ID NO: 65)

R-
AGACCGCAATTTAACAAAACACCTAAGTATGTGAAATATAGAGATGCTGGTACAGGTATCCG
TGAATACAACGATGGAACATTTGGATATGAAGCGAGACCAAGATTCAACAAGCCAAGTGAAA
CAAATGCATACAACGTAACGACAAATCAAGATGGCACAGTATCATACGGAGCTCGCCCAACA
CAAAACAAGCCAAGTGAAACAAACGCATATAACGTAACAACACATGCAAATGGTCAAGTATC
ATACGGTGCTCGCCCAACACAAAAAAAGCCAAGCAAAACAAATGCATACAACGTAACAACAC
ATGCAAATGGTCAAGTATCATATGGCGCTCGCCCGACACAAAAAAAGCCAAGCAAAACAAAT
GCATATAACGTAACAACACATGCAAATGGTCAAGTATCATACGGAGCTCGCCCGACATACAA
GAAGCCAAGCGAAACAAATGCATACAACGTAACAACACATGCAAATGGTCAAGTATCATATG
GCGCTCGCCCGACACAAAAAAGCCAAGCGAAACAAACGCATATAACGTAACAACACATGCA
GATGGTACTGCGACATATGGGCCTAGAGTAACAAAATAA (SEQ ID NO: 66)

85/2082
D1-
ATAGTAACTAAAGATTATAGTAAAGAATCAAGAGTGAATGAGAACAGTAAATACGATACACC
AATTCCAGATTGGTATCTAGGTAGTATTTTAAACAGATTAGGGGATCAAATATACTACGCTA
AGGAATTAACTAATAAATACGAATATGGTGAGAAAGAGTATAAGCAAGCGATAGATAAATTG
ATGACTAGAGTTTTGGGAGAAGATCATTATCTATTAGAAAAAAAGAAAGCACAATATGAAGC
ATACAAAAAATGGTTTGAAAAACATAAAAGTGAAAATCCACATTCTAGTTTAAAAAAGATTA
AATTTGACGATTTTGATTTATATAGATTAACGAAGAAAGAATACAATGAGTTACATCAATCA
TTAAAAGAAGCTGTTGATGAGTTTAATAGTGAAGTGAAAAATATTCAATCTAAACAAAAGGA
TTTATTACCTTAT (SEQ ID NO: 67)

D2-
GATGAAGCAACTGAAAATCGAGTAACAAATGGAATATATGATTTTGTTTGCGAGATTGACAC
ATTATACGCAGCATATTTTAATCATAGCCAATATGGTCATAATGCTAAAGAATTAAGAGCAA
AGCTAGATATAATTCTTGGTGATGCTAAAGATCCTGTTAGAATTACGAATGAAAGAATAAGA
AAAGAAATGATGGATGATTTAAATTCTATTATTGATGATTTCTTTATGGATACAAACATGAA
TAGACCATTAAACATAACTAAATTTAATCCGAATATTCATGACTATACTAATAAGCCTGAAA
ATAGAGATAACTTCGATAAATTAGTCAAAGAAACAAGAGAAGCAGTCGCAAACGCTGACGAA
TCTTGGAAAACAAGAACCGTCAAAAAT (SEQ ID NO: 68)

L-
TACGGTGAATCTGAAACAAAATCTCCTGTTGTAAAAGAAGAGAAGAAAGTTGAAGAACCTCA
ATTACCTAAAGTTGGAACCAGCAAGAGGATAAAATTACAGTTGGTACAACTGAAGAAGCAC
CATTACCAATTGCGCAACCACTAGTTAAAATTCCACAGGGCACAATTCAAGGTGAAATTGTA
AAAGGTCCGGAATATCTAACGATGGAAAATAAAACGTTACAAGGTGAAATCGTTCAAGGTCC
AGATTTCCCAACAATGGAACAAAACAGACCATCTTTAAGCGATAATTATACTCAACCGACGA
CACCGAACCCTATTTTAAAAGGTATTGAAGGAAACTCAACTAAACTTGAAATAAAACCACAA
GGTACTGAATCAACGTTAAAAGGTACTCAAGGAGAATCAAGTGATATTGAAGTTAAACCTCA
AGCAACTGAAACAACAGAAGCATCACATTATCCAGCGAGACCTCAATTTAACAAAACACCTA
AGTATGTGAAATATAGAGATGCTGGTACAGGTATCCGTGAATACAACGATGGAACATTTGGA
TATGAA (SEQ ID NO: 69)

R-
GCGAGACCAAGATTCAACAAGCCAAGCGAAACAAATGCATACAACGTAACGACAAATCAAGA
TGGCACAGTATCATATGGCGCTCGCCCGACACAAAACAAGCCAGCGAAACAAATGCATACA
ACGTAACAACACATGCAAACGGCCAAGTATCATATGGCGCCCGCCCAACATACAAGAAGCCA
AGCGAAACAAACGCATACAACGTAACGACAAATCAAGATGGCACAGTATCATATGGCGCTCG
CCCGACACAAAACAAGCCAAGCGAAACAAACGCATATAACGTAACAACACATGCAAACGGCC
AAGTATCATACGGAGCTCGTCCGACACAAAACAAGCCAGCGAAACGAACGCATATAACGTA
ACAACACATGCAAACGGTCAAGTGTCATACGGAGCTCGCCCAACACAAAACAAGCCAAGTAA
AACAAATGCATACAATGTAACAACACATGCAGATGGTACTGCGACATATGGTCCTAGAGTAA
CAAAATAA (SEQ ID NO: 70)

Newman
D1-
atgaaaaagcaaataatttcgctaggcgcattagcagttgcatctagcttatttacatggga
taacaaagcagatgcgatagtaacaaaggattatagtgggaaatcacaagttaatgctggga
gtaaaaatgggacattaatagatagcagatatttaaattcagctctatattatttggaagac
tatataattatgctataggattaactaataaatatgaatatggagataatatttataaaga
agctaaagataggttgttggaaaaggtattaaggaaagatcaatatcttttggagagaaaga
aatctcaatatgaagattataaacaatggtatgcaaattataaaaaagaaaatcctcgtaca
gatttaaaaatggctaattttcataaatataatttagaagaactttcgatgaaagaatacaa
tgaactacaggatgcattaaagagagcactggatgattttcacagagaagttaaagatatta
aggataagaattcagacttgaaaacttttt (SEQ ID NO: 71)

D2-
aatgcagcagaagaagataaagcaactaaggaagtatacgatctcgtatctgaaattgatac
attagttgtatcatattatggtgataaggattatggggagcacgcgaaagagttacgagcaa
aactggacttaatccttggagatacagacaatccacataaaattacaaatgaacgtattaaa
aaagaaatgattgatgacttaaattcaattattgatgatttctttatggaaactaaacaaaa
```

SEQUENCE TABLE NO. 2-continued

```
tagaccgaaatctataacgaaatataatcctacaacacataactataaaacaaatagtgata
ataaacctaattttgataaattagttgaagaaacgaaaaaagcagttaaagaagcagatgat
tcttggaaaaagaaaactgtcaaaaaa (SEQ ID NO: 72)

L-
tacggagaaactgaaacaaaatcgccagtagtaaaagaagagaagaaagttgaagaacctca
agcacctaaagttgataaccaacaagaggttaaaactacggctggtaaagctgaagaaacaa
cacaaccagttgcacaaccattagttaaaattccacagggcacaattacaggtgaaattgta
aaaggtccggaatatccaacgatggaaaataaaacggtacaaggtgaaatcgttcaaggtcc
cgattttctaacaatggaacaaagcggcccatcattaagcaataattatacaaacccaccgt
taacgaaccctattttagaaggtcttgaaggtagctcatctaaacttgaaataaaaccacaa
ggtactgaatcaacgttaaaaggtactcaaggagaatcaagtgatattgaagttaaacctca
agcaactgaaacaacagaagcttctcaatatggtccg (SEQ ID NO: 73)

R-
agaccgcaatttaacaaaacacctaaatatgttaaatatagagatgctggtacaggtatccg
tgaatacaacgatggaacatttggatatgaagcgagaccaagattcaataagccatcagaaa
caaatgcatataacgtaacaacacatgcaaatggtcaagtatcatacggagctcgtccgaca
tacaagaagccaagcgaaacgaatgcatacaatgtaacaacacatgcaaacggccaagtatc
atacggagctcgtccgacacaaaacaagccaagcaaaacaaacgcatataacgtaacaacac
atggaaacggccaagtatcatatggcgctcgcccaacacaaaacaagccaagcaaaacaaat
gcatacaacgtaacaacacatgcaaacggtcaagtgtcatacggagctcgcccgacacataa
gaagccaagtaaaacaaatgcatacaatgtaacaacacatgcagatggtactgcgacatatg
ggcctagagtaacaaaataa (SEQ ID NO: 74)

Full length vWbp polypeptide from strain USA 300
mknkllvlsl galcvsqiwe snrasavvsg eknpyvsesl kltnnknksr
tveeykksld dliwsfpnld nerfdnpeyk eamkkyqqrf maedealkkf
fseekkikng ntdnldylgl sheryesvfn tlkkqseefl keiedikkdn
pelkdfneee qlkcdlelnk lenqilmlgk tfyqnyrddv eslyskldli
mgykdeeran kkavnkrmle nkkedletii deffsdidkt rpnnipvled
ekqeeknhkh maqlksdtea aksdeskrsk rskrslntqn hkpasqevse
qqkaeydkra eerkarfldn qkikktpvvs leydfehkqr idnendkklv
vsaptkkpts pttytetttq vpmptverqt qqqiiynapk qlaglngesh
dfttthqspt tsnhthnnvv efeetsalpg rksgslvgis qidsshlter
ekrvikrehv reaqklvdny kdthsyldri naqqkvntls eghqkrfnkq
inkvyngk (SEQ ID NO: 75)

Additional vWbp Sequences:
USA300
GTGGTTTCTGGGGAGAAGAATCCATATGTATCTGAGTCGTTGAAACTGACTAATAATAAAAATAAATC
TAGAACAGTAGAAGAGTATAAGAAAAGCTTGGATGATTTAATATGGTCCTTTCCAAACTTAGATAATGAAAGAT
TTGATAATCCTGAATATAAAGAAGCTATGAAAAAATATCAACAGAGATTTATGGCTGAAGATGAGGCTTTGAAG
AAATTTTTTAGTGAAGAGAAAAAAATAAAAAATGGAAATACTGATAATTTAGATTATCTAGGATTATCTCATGA
AAGATATGAAAGTGTATTTAATACTTTGAAAAACAAAGTGAGGAGTTCTTAAAAGAAATTGAAGATATAAAAA
AAGATAACCCTGAATTGAAAGACTTTAATGAAGAGGAGCAATTAAAGTGCGACTTAGAATTAAACAAATTAGAA
AATCAGATATTAATGTTAGGTAAAACATTTTATCAAAACTATAGAGATGATGTTGAAAGTTTATATAGTAAGTT
AGATTTAATTATGGGATATAAAGATGAAGAAAGAGCAAATAAAAAAGCAGTTAACAAAGGATGTTAGAAAATA
AAAAAGAAGACTTAGAAACCATAATTGATGAATTTTTTAGTGATATAGATAAAACAAGACCTAATAATATTCCT
GTTTTAGAAGATGAAAAACAAGAAGAGAAAAATCATAAAAATATGGCTCAATTAAAATCTGACACTGAAGCAGC
AAAAAGTGATGAATCAAAAAGAAGCAAGAGAAGTAAAAGAAGTTTAAATACTCAAAATCACAAACCTGCATCTC
AAGAAGTTTCTGAACAACAAAAAGCTGAATATGATAAAGAGCAGAAGAAAGAAAAGCGAGATTTTTGGATAAT
CAAAAAATTAAGAAAACACCTGTAGTGTCATTAGAATATGATTTTGAGCATAAACAACGTATTGACAACGAAAA
CGACAAGAAACTTGTGGTTTCTGCACCAACAAAGAAACCAACATCACCGACTACATATACTGAAACAACGACAC
AGGTACCAATGCCTACAGTTGAGCGTCAAACTCAGCAACAAATTATTTATAATGCACCAAAACAATTGGCTGGA
TTAAATGGTGAAAGTCATGATTTCACAACAACGCATCAATCACCAACAACTTCAAATCACACGCATAATAATGT
TGTTGAATTTGAAGAAACGTCTGCTTTACCTGGTAGAAAATCAGGATCACTGGTTGGTATAAGTCAAATTGATT
CTTCTCATCTAACTGAACGTGAGAAGCGTGTAATTAAGCGTGAACACGTTAGAGAAGCTCAAAAGTTAGTTGAT
AATTATAAAGATACACATAGTTATAAAGACCGAATAAATGCACAACAAAAAGTAAATACTTTAAGTGAAGGTCA
TCAAAAACGTTTTAATAAACAAATCAATAAAGTATATAATGGCAAATAA (SEQ ID NO: 76)

N315
     GTGGTTTCTGGGGAGAAGAATCCATATGTATCAAAAGCTTTAGAATTGAAAGATAAAAGTAATAAATC
CAATTCTTACGAAAATTATAGAGATAGTTTAGAAAGTTTGATTTCATCATTATCTTTTGCTGATTATGAAAAAT
ATGAAGAGCCAGAATATGAAAAGGCTGTAAAAAAATATCAACAAAAATTTATGGCTGAAGATGATGCATTAAAA
AATTTTTTAAATGAAGAAAAGAAGATAAAAAATGCAGATATTAGCAGAAAATCGAATAATTTATTAGGTTTAAC
ACATGAAAGATATTCTTATATTTTGATACATTAAAGAAAAATAAACAAGAGTTTTTAAAAGATATTGAAGAAA
TACAACTGAAAAATAGTGATTTAAAGGACTTTAACAATACAGAGCAACATAATGCCGACGTAGAAATAAACAAT
TTAGAAAATAAAGTATTAATGGTAGGGTATACATTCTATAATACAAATAAGGACGAAGTTGAAGAATTATATAG
TGAGTTAGATTTGATTGTTGGAGAAGTTCAAGATAAGTCGGATAAAAAAAGAGCAGTAAATCAAAGGATGTTAA
ATAGAAAAAAAGAGGATTTAGAATTTATTATAGATAAATTTTTTAAAAAAATTCAACAAGAACGTCCAGAGAGT
ATACCAGCATTAACTAGTGAAAAAAATCATAATCAGACTATGGCATTAAAGTTAAAAGCAGATACAGAAGCTGC
TAAAAATGACGTATCAAAAAGAAGTAAAAGAAGTTTAAATACTCAAAATAATAAATCTACAACACAAGAAATTT
CTGAAGAACAAAAAGCTGAATATCAAAGAAAGTCAGAGGCATTAAAAGAAAGATTTATAAACAGACAAAAATCT
AAAAATGAGTCTGTGGTTTCACTAATCGATGACGAAGACGACAACGAAAACGACAGGCAACTTGTGGTTTCTGC
GCCATCAAAGAAACCAACAACACCGACTACATATACTGAAACAACGACTCAGGTACCAATGCCTACAGTTGAGC
GTCAAACTCAGCAACAAATCGTTTACAAAACACCAAAACCATTAGCTGGATTAAATGGTGAAAGTCATGATTTC
ACAACAACGCATCAATCACCAACAACTTCAAATCACACGCATAATAATGTTGTTGAATTTGAAGAAACGTCTGC
TTTACCTGGTAGAAAATCAGGATCACTGGTTGGTATAAGTCAAATTGATTCTTCTCATCTAACTGAACGTGAGA
```

SEQUENCE TABLE NO. 2-continued

```
AGCGTGTAATCAAGCGTGAACACGTTAGAGAAGCTCAAAAGTTAGTTGATAATTATAAAGATACACATAGTTAT
AAAGACCGATTAAATGCACAACAAAAAGTAAATACTTTAAGTGAAGGTCATCAAAAACGTTTTAATAAACAAAT
CAATAAAGTATACAATGGCAAATAA (SEQ ID NO: 77)
```

MRSA252
```
       GTGGTTTCTGGGGAGGAGAATCCATATAAATCTGAGTCATTGAAATTAAATGGGAAAAGAAGTACTAC
AATAACTAGTGATAAATATGAAGAAAATTTAGATATGTTAATATCGTCATTATCATTTGCAGATTATGAAAAAT
ATGAGGAACCAGAATACAAAGAAGCAGTTAAAAAGTATCAACAAAAATTTATGGCTGAAGATGATGCATTAAAA
AATTTTTTAGTGAAGAGAAAAAAATAAAAAATAGAAATACTAATACATCAAATTATCTGGGATTAACACACGAA
AGATATGAGTCAATTTATAATTCATTAAAAAATCATCGTGAAGAATTTTCAAAAGAAATCGAAGAAATTAATAA
TAAAAATCCAGTGTTAAAAGAATATAACAATGAGGAACAAACTAAAGCTGATACGGAATTAAACACTCTTGAAA
ATCAAGTACTAATGATAGGTTATACATTTTATCACTCGAATAAAAATGAAGTAGAAGATTTATATAACAAATTA
GATATGATTCTTGGTTATAAAGATGAAGAGAGAAAAAAGAAGAGGGCTACCAATCAAAGAATGTTCAATAATAA
AAAAGAGGATTTAGAAACTATTATTGATGAATTCTTTGGAGAAATTGGACAACAAAGGCCAACATCTATACCAA
CATTAGCGCCTAAAGAAGAAAAAGAAACAATATAAAAAATGCAAATAAATTAAAATCTGACACTGAAGCAGCA
AAAAATGATGAAGCAAAAAGAAGTTTAAATACCCACAATCACAAATCTGTATCTCAAGAAGTCTCTGAACAACA
AAAAGCTGACTACGAAGAAAAAGCTGAAGAAAGAAAAGCGAGATTTTTAGATAAGCAAAAAAATAAGAAAACTC
CTGTAGTTTCATTAGAATATGATTTTGAACATAAACAACGTGTTGACAACGAAAACGACAAGCAACTTGTGGTT
TCTGAGCCATCAAAGAAACCAACAACACCGCCTACATACACTGAAACAACCACACAGCTACCAATGCCTACAGT
TGAGCGTCAAACACAGCAACAAATCGTTTACAAAGCACCAAAACCATTAGCTGGATTAAATGGTGAAAGTCATG
ATTTCACAACAACGCATCAATCACCAACTACTTCAAATCACACGCATAATCATCTTATTGAAATTGAAGAAACA
TCTGCTTTACCTGGTAGAAAGACAGGTTCATTGGTTGGTTGAGTCAAATTGATTCTTCGCATTTAACTGAACG
TGAGAAGCGCGTGATTAAACGTGAACACGTGAGAGAAGCTCAAAAGTTAGTTGATAATTATAAAGATACACATA
GTTATAAAGACCGATTAAATGCCCAACAAAAGTAAATACTTTAAGTGCAGGTCATCAAAAACGTTTTAATAAA
CAAATTAATAAAGTATATAATGGCAAATAATTAATGCATGGCTGCAAAGGAAATAATGAGTTTGCCGTAAAAT
AACAACATTTTAAACTAGCAATAAATAATATCAAAGTCATCATTTCAATGATGCAATCTAGTATAGTCCACATT
CTAAACAGGTGTGGACTATTACTTTTTTCACTTTATATTACGAAAAAATTATTATGCTTAACTATCAATATCAA
TAATTAATTTTAAGCTGAAAAACAATAAAAATGTTAAGACAACGTTTACTTCAAGTTAATTATTATACTGAAAA
TTCTGGTATATAATGCTGTTAGTGAATATAACAGGAAAATTAAATTAAAAATGTTAAAATGCTGTATATAAAGGA
GAAATAACAGATGAAAAGAAATTATTAGTTTTAACTATGAGCACGCTATTTGCTACACAATTTATGAATTCAA
ATCACGCTAATGCATCAACAGAAAGTGTTGATAAAACTTTGTAGTTCCAGAATCGGGTATTAATAAAATTATT
CCAACTTACGATGAATTTAAAAAAGCACCAAAAGTAAATGTTAGTAATTTAGCTGACAACAAAAACTTTGTAGC
TTCTGAAGATAAATTGAATAAGATTGCAGATCCATCGGCAGCTAGTGATAAAATTGTAGATAAAAACTTTGCCGTAC
CAGAATCAAAATTAGGAATCATTGTACCAGAGTATAAAGAAATCAATAATCGAGTGAATGTAACAACAAACAAT
CCAGCTTCAAAACAAGTTGACAAGCAAATTGTTGCTAAAGACCCAGAGGTGAATAGATTTATTACGCAAAATAA
AGTAAACCATCGTTTCATTACTACGCAAACCCACTATAAGAAAGTTATTACTTCATACAAATCAACACATGTAC
ATAAACATGTAAACCATGCAACATCTTCTATCCATCATCACTTTACTATTAAACATCAGAAGCACCTAGATAT
ACACACCCATCTCAATCTCAATCGTTAATTATAAATCATCATTTTGCAGTTCCTGGATACCATGGTCATAAAGT
TGTAACACCAGGACAAGCTAGTATTAGAATTCATCACTTTTGTGCTGTACCTCAAATAAATAGTTTTAAGGTCA
TTCCATCATATGGTCACAATTCACATCGTATGCATGTACCAAGTTTCCAAAATAACACAACAGCAACACATCAA
AATGCAAAGTAAATAAAACTTATAACTATAAATATTTTTATACTTATAAAGTAGTCAAAGGTGTAAAAAAACA
TTTCTCATTTTCAAAATCACATGGTTGTAAAATTGTTAAACCAGCATTAAACATCAAAAATGTAAATTATCAAT
ATGCTGTTCCAAGTAATAGCCCTACACACGTTGTTCCTGAGTTTCAGGGTATCTTACCAGCACCACGAGTATAA
AAATTGACATTAAGTTTACGAGATATGATAAATACCTATTATTTTAAACATAGTCTGCAATCTATGAGGTTGTA
GGCTATGTTTTTGCAGTTTATCAATAAACACCCATCAACAAATTATACCGTTTTTCTACTTTAAAAGTTGGAA
GTAACATAATCTTAAATAAATATATTATTAATTAAGATAAATATAAGCTCGAGATTATTGTTAATAGTTTGTT
CATCGCAAGTTAATTATTGTTTCTAAAATATTGGTATATAATTTTCAATGGCGAAGAAAACAGGGTAAAAAGT
CGGTTTTTAAATCAAAGCAAATAAGGAGTAAAAAATGAAAAGGAAAGTACTAGTATTAACAATGGGCGTACTTT
GTGCGACACAATTATGGCAAACGAATAATGCAAAAGCTTTAGTGACAGAGAGTGGCGTTAATGATACTAAGCAA
TTTACTGAAGTAACATCGGAAGAAAAAGTTATAAAAGATGCTATTCGAAAGTCAATGAAAGCTTTATTTACTA
TCCCCAAAATGATTTGAAGGGATTAGGTGGAGAACACAACGATTACGAAAAAATTACATATAGCACTTCTTCTA
ATAATGTTTTAGAATTATCAATGAGTTCAAAATACGTAGGCGGTAAATCAGGAGCTATGGTTGGTATAGTGAA
ATTTACTCATCACATTTCACAGACCGCGCAAAACGTGCTATCAGACGTGATCATGTTAAAGAAGCACAAAACTT
GATTAATGATTATAAATATACGCAAATATATGAAGACTTTGCTAAAGCTACTGCAAAGGTAAGTACACTTAGTC
AGTCTCACCAAATTATTTAAATAAACAAATTGATAAAGTGAATAATAAGATAGAGAAACTGAAAAACGCTAA
(SEQ ID NO: 78)
```

MW2
D1D2-
```
GTGGTTTCTGGGGAGAAGAATCCATATGTATCTGAGTCGTTGAAACTGACTAATAATAAAAATAAATCTAGAAC
AGTAGAAGAGTATAAGAAAAGCTTGGATGATTTAATATGGTCCTTTCCAAACTTAGATAATGAAAGATTTGATA
ATCCTGAATATAAAGAAGCTATGAAAAAATATCAACAGAGATTTATGGCTGAAGATGAGGCTTTGAAGAAATTT
TTTAGTGAAGAGAAAAAATAAAAAATGGAAATACTGATAATTTAGATTATCTAGGATTATCTCATGAAAGATA
TGAAAGTGTATTTAATACTTTGAAAAAACAAAGTGAGGAGTTCTTAAAAGAAATTGAAGATATAAAAAAAGATA
ACCCTGAATTGAAAGACTTTAATGAATAG (SEQ ID NO: 79)
```

>USA300_vWbp
```
       VVSGEKNPYVSESLKLTNNKNKSRTVEEYKKSLDDLIWSFPNLDNERFDNPEYKEAMKKYQQRFMAED
EALKKFFSEEKKIKNGNTDNLDYLGLSHERYESVFNTLKKQSEEFLKEIEDIKKDNPELKDFNEEEQLKCDLEL
NKLENQILMLGKTFYQNYRDDVESLYSKLDLIMGYKDEERANKKAVNKRMLENKKEDLETIIDEFFSDIDKTRP
NNIPVLEDEKQEEKNHKNMAQLKSDTEAAKSDESKRSKRSKRSLNTQNHKPASQEVSEQQKAEYDKRAEERKAR
FLDNQKIKKTPVVSLEYDFEHKQRIDNEND (SEQ ID NO: 80)

KKLVVSAPTKKPTSPTTYTETTTQVPMPTVERQTQQQIIYNAPKQLAGLNGESHDFTTTHQSPTTSNH
THNNVVEFEETSALPGRKSGSLVGISQIDSSHLTEREKRVIKREHVREAQKLVDNYKDTHSYKDRINAQQKVNT
LSEGHQKRFNKQINKVYNGK (SEQ ID NO: 81)
```

>N315_vWbp
```
       VVSGEKNPYVSKALELKDKSNKSNSYENYRDSLESLISSLSFADYEKYEEPEYEKAVKKYQQKFMAED
DALKNFLNEEKKIKNADISRKSNNLLGLTHERYSYIFDTLKKNKQEFLKDIEEIQLKNSDLKDFNNTEQHNADV
```

SEQUENCE TABLE NO. 2-continued

```
EINNLENKVLMVGYTFYNTNKDEVEELYSELDLIVGEVQDKSDKKRAVNQRMLNRKKEDLEFIIDKFFKKIQQE
RPESIPALTSEKNHNQTMALKLKADTEAAKNDVSKRSKRSLNTQNNKSTTQEISEEQKAEYQRKSEALKERFIN
RQKSKNESVVSLIDDEDDNENDRQLVVSAP (SEQ ID NO: 82)

SKKPTTPTTYTETTTQVPMPTVERQTQQQIVYKTPKPLAGLNGESHDFTTTHQSPTTSNHTHNNVVEF
EETSALPGRKSGSLVGISQIDSSHLTEREKRVIKREHVREAQKLVDNYKDTHSYKDRLNAQQKVNTLSEGHQKR
FNKQINKVYNGK (SEQ ID NO: 83)

>MRSA252_vWbp
      VVSGEENPYKSESLKLNGKRSTTITSDKYEENLDMLISSLSFADYEKYEEPEYKEAVKKYQQKFMAED
DALKNFLVKRKK (SEQ ID NO: 84)

>MW2_vWbp
      VVSGEKNPYVSESLKLTNNKNKSRTVEEYKKSLDDLIWSFPNLDNERFDNPEYKEAMKKYQQRFMAED
EALKKFFSEEKKIKNGNTDNLDYLGLSHERYESVFNTLKKQSEEFLKEIEDIKKDNPELKDFNE
(SEQ ID NO: 85)

>Newman_vWbp
      VVSGEKNPYVSESLKLTNNKNKSRTVEEYKKSLDDLIWSFPNLDNERFDNPEYKEAMKKYQQRFMAED
EALKKFFSEEKKIKNGNTDNLDYLGLSHERYESVFNTLKKQSEEFLKEIEDIKKDNPELKDFNEEEQLKCDLEL
NKLENQILMLGKTFYQNYRDDVESLYSKLDLIMGYKDEERANKKAVNKRMLENKKEDLETIIDEFFSDIDKTRP
NNIPVLEDEKQEEKNHKNMAQLKSDTEAAKSDESKRSKRSKRSLNTQNHKPASQEVSEQQKAEYDKRAEERKAR
FLDNQKIKKTPVVSLEYDFEHKQRIDNEND (SEQ ID NO: 86)

KKLVVSAPTKKPTSPTTYTETTTQVPMPTVERQTQQQIIYNAPKQLAGLNGESHDFTTTHQSPTTSNHTHNNVV
EFEETSALPGRKSGSLVGISQIDSSHLTEREKRVIKREHVREAQKLVDNYKDTHSYKDRINAQQKVNTLSEGHQ
KRFNKQINKVYNGK (SEQ ID NO: 87)
```

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,338,298
U.S. Pat. No. 4,356,170
U.S. Pat. No. 4,367,110
U.S. Pat. No. 4,372,945
U.S. Pat. No. 4,452,901
U.S. Pat. No. 4,474,757
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,684,611
U.S. Pat. No. 4,690,915
U.S. Pat. No. 4,690,915
U.S. Pat. No. 4,748,018
U.S. Pat. No. 4,800,159
U.S. Pat. No. 4,879,236
U.S. Pat. No. 4,952,500
U.S. Pat. No. 5,084,269
U.S. Pat. No. 5,199,942
U.S. Pat. No. 5,221,605
U.S. Pat. No. 5,238,808
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,512,282
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,620,896
U.S. Pat. No. 5,648,240
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,801,234
U.S. Pat. No. 5,840,846
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,871,986
U.S. Pat. No. 5,916,776
U.S. Pat. No. 5,922,574
U.S. Pat. No. 5,925,565
U.S. Pat. No. 5,925,565
U.S. Pat. No. 5,928,905
U.S. Pat. No. 5,928,906
U.S. Pat. No. 5,932,451
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,958,895

U.S. Pat. No. 5,981,274
U.S. Pat. No. 5,994,624
U.S. Pat. No. 6,008,341
U.S. Pat. No. 6,288,214
U.S. Pat. No. 6,294,177
U.S. Pat. No. 6,651,655
U.S. Pat. No. 6,656,462
U.S. Pat. No. 6,733,754
U.S. Pat. No. 6,756,361
U.S. Pat. No. 6,770,278
U.S. Pat. No. 6,793,923
U.S. Pat. No. 6,814,971
U.S. Pat. No. 6,936,258
U.S. Patent Appln. 2002/0169288
U.S. Patent Appln. 2003/0153022
Abdallah et al., *Mol. Microbiol.*, 62, 667-679, 2006.
Abdallah et al., *Nat. Rev. Microbiol.*, 5, 883-891, 2007.
Adams & Bird, *Nephrology.* 14:462-470, 2009.
Albus, et al., *Infect Immun.* 59: 1008-1014, 1991.
An, *J. Virol.*, 71(3):2292-302, 1997.
Anavi, Sc. thesis from the department of Molecular Microbiology and Biotechnology of the Tel-Aviv University, Israel, 1998.
Andersen et al., *J. Immunol.*, 154, 3359-3372, 1995.
Andersen, et al., *Biol Chem.* 390:1279-1283, 2009.
Angel et al., *Cell,* 49:729, 1987b.
Angel et al., *Mol. Cell. Biol.*, 7:2256, 1987a.
Archer, *Clin. Infect. Dis.*, 26, 1179-1181, 1998.
Ariens, et al., *Blood.* 96:988-995, 2000.
Arrecubieta, et al., *J Infect Dis.* 198: 571-575, 2008.
Atchison and Perry, *Cell,* 46:253, 1986.
Atchison and Perry, *Cell,* 48:121, 1987.
Ausubel et al., In: *Current Protocols in Molecular Biology* John, Wiley & Sons, Inc, New York, 1996.
Baba et al., *J. Bacteriol.* 190:300-310, 2007.
Baba, et al., *Lancet.* 359: 1819-1827, 2002.
Baddour, et al., *J Infect Dis.* 165: 749-753, 1992.
Baddour, et al., *J Med Microbiol.* 41:259-263, 1994.
Bae and Schneewind, *Plasmid,* 55:58-63, 2006.
Bae et al., *Proc. Natl. Acad. Sci. USA,* 101, 12312-12317, 2004.
Balaban, et al., *Science.* 280:438-440, 1998.
Banerji et al., *Cell,* 27(2 Pt 1):299-308, 1981.
Banerji et al., *Cell,* 33(3):729-740, 1983.
Barany and Merrifield, In: *The Peptides,* Gross and Meienhofer (Eds.), *Academic Press,* NY, 1-284, 1979.
Behring. *Deutsche Medzinische Wochenschrift.* 16:1145-8, 1890.
Bellus, *J. Macromol. Sci. Pure Appl. Chem.*, A31(1): 1355-1376, 1994.
Berger, *J Pathol Bacteriol.* 55, 1943.
Berkhout et al., *Cell,* 59:273-282, 1989.
Birch-Hirschfeld, *Klinische Woschenschrift.* 13:331, 1934.
Bjerketorp, et al., *FEMS Microbiol Lett.* 234:309-314, 2004.
Bjerketorp, et al., *Microbiol.* 148:2037-2044, 2002.
Blanar et al., *EMBO J.,* 8:1139, 1989.
Blomback, et al., *Nature.* 275:501-505, 1978.
Boake, *J Immununol.* 76:89-96, 1956.
Bodine and Ley, *EMBO J.,* 6:2997, 1987.
Borrebaeck, In: *Antibody Engineering—A Practical Guide,* W. H. Freeman and Co., 1992.
Boshart et al., *Cell,* 41:521, 1985.
Bosze et al., *EMBO J.,* 5(7):1615-1623, 1986.
Boucher and Corey. *Clin. Inject. Dis.* 46:S334-S349, 2008.
Braddock et al., *Cell,* 58:269, 1989.
Brown et al., *Biochemistry,* 37:4397-4406, 1998.
Bubeck Wardenburg and Schneewind. *J. Exp. Med.* 205: 287-294, 2008.
Bubeck-Wardenburg et al., *Infect. Inmmunun.* 74:1040-1044, 2007.
Bubeck-Wardenburg et al., *Proc. Natl. Acad. Sci. USA,* 103:13831-13836, 2006.
Bulla and Siddiqui, *J. Virol.,* 62:1437, 1986.
Burke et al., *J. Inf. Dis.,* 170:1110-1119, 1994.
Burlak et al., *Cell Microbiol.,* 9:1172-1190, 2007.
Burts and Missiakas, *Mol. Microbiol.,* 69:736-46, 2008.
Burts et al., *Proc. Natl. Acad. Sci. USA,* 102:1169-1174, 2005.
Cadness-Graves, et al., *Lancet.* 2:736-738, 1943.
Camargo & Gilmore, *J Bacteriol.* 190:2253-2256, 2008.
Campbell and Villarreal, *Mol. Cell. Biol.,* 8:1993, 1988.
Campere and Tilghman, *Genes and Dev.,* 3:537, 1989.
Campo et al., *Nature,* 303:77, 1983.
Carbonelli et al., *FEMS Microbiol. Lett.,* 177(1):75-82, 1999.
Cawdery, et al., *British J Exp Pathol.* 50:408-412, 1969.
Cedergren et al., *Protein Eng.,* 6:441-448, 1993.
Celander and Haseltine, *J. Virology,* 61:269, 1987.
Celander et al., *J. Virology,* 62:1314, 1988.
Cespedes et al., *J. Inject. Dis.* 191(3):444-52, 2005.
Chambers & Deleo. *Nature Rev Microbiol.* 7: 629-641, 2009.
Champion et al., *Science,* 313:1632-1636, 2006.
Chandler et al., *Cell,* 33:489, 1983.
Chandler et al., *Proc. Natl. Acad. Sci. USA,* 94(8):3596-601, 1997.
Chang et al., *Lancet.,* 362(9381):362-369, 2003.
Chang et al., *Mol. Cell. Biol.,* 9:2153, 1989.
Chapman, et al., *J Bacteriol.* 28:343-363, 1934.
Chatterjee et al., *Proc. Natl. Acad. Sci. USA,* 86:9114, 1989.
Chen and Okayama, *Mol. Cell Biol.,* 7(8):2745-2752, 1987.
Cheng, et al., *Trends Mictobiol.* 19: 225-232, 2011.
Cheng et al., *FASEB J.,* 23:1-12, 2009.
Cheng, et al., *FASEB J.* 23(10):3393-3404, 2009.
Cheng, et al., *PLoS Pathogens.* 6, 2010.
Cheung, et al., *Infect Immun.* 63:1914-1920, 1995.
Choi et al., *Cell,* 53:519, 1988.
Chu, et al., *Am J Med.* 118:1416, 2005.
Clarke, et al., *Ad Microbial Phys.* 51:187-224, 2006.
Cocea, *Biotechniques,* 23(5):814-816, 1997.
Cohen et al., *J. Cell. Physiol.,* 5:75, 1987.
Cosgrove et al., *Infect. Control Hosp. Epidemiol.* 26:166-174, 2005.
Costa et al., *Mol. Cell. Biol.,* 8:81, 1988.
Crawley, et al., *J Thrombosis Haemostasis.* 5 Suppl 1:95-101, 2007.
Cripe et al., *EMBO J.,* 6:3745, 1987.
Culotta and Hamer, *Mol. Cell. Biol.,* 9:1376, 1989.
Dalbey and Wickner, *J. Biol. Chem.,* 260:15925-15931, 1985.
Dandolo et al., *J. Virology,* 47:55-64, 1983.
de Haas, et al., *J Exp Med.* 199:687-695, 2004.
De Villiers et al., *Nature,* 312(5991):242-246, 1984.
DeBord et al., *Infect. Immun.,* 74:4910-4914, 2006.
DeDent, et al., *Sem Inmunopathol.* 34: 317-333, 2012.
DeDent et al., *EMBO J.* 27:2656-2668, 2008.
DeDent et al., *J. Bacteriol.* 189:4473-4484, 2007.
Deisenhofer et al., Hoppe-Seyh Zeitsch. *Physiol. Chem.* 359:975-985, 1978.
Deisenhofer, *Biochemistry* 20:2361-2370, 1981.
Deivanayagam, et al., *EMBO J.* 21:6660-6672, 2002.
DeLeo, et al., *Lancet.* 375: 1557-1568, 2010.
Delvaeye & Conway, *Blood.* 114:2367-2374, 2009.

Deschamps et al., *Science,* 230:1174-1177, 1985.
Devereux et al., *Nucl. Acid Res.,* 12:387-395, 1984.
Diep et al., *J. Infect. Dis.,* 193:1495-1503, 2006a.
Diep et al., *Lancet.* 367:731-739, 2006b.
Dinges et al., *Clin. Microbiol. Rev.,* 13:16-34, 2000.
Donahue, et al., *PNAS USA.* 91: 12178-12182, 1994.
Doolittle, *Blood Rev.* 17: 33-41, 2003.
Duthie and Lorenz, *J. Gen. Microbiol.,* 6:95-107, 1952.
Duthie, *J Gen Microbiol.* 6: 95-107, 1952.
Duthie, *J Gen Microbiol.* 10:427-436, 1954.
Edbrooke et al., *Mol. Cell. Biol.,* 9:1908, 1989.
Edlund et al., *Science,* 230:912-916, 1985.
Ekstedt & Yotis, *J Bacteriol.* 80:496-500, 1960.
Ekstedt and Yotis, *Ann. N.Y. Acad. Sci.,* 80:496-500, 1960.
Emorl and Gaynes, *Clin. Microbiol. Rev.,* 6:428-442, 1993.
Enright, et al., *J Clin Microbiol.* 38: 1008-1015, 2000.
EP 0786519
EP 497524
EP 497525
Epitope Mapping Protocols In: *Methods in Molecular Biology,* Vol. 66, Morris (Ed.), 1996.
Etz, et al., *PNAS USA.* 99:6573-6578, 2002.
Fattom, et al., *Vaccine.* 23: 656-663, 2004.
Fechheimer, et al., *Proc Natl. Acad. Sci. USA,* 84:8463-8467, 1987.
Feng and Holland, *Nature,* 334:6178, 1988.
Ferry, et al., *Curr Infect Dis Report.* 7:420-428, 2005.
Field and Smith, *J. Comp. Pathol.,* 55:63, 1945.
Firak and Subramanian, *Mol. Cell. Biol.,* 6:3667, 1986.
Fitzgerald, et al., *Nature Rev Microbiol.* 4:445-457, 2006.
Foecking and Hofstetter, *Gene,* 45(1):101-105, 1986.
Fortune et al., *Proc Natl. Acad. Sci. USA,* 102:10676-10681, 2005.
Foster, *Nat. Rev. Microbiol.,* 3:948-958, 2005.
Fournier et al., *Infect. Immun.,* 45:87-93, 1984.
Fowler, et al., *New England J Med.* 355: 653-665, 2006.
Fowler, et al., *JAMA.* 293: 3012-3021, 2005.
Fraley et al., *Proc. Natl. Acad. Sci. USA,* 76:3348-3352, 1979.
Friedrich, et al., *Nature.* 425:535-539, 2003.
Fujita et al., *Cell,* 49:357, 1987.
Gailani & Renne, *Arteriosclerosis, Thrombosis & Vascular Biol.* 27:2507-2513, 2007.
Ganesh, et al., *PLoS Pathogens.* 4: e1000226, 2008.
GB Appln. 2 202 328
Geoghegan, et al., *J Biol Chem.* 285: 6208-6216, 2010.
Gilles et al., *Cell,* 33:717, 1983.
Gloss et al., *EMBO J.,* 6:3735, 1987.
Godbout et al., *Mol. Cell. Biol.,* 8:1169, 1988.
Gomez et al., *EMBO J.* 26:701-709, 2007.
Gomez et al., *J. Biol. Chem.* 281:20190-20196, 2006.
Gomez et al., *Nature Med.* 10:842-8, 2004.
Gong, et al., *Clim Vacc Immunol.* CVI 17: 1746-1752, 2010.
Gonzalez, et al., *CMLS.* 65:493-507, 2008.
Goodbourn and Maniatis, *Proc. Natl. Acad. Sci. USA,* 85:1447, 1988.
Goodbourn et al., *Cell,* 45:601, 1986.
Goodyear and Silverman, *J. Exp. Med.,* 197:1125-1139, 2003.
Goodyear, et al., *PNAS USA.* 101:11392-11397, 2004.
Gopal, *Mol. Cell Biol.,* 5:1188-1190, 1985.
Gouda et al., *Biochemistry,* 31(40):9665-72, 1992.
Gouda et al., *Biochemistry,* 37:129-36, 1998.
Graham and Van Der Eb, *Virology,* 52:456-467, 1973.
Graille et al., *Proc. Nat. Acad. Sci. USA* 97:5399-5404, 2000.
Gravenkemper, et al., *J Bacteriol.* 89:1005-1010, 1965.
Greene et al., *Immunology Today,* 10:272, 1989
Grosschedl and Baltimore, *Cell,* 41:885, 1985.
Guinn et al., *Mol. Microbiol.,* 51:359-370, 2004.
Guss et al., *Eur. J. Biochem.* 138:413-420, 1984.
Hair, et al., *Infect Immun.* 78: 1717-1727, 2010.
Hale & Smith, *Br J Exp Pathol.* 26: 209-216, 1945.
Hall, et al., *Infect Immun.* 71: 6864-6870, 2003.
Haraldsson & Jonsson, *J Comp Pathol.* 94:183-196, 1984.
Harland and Weintraub, *J. Cell Biol.,* 101(3):1094-1099, 1985.
Harlow et al., *Antibodies: A Laboratory Manual,* Cold Spring Harbor Laboratory, Cold Spring Harbor, N.Y., Chapter 8, 1988.
Harrison, *Br Med J.* 2: 149-152, 1963.
Harrison, *J Pathol Bacteriol.* 87: 145-150, 1964.
Harro, et al., *Clin Vacc Immun.* CVI 17: 1868-1874, 2010.
Hartleib, et al., *Blood.* 96:2149-2156, 2000.
Harvey et al., *Proc. Natl. Acad. Sci. USA,* 83:1084-1088, 1986.
Haslinger and Karin, *Proc. Natl. Acad. Sci. USA,* 82:8572, 1985.
Hauber and Cullen, *J. Virolog,* 62:673, 1988.
Hauel, et al., *J Med Chem.* 45: 1757-1766, 2002.
Hawiger, et al., *Nature.* 258: 643-645, 1975.
Hawiger, et al., *Biochem.* 21: 1407-1413, 1982.
Heilmann, et al., *J Infect Dis.* 186: 32-39, 2002.
Hen et al., *Nature,* 321:249, 1986.
Hendrix, et al., *J Biol Chem.* 258:3637-3644, 1983.
Hensel et al., *Lymphokine Res.,* 8:347, 1989.
Herold, et al., *JAMA.* 279:593-598, 1998.
Herr and Clarke, *Cell,* 45:461, 1986.
Hijikata-Okunomiya, *J. Thrombosis Haemostasis.* 1: 2060-2061, 2003.
Hirochika et al., *J. Virol.,* 61:2599, 1987.
Hirsch et al., *Mol. Cell. Biol.,* 10:1959, 1990.
Holbrook et al., *Virology,* 157:211, 1987.
Horlick and Benfield, *Mol. Cell. Biol.,* 9:2396, 1989.
Hsu et al., *Proc. Natl. Acad. Sci. USA,* 100:12420-12425, 2003.
Huang et al., *Cell,* 27:245, 1981.
Huber-Lang, et al., *Nature Med.* 12:682-687, 2006.
Hug et al., *Mol. Cell. Biol.,* 8:3065, 1988.
Hussain, et al., *J Bacteriol.* 183: 6778-6786, 2001.
Huston et al., In: *Methods in Enzymology,* Langone (Ed.), Academic Press, NY, 203:46-88, 1991.
Hwang et al., *Mol. Cell. Biol.,* 10:585, 1990.
Imagawa et al., *Cell,* 51:251, 1987.
Imbra and Karin, *Nature,* 323:555, 1986.
Imler et al., *Mol. Cell. Biol.,* 7:2558, 1987.
Imperiale and Nevins, *Mol. Cell. Biol.,* 4:875, 1984.
Innis et al., *Proc Natl Acad Sci USA,* 85(24):9436-9440, 1988.
Inoshima, et al., *Nat Med.* 17(10):1310-4, 2011.
Inouye and Inouye, *Nucleic Acids Res.,* 13: 3101-3109, 1985.
Jakobovits et al., *Mol. Cell. Biol.,* 8:2555, 1988.
Jameel and Siddiqui, *Mol. Cell. Biol.,* 6:710, 1986.
Jansson et al., *FEMS Immunol. Med. Microbiol.* 20:69-78 1998.
Jaynes et al., *Mol. Cell. Biol.,* 8:62, 1988.
Jensen, *Acta Path. Microbiol. Scandin.* 44:421-428, 1958.
Jensen, *APMIS: acta pathol, microbiol et immunol Scandinavica.* 115: 533-539, 2007.
Johnson et al., *Methods in Enzymol.,* 203:88-99, 1991.
Johnson et al., *Mol. Cell. Biol.,* 9:3393, 1989.
Johnstone & Smith, *Nature.* 178:982-983, 1956.
Jones, *Carb. Research,* 340:1097-1106, 2005.

Jonsson et al., *Oral Dis.,* 8(3):130-140, 2002.
Jonsson, et al., *Infect Immun.* 49: 765-769, 1985.
Josefsson, et al., *J Infect Dis.* 184: 1572-1580, 2001.
Josefsson, et al., *PLoS One.* 3: e2206, 2008.
Joyce et al., *Carbohydrate Research* 338:903-922 (2003
Kadesch and Berg, *Mol. Cell. Biol.,* 6:2593, 1986.
Kaeppler et al., *Plant Cell Rep.,* 8:415-418, 1990.
Kaida, et al., *J Biochem.* 102: 1177-1186, 1987.
Kallen, et al., *Ann Emergency Med.* 53: 358-365, 2009.
Kaneda et al., *Science,* 243:375-378, 1989.
Kanemitsu, et al., *Microbiol Immunol.* 45: 23-27, 2001.
Kang, et al., *Am J infection Control.* 40:416-20, 2011.
Kantyka, et al., *Adv Exp Med Biol.* 712:1-14, 2011.
Kapral, *J Bacteriol.* 92:1188-1195, 1966.
Karesh. Pediatric Focused Safety Review: Argatroban. Pediatric Advisory Committee Meeting, 2009.
Karin et al., *Mol. Cell. Biol.,* 7:606, 1987.
Katinka et al., *Cell,* 20:393, 1980.
Kato et al, *J. Biol. Chem.,* 266:3361-3364, 1991.
Kawabata, et al., *J Biochem.* 97: 1073-1078, 1985.
Kawabata, et al., *J Biochem.* 97:325-331, 1985.
Kawabata, et al., *J Biochem.* 98:1603-1614, 1985.
Kawamoto et al., *Mol. Cell. Biol.,* 8:267, 1988.
Kennedy, et al., *J Infect Dis.* 202: 1050-1058, 2010.
Kennedy et al., *Proc. Natl. Acad. Sci. USA* 105:1327-1332, 2008.
Kernodle, *J Infect Dis.* 203: 1692-1693; author reply 1693-1694, 2011.
Kiledjian et al., *Mol. Cell. Biol.,* 8:145, 1988.
Kim, et al., *Vaccine.* 28: 6382-6392, 2001.
Kim, et al., *FASEB J.* 25: 3605-3612, 2011.
Kim, et al., *J Exp Med.* 207:1863-1870, 2010.
Kinoshita, et al., *Microbiol Imunol.* 52: 334-348, 2008.
Klamut et al., *Mol. Cell. Biol.,* 10:193, 1990.
Klevens et al., *Clin. Infect. Dis.,* 2008; 47:927-30, 2008.
Klevens et al., *JAMA,* 298:1763-1771, 2007.
Kluytmans, et al., *Clin Microbiol Rev.* 10: 505-520, 1997.
Koch et al., *Mol. Cell. Biol.,* 9:303, 1989.
Kohler and Milstein, *Nature* 256:495-497 (1975
Kolle & Otto. Z *Hygiene.* 41, 1902.
Kollman, et al., *Biochemistry.* 48:3877-3886, 2009.
Konings, et al., *Blood.* 118(14):3942-51, 2011.
Kopec, et al., *Thrombosis et diathesis haemorrhagica.* 18:475-486, 1967.
Koreen, et al., *J Clin Microbiol.* 42: 792-799, 2004.
Krarup, et al., *PLoS One.* 2:e623, 2007.
Kriegler and Botchan, In: *Eukaryotic Viral Vectors,* Gluzman (Ed.), Cold Spring Harbor: Cold Spring Harbor Laboratory, NY, 1982.
Kriegler and Botchan, *Mol. Cell. Biol.,* 3:325, 1983.
Kriegler et al., *Cell,* 38:483, 1984a.
Kriegler et al., *Cell,* 53:45, 1988.
Kriegler et al., *In: Cancer Cells 2/Oncogenes and Viral Genes,* Van de Woude et al. eds, Cold Spring Harbor, Cold Spring Harbor Laboratory, 1984b.
Kroh, et al., *PNAS USA.* 106:7786-7791, 2009.
Kuehnert, et al., *J Infect Dis.* 193: 172-179, 2006.
Kuhl et al., *Cell,* 50:1057, 1987.
Kuklin et al., *Infect. Immun.,* 74:2215-23, 2006.
Kunz et al., *Nucl. Acids Res.,* 17:1121, 1989.
Kuroda et al., *Lancet.,* 357:1225-1240, 2001.
Kwiecinski, et al., *J Infect Dis.* 202:1041-1049, 2010.
Kyte and Doolittle, *J. Mol. Biol.,* 157(1):105-132, 1982.
Lack, *Nature.* 161:559, 1948.
Lagergard et al.,*Eur. J. Clin. Microbiol. Infect. Dis.,* 11:341-5, 1992.
Lam, et al., *J Bacteriol.* 86:611-615, 1963.
Lam, et al., *J Bacteriol.* 86:87-91, 1963.
Lancefield, *J Immunol.* 89: 307-313, 1962.
Lancefield, *J Exp Med.* 47: 91-103, 1928.
Larsen et al., *Proc Natl. Acad. Sci. USA.,* 83:8283, 1986, 1963.
Laspia et al., *Cell,* 59:283, 1989.
Latimer et al., *Mol. Cell. Biol.,* 10:760, 1990.
Lattar, et al., *Infect Immun.* 77:1968-1975, 2009.
Lee et al., *Nature,* 294:228, 1981.
Lee et al., *Nucleic Acids Res.,* 12:4191-206, 1984.
Lee, et al., *J Infect Dis.* 156: 741-750, 1987.
Lee, *Trends Microbiol.* 4(4): 162-166, 1996.
Levenson et al., *Hum. Gene Ther.,* 9(8):1233-1236, 1998.
Levine M M, editor. New generation vaccines. 4th ed. New York: Informa Healthcare USA. xxvii, 1011, 2010
Levinson et al., *Nature,* 295:79, 1982.
Lin et al., *Mol. Cell. Biol.,* 10:850, 1990.
Lin, et al., *J Bacteriol.* 176: 7005-7016, 1994.
Liu, et al., *Clin Infect Dis.* 52: 285-292, 2011.
Loeb, *J Med Res.* 10:407-419, 1903.
Lominski, *J Gen Microbiol.* 3: ix, 1949.
Lominski & Roberts, *J Pathol Bacteriol.* 58: 187-199, 1946.
Lominski, et al., *Lancet.* 1: 1315-1318, 1962.
Loof, et al., *Blood.* 118:2589-98, 2011.
Lorand, *Arteriosclerosis, Thrombosis, and Vascular Biol.* 20:2-9, 2000.
Lord, *Arteriosclerosis, Thrombosis & Vascular Biol.* 31:494-499, 2011.
Lowy, *N Engl J Med.* 339:520-532, 1998.
Luria et al., *EMBO J.,* 6:3307, 1987.
Lusky and Botchan, *Proc. Natl. Acad. Sci. USA,* 83:3609, 1986.
Lusky et al., *Mol. Cell. Biol.,* 3:1108, 1983.
Macejak and Sarnow, *Nature,* 353:90-94, 1991.
MacGurn et al., *Mol. Microbiol.,* 57:1653-1663, 2005.
Mainiero, et al., *J Bacteriol.* 192: 613-623, 2010.
Maira-Litran et al., *Infect. Immun.,* 70:4433-4440, 2002.
Maira-Litran et al., *Vaccine,* 22:872-879, 2004.
Majors and Varmus, *Proc. Natl. Acad. Sci. USA,* 80:5866, 1983.
Markwardt F (1955) Untersuchungen √°ber Hirudin: naturwiss. F, 1955.
Markwardt, *Untersuchungen über Hirudin. Naturwissenschaften,* 41:537-538, 1955.
Mazmanian et al., *Mol. Microbiol.,* 40(5): 1049-1057, 2001.
Mazmanian et al., *Proc. Natl. Acad. Sci. USA,* 97:5510-5515, 2000.
Mazmanian et al., *Science,* 285(5428):760-3, 1999.
Mazmanian, et al., *Science.* 299:906-909, 2003.
McAdow, et al., *PLoS Pathogens.* 7: e1002307, 2011.
McAdow, et al., *J Inn Immun.* 4: 141-148, 2012.
McAdow, et al., Coagulases as determinants of protective immune responses against *Staphylococcus aureus*. In preparation, 2012.
McAleese, et al., *Microbiology.* 149:99-109, 2003.
McCarthy & Lindsay, *BMC Microbiol.* 10: 173, 2010.
McDevitt, et al., *Mol Microbiol.* 16: 895-907, 1995.
McDevitt, et al., *Euro J Biochem/FEBS.* 247: 416-424, 1997.
McDevitt, et al., *Mol Microbiol.* 11:237-248, 1994.
McLaughlin et al., *PLoS Pathog.,* 3:e105, 2007.
McNeall et al., *Gene,* 76:81, 1989.
Melles, et al., *FEMS Immunol Med Microbiol.* 52:287-292, 2008.
Mernaugh et al., In: *Molecular Methods in Plant Pathology,* Singh et al. (Eds.), CRC Press Inc., Boca Raton, Fla., 359-365, 1995.
Merrifield, *Science,* 232(4748):341-347, 1986.

Miksicek et al., *Cell*, 46:203, 1986.
Mora, et al., *PNAS USA*. 102: 15641-15646, 2005.
Mordacq and Linzer, *Genes and Dev.*, 3:760, 1989.
Moreau et al., *Carbohvdrate Res.*, 201:285-297, 1990.
Moreau et al., *Nucl. Acids Res.*, 9:6047, 1981.
Moreillon, et al., *Infect Immun.* 63:4738-4743, 1995.
Mosmann and Coffman, *Ann. Rev. Immunol.*, 7:145-173, 1989.
Much, *Biochem Z.* 14:143-155, 1908.
Muesing et al., *Cell*, 48:691, 1987.
Musher et al., *Medicine* (Baltimore), 73:186-208, 1994.
Mutch, et al., *Blood.* 115:3980-3988, 2010.
Navarre and Schneewind, *J. Biol. Chem.*, 274:15847-15856, 1999.
Na'was T, et al., *J Clin Immunol.* 36:414-420, 1998.
Needleman & Wunsch, *J. Mol. Biol.*, 48:443, 1970.
Ng et al., *Nuc. Acids Res.*, 17:601, 1989.
Ni Eidhin, et al., *Mol Microbiol.* 30:245-257, 1998.
Nicolau and Sene, *Biochim. Biophys. Acta*, 721:185-190, 1982.
Nicolau et al., *Methods Enzymol.*, 149:157-176, 1987.
Niemann, et al., *Circulation.* 110:193-200, 2004.
Nilsson, et al., *J Clin Invest.* 101: 2640-2649, 1998.
Noble, et al., *FEMS Microbiol Left.* 72:195-198, 1992.
Novick, *Mol. Microbiol.*, 48:1429-1449, 2003.
Nuccitelli, et al., *PNAS USA.* 108: 10278-10283, 2011.
O'Seaghdha et al., *FEBS J.* 273:4831-4841, 2006.
O'Brien, et al., *Mol Microbiol.* 44:1033-1044, 2002.
Omirulleh et al., *Plant Mol. Biol.*, 21(3):415-28, 1993.
Ondek et al., *EMBO J.*, 6:1017, 1987.
Ornitz et al., *Mol. Cell. Biol.*, 7:3466, 1987.
O'Seaghdha, et al. *FEBS J.* 273: 4831-4841, 2006.
Pallen, Trends *Microbiol.*, 10:209-212, 2002.
Palma, et al., *Infect Immun.* 64: 5284-5289, 1996.
Palma, et al., *J Biol Chem.* 276: 31691-31697, 2001.
Palma, et al., *J Biol Chem.* 273: 13177-13181, 1998.
Palmiter et al., *Nature*, 300:611, 1982.
Palmqvist et al., *Microbes. Infect.*, 7:1501-11, 2005.
Palmqvist, et al., *Microbes Infect.* 6: 188-195, 2004.
Panizzi et al., *J. Biol. Chem.*, 281:1179-1187, 2006.
Panizzi, et al., *Cell Mol Life Sci.* 61: 2793-2798, 2004.
Panizzi, et al., *Nat Med.* 17: 1142-1146, 2011.
Patel, et al., *Infect Contr Hosp Epidemiol.* 32: 881-888, 2011.
Paul-Satyaseela, et al., *Epidenmiol Infect.* 132:831-838, 2004.
PCT Appln. PCT/US89/01025
PCT Appln. WO 00/02523
PCT Appln. WO 00/12132
PCT Appln. WO 00/12689
PCT Appln. WO 00/15238
PCT Appln. WO 01/34809
PCT Appln. WO 01/60852
PCT Appln. WO 01/98499
PCT Appln. WO 02/059148
PCT Appln. WO 02/094868
PCT Appln. WO 03/53462
PCT Appln. WO 04/43407
PCT Appln. WO 06/032472
PCT Appln. WO 06/032475
PCT Appln. WO 06/032500
PCT Appln. WO 07/113222
PCT Appln. WO 07/113223
PCT Appln. WO 94/09699
PCT Appln. WO 95/06128
PCT Appln. WO 95/08348
PCT Appln. WO 98/57994
Pearson & Lipman, *Proc. Natl. Acad. Sci. USA*, 85:2444, 1988.
Pech et al., *Mol. Cell. Biol.*, 9:396, 1989.
Pelletier and Sonenberg, *Nature*, 334(6180):320-325, 1988.
Perez-Stable and Constantini, *Mol. Cell. Biol.*, 10:1116, 1990.
Peterson, et al., *Infect Immun.* 15:760-764, 1997.
Phonimdaeng, et al., *J Gen Microbiol.* 134:75-83, 1988.
Phonimdaeng, et al., *Mol Microbiol.* 4:393-404, 1990.
Picard and Schaffner, *Nature*, 307:83, 1984.
Pinkert et al., *Genes and Dev.*, 1:268, 1987.
Plotkin, S A, Orenstein W A, editors (2004) Vaccines. 4th ed. Philadelphia, Pa.: Saunders. xxi, 1662 p. p. 2004
Ponta et al., *Proc. Natl. Acad. Sci. USA*, 82:1020, 1985.
Porton et al., *Mol. Cell. Biol.*, 10:1076, 1990.
Potrykus et al., *Mol. Gen. Genet.*, 199(2):169-177, 1985.
Powers, et al., *J Infect Dis. Doi:* 10.1093/infdis/jis192, 2012.
Procyk & Blomback, *Biochemistry.* 29:1501-1507, 1990.
Projan, et al., *Curr Opin Pharmacol.* 6: 473-479, 2006.
Pugsley, *Microbiol. Rev.*, 57:50-108, 1993.
Pym et al., *Mol. Microbiol.*, 46; 709-717, 2002.
Pym et al., *Nat. Med.*, 9:533-539, 2003.
Que, et al., *Infect Immnun.* 68:3516-3522, 2000.
Queen and Baltimore, *Cell*, 35:741, 1983.
Quinn et al., *Mol. Cell. Biol.*, 9:4713, 1989.
Rammelkamp, et al., *J Exp Med.* 91: 295-307, 1950.
Rammelkamp, et al., *Ann NY Acad Sci.* 65: 144-151, 1956.
Redondo et al., *Science*, 247:1225, 1990.
Reisman and Rotter, *Mol. Cell. Biol.*, 9:3571, 1989.
Remington's Pharmaceutical Sciences, 18th Ed. Mack Printing Company, 1289-1329, 1990.
Resendez Jr. et al., *Mol. Cell. Biol.*, 8:4579, 1988.
Rijken & Lijnen, *J Thrombosis & Haemostasis.* 7:4-13, 2009.
Ripe et al., *Mol. Cell. Biol.*, 9:2224, 1989.
Rippe, et al., *Mol. Cell Biol.*, 10:689-695, 1990.
Rittling et al., *Nuc. Acids Res.*, 17:1619, 1989.
Roben et al., *J. Immunol.* 154:6437-6445, 1995.
Rogers, et al., *Ann NY Acad Sci.* 128: 274-284, 1965.
Rooijakkers, et al., *Nature Immunol.* 6:920-927, 2005.
Rosen et al., *Cell*, 41:813, 1988.
Rothfork, et al., *J Inmmunol.* 171: 5389-5395, 2003.
Ryan, K. J., & Ray. C. G. (Eds.). Sherris Medical Microbiology: An Introduction to Infectious Disease. (Fourth Edition. ed.). New York.: McGraw-Hill, 2004.
Sakai et al., *Genes and Dev.*, 2:1144, 1988.
Sakharov, et al. *J Biol Chem.* 271:27912-27918, 1996.
Salid-Salim et al., *Inject. Control Hosp. Epidemiol.* 24:451-455, 2003.
Sambrook et al., In: *Molecular cloning*, Cold Spring Harbor Laboratory Press, Cold Spring Harbor, N.Y., 2001.
Saravolatz, et al., *Ann Int Med.* 97:325-329, 1982.
Sawai, et al., *Infect Immunity.* 65:466-471, 1997.
Schaffner et al., *J. Mol. Biol.*, 201:81, 1988.
Schneewind et al., *Cell* 70:267-281, 1992.
Schneewind et al., *EMBO*, 12:4803-4811, 1993.
Schneewind & Missiakas, *PNAS USA.* 108: 10029-10030, 2011.
Schneewind, et al., *Science.* 268:103-106, 1995.
Searle et al., *Mol. Cell. Biol.*, 5:1480, 1985.
Seki, et al., *Microbiol Immunol.* 33:981-990, 1989.
Sharp and Marciniak. *Cell*, 59:229, 1989.
Shaul and Ben-Levy, *EMBO J.*, 6:1913, 1987.
Shaw et al., *Microbiology*, 150:217-228, 2004.
Sheagren, *N Engl. J. Med.* 310:1368-1373, 1984.
Sherman et al., *Mol. Cell. Biol.*, 9:50, 1989.
Shinefield, et al., *New England J Med.* 346: 491-496, 2002.

Shopsin et al., *J. Clin. Microbiol.*, 37:3556-63, 1999.
Sibbald et al., *Microbiol. Mol Biol. Rev.*, 70:755-788, 2006.
Sievert, et al., *Clin Infect Dis.* 46:668-674, 2008.
Silberman, et al., *Brit J Haemotol.* 24: 101-113, 1973.
Silverman and Goodyear. *Nat. Rev. Immunol.*, 6:465-75, 2006.
Sjodahl, *Eur. J. Biochem.* 73:343-351, 1977.
Sjoquist et al., *Eur. J. Biochem.* 30:190-194, 1972.
Sleigh and Lockett, *J. EMBO*, 4:3831, 1985.
Smith & Waterman, *Adv. Appl. Math.*, 2:482, 1981.
Smith & Johnstone. *Nature.* 178: 982-983, 1956.
Smith et al., *Brit. J. Exp. Pathol.*, 28:57, 1947.
Sorensen et al., *Infect. Immun.*, 63:1710-1717, 1995.
Soulier, et al., *Thrombosis et diathesis haemorrhagica.* 17:321-334, 1967.
Spalholz et al., *Cell*, 42:183, 1985.
Spandau and Lee, *J. Virology.* 62:427, 1988.
Spandidos and Wilkie, *EMBO J.*, 2:1193, 1983.
Spink, et al., *J Clin Invest.* 21:353-356, 1942.
Stanley et al., *Proc. Natl. Acad. Sci. USA*, 100:13001-13006, 2003.
Stephens and Hentschel, *Biochem. J.*, 248:1, 1987.
Stewart and Young, In: *Solid Phase Peptide Synthesis*, 2d. ed., Pierce Chemical Co., 1984.
Stranger-Jones et al., *Proc. Nat. Acad. Sci. USA*, 103:16942-16947, 2006.
Streitfeld, et al., *Nature.* 184(Suppl 21): 1665-1666, 1959.
Strong, et al., *Biochem.* 21: 1414-1420, 1982.
Stuart et al., *Nature*, 317:828, 1985.
Studier et al., *Methods Enzmol.* 185:60-89 1990.
Stutzmann, et al., *Infect Immun.* 69:657-664, 2001.
Sullivan and Peterlin, *Mol. Cell. Biol.*, 7:3315, 1987.
Sutter, et al., *FEMS Immunol Med Microbiol.* 63:16-24, 2011.
Swartzendruber and Lehman, *J. Cell. Physiology*, 85:179, 1975.
Tager & Drumman, *Ann NY Acad Sci.* 128: 92-111, 1965.
Tager & Hales, *J Immunol.* 60: 1-9, 1948.
Takebe et al., *Mol. Cell. Biol.*, 8:466, 1988.
Tam et al., *J. Am. Chem. Soc.*, 105:6442, 1983.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Tenover, et al., *Antimicrob Agents Chemother.* 56: 1324-1330, 2012.
Thammavongsa, et al., *J Exp Med.* 206:2417-2427, 2009.
Thiesen et al., *J. Virology*, 62:614, 1988.
Thomson et al., *J. Immunol.*, 157(2):822-826, 1996.
Tigges et al., *J. Immunol.*, 156(10):3901-3910, 1996.
Ton-That et al., *Proc. Natl. Acad. Sci. USA*, 96(22):12424-9, 1999.
Treisman, *Cell*, 42:889, 1985.
Tronche et al., *Mol. Biol. Med.*, 7:173, 1990.
Trudel and Constantini, *Genes and Dev.*, 6:954, 1987.
Tuchscherr, et al., *Infect Immun.* 73:7932-7937, 2005.
Tyndell et al., *Nuc. Acids. Res.*, 9:6231, 1981.
Uhlen et al., *J. Biol. Chem.* 259:1695-1702 and 13628 (Corr.) 1984.
Umeda, et al., *J Bacteriol.* 141:838-844, 1980.
van den Ent and Lowe, *FEBS Lett.*, 579:3837-3841, 2005.
van Wely et al., *FEMS Microbiol. Rev.*, 25:437-454, 2001.
Vanassche, et al., *J Clin Microbiol.* 48: 4248-4250, 2010.
Vanassche, et al., *J Thrombosis Haemostasis.* 9: 2436-2446, 2011.
Vanassche, et al., *J Thrombosis Haemostasis.* 107, 2012.
Vannice and Levinson, *J. Virology*, 62:1305, 1988.
Vasseur et al., *Proc Natl. Acad. Sci. USA*, 77:1068, 1980.
Vaughan, et al., *Nat. Biotech.* 16; 535-539, 1998.
Walker & Nesheim, *J Biol Chem.* 274:5201-5212, 1999.
Walsh, *Science.* 261: 308-309, 1993.
Walsh, et al., *Microbiol.* 154: 550-558, 2008.
Walsh, *Am J Med.* 4:782-782, 2010.
Wang and Calame, *Cell*, 47:241, 1986.
Wang, et al., *PLoS Pathogens.* 6:e1000763, 2010.
Ware, et al., *Protein Sci.* 8: 2663-2671, 1999.
Watanabe, et al., *PLoS One. S*, 4: e5714, 2009.
Watanabe, et al., *J Bacteriol.* 187:3698-3707, 2005.
Weber et al., *Cell*, 36:983, 1984.
Weems, et al., *Antimicrob Agents Chemother.* 50: 2751-2755, 2006.
Weidenmaier, et al., *Nature Med.* 10:243-245, 2004.
Weigel, et al., *Science.* 302:1569-1571, 2003.
Weinberger et al. *Mol. Cell. Biol.*, 8:988, 1984.
Weiss et al., *J. Antimicrob. Chemother.*, 53(3):480-6, 2004.
Wilke, et al., *PNAS USA.* 107:13473-13478, 2010.
Winoto and Baltimore, *Cell*, 59:649, 1989.
Wolberg, *Haemophilia.* 16 Suppl 3:7-12, 2010.
Wong et al., *Gene*, 10:87-94, 1980.
Xu et al., *J. Infect. Dis.*, 189:2323-2333, 2004.
Xu et al., *Mol. Microbiol.*, 66(3):787-800, 2007.
Yang, et al., *PNAS USA.* 97:14156-14161, 2000.
Yeaman, et al., *Antimicrobial Agents Chemotherapy.* 36:1665-1670, 1992.
Yutzey et al. *Mol. Cell. Biol.*, 9:1397, 1989.
Zajdel. *Thrombosis Red.* 6:501-510, 1975.

The invention claimed is:

1. An immunogenic composition comprising a first staphylococcal coagulase Domains 1-2 from a first staphylococcal strain and a second staphylococcal coagulase Domains 1-2 from a second staphylococcal strain, wherein the first and second staphylococcal strains are different from each other, wherein each Domains 1-2 is 80% identical in sequence to a Domains 1-2 sequence in SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, or SEQ ID NO: 41, and wherein at least one Domains 1-2 is comprised in a less than full-length coagulase protein that is truncated on the C terminus.

2. The composition of claim 1, wherein the less than full-length coagulase protein lacks all or part of a L or R Domain segment.

3. The composition of claim 1, wherein the less than full-length coagulase protein lacks all or part of a L or F Domain segment.

4. The composition of claim 1, wherein one of the Domains 1-2 is from a S. aureus Newman, 85/2082, MW2, MSSA476, N315, Mu50, MRSA252, CowanI, WIS or USA300 strain.

5. The composition of claim 1, wherein one of the Domains 1-2 is a Coa Domains 1-2 at least 80% identical in sequence to SEQ ID NO: 33, SEQ ID NO: 34, SEQ ID NO: 35, SEQ ID NO: 36, or SEQ ID NO: 37.

6. The composition of claim 1, wherein one of the Domains 1-2 is a vWbp Domains 1-2 at least 80% identical in sequence to SEQ ID NO: 38, SEQ ID NO: 39, SEQ ID NO: 40, or SEQ ID NO: 41.

7. A method for treating a staphylococcal infection in a subject comprising administering to the subject an effective amount of a composition of claim 1.

8. The composition of claim 1, wherein each Domains 1-2 is at least 85%, 90% or 95% identical to an amino acid sequence of SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, or SEQ ID NO: 41.

9. The composition of claim 1, wherein one of the Domains 1-2 is a vWbp Domains 1-2 from a S. aureus N315 or USA300.

10. The composition of claim 1, wherein one of the Domains 1-2 is a Coa Domains 1-2 and comprises a L or R Domain from a staphylococcal Coa protein.

11. The composition of claim 1, wherein one of the Domains 1-2 is a vWbp Domains 1-2 and comprises an L or Fgb domain from a staphylococcal vWbp protein.

12. The composition of claim 1, comprising at least three, four or five different staphylococcal coagulase Domains 1-2.

13. The composition of claim 12, comprising at least four different staphylococcal coagulase Domains 1-2 wherein the different Domains 1-2 are staphylococcal Coa Domains 1-2 from strains MRSA252, MW2, N315 and USA300.

14. The composition of claim 1, wherein the first and second staphylococcal coagulase Domains 1-2 are comprised in a fusion protein.

15. The composition of claim 1, further comprising one or more additional staphylococcal antigen(s).

16. The composition of claim 15, wherein the additional staphylococcal antigen(s) is Emp, EsxA, EsxB, EsaC, Eap, Ebh, EsaB, Coa, vWbp, vWh, Hla, SdrC, SdrD, SdrE, IsdA, IsdB, IsdC, ClfA, ClfB, SasF and/or a nontoxigenic SpA.

17. The composition of claim 1, further comprising an adjuvant.

18. The composition of claim 1, wherein the first and second staphylococcal coagulase Domains 1-2 are recombinant polypeptide(s).

19. The composition of claim 1, further comprising at least four different staphylococcal coagulase Domains 1-2 wherein the composition comprises at least staphylococcal Coa Domains 1-2 from strains MRSA252, MW2, N315 and USA300 and vWbp Domains 1-2 from a S. aureus N315 and USA300.

20. The composition of claim 19, wherein the composition comprises a R Domain from a staphylococcal Coa protein or a CT domain of vWbp.

21. A method for treating and/or preventing a staphylococcal infection in a subject comprising administering to the subject an effective amount of a composition of claim 19.

* * * * *

SEQUENCE LISTING

<160> NUMBER OF SEQ ID NOS: 87

<210> SEQ ID NO 1
<211> LENGTH: 41
<212> TYPE: DNA
<213> ORGANISM: Artificial Sequence
<220> FEATURE:
<223> OTHER INFORMATION: Synthetic Primer

<400> SEQUENCE: 1
cgcggatcca tagtaacaaa ggattatagt aaagaatcaa g         41

<210> SEQ ID NO 2
<211> LENGTH: 33
<212> TYPE: DNA

```
<213> ORGANISM: Artificial Sequence
<220> FEATURE:
<223> OTHER INFORMATION: Synthetic Primer

<400> SEQUENCE: 2
tcccccgggt tattttgtta ctctaggccc ata                           33

<210> SEQ ID NO 3
<211> LENGTH: 36
<212> TYPE: DNA
<213> ORGANISM: Artificial Sequence
<220> FEATURE:
<223> OTHER INFORMATION: Synthetic Primer

<400> SEQUENCE: 3
cgcggatcca tagtaacaaa ggattatagt gggaaa                        36

<210> SEQ ID NO 4
<211> LENGTH: 33
<212> TYPE: DNA
<213> ORGANISM: Artificial Sequence
<220> FEATURE:
<223> OTHER INFORMATION: Synthetic Primer

<400> SEQUENCE: 4
tcccccgggt tattttgtta ctctaggccc ata                           33

<210> SEQ ID NO 5
<211> LENGTH: 43
<212> TYPE: DNA
<213> ORGANISM: Artificial Sequence
<220> FEATURE:
<223> OTHER INFORMATION: Synthetic Primer

<400> SEQUENCE: 5
cgcggatcca tagtaactaa agattatagt aaagaatcaa gag                43

<210> SEQ ID NO 6
<211> LENGTH: 37
<212> TYPE: DNA
<213> ORGANISM: Artificial Sequence
<220> FEATURE:
<223> OTHER INFORMATION: Synthetic Primer

<400> SEQUENCE: 6
tcccccgggt tattttgtta ctctaggacc atatgtc                       37

<210> SEQ ID NO 7
<211> LENGTH: 37
<212> TYPE: DNA
<213> ORGANISM: Artificial Sequence
<220> FEATURE:
<223> OTHER INFORMATION: Synthetic Primer

<400> SEQUENCE: 7
cgcggatcca tagtaacaaa ggattatagt gggaaat                       37

<210> SEQ ID NO 8
<211> LENGTH: 33
<212> TYPE: DNA
<213> ORGANISM: Artificial Sequence
<220> FEATURE:
<223> OTHER INFORMATION: Synthetic Primer

<400> SEQUENCE: 8
tcccccgggt tattttgtta ctctaggccc ata                           33
```

<210> SEQ ID NO 9
<211> LENGTH: 37
<212> TYPE: DNA
<213> ORGANISM: Artificial Sequence
<220> FEATURE:
<223> OTHER INFORMATION: Synthetic Primer

<400> SEQUENCE: 9
cgcggatcca tagtaacaaa ggattatagt gggaaat           37

<210> SEQ ID NO 10
<211> LENGTH: 37
<212> TYPE: DNA
<213> ORGANISM: Artificial Sequence
<220> FEATURE:
<223> OTHER INFORMATION: Synthetic Primer

<400> SEQUENCE: 10
tcccccgggt tattttgtta ctctaggacc atatgtc           37

<210> SEQ ID NO 11
<211> LENGTH: 43
<212> TYPE: DNA
<213> ORGANISM: Artificial Sequence
<220> FEATURE:
<223> OTHER INFORMATION: Synthetic Primer

<400> SEQUENCE: 11
cgcggatcca tagtaactaa agattatagt aaagaatcaa gag       43

<210> SEQ ID NO 12
<211> LENGTH: 37
<212> TYPE: DNA
<213> ORGANISM: Artificial Sequence
<220> FEATURE:
<223> OTHER INFORMATION: Synthetic Primer

<400> SEQUENCE: 12
tcccccgggt tattttgtta ctctaggacc atatgtc           37

<210> SEQ ID NO 13
<211> LENGTH: 27
<212> TYPE: DNA
<213> ORGANISM: Artificial Sequence
<220> FEATURE:
<223> OTHER INFORMATION: Synthetic Primer

<400> SEQUENCE: 13
ccgctcgagg tggtttctgg ggagaag                       27

<210> SEQ ID NO 14
<211> LENGTH: 37
<212> TYPE: DNA
<213> ORGANISM: Artificial Sequence
<220> FEATURE:
<223> OTHER INFORMATION: Synthetic Primer

<400> SEQUENCE: 14
cgggatcctt atttgccatt atatacttta ttgattt            37

<210> SEQ ID NO 15
<211> LENGTH: 27
<212> TYPE: DNA
<213> ORGANISM: Artificial Sequence
<220> FEATURE:

```
<223> OTHER INFORMATION: Synthetic Primer

<400> SEQUENCE: 15
ccgctcgagg tggtttctgg ggagaag                                           27

<210> SEQ ID NO 16
<211> LENGTH: 33
<212> TYPE: DNA
<213> ORGANISM: Artificial Sequence
<220> FEATURE:
<223> OTHER INFORMATION: Synthetic Primer

<400> SEQUENCE: 16
cgggatcctt atttgccatt gtatacttta ttg                                    33

<210> SEQ ID NO 17
<211> LENGTH: 44
<212> TYPE: DNA
<213> ORGANISM: Artificial Sequence
<220> FEATURE:
<223> OTHER INFORMATION: Synthetic Primer

<400> SEQUENCE: 17
catgccatgg cctaggatag taacaaagga ttatagtggg aaat                        44

<210> SEQ ID NO 18
<211> LENGTH: 32
<212> TYPE: DNA
<213> ORGANISM: Artificial Sequence
<220> FEATURE:
<223> OTHER INFORMATION: Synthetic Primer

<400> SEQUENCE: 18
cgggatcctt attttgttac tctaggccca ta                                     32

<210> SEQ ID NO 19
<211> LENGTH: 45
<212> TYPE: DNA
<213> ORGANISM: Artificial Sequence
<220> FEATURE:
<223> OTHER INFORMATION: Synthetic Primer

<400> SEQUENCE: 19
catgccatgg ctcgagatag taacaaagga ttatagtaaa gaatc                       45

<210> SEQ ID NO 20
<211> LENGTH: 24
<212> TYPE: DNA
<213> ORGANISM: Artificial Sequence
<220> FEATURE:
<223> OTHER INFORMATION: Synthetic Primer

<400> SEQUENCE: 20
cctaggcgga ccatattgag aagc                                              24

<210> SEQ ID NO 21
<211> LENGTH: 43
<212> TYPE: DNA
<213> ORGANISM: Artificial Sequence
<220> FEATURE:
<223> OTHER INFORMATION: Synthetic Primer

<400> SEQUENCE: 21
catgccatgg ccgcggatag taacaaagga ttatagtggg aaa                         43
```

<210> SEQ ID NO 22
<211> LENGTH: 32
<212> TYPE: DNA
<213> ORGANISM: Artificial Sequence
<220> FEATURE:
<223> OTHER INFORMATION: Synthetic Primer

<400> SEQUENCE: 22
ggctcgagtt ttttgacagt tttattttc ca                          32

<210> SEQ ID NO 23
<211> LENGTH: 50
<212> TYPE: DNA
<213> ORGANISM: Artificial Sequence
<220> FEATURE:
<223> OTHER INFORMATION: Synthetic Primer

<400> SEQUENCE: 23
catgccatgg cccgggatag taactaaaga ttatagtaaa gaatcaagag       50

<210> SEQ ID NO 24
<211> LENGTH: 38
<212> TYPE: DNA
<213> ORGANISM: Artificial Sequence
<220> FEATURE:
<223> OTHER INFORMATION: Synthetic Primer

<400> SEQUENCE: 24
tccccgcgga tttttgacgg ttcttgtttt ccaagatt                    38

<210> SEQ ID NO 25
<211> LENGTH: 34
<212> TYPE: DNA
<213> ORGANISM: Artificial Sequence
<220> FEATURE:
<223> OTHER INFORMATION: Synthetic Primer

<400> SEQUENCE: 25
catgccatgg cctagggtgg tttctgggga gaag                        34

<210> SEQ ID NO 26
<211> LENGTH: 37
<212> TYPE: DNA
<213> ORGANISM: Artificial Sequence
<220> FEATURE:
<223> OTHER INFORMATION: Synthetic Primer

<400> SEQUENCE: 26
cgggatcctt atttgccatt atatacttta ttgattt                     37

<210> SEQ ID NO 27
<211> LENGTH: 34
<212> TYPE: DNA
<213> ORGANISM: Artificial Sequence
<220> FEATURE:
<223> OTHER INFORMATION: Synthetic Primer

<400> SEQUENCE: 27
catgccatgg ctcgaggtgg tttctgggga gaag                        34

<210> SEQ ID NO 28
<211> LENGTH: 32
<212> TYPE: DNA
<213> ORGANISM: Artificial Sequence
<220> FEATURE:
<223> OTHER INFORMATION: Synthetic Primer

```
<400> SEQUENCE: 28
cctaggtgta ttgttaaagt cctttaaatc ac                          32

<210> SEQ ID NO 29
<211> LENGTH: 76
<212> TYPE: DNA
<213> ORGANISM: Artificial Sequence
<220> FEATURE:
<223> OTHER INFORMATION: Synthetic Primer

<400> SEQUENCE: 29
catgccatgg gcagcagcca tcatcatcat catcacagca gcatagtaac taaagattat    60
agtaaagaat caagag                                                    76

<210> SEQ ID NO 30
<211> LENGTH: 60
<212> TYPE: DNA
<213> ORGANISM: Artificial Sequence
<220> FEATURE:
<223> OTHER INFORMATION: Synthetic Primer

<400> SEQUENCE: 30
catgccatgg gcagcagcca tcatcatcat catcacagca gcgtggtttc tggggagaag    60

<210> SEQ ID NO 31
<211> LENGTH: 56
<212> TYPE: DNA
<213> ORGANISM: Artificial Sequence
<220> FEATURE:
<223> OTHER INFORMATION: Synthetic Primer

<400> SEQUENCE: 31
cgggatcctt acttctcaaa ttgaggatga gaccattttg ttactctagg cccata        56

<210> SEQ ID NO 32
<211> LENGTH: 61
<212> TYPE: DNA
<213> ORGANISM: Artificial Sequence
<220> FEATURE:
<223> OTHER INFORMATION: Synthetic Primer

<400> SEQUENCE: 32
cgggatcctt acttctcaaa ttgaggatga gaccatttgc cattatatac tttattgatt    60
t                                                                    61

<210> SEQ ID NO 33
<211> LENGTH: 282
<212> TYPE: PRT
<213> ORGANISM: Staphylococcus aureus

<400> SEQUENCE: 33

Ile Val Thr Lys Asp Tyr Ser Lys Glu Ser Arg Val Asn Glu Asn Ser
1               5                   10                  15

Lys Tyr Asp Thr Pro Ile Pro Asp Trp Tyr Leu Gly Ser Ile Leu Asn
            20                  25                  30

Arg Leu Gly Asp Gln Ile Tyr Tyr Ala Lys Glu Leu Thr Asn Lys Tyr
        35                  40                  45

Glu Tyr Gly Glu Lys Glu Tyr Lys Gln Ala Ile Asp Lys Leu Met Thr
    50                  55                  60

Arg Val Leu Gly Glu Asp His Tyr Leu Leu Glu Lys Lys Lys Ala Gln
65                  70                  75                  80
```

```
Tyr Glu Ala Tyr Lys Lys Trp Phe Glu Lys His Lys Ser Glu Asn Pro
             85                  90                  95

His Ser Ser Leu Lys Lys Ile Lys Phe Asp Asp Phe Asp Leu Tyr Arg
            100                 105                 110

Leu Thr Lys Lys Glu Tyr Asn Glu Leu His Gln Ser Leu Lys Glu Ala
            115                 120                 125

Val Asp Glu Phe Asn Ser Glu Val Lys Asn Ile Gln Ser Lys Gln Lys
            130                 135                 140

Asp Leu Leu Pro Tyr Asp Glu Ala Thr Glu Asn Arg Val Thr Asn Gly
145                 150                 155                 160

Ile Tyr Asp Phe Val Cys Glu Ile Asp Thr Leu Tyr Ala Ala Tyr Phe
                165                 170                 175

Asn His Ser Gln Tyr Gly His Asn Ala Lys Glu Leu Arg Ala Lys Leu
            180                 185                 190

Asp Ile Ile Leu Gly Asp Ala Lys Asp Pro Val Arg Ile Thr Asn Glu
            195                 200                 205

Arg Ile Arg Lys Glu Met Met Asp Asp Leu Asn Ser Ile Ile Asp Asp
210                 215                 220

Phe Phe Met Asp Thr Asn Met Asn Arg Pro Leu Asn Ile Thr Lys Phe
225                 230                 235                 240

Asn Pro Asn Ile His Asp Tyr Thr Asn Lys Pro Glu Asn Arg Asp Asn
                245                 250                 255

Phe Asp Lys Leu Val Lys Glu Thr Arg Glu Ala Ile Ala Asn Ala Asp
            260                 265                 270

Glu Ser Trp Lys Thr Arg Thr Val Lys Asn
275                 280

<210> SEQ ID NO 34
<211> LENGTH: 279
<212> TYPE: PRT
<213> ORGANISM: Staphylococcus aureus

<400> SEQUENCE: 34

Ile Val Thr Lys Asp Tyr Ser Gly Lys Ser Gln Val Asn Ala Gly Ser
1               5                   10                  15

Lys Asn Gly Lys Gln Ile Ala Asp Gly Tyr Tyr Trp Gly Ile Ile Glu
            20                  25                  30

Asn Leu Glu Asn Gln Phe Tyr Asn Ile Phe His Leu Leu Asp Gln His
            35                  40                  45

Lys Tyr Ala Glu Lys Glu Tyr Lys Asp Ala Val Asp Lys Leu Lys Thr
        50                  55                  60

Arg Val Leu Glu Glu Asp Gln Tyr Leu Leu Glu Arg Lys Lys Glu Lys
65                  70                  75                  80

Tyr Glu Ile Tyr Lys Glu Leu Tyr Lys Lys Tyr Lys Lys Glu Asn Pro
                85                  90                  95

Asn Thr Gln Val Lys Met Lys Ala Phe Asp Lys Tyr Asp Leu Gly Asp
            100                 105                 110

Leu Thr Met Glu Glu Tyr Asn Asp Leu Ser Lys Leu Leu Thr Lys Ala
            115                 120                 125

Leu Asp Asn Phe Lys Leu Glu Val Lys Ile Glu Ser Glu Asn Pro
            130                 135                 140

Asp Leu Lys Pro Tyr Ser Glu Ser Glu Arg Thr Ala Tyr Gly Lys
145                 150                 155                 160

Ile Asp Ser Leu Val Asp Gln Ala Tyr Ser Val Tyr Phe Ala Tyr Val
                165                 170                 175
```

```
Thr Asp Ala Gln His Lys Thr Glu Ala Leu Asn Leu Arg Ala Lys Ile
                180                 185                 190

Asp Leu Ile Leu Gly Asp Glu Lys Asp Pro Ile Arg Val Thr Asn Gln
            195                 200                 205

Arg Thr Glu Lys Glu Met Ile Lys Asp Leu Glu Ser Ile Ile Asp Asp
210                 215                 220

Phe Phe Ile Glu Thr Lys Leu Asn Arg Pro Lys His Ile Thr Arg Tyr
225                 230                 235                 240

Asp Gly Thr Lys His Asp Tyr His Lys His Lys Asp Gly Phe Asp Ala
                245                 250                 255

Leu Val Lys Glu Thr Arg Glu Ala Val Ala Lys Ala Asp Glu Ser Trp
            260                 265                 270

Lys Asn Lys Thr Val Lys Lys
            275

<210> SEQ ID NO 35
<211> LENGTH: 279
<212> TYPE: PRT
<213> ORGANISM: Staphylococcus aureus

<400> SEQUENCE: 35

Ile Val Thr Lys Asp Tyr Ser Gly Lys Ser Gln Val Asn Ala Gly Ser
1               5                   10                  15

Lys Asn Gly Lys Gln Ile Ala Asp Gly Tyr Tyr Trp Gly Ile Ile Glu
            20                  25                  30

Asn Leu Glu Asn Gln Phe Tyr Asn Ile Phe His Leu Leu Asp Gln His
            35                  40                  45

Lys Tyr Ala Glu Lys Glu Tyr Lys Asp Ala Leu Asp Lys Leu Lys Thr
        50                  55                  60

Arg Val Leu Glu Glu Asp Gln Tyr Leu Leu Glu Arg Lys Lys Glu Lys
65                  70                  75                  80

Tyr Glu Ile Tyr Lys Glu Leu Tyr Lys Lys Tyr Lys Lys Glu Asn Pro
                85                  90                  95

Asn Thr Gln Val Lys Met Lys Ala Phe Asp Lys Tyr Asp Leu Gly Asp
            100                 105                 110

Leu Thr Met Glu Glu Tyr Asn Asp Leu Ser Lys Leu Leu Thr Lys Ala
            115                 120                 125

Leu Asp Asn Phe Lys Leu Glu Val Lys Lys Ile Glu Ser Glu Asn Pro
130                 135                 140

Asp Leu Arg Pro Tyr Ser Glu Ser Glu Arg Thr Ala Tyr Gly Lys
145                 150                 155                 160

Ile Asp Ser Leu Val Asp Gln Ala Tyr Ser Val Tyr Phe Ala Tyr Val
                165                 170                 175

Thr Asp Ala Gln His Lys Thr Glu Ala Leu Asn Leu Arg Ala Lys Ile
                180                 185                 190

Asp Leu Ile Leu Gly Asp Glu Lys Asp Pro Ile Arg Val Thr Asn Gln
            195                 200                 205

Arg Thr Glu Lys Glu Met Ile Lys Asp Leu Glu Ser Ile Ile Asp Asp
210                 215                 220

Phe Phe Ile Glu Thr Lys Leu Asn Arg Pro Gln His Ile Thr Arg Tyr
225                 230                 235                 240

Asp Gly Thr Lys His Asp Tyr His Lys His Lys Asp Gly Phe Asp Ala
                245                 250                 255

Leu Val Lys Glu Thr Arg Glu Ala Val Ser Lys Ala Asp Glu Ser Trp
```

```
                    260                 265                 270

Lys Thr Lys Thr Val Lys Lys
        275

<210> SEQ ID NO 36
<211> LENGTH: 277
<212> TYPE: PRT
<213> ORGANISM: Staphylococcus aureus

<400> SEQUENCE: 36

Ile Val Thr Lys Asp Tyr Ser Lys Glu Ser Arg Val Asn Glu Lys Ser
1               5                   10                  15

Lys Lys Gly Ala Thr Val Ser Asp Tyr Tyr Trp Lys Ile Ile Asp
            20                  25                  30

Ser Leu Glu Ala Gln Phe Thr Gly Ala Ile Asp Leu Leu Glu Asp Tyr
        35                  40                  45

Lys Tyr Gly Asp Pro Ile Tyr Lys Glu Ala Lys Asp Arg Leu Met Thr
    50                  55                  60

Arg Val Leu Gly Glu Asp Gln Tyr Leu Leu Lys Lys Ile Asp Glu
65                  70                  75                  80

Tyr Glu Leu Tyr Lys Lys Trp Tyr Lys Ser Ser Asn Lys Asn Thr Asn
                85                  90                  95

Met Leu Thr Phe His Lys Tyr Asn Leu Tyr Asn Leu Thr Met Asn Glu
            100                 105                 110

Tyr Asn Asp Ile Phe Asn Ser Leu Lys Asp Ala Val Tyr Gln Phe Asn
        115                 120                 125

Lys Glu Val Lys Glu Ile Glu His Lys Asn Val Asp Leu Lys Gln Phe
    130                 135                 140

Asp Lys Asp Gly Glu Asp Lys Ala Thr Lys Glu Val Tyr Asp Leu Val
145                 150                 155                 160

Ser Glu Ile Asp Thr Leu Val Val Thr Tyr Tyr Ala Asp Lys Asp Tyr
                165                 170                 175

Gly Glu His Ala Lys Glu Leu Arg Ala Lys Leu Asp Leu Ile Leu Gly
            180                 185                 190

Asp Thr Asp Asn Pro His Lys Ile Thr Asn Glu Arg Ile Lys Lys Glu
        195                 200                 205

Met Ile Asp Asp Leu Asn Ser Ile Ile Asp Asp Phe Phe Met Glu Thr
    210                 215                 220

Lys Gln Asn Arg Pro Asn Ser Ile Thr Lys Tyr Asp Pro Thr Lys His
225                 230                 235                 240

Asn Phe Lys Glu Lys Ser Glu Asn Lys Pro Asn Phe Asp Lys Leu Val
                245                 250                 255

Glu Glu Thr Lys Lys Ala Val Lys Glu Ala Asp Glu Ser Trp Lys Asn
            260                 265                 270

Lys Thr Val Lys Lys
        275

<210> SEQ ID NO 37
<211> LENGTH: 282
<212> TYPE: PRT
<213> ORGANISM: Staphylococcus aureus

<400> SEQUENCE: 37

Ile Val Thr Lys Asp Tyr Ser Gly Lys Ser Gln Val Asn Ala Gly Ser
1               5                   10                  15

Lys Asn Gly Thr Leu Ile Asp Ser Arg Tyr Leu Asn Ser Ala Leu Tyr
```

```
            20                  25                  30
Tyr Leu Glu Asp Tyr Ile Ile Tyr Ala Ile Gly Leu Thr Asn Lys Tyr
            35                  40                  45
Glu Tyr Gly Asp Asn Ile Tyr Lys Glu Ala Lys Asp Arg Leu Leu Glu
        50                  55                  60
Lys Val Leu Arg Glu Asp Gln Tyr Leu Leu Glu Arg Lys Lys Ser Gln
65                  70                  75                  80
Tyr Glu Asp Tyr Lys Gln Trp Tyr Ala Asn Tyr Lys Lys Glu Asn Pro
                85                  90                  95
Arg Thr Asp Leu Lys Met Ala Asn Phe His Lys Tyr Asn Leu Glu Glu
            100                 105                 110
Leu Ser Met Lys Glu Tyr Asn Glu Leu Gln Asp Ala Leu Lys Arg Ala
        115                 120                 125
Leu Asp Asp Phe His Arg Glu Val Lys Asp Ile Lys Asp Lys Asn Ser
    130                 135                 140
Asp Leu Lys Thr Phe Asn Ala Ala Glu Glu Asp Lys Ala Thr Lys Glu
145                 150                 155                 160
Val Tyr Asp Leu Val Ser Glu Ile Asp Thr Leu Val Val Ser Tyr Tyr
                165                 170                 175
Gly Asp Lys Asp Tyr Gly Glu His Ala Lys Glu Leu Arg Ala Lys Leu
            180                 185                 190
Asp Leu Ile Leu Gly Asp Thr Asp Asn Pro His Lys Ile Thr Asn Glu
        195                 200                 205
Arg Ile Lys Lys Glu Met Ile Asp Asp Leu Asn Ser Ile Ile Asp Asp
    210                 215                 220
Phe Phe Met Glu Thr Lys Gln Asn Arg Pro Lys Ser Ile Thr Lys Tyr
225                 230                 235                 240
Asn Pro Thr Thr His Asn Tyr Lys Thr Asn Ser Asp Asn Lys Pro Asn
                245                 250                 255
Phe Asp Lys Leu Val Glu Glu Thr Lys Lys Ala Val Lys Glu Ala Asp
            260                 265                 270
Asp Ser Trp Lys Lys Lys Thr Val Lys Lys
        275                 280

<210> SEQ ID NO 38
<211> LENGTH: 135
<212> TYPE: PRT
<213> ORGANISM: Staphylococcus aureus

<400> SEQUENCE: 38

Val Val Ser Gly Glu Lys Asn Pro Tyr Val Ser Lys Ala Leu Glu Leu
1               5                   10                  15
Lys Asp Lys Ser Asn Lys Ser Asn Ser Tyr Glu Asn Tyr Arg Asp Ser
            20                  25                  30
Leu Glu Ser Leu Ile Ser Ser Leu Ser Phe Ala Asp Tyr Glu Lys Tyr
        35                  40                  45
Glu Glu Pro Glu Tyr Glu Lys Ala Val Lys Lys Tyr Gln Gln Lys Phe
    50                  55                  60
Met Ala Glu Asp Asp Ala Leu Lys Asn Phe Leu Asn Glu Glu Lys Lys
65                  70                  75                  80
Ile Lys Asn Ala Asp Ile Ser Arg Lys Ser Asn Asn Leu Leu Gly Leu
                85                  90                  95
Thr His Glu Arg Tyr Ser Tyr Ile Phe Asp Thr Leu Lys Lys Asn Lys
            100                 105                 110
```

Gln Glu Phe Leu Lys Asp Ile Glu Glu Ile Gln Leu Lys Asn Ser Asp
            115                 120                 125

Leu Lys Asp Phe Asn Asn Thr
    130                 135

<210> SEQ ID NO 39
<211> LENGTH: 132
<212> TYPE: PRT
<213> ORGANISM: Staphylococcus aureus

<400> SEQUENCE: 39

Val Val Ser Gly Glu Lys Asn Pro Tyr Val Ser Glu Ser Leu Lys Leu
1               5                   10                  15

Thr Asn Asn Lys Asn Lys Ser Arg Thr Val Glu Glu Tyr Lys Lys Ser
            20                  25                  30

Leu Asp Asp Leu Ile Trp Ser Phe Pro Asn Leu Asp Asn Glu Arg Phe
        35                  40                  45

Asp Asn Pro Glu Tyr Lys Glu Ala Met Lys Lys Tyr Gln Gln Arg Phe
    50                  55                  60

Met Ala Glu Asp Glu Ala Leu Lys Lys Phe Phe Ser Glu Glu Lys Lys
65                  70                  75                  80

Ile Lys Asn Gly Asn Thr Asp Asn Leu Asp Tyr Leu Gly Leu Ser His
                85                  90                  95

Glu Arg Tyr Glu Ser Val Phe Asn Thr Leu Lys Lys Gln Ser Glu Glu
            100                 105                 110

Phe Leu Lys Glu Ile Glu Asp Ile Lys Lys Asp Asn Pro Glu Leu Lys
        115                 120                 125

Asp Phe Asn Glu
    130

<210> SEQ ID NO 40
<211> LENGTH: 482
<212> TYPE: PRT
<213> ORGANISM: Staphylococcus aureus

<400> SEQUENCE: 40

Val Val Ser Gly Glu Lys Asn Pro Tyr Val Ser Glu Ser Leu Lys Leu
1               5                   10                  15

Thr Asn Asn Lys Asn Lys Ser Arg Thr Val Glu Glu Tyr Lys Lys Ser
            20                  25                  30

Leu Asp Asp Leu Ile Trp Ser Phe Pro Asn Leu Asp Asn Glu Arg Phe
        35                  40                  45

Asp Asn Pro Glu Tyr Lys Glu Ala Met Lys Lys Tyr Gln Gln Arg Phe
    50                  55                  60

Met Ala Glu Asp Glu Ala Leu Lys Lys Phe Phe Ser Glu Glu Lys Lys
65                  70                  75                  80

Ile Lys Asn Gly Asn Thr Asp Asn Leu Asp Tyr Leu Gly Leu Ser His
                85                  90                  95

Glu Arg Tyr Glu Ser Val Phe Asn Thr Leu Lys Lys Gln Ser Glu Glu
            100                 105                 110

Phe Leu Lys Glu Ile Glu Asp Ile Lys Lys Asp Asn Pro Glu Leu Lys
        115                 120                 125

Asp Phe Asn Glu Glu Glu Gln Leu Lys Cys Asp Leu Glu Leu Asn Lys
    130                 135                 140

Leu Glu Asn Gln Ile Leu Met Leu Gly Lys Thr Phe Tyr Gln Asn Tyr
145                 150                 155                 160

Arg Asp Asp Val Glu Ser Leu Tyr Ser Lys Leu Asp Leu Ile Met Gly
                165                 170                 175

Tyr Lys Asp Glu Glu Arg Ala Asn Lys Lys Ala Val Asn Lys Arg Met
            180                 185                 190

Leu Glu Asn Lys Lys Glu Asp Leu Glu Thr Ile Ile Asp Glu Phe Phe
            195                 200                 205

Ser Asp Ile Asp Lys Thr Arg Pro Asn Asn Ile Pro Val Leu Glu Asp
            210                 215                 220

Glu Lys Gln Glu Glu Asn His Lys Asn Met Ala Gln Leu Lys Ser
225                 230                 235                 240

Asp Thr Glu Ala Ala Lys Ser Asp Glu Ser Lys Arg Ser Lys Arg Ser
                245                 250                 255

Lys Arg Ser Leu Asn Thr Gln Asn His Lys Pro Ala Ser Gln Glu Val
            260                 265                 270

Ser Glu Gln Gln Lys Ala Glu Tyr Asp Lys Arg Ala Glu Arg Lys
            275                 280                 285

Ala Arg Phe Leu Asp Asn Gln Lys Ile Lys Lys Thr Pro Val Val Ser
    290                 295                 300

Leu Glu Tyr Asp Phe Glu His Lys Gln Arg Ile Asp Asn Glu Asn Asp
305                 310                 315                 320

Lys Lys Leu Val Val Ser Ala Pro Thr Lys Lys Pro Thr Ser Pro Thr
                325                 330                 335

Thr Tyr Thr Glu Thr Thr Thr Gln Val Pro Met Pro Thr Val Glu Arg
            340                 345                 350

Gln Thr Gln Gln Gln Ile Ile Tyr Asn Ala Pro Lys Gln Leu Ala Gly
            355                 360                 365

Leu Asn Gly Glu Ser His Asp Phe Thr Thr Thr His Gln Ser Pro Thr
    370                 375                 380

Thr Ser Asn His Thr His Asn Asn Val Glu Phe Glu Glu Thr Ser
385                 390                 395                 400

Ala Leu Pro Gly Arg Lys Ser Gly Ser Leu Val Gly Ile Ser Gln Ile
                405                 410                 415

Asp Ser Ser His Leu Thr Glu Arg Glu Lys Arg Val Ile Lys Arg Glu
            420                 425                 430

His Val Arg Glu Ala Gln Lys Leu Val Asp Asn Tyr Lys Asp Thr His
            435                 440                 445

Ser Tyr Lys Asp Arg Ile Asn Ala Gln Gln Lys Val Asn Thr Leu Ser
    450                 455                 460

Glu Gly His Gln Lys Arg Phe Asn Lys Gln Ile Asn Lys Val Tyr Asn
465                 470                 475                 480

Gly Lys

<210> SEQ ID NO 41
<211> LENGTH: 434
<212> TYPE: PRT
<213> ORGANISM: Staphylococcus aureus

<400> SEQUENCE: 41

Ile Val Thr Lys Asp Tyr Ser Lys Glu Ser Arg Val Asn Glu Lys Ser
1               5                   10                  15

Lys Lys Gly Ala Thr Val Ser Asp Tyr Tyr Tyr Trp Lys Ile Ile Asp
            20                  25                  30

Ser Leu Glu Ala Gln Phe Thr Gly Ala Ile Asp Leu Leu Glu Asp Tyr
        35                  40                  45

```
Lys Tyr Gly Asp Pro Ile Tyr Lys Glu Ala Lys Asp Arg Leu Met Thr
 50                  55                  60

Arg Val Leu Gly Glu Asp Gln Tyr Leu Lys Lys Lys Ile Asp Glu
 65                  70                  75                  80

Tyr Glu Leu Tyr Lys Lys Trp Tyr Lys Ser Ser Asn Lys Asn Thr Asn
                 85                  90                  95

Met Leu Thr Phe His Lys Tyr Asn Leu Tyr Asn Leu Thr Met Asn Glu
            100                 105                 110

Tyr Asn Asp Ile Phe Asn Ser Leu Lys Asp Ala Val Tyr Gln Phe Asn
            115                 120                 125

Lys Glu Val Lys Glu Ile Glu His Lys Asn Val Asp Leu Lys Gln Phe
130                 135                 140

Asp Lys Asp Gly Glu Asp Lys Ala Thr Lys Glu Val Tyr Asp Leu Val
145                 150                 155                 160

Ser Glu Ile Asp Thr Leu Val Val Thr Tyr Ala Asp Lys Asp Tyr
                165                 170                 175

Gly Glu His Ala Lys Glu Leu Arg Ala Lys Leu Asp Leu Ile Leu Gly
            180                 185                 190

Asp Thr Asp Asn Pro His Lys Ile Thr Asn Glu Arg Ile Lys Lys Glu
            195                 200                 205

Met Ile Asp Asp Leu Asn Ser Ile Ile Asp Asp Phe Phe Met Glu Thr
210                 215                 220

Lys Gln Asn Arg Pro Asn Ser Ile Thr Lys Tyr Asp Pro Thr Lys His
225                 230                 235                 240

Asn Phe Lys Glu Lys Ser Glu Asn Lys Pro Asn Phe Asp Lys Leu Val
                245                 250                 255

Glu Glu Thr Lys Lys Ala Val Lys Glu Ala Asp Glu Ser Trp Lys Asn
            260                 265                 270

Lys Thr Val Lys Lys Tyr Glu Glu Thr Val Thr Lys Ser Pro Val Val
            275                 280                 285

Lys Glu Glu Lys Lys Val Glu Glu Pro Gln Leu Pro Lys Val Gly Asn
            290                 295                 300

Gln Gln Glu Val Lys Thr Thr Ala Gly Lys Ala Glu Glu Thr Thr Gln
305                 310                 315                 320

Pro Val Ala Gln Pro Leu Val Lys Ile Pro Gln Glu Thr Ile Tyr Gly
                325                 330                 335

Glu Thr Val Lys Gly Pro Glu Tyr Pro Thr Met Glu Asn Lys Thr Leu
            340                 345                 350

Gln Gly Glu Ile Val Gln Gly Pro Asp Phe Leu Thr Met Glu Gln Asn
            355                 360                 365

Arg Pro Ser Leu Ser Asp Asn Tyr Thr Gln Pro Thr Thr Pro Asn Pro
370                 375                 380

Ile Leu Glu Gly Leu Glu Gly Ser Ser Ser Lys Leu Glu Ile Lys Pro
385                 390                 395                 400

Gln Gly Thr Glu Ser Thr Leu Lys Gly Ile Gln Gly Glu Ser Ser Asp
                405                 410                 415

Ile Glu Val Lys Pro Gln Ala Thr Glu Thr Thr Glu Ala Ser Gln Tyr
            420                 425                 430

Gly Pro

<210> SEQ ID NO 42
<211> LENGTH: 609
<212> TYPE: PRT
<213> ORGANISM: Staphylococcus aureus
```

<400> SEQUENCE: 42

```
Met Lys Lys Gln Ile Ile Ser Leu Gly Ala Leu Ala Val Ala Ser Ser
 1               5                  10                  15

Leu Phe Thr Trp Asp Asn Lys Ala Asp Ala Ile Val Thr Lys Asp Tyr
             20                  25                  30

Ser Gly Lys Ser Gln Val Asn Ala Gly Ser Lys Asn Gly Thr Leu Ile
         35                  40                  45

Asp Ser Arg Tyr Leu Asn Ser Ala Leu Tyr Tyr Leu Glu Asp Tyr Ile
     50                  55                  60

Ile Tyr Ala Ile Gly Leu Thr Asn Lys Tyr Glu Tyr Gly Asp Asn Ile
 65                  70                  75                  80

Tyr Lys Glu Ala Lys Asp Arg Leu Leu Glu Lys Val Leu Arg Glu Asp
                 85                  90                  95

Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
        115                 120                 125

Ala Asn Phe His Lys Tyr Asn Leu Glu Glu Leu Ser Met Lys Glu Tyr
    130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Asp Phe Phe Met Glu Thr Lys
                245                 250                 255

Gln Asn Arg Pro Lys Ser Ile Thr Lys Tyr Asn Pro Thr Thr His Asn
            260                 265                 270

Tyr Lys Thr Asn Ser Asp Asn Lys Pro Asn Phe Asp Lys Leu Val Glu
        275                 280                 285

Glu Thr Lys Lys Ala Val Lys Glu Ala Asp Asp Ser Trp Lys Lys Lys
    290                 295                 300

Thr Val Lys Lys Tyr Gly Glu Thr Glu Thr Lys Ser Pro Val Val Lys
305                 310                 315                 320

Glu Glu Lys Lys Val Glu Glu Pro Gln Ala Pro Lys Val Asp Asn Gln
                325                 330                 335

Gln Glu Val Lys Thr Thr Ala Gly Lys Ala Glu Glu Thr Gln Pro
            340                 345                 350

Val Ala Gln Pro Leu Val Lys Ile Pro Gln Gly Thr Ile Thr Gly Glu
        355                 360                 365

Ile Val Lys Gly Pro Glu Tyr Pro Thr Met Glu Asn Lys Thr Val Gln
    370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
```

```
                405                 410                 415
Leu Glu Gly Leu Glu Gly Ser Ser Lys Leu Glu Ile Lys Pro Gln
            420                 425                 430
Gly Thr Glu Ser Thr Leu Lys Gly Thr Gln Gly Glu Ser Ser Asp Ile
                435                 440                 445
Glu Val Lys Pro Gln Ala Thr Glu Thr Thr Glu Ala Ser Gln Tyr Gly
        450                 455                 460
Pro Arg Pro Gln Phe Asn Lys Thr Pro Lys Tyr Val Lys Tyr Arg Asp
465                 470                 475                 480
Ala Gly Thr Gly Ile Arg Glu Tyr Asn Asp Gly Thr Phe Gly Tyr Glu
                485                 490                 495
Ala Arg Pro Arg Phe Asn Lys Pro Ser Glu Thr Asn Ala Tyr Asn Val
            500                 505                 510
Thr Thr His Ala Asn Gly Gln Val Ser Tyr Gly Ala Arg Pro Thr Gln
            515                 520                 525
Asn Lys Pro Ser Lys Thr Asn Ala Tyr Asn Val Thr Thr His Gly Asn
        530                 535                 540
Gly Gln Val Ser Tyr Gly Ala Arg Pro Thr Gln Asn Lys Pro Ser Lys
545                 550                 555                 560
Thr Asn Ala Tyr Asn Val Thr Thr His Ala Asn Gly Gln Val Ser Tyr
                565                 570                 575
Gly Ala Arg Pro Thr Tyr Lys Lys Pro Ser Lys Thr Asn Ala Tyr Asn
            580                 585                 590
Val Thr Thr His Ala Asp Gly Thr Ala Thr Tyr Gly Pro Arg Val Thr
            595                 600                 605
Lys

<210> SEQ ID NO 43
<211> LENGTH: 447
<212> TYPE: DNA
<213> ORGANISM: Staphylococcus aureus

<400> SEQUENCE: 43
atagtaacaa aggattatag tgggaaatca caagttaatg ctgggagtaa aaatgggaca      60
ttaatagata gcagatattt aaattcagct ctatattatt tggaagacta tataatttat    120
gctataggat taactaataa atatgaatat ggagataata tttataaaga agctaaagat    180
aggttgttgg aaaaggtatt aagggaagat caatatcttt tggagagaaa gaaatctcaa    240
tatgaagatt ataaacaatg gtatgcaaat tataaaaaag aaaatcctcg tacagattta    300
aaaatggcta attttcataa atataattta gaagaacttt cgatgaaaga atacaatgaa    360
ctacaggatg cattaaagag agcactggat gattttcaca gaagagttaa agatattaag    420
gataagaatt cagacttgaa aactttt                                        447

<210> SEQ ID NO 44
<211> LENGTH: 399
<212> TYPE: DNA
<213> ORGANISM: Staphylococcus aureus

<400> SEQUENCE: 44
aatgcagcag aagaagataa agcaactaag gaagtatacg atctcgtatc tgaaattgat     60
acattagttg tatcatatta tggtgataag gattatgggg agcacgcgaa agagttacga    120
gcaaaactgg acttaatcct tggagataca gacaatccac ataaaattac aaatgaacgt    180
attaaaaaag aaatgattga tgacttaaat tcaattattg atgatttctt tatggaaact    240
```

| | |
|---|---|
| aaacaaaata gaccgaaatc tataacgaaa tataatccta caacacataa ctataaaaca | 300 |
| aatagtgata ataaacctaa ttttgataaa ttagttgaag aaacgaaaaa agcagttaaa | 360 |
| gaagcagatg attcttggaa aaagaaaact gtcaaaaaa | 399 |

<210> SEQ ID NO 45
<211> LENGTH: 471
<212> TYPE: DNA
<213> ORGANISM: Staphylococcus aureus

<400> SEQUENCE: 45

| | |
|---|---|
| tacggagaaa ctgaaacaaa atcgccagta gtaaagaag agaagaaagt tgaagaacct | 60 |
| caagcaccta aagttgataa ccaacaagag gttaaaacta cggctggtaa agctgaagaa | 120 |
| acaacacaac cagttgcaca accattagtt aaaattccac agggcacaat tacaggtgaa | 180 |
| attgtaaaag gtccggaata tccaacgatg gaaaataaaa cggtacaagg tgaaatcgtt | 240 |
| caaggtcccg attttctaac aatggaacaa agcggcccat cattaagcaa taattataca | 300 |
| aacccaccgt taacgaaccc tatttagaa ggtcttgaag gtagctcatc taaacttgaa | 360 |
| ataaaaccac aaggtactga atcaacgtta aaaggtactc aaggagaatc aagtgatatt | 420 |
| gaagttaaac ctcaagcaac tgaaacaaca gaagcttctc aatatggtcc g | 471 |

<210> SEQ ID NO 46
<211> LENGTH: 435
<212> TYPE: DNA
<213> ORGANISM: Staphylococcus aureus

<400> SEQUENCE: 46

| | |
|---|---|
| agaccgcaat ttaacaaaac acctaaatat gttaaatata gagatgctgg tacaggtatc | 60 |
| cgtgaataca acgatggaac atttggatat gaagcgagac caagattcaa taagccatca | 120 |
| gaaacaaatg catataacgt aacaacacat gcaaatggtc aagtatcata cggagctcgt | 180 |
| ccgacacaaa acaagccaag caaaacaaac gcatataacg taacaacaca tggaaacggc | 240 |
| caagtatcat atggcgctcg cccaacacaa aacaagccaa gcaaaacaaa tgcatacaac | 300 |
| gtaacaacac atgcaaacgg tcaagtgtca tacggagctc gcccgacata caagaagcca | 360 |
| agtaaaacaa atgcatacaa tgtaacaaca catgcagatg gtactgcgac atatgggcct | 420 |
| agagtaacaa aataa | 435 |

<210> SEQ ID NO 47
<211> LENGTH: 510
<212> TYPE: DNA
<213> ORGANISM: Staphylococcus aureus

<400> SEQUENCE: 47

| | |
|---|---|
| atgaaaaagc aaataatttc gctaggcgca ttagcagttg catctagctt atttacatgg | 60 |
| gataacaaag cagatgcgat agtaacaaag gattatagta agaatcaag agtgaatgag | 120 |
| aaaagtaaaa agggagctac tgtttcagat tattactatt ggaaaataat tgatagttta | 180 |
| gaggcacaat ttactggagc aatagactta ttggaagatt ataaatatgg agatcctatc | 240 |
| tataaagaag cgaaagatag attgatgaca agagtattag gagaagacca gtatttatta | 300 |
| aagaaaaaga ttgatgaata tgagctttat aaaagtggt ataaaagttc aaataagaac | 360 |
| actaatatgc ttactttcca taatataat ctttacaatt taacaatgaa tgaatataac | 420 |
| gatatttta actcttgaa agatgcagtt tatcaattta ataagaagt taagaaaata | 480 |

```
gagcataaaa atgttgactt gaagcagttt                                      510
```

<210> SEQ ID NO 48
<211> LENGTH: 399
<212> TYPE: DNA
<213> ORGANISM: Staphylococcus aureus

<400> SEQUENCE: 48

```
gataaagatg gagaagacaa ggcaactaaa gaagtttatg accttgtttc tgaaattgat     60
acattagttg taacttatta tgctgataag gattatgggg agcatgcgaa agagttacga   120
gcaaaactgg acttaatcct tggagataca gacaatccac ataaaattac aaatgagcgt   180
ataaaaaaag aaatgatcga tgacttaaat tcaattatag atgatttctt tatggagact   240
aaacaaaata gaccgaattc tataacaaaa tatgatccaa caaaacacaa ttttaaagag   300
aagagtgaaa ataaacctaa ttttgataaa ttagttgaag aaacaaaaaa agcagttaaa   360
gaagcagacg aatcttggaa aaataaaact gtcaaaaaa                           399
```

<210> SEQ ID NO 49
<211> LENGTH: 471
<212> TYPE: DNA
<213> ORGANISM: Staphylococcus aureus

<400> SEQUENCE: 49

```
tacgaggaaa ctgtaacaaa atctcctgtt gtaaagaag agaagaaagt tgaagaacct     60
caattaccta agttggaaa ccagcaagag gttaaaacta cggctggtaa agctgaagaa   120
acaacacaac cagtggcaca gccattagta aaaattccac aagaaacaat ctatggtgaa   180
actgtaaaag gtccagaata tccaacgatg gaaaataaaa cgttacaagg tgaaatcgtt   240
caaggtcccg attttctaac aatggaacaa aacagaccat ctttaagcga taattatact   300
caaccgacga caccgaaccc tattttagaa ggtcttgaag gtagctcatc taaacttgaa   360
ataaaaccac aaggtactga atcaacgttg aaaggtattc aaggagaatc aagtgatatt   420
gaagttaaac ctcaagcaac tgaaacaaca gaagcttctc aatatggtcc g             471
```

<210> SEQ ID NO 50
<211> LENGTH: 597
<212> TYPE: DNA
<213> ORGANISM: Staphylococcus aureus

<400> SEQUENCE: 50

```
agaccgcaat ttaacaaaac acctaagtat gtgaaatata gagatgctgg tacaggtatc     60
cgtgaataca acgatggaac atttggatat gaagcgagac caagattcaa caagccaagt   120
gaaacaaatg catacaacgt aacgacaaat caagatggca cagtatcata cggagctcgc   180
ccaacacaaa acaagccaag tgaaacaaac gcatataacg taacaacaca tgcaaatggt   240
caagtatcat acggtgctcg cccaacacaa aaaaagccaa gcaaaacaaa tgcatacaac   300
gtaacaacac atgcaaatgg tcaagtatca tatggcgctc gcccgacaca aaaaaagcca   360
agcaaaacaa atgcatataa cgtaacaaca catgcaaatg gtcaagtatc atacggagct   420
cgcccgacat acaagaagcc aagcgaaaca atgcataca acgtaacaac acatgcaaat   480
ggtcaagtat catatggcgc tcgcccgaca caaaaaaagc caagcgaaac aaacgcatat   540
aacgtaacaa cacatgcaga tggtactgcg acatatgggc ctagagtaac aaaataa     597
```

<210> SEQ ID NO 51
<211> LENGTH: 525

```
<212> TYPE: DNA
<213> ORGANISM: Staphylococcus aureus

<400> SEQUENCE: 51
atgaaaaagc aaataatttc gctaggcgca ttagcagttg catctagctt atttacatgg      60
gataacaaag cagatgcgat agtaacaaag gattatagtg ggaaatcaca agttaatgct     120
gggagtaaaa atgggaaaca aattgcagat ggatattatt ggggaataat tgaaaatcta     180 gaaaccagt tttacaatat ttttcattta ctggatcagc ataaatatgc agaaaaagaa      240
tataaagatg cagtagataa attaaaaact agagttttag aggaagacca atacctgcta     300
gaaagaaaaa aagaaaaata cgaaatttat aaagaactat ataaaaata caaaaaagag      360 aatcctaata ctcaagttaa atgaaagca tttgataaat cgatcttgg cgatttaact       420 atggaagaat acaatgactt atcaaaatta ttaacaaaag cattggataa ctttaagtta     480
gaagtaaaga aaattgaatc agagaatcca gatttaaaac catat                     525

<210> SEQ ID NO 52
<211> LENGTH: 390
<212> TYPE: DNA
<213> ORGANISM: Staphylococcus aureus

<400> SEQUENCE: 52
tctgaaagcg aagaaagaac agcatatggt aaaatagatt cacttgttga tcaagcatat      60
agtgtatatt ttgcctacgt tacagatgca caacataaaa cagaagcatt aaatcttagg     120
gcgaaaattg atttgatttt aggtgatgaa aaagatccaa ttagagttac gaatcaacgt     180
actgaaaaag aaatgattaa agatttagaa tctattattg atgatttctt cattgaaacc     240
aagttgaata gacctaaaca cattactagg tatgatggaa ctaaacatga ttaccataaa     300
cataaagatg gatttgatgc tctagttaaa gaaacaagag aagcggttgc aaaggctgac     360
gaatcttgga aaataaaac tgtcaaaaaa                                        390

<210> SEQ ID NO 53
<211> LENGTH: 564
<212> TYPE: DNA
<213> ORGANISM: Staphylococcus aureus

<400> SEQUENCE: 53
tacgaggaaa ctgtaacaaa atctccagtt gtaaagaag agaagaaagt tgaagaacct       60
caatcaccta aatttgataa ccaacaagag gttaaaatta cagttgataa agctgaagaa     120
acaacacaac cagtggcaca gccattagtt aaaattccac agggcacaat tacaggtgaa     180
attgtaaaag gtccggaata tccaacgatg gaaaataaaa cgttacaagg tgaaatcgtt     240
caaggtccag atttcccaac aatggaacaa acagaccat ctttaagcga taattatact      300
caaccgacga caccgaaccc tatttttagaa ggtcttgaag tagctcatc taaacttgaa     360 ataaaaccac aagtactgaa atcaacgtta aaaggtactc aaggagaatc aagtgatatt     420
gaagttaaac ctcaagcatc tgaaacaaca gaagcatcac attatccagc aagacctcaa     480
tttaacaaaa cacctaaata tgttaaatat agagatgctg gtacaggtat ccgtgaatac     540
aacgatggaa catttggata tgaa                                             564

<210> SEQ ID NO 54
<211> LENGTH: 423
<212> TYPE: DNA
<213> ORGANISM: Staphylococcus aureus
```

<400> SEQUENCE: 54

```
gcgagaccaa gattcaataa gccatcagaa acaaacgcat acaacgtaac gacaaatcaa      60
gatggcacag taacatatgg cgctcgccca acacaaaaca aaccaagcaa acaaatgca      120
tacaacgtaa caacacatgc aaatggtcaa gtatcatatg cgctcgccc gacacaaaac      180
aagccaagca aaacaaatgc ataacgta acaacacatg caaatggtca agtatcatac      240
ggagctcgcc cgacacaaaa caagccaagc aaaacaaatg catataacgt aacaacacac      300
gcaaacggtc aagtgtcata cggagctcgc ccgacataca agaagccaag taaaacaaat      360
gcatacaatg taacaacaca tgcagatggt actgcgacat atgggcctag agtaacaaaa      420
taa                                                                   423
```

<210> SEQ ID NO 55
<211> LENGTH: 525
<212> TYPE: DNA
<213> ORGANISM: Staphylococcus aureus

<400> SEQUENCE: 55

```
atgaaaaagc aaataatttc gctaggcgca ttagcagttg catctagctt atttacatgg      60
gataacaaag cagatgcgat agtaactaaa gattatagta agaatcaag agtgaatgag      120
aacagtaaat acgatacacc aattccagat tggtatctag gtagtatttt aaacagatta      180
ggggatcaaa tatactacgc taaggaatta actaataaat acgaatatgg tgagaaagag      240
tataagcaag cgatagataa attgatgact agagttttgg gagaagatca ttatctatta      300
gaaaaaaga aagcacaata tgaagcatac aaaaaatggt ttgaaaaaca taaaagtgaa      360
aatccacatt ctagttttaaa aaagattaaa tttgacgatt ttgatttata tagattaacg      420
aagaaagaat acaatgagtt acatcaatca ttaaaagaag ctgttgatga gtttaatagt      480
gaagtgaaaa atattcaatc taaacaaaag gatttattac cttat                     525
```

<210> SEQ ID NO 56
<211> LENGTH: 399
<212> TYPE: DNA
<213> ORGANISM: Staphylococcus aureus

<400> SEQUENCE: 56

```
gatgaagcaa ctgaaaatcg agtaacaaat ggaatatatg attttgtttg cgagattgac      60
acattatacg cagcatattt taatcatagc caatatggtc ataatgctaa agaattaaga     120
gcaaagctag atataattct tggtgatgct aaagatcctg ttagaattac gaatgaaaga     180
ataagaaaag aaatgatgga tgatttaaat tctattattg atgatttctt tatggataca     240
aacatgaata gaccattaaa cataactaaa tttaatccga atattcatga ctatactaat     300
aagcctgaaa atagagataa cttcgataaa ttagtcaaag aaacaagaga agcaatcgca     360
aacgctgacg aatcttggaa acaagaacc gtcaaaaat                             399
```

<210> SEQ ID NO 57
<211> LENGTH: 564
<212> TYPE: DNA
<213> ORGANISM: Staphylococcus aureus

<400> SEQUENCE: 57

```
tacggtgaat ctgaaacaaa atctcctgtt gtaaagaag agaagaaagt tgaagaacct       60
caattaccta agttggaaa ccagcaagag gataaaatta cagttggtac aactgaagaa      120
gcaccattac caattgcgca accactagtt aaaattccac agggcacaat tcaaggtgaa     180
```

```
attgtaaaag gtccggaata tctaacgatg gaaaataaaa cgttacaagg tgaaatcgtt    240
caaggtccag atttcccaac aatgaacaa  acagaccat  ctttaagcga taattatact    300
caaccgacga caccgaaccc tattttaaaa ggtattgaag gaaactcaac taaacttgaa    360
ataaaaccac aaggtactga atcaacgtta aaaggtactc aaggagaatc aagtgatatt    420
gaagttaaac ctcaagcaac tgaaacaaca gaagcatcac attatccagc gagacctcaa    480
tttaacaaaa cacctaagta tgtgaaatat agagatgctg gtacaggtat ccgtgaatac    540
aacgatggaa catttggata tgaa                                           564

<210> SEQ ID NO 58
<211> LENGTH: 342
<212> TYPE: DNA
<213> ORGANISM: Staphylococcus aureus

<400> SEQUENCE: 58
gcgagaccaa gattcaacaa gccaagcgaa acaaatgcat acaacgtaac gacaaatcaa     60
gatggcacag tatcatatgg cgctcgcccg acacaaaaca agccaagcga acaaacgca    120 tataacgtaa caacacatgc aaacggccaa gtatcatacg gagctcgtcc gacacaaaac    180
aagccaagcg aaacgaacgc atataacgta acaacacatg caaacggtca agtgtcatac    240
ggagctcgcc caacacaaaa caagccaagt aaaacaaatg catacaatgt aacaacacat    300
gcagatggta ctgcgacata tggtcctaga gtaacaaaat aa                       342

<210> SEQ ID NO 59
<211> LENGTH: 447
<212> TYPE: DNA
<213> ORGANISM: Staphylococcus aureus

<400> SEQUENCE: 59
atagtaacaa aggattatag tgggaaatca caagttaatg ctgggagtaa aaatgggaaa     60
caaattgcag atggatatta ttggggaata attgaaaatc tagagaacca gttttacaat    120
atttttcatt tattggatca gcataaatat gcagaaaaag aatataaaga tgcattagat    180
aaattaaaaa ctagagtttt agaggaagac caatacctgc tagaaagaaa aaaagaaaaa    240
tacgaaattt ataaagaact atataaaaaa tacaaaaaag agaatcctaa tactcaggtt    300
aaaatgaaag catttgataa atacgatctt ggcgatttaa ctatggaaga atacaatgac    360
ttatcaaaat tattaacaaa agcattggat aactttaagt tagaagtaaa gaaaattgaa    420
tcagagaatc cagatttaag accatat                                        447

<210> SEQ ID NO 60
<211> LENGTH: 390
<212> TYPE: DNA
<213> ORGANISM: Staphylococcus aureus

<400> SEQUENCE: 60
tctgaaagtg aagagagaac agcatatggt aaaatagatt cacttgttga tcaagcatat     60
agtgtatatt ttgcctacgt tacagatgct caacataaaa cagaagcatt aaatcttagg    120
gcaaaaatag atttgatttt aggtgatgaa aaagatccaa ttagagtgac gaatcaacgt    180
actgaaaaag aaatgattaa agatttagaa tctattattg atgatttctt cattgaaaca    240
aagttgaata gacctcaaca cattactaga tatgatggaa ctaaacatga ttaccataaa    300
cataaagatg gatttgatgc tttagttaaa gaaacaagag aagcggtttc taaggctgac    360
```

```
gaatcttgga aaactaaaac tgtcaaaaaa                                   390
```

<210> SEQ ID NO 61
<211> LENGTH: 597
<212> TYPE: DNA
<213> ORGANISM: Staphylococcus aureus

<400> SEQUENCE: 61

```
tacggggaaa ctgaaacaaa atatcctgtt gtaaagaag agaagaaagt tgaagaacct    60
caatcaccta agtttctga aaagtggat gttcaggaaa cggttggtac aactgaagaa   120
gcaccattac caattgcgca accactagtt aaattaccac aaattgggac tcaaggcgaa   180
attgtaaaag gtcccgacta ccaactatg gaaataaaa cgttacaagg tgtaattgtt   240
caaggtccag atttcccaac aatggaacaa acagaccat ctttaagtga caattataca   300
caaccatctg tgactttacc gtcaattaca ggtgaaagta caccaacgaa ccctatttta   360
aaaggtattg aaggaaactc atctaaactt gaaataaaac cacaaggtac tgaatcaacg   420
ttgaaaggta ttcaaggaga atcaagtgat attgaagtta accctcaagc aactgaaaca   480
acagaagcat cacattatcc agcgagaccg caatttaaca aaacacctaa atatgtgaaa   540
tatagagatg ctggtacagg tattcgtgaa tacaacgatg gaacttttgg atatgaa     597
```

<210> SEQ ID NO 62
<211> LENGTH: 504
<212> TYPE: DNA
<213> ORGANISM: Staphylococcus aureus

<400> SEQUENCE: 62

```
gcgagaccaa gattcaacaa gccatcagaa acaaacgcat acaacgtaac gacaaatcaa    60
gatggcacag tatcatatgg ggctcgccca acacaaaaca agccaagcaa aacaaatgca   120
tataacgtaa caacacatgc aaacggccaa gtatcatatg gcgctcgccc gacatacaac   180
aagccaagtg aaacaaatgc atacaacgta acgacaaatc gagatggcac agtatcatat   240
ggcgctcgcc cgacacaaaa caagccaagc gaaacgaatg catataacgt aacaacacac   300
ggaaatggcc aagtatcata tggcgctcgt ccgacacaaa agaagccaag caaaacaaat   360
gcatataacg taacaacaca tgcaaacggc caagtatcat atggcgctcg tccgacatac   420
aacaagccaa gtaaaacaaa tgcatacaat gtaacaacac atgcagatgg tactgcgaca   480
tatggtccta gagtaacaaa ataa                                         504
```

<210> SEQ ID NO 63
<211> LENGTH: 546
<212> TYPE: DNA
<213> ORGANISM: Staphylococcus aureus

<400> SEQUENCE: 63

```
gattgggcaa ttacattttg gaggaattaa aaaattatga aaagcaaat aatttcgcta    60
ggcgcattag cagttgcatc tagcttattt acatgggata caaagcaga tgcgatagta   120
acaaaggatt atagtaaaga atcaagagtg aatgagaaaa gtaaaaaggg agctactgtt   180
tcagattatt actattggaa ataattgat agtttagagg cacaatttac tggagcaata   240
gacttattgg aagattataa atatggagat cctatctata agaagcgaa agatagattg   300
atgacaagag tattaggaga agaccagtat ttattaaaga aaagattga tgaatatgag   360
ctttatataa agtggtataa aagttcaaat aagaacacta atatgcttac tttccataaa   420
tataatcttt acaatttaac aatgaatgaa tataacgata ttttttaactc tttgaaagat   480
```

```
gcagtttatc aatttaataa agaagttaaa gaaatagagc ataaaaatgt tgacttgaag    540
cagttt                                                              546

<210> SEQ ID NO 64
<211> LENGTH: 399
<212> TYPE: DNA
<213> ORGANISM: Staphylococcus aureus

<400> SEQUENCE: 64
gataaagatg gagaagacaa ggcaactaaa gaagtttatg accttgtttc tgaaattgat     60
acattagttg taacttatta tgctgataag gattatgggg agcatgcgaa agagttacga    120
gcaaaactgg acttaatcct tggagataca gacaatccac ataaaattac aaatgagcgt    180
ataaaaaaag aaatgatcga tgacttaaat tcaattatag atgatttctt tatggagact    240
aaacaaaata gaccgaattc tataacaaaa tatgatccaa caaaacacaa ttttaaagag    300
aagagtgaaa ataaacctaa ttttgataaa ttagttgaag aaacaaaaaa agcagttaaa    360
gaagcagacg aatcttggaa aaataaaact gtcaaaaaa                            399

<210> SEQ ID NO 65
<211> LENGTH: 471
<212> TYPE: DNA
<213> ORGANISM: Staphylococcus aureus

<400> SEQUENCE: 65
tacgaggaaa ctgtaacaaa atctcctgtt gtaaaagaag agaagaaagt tgaagaacct     60
caattaccta agttggaaaa ccagcaagag gttaaaacta cggctggtaa agctgaagaa    120
acaacacaac cagtggcaca gccattagta aaaattccac aagaaacaat ctatggtgaa    180
actgtaaaag gtccagaata tccaacgatg gaaaataaaa cgttacaagg tgaaatcgtt    240
caaggtcccg attttctaac aatggaacaa aacagaccat ctttaagcga taattatact    300
caaccgacga caccgaaccc tattttagaa ggtcttgaag gtagctcatc taaacttgaa    360
ataaaaccac aaggtactga atcaacgttg aaaggtattc aaggagaatc aagtgatatt    420
gaagttaaac ctcaagcaac tgaaacaaca gaagcttctc aatatggtcc g              471

<210> SEQ ID NO 66
<211> LENGTH: 597
<212> TYPE: DNA
<213> ORGANISM: Staphylococcus aureus

<400> SEQUENCE: 66
agaccgcaat ttaacaaaac acctaagtat gtgaaatata gagatgctgg tacaggtatc     60
cgtgaataca cgatggaac atttggatat gaagcgagac caagattcaa caagccaagt    120
gaaacaaatg catacaacgt aacgacaaat caagatggca cagtatcata cggagctcgc    180
ccaacacaaa acaagccaag tgaaacaaac gcatataacg taacaacaca tgcaaatggt    240
caagtatcat acggtgctcg cccaacacaa aaaagccaa gcaaaacaaa tgcatacaac    300
gtaacaacac atgcaaatgg tcaagtatca tatggcgctc gcccgacaca aaaaagccaa    360
agcaaaacaa atgcatataa cgtaacaaca catgcaaatg gtcaagtatc atacggagct    420
cgcccgacat acaagaagcc aagcgaaaca aatgcataca acgtaacaac acatgcaaat    480
ggtcaagtat catatggcgc tcgcccgaca caaaaaaagc caagcgaaac aaacgcatat    540
aacgtaacaa cacatgcaga tggtactgcg acatatgggc ctagagtaac aaaataa       597
```

<210> SEQ ID NO 67
<211> LENGTH: 447
<212> TYPE: DNA
<213> ORGANISM: Staphylococcus aureus

<400> SEQUENCE: 67

| | | | | | |
|---|---|---|---|---|---|
| atagtaacta | aagattatag | taaagaatca | agagtgaatg | agaacagtaa | atacgataca | 60 |
| ccaattccag | attggtatct | aggtagtatt | ttaaacagat | tagggatca | aatatactac | 120 |
| gctaaggaat | taactaataa | atacgaatat | ggtgagaaag | agtataagca | agcgatagat | 180 |
| aaattgatga | ctagagtttt | gggagaagat | cattatctat | tagaaaaaaa | gaaagcacaa | 240 |
| tatgaagcat | acaaaaaatg | gtttgaaaaa | cataaaagtg | aaaatccaca | ttctagttta | 300 |
| aaaaagatta | aatttgacga | ttttgattta | tatagattaa | cgaagaaaga | atacaatgag | 360 |
| ttacatcaat | cattaaaaga | agctgttgat | gagtttaata | gtgaagtgaa | aaatattcaa | 420 |
| tctaaacaaa | aggatttatt | accttat | | | | 447 |

<210> SEQ ID NO 68
<211> LENGTH: 399
<212> TYPE: DNA
<213> ORGANISM: Staphylococcus aureus

<400> SEQUENCE: 68

| | | | | | |
|---|---|---|---|---|---|
| gatgaagcaa | ctgaaaatcg | agtaacaaat | ggaatatatg | attttgtttg | cgagattgac | 60 |
| acattatacg | cagcatattt | taatcatagc | caatatggtc | ataatgctaa | agaattaaga | 120 |
| gcaaagctag | atataattct | tggtgatgct | aaagatcctg | ttagaattac | gaatgaaaga | 180 |
| ataagaaaag | aaatgatgga | tgatttaaat | tctattattg | atgatttctt | tatggataca | 240 |
| aacatgaata | gaccattaaa | cataactaaa | tttaatccga | atattcatga | ctatactaat | 300 |
| aagcctgaaa | atagagataa | cttcgataaa | ttagtcaaag | aaacaagaga | agcagtcgca | 360 |
| aacgctgacg | aatcttggaa | acaagaacc | gtcaaaaat | | | 399 |

<210> SEQ ID NO 69
<211> LENGTH: 564
<212> TYPE: DNA
<213> ORGANISM: Staphylococcus aureus

<400> SEQUENCE: 69

| | | | | | |
|---|---|---|---|---|---|
| tacggtgaat | ctgaaacaaa | atctcctgtt | gtaaagaag | agaagaaagt | tgaagaacct | 60 |
| caattaccta | agttggaaaa | ccagcaagag | gataaaatta | cagttggtac | aactgaagaa | 120 |
| gcaccattac | caattgcgca | accactagtt | aaaattccac | agggcacaat | tcaaggtgaa | 180 |
| attgtaaaag | gtccggaata | tctaacgatg | gaaaataaaa | cgttacaagg | tgaaatcgtt | 240 |
| caaggtccag | atttcccaac | aatggaacaa | aacagaccat | ctttaagcga | taattatact | 300 |
| caaccgacga | caccgaaccc | tattttaaaa | ggtattgaag | gaaactcaac | taaacttgaa | 360 |
| ataaaaccac | aaggtactga | atcaacgtta | aaaggtactc | aaggagaatc | aagtgatatt | 420 |
| gaagttaaac | ctcaagcaac | tgaaacaaca | gaagcatcac | attatccagc | gagacctcaa | 480 |
| tttaacaaaa | cacctaagta | tgtgaaatat | agagatgctg | gtacaggtat | ccgtgaatac | 540 |
| aacgatggaa | catttggata | tgaa | | | | 564 |

<210> SEQ ID NO 70
<211> LENGTH: 504
<212> TYPE: DNA
<213> ORGANISM: Staphylococcus aureus -continued

<400> SEQUENCE: 70

| gcgagaccaa | gattcaacaa | gccaagcgaa | acaaatgcat | acaacgtaac | gacaaatcaa | 60 |
| gatggcacag | tatcatatgg | cgctcgcccg | acacaaaaca | aaccaagcga | aacaaatgca | 120 |
| tacaacgtaa | caacacatgc | aaacggccaa | gtatcatatg | cgcccgccc  | aacatacaag | 180 |
| aagccaagcg | aaacaaacgc | atacaacgta | acgacaaatc | aagatggcac | agtatcatat | 240 |
| ggcgctcgcc | cgacacaaaa | caagccaagc | gaaacaaacg | catataacgt | aacaacacat | 300 |
| gcaaacggcc | aagtatcata | cggagctcgt | ccgacacaaa | acaagccaag | cgaaacgaac | 360 |
| gcatataacg | taacaacaca | tgcaaacggt | caagtgtcat | acggagctcg | cccaacacaa | 420 |
| aacaagccaa | gtaaaacaaa | tgcatacaat | gtaacaacac | atgcagatgg | tactgcgaca | 480 |
| tatggtccta | gagtaacaaa | ataa | | | | 504 |

<210> SEQ ID NO 71
<211> LENGTH: 525
<212> TYPE: DNA
<213> ORGANISM: Staphylococcus aureus

<400> SEQUENCE: 71

| atgaaaaagc | aaataatttc | gctaggcgca | ttagcagttg | catctagctt | atttacatgg | 60 |
| gataacaaag | cagatgcgat | agtaacaaag | gattatagtg | ggaaatcaca | agttaatgct | 120 |
| gggagtaaaa | atgggacatt | aatagatagc | agatatttaa | attcagctct | atattatttg | 180 |
| gaagactata | taatttatgc | tataggatta | actaataaat | atgaatatgg | agataatatt | 240 |
| tataaagaag | ctaaagatag | gttgttggaa | aaggtattaa | gggaagatca | atatcttttg | 300 |
| gagagaaaga | atctcaata  | tgaagattat | aaacaatggt | atgcaaatta | taaaaagaa  | 360 |
| aatcctcgta | cagatttaaa | aatggctaat | tttcataaat | ataatttaga | agaactttcg | 420 |
| atgaaagaat | acaatgaact | acaggatgca | ttaagagag  | cactggatga | ttttcacaga | 480 |
| gaagttaaag | atattaagga | taagaattca | gacttgaaaa | ctttt | | 525 |

<210> SEQ ID NO 72
<211> LENGTH: 399
<212> TYPE: DNA
<213> ORGANISM: Staphylococcus aureus

<400> SEQUENCE: 72

| aatgcagcag | aagaagataa | agcaactaag | gaagtatacg | atctcgtatc | tgaaattgat | 60 |
| acattagttg | tatcatatta | tggtgataag | gattatgggg | agcacgcgaa | agagttacga | 120 |
| gcaaaactgg | acttaatcct | tggagataca | gacaatccac | ataaaattac | aaatgaacgt | 180 |
| attaaaaaag | aaatgattga | tgacttaaat | tcaattattg | atgatttctt | tatggaaact | 240 |
| aaacaaaata | gaccgaaatc | tataacgaaa | tataatccta | caacacataa | ctataaaaca | 300 |
| aatagtgata | taaacctaa  | ttttgataaa | ttagttgaag | aaacgaaaaa | agcagttaaa | 360 |
| gaagcagatg | attcttggaa | aaagaaaact | gtcaaaaaa  | | | 399 |

<210> SEQ ID NO 73
<211> LENGTH: 471
<212> TYPE: DNA
<213> ORGANISM: Staphylococcus aureus

<400> SEQUENCE: 73

| tacggagaaa | ctgaaacaaa | atcgccagta | gtaaaagaag | agaagaaagt | tgaagaacct | 60 |

-continued

```
caagcaccta aagttgataa ccaacaagag gttaaaacta cggctggtaa agctgaagaa      120
acaacacaac cagttgcaca accattagtt aaaattccac agggcacaat tacaggtgaa      180
attgtaaaag gtccggaata tccaacgatg gaaaataaaa cggtacaagg tgaaatcgtt      240
caaggtcccg attttctaac aatggaacaa agcggcccat cattaagcaa taattataca      300
aacccaccgt taacgaaccc tattttagaa ggtcttgaag gtagctcatc taaacttgaa      360
ataaaaccac aaggtactga atcaacgtta aaaggtactc aaggagaatc aagtgatatt      420
gaagttaaac ctcaagcaac tgaaacaaca gaagcttctc aatatggtcc g              471
```

<210> SEQ ID NO 74
<211> LENGTH: 516
<212> TYPE: DNA
<213> ORGANISM: Staphylococcus aureus

<400> SEQUENCE: 74

```
agaccgcaat ttaacaaaac acctaaatat gttaaatata gagatgctgg tacaggtatc       60
cgtgaataca acgatggaac atttggatat gaagcgagac caagattcaa taagccatca      120
gaaacaaatg catataacgt aacaacacat gcaaatggtc aagtatcata cggagctcgt      180
ccgacataca agaagccaag cgaaacgaat gcatacaatg taacaacaca tgcaaacggc      240
caagtatcat acggagctcg tccgacacaa acaagccaa gcaaaacaaa cgcatataac       300
gtaacaacac atgaaacgg ccaagtatca tatggcgctc gcccaacaca aaacaagcca      360
agcaaaacaa atgcatacaa cgtaacaaca catgcaaacg gtcaagtgtc atacggagct      420
cgcccgacat acaagaagcc aagtaaaaca aatgcataca atgtaacaac acatgcagat      480
ggtactgcga catatgggcc tagagtaaca aaataa                               516
```

<210> SEQ ID NO 75
<211> LENGTH: 508
<212> TYPE: PRT
<213> ORGANISM: Staphylococcus aureus

<400> SEQUENCE: 75

Met Lys Asn Lys Leu Leu Val Leu Ser Leu Gly Ala Leu Cys Val Ser
1               5                   10                  15

Gln Ile Trp Glu Ser Asn Arg Ala Ser Ala Val Val Ser Gly Glu Lys
            20                  25                  30

Asn Pro Tyr Val Ser Glu Ser Leu Lys Leu Thr Asn Lys Asn Lys
        35                  40                  45

Ser Arg Thr Val Glu Glu Tyr Lys Lys Ser Leu Asp Asp Leu Ile Trp
    50                  55                  60

Ser Phe Pro Asn Leu Asp Asn Glu Arg Phe Asp Asn Pro Glu Tyr Lys
65                  70                  75                  80

Glu Ala Met Lys Lys Tyr Gln Gln Arg Phe Met Ala Glu Asp Glu Ala
                85                  90                  95

Leu Lys Lys Phe Phe Ser Glu Glu Lys Lys Ile Lys Asn Gly Asn Thr
            100                 105                 110

Asp Asn Leu Asp Tyr Leu Gly Leu Ser His Glu Arg Tyr Glu Ser Val
        115                 120                 125

Phe Asn Thr Leu Lys Lys Gln Ser Glu Glu Phe Leu Lys Glu Ile Glu
    130                 135                 140

Asp Ile Lys Lys Asp Asn Pro Glu Leu Lys Asp Phe Asn Glu Glu Glu
145                 150                 155                 160

Gln Leu Lys Cys Asp Leu Glu Leu Asn Lys Leu Glu Asn Gln Ile Leu

```
            165                 170                 175
Met Leu Gly Lys Thr Phe Tyr Gln Asn Tyr Arg Asp Asp Val Glu Ser
        180                 185                 190

Leu Tyr Ser Lys Leu Asp Leu Ile Met Gly Tyr Lys Asp Glu Glu Arg
        195                 200                 205

Ala Asn Lys Lys Ala Val Asn Lys Arg Met Leu Glu Asn Lys Lys Glu
        210                 215                 220

Asp Leu Glu Thr Ile Ile Asp Glu Phe Phe Ser Asp Ile Asp Lys Thr
225                 230                 235                 240

Arg Pro Asn Asn Ile Pro Val Leu Glu Asp Glu Lys Gln Glu Glu Lys
                245                 250                 255

Asn His Lys Asn Met Ala Gln Leu Lys Ser Asp Thr Glu Ala Ala Lys
            260                 265                 270

Ser Asp Glu Ser Lys Arg Ser Lys Arg Ser Lys Arg Ser Leu Asn Thr
        275                 280                 285

Gln Asn His Lys Pro Ala Ser Gln Glu Val Ser Glu Gln Gln Lys Ala
        290                 295                 300

Glu Tyr Asp Lys Arg Ala Glu Glu Arg Lys Ala Arg Phe Leu Asp Asn
305                 310                 315                 320

Gln Lys Ile Lys Lys Thr Pro Val Val Ser Leu Glu Tyr Asp Phe Glu
                325                 330                 335

His Lys Gln Arg Ile Asp Asn Glu Asn Asp Lys Lys Leu Val Val Ser
            340                 345                 350

Ala Pro Thr Lys Lys Pro Thr Ser Pro Thr Thr Tyr Thr Glu Thr Thr
        355                 360                 365

Thr Gln Val Pro Met Pro Thr Val Glu Arg Gln Thr Gln Gln Gln Ile
    370                 375                 380

Ile Tyr Asn Ala Pro Lys Gln Leu Ala Gly Leu Asn Gly Glu Ser His
385                 390                 395                 400

Asp Phe Thr Thr Thr His Gln Ser Pro Thr Thr Ser Asn His Thr His
                405                 410                 415

Asn Asn Val Val Glu Phe Glu Glu Thr Ser Ala Leu Pro Gly Arg Lys
            420                 425                 430

Ser Gly Ser Leu Val Gly Ile Ser Gln Ile Asp Ser Ser His Leu Thr
        435                 440                 445

Glu Arg Glu Lys Arg Val Ile Lys Arg Glu His Val Arg Glu Ala Gln
    450                 455                 460

Lys Leu Val Asp Asn Tyr Lys Asp Thr His Ser Tyr Lys Asp Arg Ile
465                 470                 475                 480

Asn Ala Gln Gln Lys Val Asn Thr Leu Ser Glu Gly His Gln Lys Arg
                485                 490                 495

Phe Asn Lys Gln Ile Asn Lys Val Tyr Asn Gly Lys
            500                 505

<210> SEQ ID NO 76
<211> LENGTH: 1449
<212> TYPE: DNA
<213> ORGANISM: Staphylococcus aureus

<400> SEQUENCE: 76
gtggtttctg gggagaagaa tccatatgta tctgagtcgt tgaaactgac taataataaa      60
aataaatcta gaacagtaga agagtataag aaaagcttgg atgatttaat atggtccttt    120
ccaaacttag ataatgaaag atttgataat cctgaatata agaagctat gaaaaatat     180
```

| caacagagat ttatggctga agatgaggct ttgaagaaat tttttagtga agagaaaaaa | 240 |
| ataaaaaatg gaaatactga taatttagat tatctaggat tatctcatga agatatgaa | 300 |
| agtgtattta atactttgaa aaacaaagt gaggagttct taaaagaaat tgaagatata | 360 |
| aaaaaagata accctgaatt gaaagacttt aatgaagagg agcaattaaa gtgcgactta | 420 |
| gaattaaaca aattagaaaa tcagatatta atgttaggta aaacatttta tcaaaactat | 480 |
| agagatgatg ttgaaagttt atatagtaag ttagatttaa ttatgggata taaagatgaa | 540 |
| gaaagagcaa ataaaaagc agttaacaaa aggatgttag aaaataaaaa agaagactta | 600 |
| gaaaccataa ttgatgaatt ttttagtgat atagataaaa caagacctaa taatattcct | 660 |
| gttttagaag atgaaaaaca agaagagaaa aatcataaaa atatggctca attaaaatct | 720 |
| gacactgaag cagcaaaaag tgatgaatca aaagaagca agagaagtaa aagaagttta | 780 |
| aatactcaaa atcacaaacc tgcatctcaa gaagtttctg aacaacaaaa agctgaatat | 840 |
| gataaaagag cagaagaaag aaaagcgaga ttttggata tcaaaaaat taagaaaaca | 900 |
| cctgtagtgt cattagaata tgattttgag cataaacaac gtattgacaa cgaaaacgac | 960 |
| aagaaacttg tggtttctgc accaacaaag aaaccaacat caccgactac atatactgaa | 1020 |
| acaacgacac aggtaccaat gcctacagtt gagcgtcaaa ctcagcaaca aattatttat | 1080 |
| aatgcaccaa acaattggc tggattaaat ggtgaaagtc atgatttcac aacaacgcat | 1140 |
| caatcaccaa caacttcaaa tcacacgcat aataatgttg ttgaatttga agaaacgtct | 1200 |
| gctttacctg gtagaaaatc aggatcactg gttggtataa gtcaaattga ttcttctcat | 1260 |
| ctaactgaac gtgagaagcg tgtaattaag cgtgaacacg ttagagaagc tcaaaagtta | 1320 |
| gttgataatt ataaagatac acatagttat aaagaccgaa taaatgcaca acaaaaagta | 1380 |
| aatactttaa gtgaaggtca tcaaaaacgt tttaataaac aaatcaataa agtatataat | 1440 |
| ggcaaataa | 1449 |

<210> SEQ ID NO 77
<211> LENGTH: 1425
<212> TYPE: DNA
<213> ORGANISM: Staphylococcus aureus

<400> SEQUENCE: 77

| gtggtttctg gggagaagaa tccatatgta tcaaaagctt tagaattgaa agataaaagt | 60 |
| aataaatcca attcttacga aaattataga gatagtttag aaagtttgat ttcatcatta | 120 |
| tcttttgctg attatgaaaa atatgaagag ccagaatatg aaaaggctgt aaaaaaatat | 180 |
| caacaaaaat ttatggctga agatgatgca ttaaaaaatt ttttaaatga agaaaagaag | 240 |
| ataaaaaatg cagatattag cagaaaatcg ataatttat taggtttaac acatgaaaga | 300 |
| tattcttata tttttgatac attaaagaaa ataaacaag agttttaaa agatattgaa | 360 |
| gaaatacaac tgaaaatag tgatttaaag gactttaaca atacagagca acataatgcc | 420 |
| gacgtagaaa taaacaattt agaaaataaa gtattaatgg tagggtatac attctataat | 480 |
| acaaataagg acgaagttga agaattatat agtgagttag atttgattgt tggagaagtt | 540 |
| caagataagt cggataaaaa aagagcagta atcaaagga tgttaaatag aaaaaaagag | 600 |
| gatttagaat ttattataga taaatttttt aaaaaaattc aacaagaacg tccagagagt | 660 |
| ataccagcat taactagtga aaaaaatcat aatcagacta tggcattaaa gttaaaagca | 720 |
| gatacagaag ctgctaaaaa tgacgtatca aaaagagta aagaagttt aaatactcaa | 780 |
| aataataaat ctacaacaca agaaatttct gaagaacaaa aagctgaata tcaaagaaag | 840 |

```
tcagaggcat taaagaaag atttataaac agacaaaaat ctaaaaatga gtctgtggtt      900
tcactaatcg atgacgaaga cgacaacgaa acgacaggc aacttgtggt ttctgcgcca      960
tcaaagaaac caacaacacc gactacatat actgaaacaa cgactcaggt accaatgcct     1020
acagttgagc gtcaaactca gcaacaaatc gtttacaaaa caccaaaacc attagctgga     1080
ttaaatggtg aaagtcatga tttcacaaca acgcatcaat caccaacaac ttcaaatcat     1140
acgcataata atgttgttga atttgaagaa acgtctgctt tacctggtag aaaatcagga     1200
tcactggttg gtataagtca aattgattct tctcatctaa ctgaacgtga gaagcgtgta     1260
atcaagcgtg aacacgttag agaagctcaa aagttagttg ataattataa agatacacat     1320
agttataaag accgattaaa tgcacaacaa aaagtaaata ctttaagtga aggtcatcaa     1380
aaacgtttta ataaacaaat caataaagta tacaatggca aataa                    1425
```

<210> SEQ ID NO 78
<211> LENGTH: 3694
<212> TYPE: DNA
<213> ORGANISM: Staphylococcus aureus

<400> SEQUENCE: 78

```
gtggtttctg gggaggagaa tccatataaa tctgagtcat tgaaattaaa tgggaaaaga       60
agtactacaa taactagtga taaatatgaa gaaaatttag atatgttaat atcgtcatta      120
tcatttgcag attatgaaaa atatgaggaa ccagaataca agaagcagt taaaaagtat       180 caacaaaaat ttatggctga agatgatgca ttaaaaaatt ttttagtgaa gagaaaaaaa      240
taaaaaatag aaatactaat acatcaaatt atctgggatt aacacacgaa agatatgagt      300
caatttataa ttcattaaaa aatcatcgtg aagaattttc aaaagaaatc gaagaaatta      360
ataataaaaa tccagtgtta aaagaatata acaatgagga acaaactaaa gctgatacgg      420
aattaaacac tcttgaaaat caagtactaa tgataggtta tacattttat cactcgaata      480
aaaatgaagt agaagattta tataacaaat tagatatgat tcttggttat aaagatgaag      540
agagaaaaaa gaagagggct accaatcaaa gaatgttcaa taataaaaaa gaggatttag      600
aaactattat tgatgaattc tttggagaaa ttggacaaca aaggccaaca tctataccaa      660
cattagcgcc taaagaagaa aaagaaacaa atataaaaaa tgcaaataaa ttaaaatctg      720
acactgaagc agcaaaaaat gatgaagcaa aaagaagttt aaatacccac aatcacaaat      780
ctgtatctca agaagtctct gaacaacaaa aagctgacta cgaaagaaaa gctgaagaaa      840
gaaaagcgag attttagat aagcaaaaaa ataagaaaac tcctgtagtt tcattagaat      900
atgattttga acataaacaa cgtgttgaca acgaaaacga caagcaactt gtggtttctg      960
agccatcaaa gaaccaaca acaccgccta catacactga acaaccaca cagctaccaa     1020 tgcctacagt tgagcgtcaa acacagcaac aaatcgttta caaagcacca aaaccattag     1080
ctggattaaa tggtgaaagt catgatttca acaacgca tcaatcacca actacttcaa     1140
atcacacgca taatcatctt attgaaattg aagaaacatc tgctttacct ggtagaaaga     1200
caggttcatt ggttggtttg agtcaaattg attcttcgca tttaactgaa cgtgagaagc     1260
gcgtgattaa acgtgaacac gtgagagaag ctcaaaagtt agttgataat tataagata     1320 cacatagtta taagaccga ttaaatgccc aacaaaagt aaatactta agtgcaggtc     1380 atcaaaaacg ttttaataaa caattaata agtatataa tggcaaataa ttaatgcatg     1440
gctgcaaagg aaataatgag tttgccgtaa aaataacaac atttaaact agcaataaat     1500
```

```
aatatcaaag tcatcatttc aatgatgcaa tctagtatag tccacattct aaacaggtgt    1560
ggactattac ttttttcact ttatattacg aaaaaattat tatgcttaac tatcaatatc    1620
aataattaat tttaagctga aaaacaataa aaatgttaag acaacgttta cttcaagtta    1680
attattatac tgaaaattct ggtatataat gctgttagtg aatataacag aaaaattaaa    1740
ttggttatga tattgagtct atataaagga gaaataacag atgaaaaaga aattattagt    1800
tttaactatg agcacgctat ttgctacaca atttatgaat tcaaatcacg ctaatgcatc    1860
aacagaaagt gttgataaaa actttgtagt tccagaatcg ggtattaata aaattattcc    1920
aacttacgat gaatttaaaa aagcaccaaa agtaaatgtt agtaatttag ctgacaacaa    1980
aaactttgta gcttctgaag ataaattgaa taagattgca gatccatcgg cagctagtaa    2040
aattgtagat aaaaactttg ccgtaccaga atcaaaatta ggaatcattg taccagagta    2100
taaagaaatc aataatcgag tgaatgtaac aacaaacaat ccagcttcaa aacaagttga    2160
caagcaaatt gttgctaaag acccagaggt gaatagattt attacgcaaa ataaagtaaa    2220
ccatcgtttc attactacgc aaacccacta taagaaagtt attacttcat acaaatcaac    2280
acatgtacat aaacatgtaa accatgcaac atcttctatc catcatcact ttactattaa    2340
accatcagaa gcacctagat atacacaccc atctcaatct caatcgttaa ttataaatca    2400
tcattttgca gttcctggat accatggtca taagttgta acaccaggac aagctagtat    2460
```



```
tcattttgca gttcctggat accatggtca taagttgta  acaccaggac aagctagtat    2460
tagaattcat cactttgtg ctgtacctca aataaatagt tttaaggtca ttccatcata    2520
tggtcacaat tcacatcgta tgcatgtacc aagtttccaa aataacacaa cagcaacaca    2580
tcaaaatgca aagtaaata aaacttataa ctataaatat ttttatactt ataaagtagt    2640 caaggtgta aaaaaacatt tctcattttc aaaatcacat ggttgtaaaa ttgttaaacc    2700
agcattaaac atcaaaaatg taaattatca atatgctgtt ccaagtaata gccctacaca    2760
cgttgttcct gagtttcagg gtatcttacc agcaccacga gtataaaaat tgacattaag    2820
tttacgagat atgataaata cctattattt taaacatagt ctgcaatcta tgaggttgta    2880
ggctatgttt tttgcagttt atcaataaac acccatcaac aaattatacc gttttctac    2940 tttaaaagtt ggaagtaaca taatcttaaa taaatatatt attaattaag ataaatataa    3000
gactcgagat tattgttaat agtttgttca tcgcaagtta attattgttt ctaaaatatt    3060
ggtatataat tttcaatggc gaagaaaaca gggtaaaaaa gtcggttttt aaatcaaagc    3120
aaataaggag taaaaaatga aaaggaaagt actagtatta acaatgggcg tactttgtgc    3180
gacacaatta tggcaaacga ataatgcaaa agctttagtg acagagagtg gcgttaatga    3240
tactaagcaa tttactgaag taacatcgga agaaaaagtt ataaagatg ctatttcgaa    3300 agtcaatgaa agctttatttt actatcccca aaatgatttg aagggattag gtggagaaca    3360
caacgattac gaaaaaatta catatagcac ttcttctaat aatgttttag aattatcaat    3420
gagttcaaaa tacgtaggcg gtaaatcagg agctatggtt ggttatagtg aaatttactc    3480
atcacatttc acagaccgcg acaaacgtgc tatcagacgt gatcatgtta aagaagcaca    3540
aaacttgatt aatgattata atatacgca aatatatgaa gactttgcta aagctactgc    3600
aaaggtaagt acacttagtc agtctccacca aaattatttta aataaacaaa ttgataaagt    3660
gaataataag atagagaaaa ctgaaaaacg ctaa                                3694
```

<210> SEQ ID NO 79
<211> LENGTH: 399
<212> TYPE: DNA
<213> ORGANISM: Staphylococcus aureus

<400> SEQUENCE: 79

```
gtggtttctg gggagaagaa tccatatgta tctgagtcgt tgaaactgac taataataaa      60
aataaatcta gaacagtaga agagtataag aaaagcttgg atgatttaat atggtccttt     120
ccaaacttag ataatgaaag atttgataat cctgaatata agaagctat gaaaaaatat      180 caacagagat ttatggctga agatgaggct ttgaagaaat ttttagtga agagaaaaaa      240 ataaaaaatg gaaatactga taatttagat tatctaggat tatctcatga agatatgaa      300 agtgtattta atactttgaa aaacaaagt gaggagttct taaaagaaat tgaagatata      360
aaaaaagata accctgaatt gaaagactt aatgaatag                             399
```

<210> SEQ ID NO 80
<211> LENGTH: 320
<212> TYPE: PRT
<213> ORGANISM: Staphylococcus aureus

<400> SEQUENCE: 80

| Val | Val | Ser | Gly | Glu | Lys | Asn | Pro | Tyr | Val | Ser | Glu | Ser | Leu | Lys | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Thr | Asn | Asn | Lys | Asn | Lys | Ser | Arg | Thr | Val | Glu | Glu | Tyr | Lys | Lys | Ser |
|     |     |     | 20  |     |     |     |     | 25  |     |     |     |     | 30  |     |     |

| Leu | Asp | Asp | Leu | Ile | Trp | Ser | Phe | Pro | Asn | Leu | Asp | Asn | Glu | Arg | Phe |
|     |     |     | 35  |     |     |     |     | 40  |     |     |     |     | 45  |     |     |

| Asp | Asn | Pro | Glu | Tyr | Lys | Glu | Ala | Met | Lys | Lys | Tyr | Gln | Gln | Arg | Phe |
|     |     | 50  |     |     |     |     | 55  |     |     |     |     | 60  |     |     |     |

| Met | Ala | Glu | Asp | Glu | Ala | Leu | Lys | Lys | Phe | Phe | Ser | Glu | Glu | Lys | Lys |
| 65  |     |     |     |     | 70  |     |     |     |     | 75  |     |     |     |     | 80  |

| Ile | Lys | Asn | Gly | Asn | Thr | Asp | Asn | Leu | Asp | Tyr | Leu | Gly | Leu | Ser | His |
|     |     |     |     | 85  |     |     |     |     | 90  |     |     |     |     | 95  |     |

| Glu | Arg | Tyr | Glu | Ser | Val | Phe | Asn | Thr | Leu | Lys | Lys | Gln | Ser | Glu | Glu |
|     |     |     | 100 |     |     |     |     | 105 |     |     |     |     | 110 |     |     |

| Phe | Leu | Lys | Glu | Ile | Glu | Asp | Ile | Lys | Lys | Asp | Asn | Pro | Glu | Leu | Lys |
|     |     |     | 115 |     |     |     |     | 120 |     |     |     |     | 125 |     |     |

| Asp | Phe | Asn | Glu | Glu | Gln | Leu | Lys | Cys | Asp | Leu | Glu | Leu | Asn | Lys |
|     |     |     | 130 |     |     |     |     | 135 |     |     |     |     | 140 |     |

| Leu | Glu | Asn | Gln | Ile | Leu | Met | Leu | Gly | Lys | Thr | Phe | Tyr | Gln | Asn | Tyr |
| 145 |     |     |     |     | 150 |     |     |     |     | 155 |     |     |     |     | 160 |

| Arg | Asp | Asp | Val | Glu | Ser | Leu | Tyr | Ser | Lys | Leu | Asp | Leu | Ile | Met | Gly |
|     |     |     |     | 165 |     |     |     |     | 170 |     |     |     |     | 175 |     |

| Tyr | Lys | Asp | Glu | Glu | Arg | Ala | Asn | Lys | Lys | Ala | Val | Asn | Lys | Arg | Met |
|     |     |     | 180 |     |     |     |     | 185 |     |     |     |     | 190 |     |     |

| Leu | Glu | Asn | Lys | Lys | Glu | Asp | Leu | Glu | Thr | Ile | Ile | Asp | Glu | Phe | Phe |
|     |     |     | 195 |     |     |     |     | 200 |     |     |     |     | 205 |     |     |

| Ser | Asp | Ile | Asp | Lys | Thr | Arg | Pro | Asn | Asn | Ile | Pro | Val | Leu | Glu | Asp |
|     |     |     | 210 |     |     |     |     | 215 |     |     |     |     | 220 |     |     |

| Glu | Lys | Gln | Glu | Glu | Lys | Asn | His | Lys | Asn | Met | Ala | Gln | Leu | Lys | Ser |
| 225 |     |     |     |     | 230 |     |     |     |     | 235 |     |     |     |     | 240 |

| Asp | Thr | Glu | Ala | Ala | Lys | Ser | Asp | Glu | Ser | Lys | Arg | Ser | Lys | Arg | Ser |
|     |     |     |     | 245 |     |     |     |     | 250 |     |     |     |     | 255 |     |

| Lys | Arg | Ser | Leu | Asn | Thr | Gln | Asn | His | Lys | Pro | Ala | Ser | Gln | Glu | Val |
|     |     |     | 260 |     |     |     |     | 265 |     |     |     |     | 270 |     |     |

| Ser | Glu | Gln | Gln | Lys | Ala | Glu | Tyr | Asp | Lys | Arg | Ala | Glu | Glu | Arg | Lys |
|     |     |     | 275 |     |     |     |     | 280 |     |     |     |     | 285 |     |     |

Ala Arg Phe Leu Asp Asn Gln Lys Ile Lys Lys Thr Pro Val Val Ser
290                 295                 300

Leu Glu Tyr Asp Phe Glu His Lys Gln Arg Ile Asp Asn Glu Asn Asp
305                 310                 315                 320

<210> SEQ ID NO 81
<211> LENGTH: 162
<212> TYPE: PRT
<213> ORGANISM: Staphylococcus aureus

<400> SEQUENCE: 81

Lys Lys Leu Val Val Ser Ala Pro Thr Lys Pro Thr Ser Pro Thr
1               5                   10                  15

Thr Tyr Thr Glu Thr Thr Thr Gln Val Pro Met Pro Thr Val Glu Arg
                20                  25                  30

Gln Thr Gln Gln Gln Ile Ile Tyr Asn Ala Pro Lys Gln Leu Ala Gly
            35                  40                  45

Leu Asn Gly Glu Ser His Asp Phe Thr Thr His Gln Ser Pro Thr
50                  55                  60

Thr Ser Asn His Thr His Asn Asn Val Val Glu Phe Glu Glu Thr Ser
65                  70                  75                  80

Ala Leu Pro Gly Arg Lys Ser Gly Ser Leu Val Gly Ile Ser Gln Ile
                85                  90                  95

Asp Ser Ser His Leu Thr Glu Arg Glu Lys Arg Val Ile Lys Arg Glu
            100                 105                 110

His Val Arg Glu Ala Gln Lys Leu Val Asp Asn Tyr Lys Asp Thr His
        115                 120                 125

Ser Tyr Lys Asp Arg Ile Asn Ala Gln Gln Lys Val Asn Thr Leu Ser
130                 135                 140

Glu Gly His Gln Lys Arg Phe Asn Lys Gln Ile Asn Lys Val Tyr Asn
145                 150                 155                 160

Gly Lys

<210> SEQ ID NO 82
<211> LENGTH: 320
<212> TYPE: PRT
<213> ORGANISM: Staphylococcus aureus

<400> SEQUENCE: 82

Val Val Ser Gly Glu Lys Asn Pro Tyr Val Ser Lys Ala Leu Glu Leu
1               5                   10                  15

Lys Asp Lys Ser Asn Lys Ser Asn Ser Tyr Glu Asn Tyr Arg Asp Ser
                20                  25                  30

Leu Glu Ser Leu Ile Ser Ser Leu Ser Phe Ala Asp Tyr Glu Lys Tyr
            35                  40                  45

Glu Glu Pro Glu Tyr Glu Lys Ala Val Lys Lys Tyr Gln Gln Lys Phe
        50                  55                  60

Met Ala Glu Asp Ala Leu Lys Asn Phe Leu Asn Glu Lys Lys
65                  70                  75                  80

Ile Lys Asn Ala Asp Ile Ser Arg Lys Ser Asn Asn Leu Leu Gly Leu
                85                  90                  95

Thr His Glu Arg Tyr Ser Tyr Ile Phe Asp Thr Leu Lys Lys Asn Lys
            100                 105                 110

Gln Glu Phe Leu Lys Asp Ile Glu Glu Ile Gln Leu Lys Asn Ser Asp
        115                 120                 125

Leu Lys Asp Phe Asn Asn Thr Glu Gln His Asn Ala Asp Val Glu Ile

```
            130                 135                 140
Asn Asn Leu Glu Asn Lys Val Leu Met Val Gly Tyr Thr Phe Tyr Asn
145                 150                 155                 160

Thr Asn Lys Asp Glu Val Glu Leu Tyr Ser Glu Leu Asp Leu Ile
                165                 170                 175

Val Gly Glu Val Gln Asp Lys Ser Asp Lys Lys Arg Ala Val Asn Gln
                180                 185                 190

Arg Met Leu Asn Arg Lys Lys Glu Asp Leu Glu Phe Ile Ile Asp Lys
                195                 200                 205

Phe Phe Lys Lys Ile Gln Gln Glu Arg Pro Glu Ser Ile Pro Ala Leu
            210                 215                 220

Thr Ser Glu Lys Asn His Asn Gln Thr Met Ala Leu Lys Leu Lys Ala
225                 230                 235                 240

Asp Thr Glu Ala Ala Lys Asn Asp Val Ser Lys Arg Ser Lys Arg Ser
                245                 250                 255

Leu Asn Thr Gln Asn Asn Lys Ser Thr Thr Gln Glu Ile Ser Glu Glu
                260                 265                 270

Gln Lys Ala Glu Tyr Gln Arg Lys Ser Glu Ala Leu Lys Glu Arg Phe
            275                 280                 285

Ile Asn Arg Gln Lys Ser Lys Asn Glu Ser Val Val Ser Leu Ile Asp
            290                 295                 300

Asp Glu Asp Asp Asn Glu Asn Asp Arg Gln Leu Val Val Ser Ala Pro
305                 310                 315                 320

<210> SEQ ID NO 83
<211> LENGTH: 154
<212> TYPE: PRT
<213> ORGANISM: Staphylococcus aureus

<400> SEQUENCE: 83

Ser Lys Lys Pro Thr Thr Pro Thr Thr Tyr Thr Glu Thr Thr Thr Gln
1               5                   10                  15

Val Pro Met Pro Thr Val Glu Arg Gln Thr Gln Gln Ile Val Tyr
                20                  25                  30

Lys Thr Pro Lys Pro Leu Ala Gly Leu Asn Gly Glu Ser His Asp Phe
            35                  40                  45

Thr Thr Thr His Gln Ser Pro Thr Thr Ser Asn His Thr His Asn Asn
            50                  55                  60

Val Val Glu Phe Glu Glu Thr Ser Ala Leu Pro Gly Arg Lys Ser Gly
65                  70                  75                  80

Ser Leu Val Gly Ile Ser Gln Ile Asp Ser Ser His Leu Thr Glu Arg
                85                  90                  95

Glu Lys Arg Val Ile Lys Arg Glu His Val Arg Glu Ala Gln Lys Leu
            100                 105                 110

Val Asp Asn Tyr Lys Asp Thr His Ser Tyr Lys Asp Arg Leu Asn Ala
            115                 120                 125

Gln Gln Lys Val Asn Thr Leu Ser Glu Gly His Gln Lys Arg Phe Asn
            130                 135                 140

Lys Gln Ile Asn Lys Val Tyr Asn Gly Lys
145                 150

<210> SEQ ID NO 84
<211> LENGTH: 80
<212> TYPE: PRT
<213> ORGANISM: Staphylococcus aureus
```

```
<400> SEQUENCE: 84

Val Val Ser Gly Glu Asn Pro Tyr Lys Ser Glu Ser Leu Lys Leu
1               5                   10                  15

Asn Gly Lys Arg Ser Thr Thr Ile Thr Ser Asp Lys Tyr Glu Glu Asn
            20                  25                  30

Leu Asp Met Leu Ile Ser Ser Leu Ser Phe Ala Asp Tyr Glu Lys Tyr
            35                  40                  45

Glu Glu Pro Glu Tyr Lys Glu Ala Val Lys Lys Tyr Gln Gln Lys Phe
            50                  55                  60

Met Ala Glu Asp Asp Ala Leu Lys Asn Phe Leu Val Lys Arg Lys Lys
65                  70                  75                  80

<210> SEQ ID NO 85
<211> LENGTH: 132
<212> TYPE: PRT
<213> ORGANISM: Staphylococcus aureus

<400> SEQUENCE: 85

Val Val Ser Gly Glu Lys Asn Pro Tyr Val Ser Glu Ser Leu Lys Leu
1               5                   10                  15

Thr Asn Asn Lys Asn Lys Ser Arg Thr Val Glu Glu Tyr Lys Lys Ser
            20                  25                  30

Leu Asp Asp Leu Ile Trp Ser Phe Pro Asn Leu Asp Asn Glu Arg Phe
            35                  40                  45

Asp Asn Pro Glu Tyr Lys Glu Ala Met Lys Lys Tyr Gln Gln Arg Phe
            50                  55                  60

Met Ala Glu Asp Glu Ala Leu Lys Lys Phe Phe Ser Glu Glu Lys Lys
65                  70                  75                  80

Ile Lys Asn Gly Asn Thr Asp Asn Leu Asp Tyr Leu Gly Leu Ser His
            85                  90                  95

Glu Arg Tyr Glu Ser Val Phe Asn Thr Leu Lys Lys Gln Ser Glu Glu
            100                 105                 110

Phe Leu Lys Glu Ile Glu Asp Ile Lys Lys Asp Asn Pro Glu Leu Lys
            115                 120                 125

Asp Phe Asn Glu
            130

<210> SEQ ID NO 86
<211> LENGTH: 320
<212> TYPE: PRT
<213> ORGANISM: Staphylococcus aureus

<400> SEQUENCE: 86

Val Val Ser Gly Glu Lys Asn Pro Tyr Val Ser Glu Ser Leu Lys Leu
1               5                   10                  15

Thr Asn Asn Lys Asn Lys Ser Arg Thr Val Glu Glu Tyr Lys Lys Ser
            20                  25                  30

Leu Asp Asp Leu Ile Trp Ser Phe Pro Asn Leu Asp Asn Glu Arg Phe
            35                  40                  45

Asp Asn Pro Glu Tyr Lys Glu Ala Met Lys Lys Tyr Gln Gln Arg Phe
            50                  55                  60

Met Ala Glu Asp Glu Ala Leu Lys Lys Phe Phe Ser Glu Glu Lys Lys
65                  70                  75                  80

Ile Lys Asn Gly Asn Thr Asp Asn Leu Asp Tyr Leu Gly Leu Ser His
            85                  90                  95

Glu Arg Tyr Glu Ser Val Phe Asn Thr Leu Lys Lys Gln Ser Glu Glu
```

```
                     100                 105                 110
Phe Leu Lys Glu Ile Glu Asp Ile Lys Lys Asp Asn Pro Glu Leu Lys
            115                 120                 125

Asp Phe Asn Glu Glu Glu Gln Leu Lys Cys Asp Leu Glu Leu Asn Lys
130                 135                 140

Leu Glu Asn Gln Ile Leu Met Leu Gly Lys Thr Phe Tyr Gln Asn Tyr
145                 150                 155                 160

Arg Asp Asp Val Glu Ser Leu Tyr Ser Lys Leu Asp Leu Ile Met Gly
                165                 170                 175

Tyr Lys Asp Glu Glu Arg Ala Asn Lys Lys Ala Val Asn Lys Arg Met
            180                 185                 190

Leu Glu Asn Lys Lys Glu Asp Leu Glu Thr Ile Ile Asp Glu Phe Phe
            195                 200                 205

Ser Asp Ile Asp Lys Thr Arg Pro Asn Asn Ile Pro Val Leu Glu Asp
210                 215                 220

Glu Lys Gln Glu Glu Lys Asn His Lys Asn Met Ala Gln Leu Lys Ser
225                 230                 235                 240

Asp Thr Glu Ala Ala Lys Ser Asp Glu Ser Lys Arg Ser Lys Arg Ser
                245                 250                 255

Lys Arg Ser Leu Asn Thr Gln Asn His Lys Pro Ala Ser Gln Glu Val
            260                 265                 270

Ser Glu Gln Gln Lys Ala Glu Tyr Asp Lys Arg Ala Glu Glu Arg Lys
            275                 280                 285

Ala Arg Phe Leu Asp Asn Gln Lys Ile Lys Lys Thr Pro Val Val Ser
            290                 295                 300

Leu Glu Tyr Asp Phe Glu His Lys Gln Arg Ile Asp Asn Glu Asn Asp
305                 310                 315                 320

<210> SEQ ID NO 87
<211> LENGTH: 162
<212> TYPE: PRT
<213> ORGANISM: Staphylococcus aureus

<400> SEQUENCE: 87

Lys Lys Leu Val Val Ser Ala Pro Thr Lys Pro Thr Ser Pro Thr
1               5                   10                  15

Thr Tyr Thr Glu Thr Thr Thr Gln Val Pro Met Pro Thr Val Glu Arg
                20                  25                  30

Gln Thr Gln Gln Gln Ile Ile Tyr Asn Ala Pro Lys Gln Leu Ala Gly
            35                  40                  45

Leu Asn Gly Glu Ser His Asp Phe Thr Thr Thr His Gln Ser Pro Thr
50                  55                  60

Thr Ser Asn His Thr His Asn Asn Val Val Glu Phe Glu Glu Thr Ser
65                  70                  75                  80

Ala Leu Pro Gly Arg Lys Ser Gly Ser Leu Val Gly Ile Ser Gln Ile
                85                  90                  95

Asp Ser Ser His Leu Thr Glu Arg Glu Lys Arg Val Ile Lys Arg Glu
            100                 105                 110

His Val Arg Glu Ala Gln Lys Leu Val Asp Asn Tyr Lys Asp Thr His
            115                 120                 125

Ser Tyr Lys Asp Arg Ile Asn Ala Gln Gln Lys Val Asn Thr Leu Ser
            130                 135                 140
```

```
Glu Gly His Gln Lys Arg Phe Asn Lys Gln Ile Asn Lys Val Tyr Asn
145                 150                 155                 160
Gly Lys
```